US007888010B2

(12) United States Patent
Brown et al.

(10) Patent No.: US 7,888,010 B2
(45) Date of Patent: Feb. 15, 2011

(54) METHODS AND COMPOSITIONS INVOLVING MICRORNA

(75) Inventors: David Brown, Austin, TX (US); Kerri Keiger, Austin, TX (US); Emmanuel Labourier, Austin, TX (US); Jeffrey Shelton, Austin, TX (US); Jaclyn Shingara, Austin, TX (US)

(73) Assignee: Asuragen, Inc., Austin, TX (US)

( * ) Notice: Subject to any disclaimer, the term of this patent is extended or adjusted under 35 U.S.C. 154(b) by 0 days.

(21) Appl. No.: 11/141,707

(22) Filed: May 31, 2005

(65) Prior Publication Data

US 2007/0161004 A1 Jul. 12, 2007

Related U.S. Application Data

(60) Provisional application No. 60/575,743, filed on May 28, 2004, provisional application No. 60/649,584, filed on Feb. 3, 2005.

(51) Int. Cl.
C07H 21/04 (2006.01)
(52) U.S. Cl. .................... 435/6; 435/325; 435/375; 536/24.5; 536/24.31; 536/24.1
(58) Field of Classification Search ................ None
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,876,187 A | 10/1989 | Duck et al. | 435/6 |
| 4,999,290 A | 3/1991 | Lee | 435/6 |
| 5,011,769 A | 4/1991 | Duck et al. | 435/6 |
| 5,188,934 A | 2/1993 | Menchen et al. | 435/6 |
| 5,256,555 A | 10/1993 | Milburn et al. | 435/195 |
| 5,260,191 A | 11/1993 | Yang | 435/6 |
| 5,262,311 A | 11/1993 | Pardee et al. | 435/91.2 |
| 5,366,860 A | 11/1994 | Bergot et al. | 435/6 |
| 5,432,272 A | 7/1995 | Benner | 536/25.3 |
| 5,486,603 A | 1/1996 | Buhr | 536/24.3 |
| 5,538,848 A | 7/1996 | Livak et al. | 435/5 |
| 5,543,296 A | 8/1996 | Sobol et al. | 435/6 |
| 5,545,522 A | 8/1996 | Van Gelder et al. | 435/6 |
| 5,660,988 A | 8/1997 | Duck et al. | 435/6 |
| 5,723,591 A | 3/1998 | Livak et al. | 536/22.1 |
| 5,739,169 A | 4/1998 | Ocain et al. | 514/658 |
| 5,766,888 A | 6/1998 | Sobol et al. | 435/91.2 |
| 5,800,996 A | 9/1998 | Lee et al. | 435/6 |
| 5,801,005 A | 9/1998 | Cheever et al. | 435/724 |
| 5,801,155 A | 9/1998 | Kutyavin et al. | 514/44 |
| 5,824,311 A | 10/1998 | Greene et al. | 424/438.1 |
| 5,830,880 A | 11/1998 | Sedlacek et al. | 514/44 |
| 5,847,162 A | 12/1998 | Lee et al. | 549/227 |
| 5,859,221 A | 1/1999 | Cook et al. | 536/23.1 |
| 5,861,245 A | 1/1999 | McClelland | 435/6 |
| 5,863,727 A | 1/1999 | Lee et al. | 435/6 |
| 5,871,697 A | 2/1999 | Rothberg et al. | 422/68.1 |
| 5,898,031 A | 4/1999 | Crooke | 435/172.3 |
| 5,925,517 A | 7/1999 | Tyagi et al. | 435/6 |
| 5,936,087 A | 8/1999 | Benson et al. | 546/33 |
| 5,942,398 A | 8/1999 | Tartaglia et al. | 435/6 |
| 5,945,526 A | 8/1999 | Lee et al. | 536/26.6 |
| 5,965,364 A | 10/1999 | Benner | 435/6 |
| 5,976,567 A | 11/1999 | Wheeler et al. | 424/450 |
| 5,998,203 A | 12/1999 | Matulic-Adamic et al. | 435/325 |
| 6,001,983 A | 12/1999 | Benner | 536/23.1 |
| 6,004,755 A | 12/1999 | Wang | 435/6 |
| 6,008,379 A | 12/1999 | Benson et al. | 549/224 |
| 6,020,481 A | 2/2000 | Benson et al. | 536/26.6 |
| 6,037,129 A | 3/2000 | Cole et al. | 435/6 |
| 6,040,138 A * | 3/2000 | Lockhart et al. | 435/6 |
| 6,051,719 A | 4/2000 | Benson et al. | 548/416 |
| 6,057,105 A | 5/2000 | Hoon et al. | 435/6 |
| 6,084,102 A | 7/2000 | Kutyavin et al. | 548/100 |
| 6,096,314 A | 8/2000 | Cohen et al. | 424/185.1 |
| 6,103,476 A | 8/2000 | Tyagi et al. | 435/6 |
| 6,107,094 A | 8/2000 | Crooke | 435/455 |
| 6,111,095 A | 8/2000 | Benseler et al. | 536/25.3 |
| 6,132,997 A | 10/2000 | Shannon | 435/91.21 |
| 6,140,054 A | 10/2000 | Wittwer et al. | 435/6 |
| 6,140,500 A | 10/2000 | Yan et al. | 544/99 |
| 6,150,097 A | 11/2000 | Tyagi et al. | 435/6 |
| 6,153,737 A | 11/2000 | Manoharan et al. | 536/22.1 |
| 6,174,670 B1 | 1/2001 | Wittwer et al. | 435/6 |

(Continued)

FOREIGN PATENT DOCUMENTS

EP 0416817 3/1991

(Continued)

OTHER PUBLICATIONS

Kabbarah et al. (Mar. 2003) American J. Pathology 162:755-762.*

(Continued)

*Primary Examiner*—Kimberly Chong
(74) *Attorney, Agent, or Firm*—Fulbright & Jaworski LLP

(57) ABSTRACT

The present invention concerns methods and compositions for isolating, enriching, and/or labeling miRNA molecules and for preparing and using arrays or other detection techniques for miRNA analysis. Moreover, the present invention concerns methods and compositions for generating miRNA profiles and employing such profiles for therapeutic, diagnostic, and prognostic applications.

14 Claims, 26 Drawing Sheets

U.S. PATENT DOCUMENTS

| | | |
|---|---|---|
| 6,184,037 B1 | 2/2001 | Rolland et al. ............... 435/455 |
| 6,191,278 B1 | 2/2001 | Lee et al. ....................... 546/41 |
| 6,232,066 B1 | 5/2001 | Felder et al. ..................... 435/6 |
| 6,238,869 B1 | 5/2001 | Kris et al. ....................... 435/6 |
| 6,287,792 B1 | 9/2001 | Pardridge et al. ............. 435/7.5 |
| 6,344,316 B1* | 2/2002 | Lockhart et al. ................ 506/9 |
| 6,355,421 B1 | 3/2002 | Coull et al. ..................... 435/6 |
| 6,383,752 B1 | 5/2002 | Agrawal et al. .................. 435/6 |
| 6,418,382 B2 | 7/2002 | Rothberg et al. .............. 702/20 |
| 6,435,245 B1 | 8/2002 | Sette et al. ................... 156/745 |
| 6,458,382 B1 | 10/2002 | Herweijer et al. ............ 424/450 |
| 6,458,533 B1 | 10/2002 | Felder et al. .................... 435/6 |
| 6,476,205 B1 | 11/2002 | Buhr ........................ 536/23.1 |
| 6,485,901 B1 | 11/2002 | Gildea et al. .................... 435/5 |
| 6,506,559 B1 | 1/2003 | Fire et al. ....................... 435/6 |
| 6,511,832 B1 | 1/2003 | Guarino et al. ............. 435/91.1 |
| 6,548,250 B1 | 4/2003 | Sorge ............................ 435/6 |
| 6,573,048 B1 | 6/2003 | VanAtta et al. ................. 435/6 |
| 6,573,099 B2 | 6/2003 | Graham ...................... 435/455 |
| 6,586,218 B2 | 7/2003 | Milburn et al. ............... 435/195 |
| 6,586,219 B2 | 7/2003 | Milburn et al. ............... 435/195 |
| 6,589,743 B2 | 7/2003 | Sorge ............................ 435/6 |
| 6,590,091 B2 | 7/2003 | Albagli et al. ............. 536/24.3 |
| 6,593,091 B2 | 7/2003 | Keys et al. ...................... 435/6 |
| 6,596,490 B2 | 7/2003 | Dattagupta ..................... 435/6 |
| 6,706,480 B1 | 3/2004 | Armour ......................... 435/6 |
| 6,720,138 B2 | 4/2004 | Sharma et al. .................. 435/6 |
| 6,723,509 B2 | 4/2004 | Ach .............................. 435/6 |
| 6,730,477 B1 | 5/2004 | Sun et al. ....................... 435/6 |
| 6,787,335 B2 | 9/2004 | Salceda et al. .............. 435/69.1 |
| 6,797,471 B2 | 9/2004 | Katz et al. ...................... 435/6 |
| 6,815,432 B2 | 11/2004 | Wheeler et al. ................ 514/44 |
| 6,858,225 B2 | 2/2005 | Semple et al. ............... 424/450 |
| 6,964,847 B1 | 11/2005 | Englert .......................... 435/6 |
| 6,967,016 B2 | 11/2005 | Van Gemen et al. ......... 424/9.2 |
| 6,998,268 B2 | 2/2006 | Terada et al. ................. 435/455 |
| 7,001,724 B1 | 2/2006 | Greenfield ..................... 435/6 |
| 7,005,261 B1 | 2/2006 | Lloyd et al. .................... 435/6 |
| 7,014,838 B2 | 3/2006 | Mueller et al. .............. 424/1.69 |
| 7,015,047 B2 | 3/2006 | Huang et al. ................. 436/526 |
| 7,056,704 B2 | 6/2006 | Tuschl et al. ............... 435/91.1 |
| 7,078,180 B2 | 7/2006 | Genetta ..................... 435/7.23 |
| 7,078,196 B2 | 7/2006 | Tuschl et al. ............... 435/91.1 |
| 7,109,167 B2 | 9/2006 | Von Wronski et al. ......... 514/12 |
| 7,141,372 B2 | 11/2006 | Spivack et al. .................. 435/6 |
| 7,171,311 B2 | 1/2007 | Dai et al. ...................... 702/219 |
| 7,192,586 B2 | 3/2007 | Bander .................... 424/155.1 |
| 7,205,105 B2 | 4/2007 | Afonina et al. ................. 435/6 |
| 7,232,806 B2 | 6/2007 | Tuschl et al. ................. 514/44 |
| 7,282,564 B2 | 10/2007 | Mello et al. .................. 530/350 |
| 7,297,480 B2 | 11/2007 | Vogt ............................ 435/6 |
| 7,306,906 B2 | 12/2007 | Maruyama et al. ............. 435/6 |
| 7,307,067 B2 | 12/2007 | Sarnow et al. ................ 514/44 |
| 7,354,725 B2 | 4/2008 | Muraca ..................... 435/7.1 |
| 7,365,058 B2 | 4/2008 | Stoffel et al. ................. 514/44 |
| 7,368,098 B2 | 5/2008 | Mueller et al. ............. 424/1.49 |
| 7,390,792 B2 | 6/2008 | Srivastava et al. ............. 514/44 |
| 7,402,389 B2 | 7/2008 | Mousses et al. ................ 435/6 |
| 7,452,987 B2 | 11/2008 | Giese et al. ................ 536/24.5 |
| 7,459,547 B2 | 12/2008 | Zamore et al. ............. 536/24.5 |
| 7,473,525 B2 | 1/2009 | Kreutzer et al. ................ 435/6 |
| 7,495,073 B2 | 2/2009 | Hsu et al. .................... 530/350 |
| 7,582,744 B2 | 9/2009 | Manoharan et al. ........ 536/24.5 |
| 7,592,441 B2 | 9/2009 | Bentwich et al. ........... 536/24.5 |
| 7,642,348 B2 | 1/2010 | Bentwich et al. ........... 536/24.5 |
| 7,655,785 B1 | 2/2010 | Bentwich .................. 536/24.1 |
| 7,683,036 B2 | 3/2010 | Esau et al. .................... 514/44 |
| 7,723,510 B1 | 5/2010 | Tuschl et al. .............. 536/24.5 |
| 2002/0006630 A1 | 1/2002 | Sirbasku ........................ 514/1 |
| 2002/0037540 A1 | 3/2002 | Ali et al. .................... 424/1.49 |
| 2002/0065396 A1 | 5/2002 | Yang et al. ................. 424/1.49 |
| 2002/0065406 A1 | 5/2002 | Meyers ........................... 435/6 |
| 2002/0068307 A1 | 6/2002 | Pluta et al. .................. 435/7.23 |
| 2002/0086356 A1 | 7/2002 | Tuschl et al. ............... 435/69.1 |
| 2002/0094546 A1 | 7/2002 | Shimkets et al. ............ 435/69.4 |
| 2002/0119156 A1 | 8/2002 | Chen et al. ................ 424/155.1 |
| 2002/0165189 A1 | 11/2002 | Crooke ........................ 514/44 |
| 2003/0009295 A1 | 1/2003 | Markowitz et al. ............ 702/20 |
| 2003/0027783 A1 | 2/2003 | Zernicka-Goetz et al. ..... 514/44 |
| 2003/0031678 A1 | 2/2003 | Ali et al. .................... 424/185.1 |
| 2003/0033614 A1 | 2/2003 | French et al. ................... 800/3 |
| 2003/0084471 A1 | 5/2003 | Beach et al. .................. 800/278 |
| 2003/0099976 A1 | 5/2003 | Chang ........................... 435/6 |
| 2003/0108923 A1 | 6/2003 | Tuschl et al. ................... 435/6 |
| 2003/0124114 A1 | 7/2003 | McIntire et al. ........... 424/94.63 |
| 2003/0157030 A1 | 8/2003 | Davis et al. .................... 424/46 |
| 2003/0170623 A1 | 9/2003 | Chen et al. ..................... 435/6 |
| 2003/0175768 A1 | 9/2003 | Carson et al. ................... 435/6 |
| 2003/0180298 A1 | 9/2003 | Old et al. ................... 424/144.1 |
| 2003/0204322 A1 | 10/2003 | Loehrlein et al. .............. 702/20 |
| 2003/0215842 A1 | 11/2003 | Sledziewski et al. ............ 435/6 |
| 2004/0001841 A1 | 1/2004 | Nagavarapu et al. ...... 424/178.1 |
| 2004/0010001 A1 | 1/2004 | Au et al. ....................... 514/283 |
| 2004/0029121 A1 | 2/2004 | Cottrell et al. .................. 435/6 |
| 2004/0029128 A1 | 2/2004 | Cottrell et al. .................. 435/6 |
| 2004/0053411 A1 | 3/2004 | Cullen et al. ................... 514/44 |
| 2004/0058373 A1 | 3/2004 | Winkler et al. ............. 435/91.2 |
| 2004/0063197 A1 | 4/2004 | Tilles et al. ............... 435/287.2 |
| 2004/0063654 A1 | 4/2004 | Davis et al. .................... 514/44 |
| 2004/0072164 A1 | 4/2004 | Maruyama et al. ............. 435/6 |
| 2004/0086504 A1 | 5/2004 | Sampath et al. ........... 424/143.1 |
| 2004/0110191 A1 | 6/2004 | Winkler et al. ................. 435/6 |
| 2004/0114800 A1 | 6/2004 | Ponomarev et al. ......... 382/173 |
| 2004/0115630 A1 | 6/2004 | Olek et al. ...................... 435/6 |
| 2004/0115671 A1 | 6/2004 | Zlokovic et al. ................ 435/6 |
| 2004/0147027 A1 | 7/2004 | Troy et al. .................... 435/458 |
| 2004/0152112 A1 | 8/2004 | Croce et al. .................... 435/6 |
| 2004/0166511 A1 | 8/2004 | Clasina Timmermans et al. ............................ 435/6 |
| 2004/0175732 A1* | 9/2004 | Rana ............................. 435/6 |
| 2004/0203145 A1 | 10/2004 | Zamore et al. ............... 435/375 |
| 2004/0214198 A1 | 10/2004 | Rana ............................. 435/6 |
| 2004/0215651 A1 | 10/2004 | Markowitz et al. .......... 707/102 |
| 2004/0224337 A1 | 11/2004 | Foehr et al. ..................... 435/6 |
| 2004/0229211 A1 | 11/2004 | Yeung ........................... 435/5 |
| 2004/0236516 A1 | 11/2004 | Brandon ....................... 702/20 |
| 2004/0243362 A1 | 12/2004 | Liebman ........................ 703/2 |
| 2004/0259247 A1 | 12/2004 | Tuschl et al. ................ 435/375 |
| 2005/0020521 A1 | 1/2005 | Rana ............................ 514/44 |
| 2005/0026278 A1 | 2/2005 | Tuschl et al. ................ 435/375 |
| 2005/0033030 A1 | 2/2005 | Lo et al. ................. 530/388.15 |
| 2005/0037362 A1* | 2/2005 | Remacle et al. ................. 435/6 |
| 2005/0059005 A1* | 3/2005 | Tuschl et al. ................... 435/6 |
| 2005/0059024 A1* | 3/2005 | Conrad .......................... 435/6 |
| 2005/0065333 A1 | 3/2005 | Seth ......................... 536/23.5 |
| 2005/0074788 A1 | 4/2005 | Dahlberg et al. ................ 435/6 |
| 2005/0075492 A1 | 4/2005 | Chen et al. .................. 536/23.1 |
| 2005/0095646 A1 | 5/2005 | Sherman .................... 435/7.1 |
| 2005/0112604 A1 | 5/2005 | Fujimoto et al. ................ 435/6 |
| 2005/0125161 A1 | 6/2005 | Cairney et al. ................ 702/20 |
| 2005/0130170 A1 | 6/2005 | Harvey et al. ................... 435/6 |
| 2005/0130172 A1 | 6/2005 | Beard et al. .................... 435/6 |
| 2005/0142556 A1 | 6/2005 | Hoon et al. ..................... 435/6 |
| 2005/0153337 A1 | 7/2005 | Manoharan .................... 435/6 |
| 2005/0176018 A1 | 8/2005 | Thompson et al. ............. 435/6 |
| 2005/0181382 A1 | 8/2005 | Zamore et al. .................. 435/6 |
| 2005/0182005 A1 | 8/2005 | Tuschl et al. ................. 514/44 |
| 2005/0186586 A1 | 8/2005 | Zamore et al. .................. 435/6 |
| 2005/0208493 A1 | 9/2005 | Alon .............................. 435/6 |
| 2005/0234006 A1 | 10/2005 | Tuschl et al. ................. 514/44 |
| 2005/0234007 A1 | 10/2005 | Tuschl et al. ................. 514/44 |
| 2005/0261218 A1 | 11/2005 | Esau et al. .................... 514/44 |
| 2005/0266418 A1 | 12/2005 | Chen et al. ..................... 435/6 |
| 2005/0287539 A1 | 12/2005 | Labourier et al. ............... 435/6 |

| | | | |
|---|---|---|---|
| 2006/0051768 A1 | 3/2006 | Hoon et al. ............... 435/6 |
| 2006/0078894 A1 | 4/2006 | Winkler et al. ............. 435/6 |
| 2006/0088521 A1 | 4/2006 | Mahadevan ............. 424/133.1 |
| 2006/0095980 A1 | 5/2006 | Petitte et al. ............. 800/19 |
| 2006/0105350 A1 | 5/2006 | Qiao et al. ............... 435/6 |
| 2006/0105360 A1 | 5/2006 | Croce et al. .............. 435/6 |
| 2006/0134639 A1* | 6/2006 | Huffel et al. .............. 435/6 |
| 2006/0134661 A1 | 6/2006 | Essner ................... 435/6 |
| 2006/0154275 A1 | 7/2006 | Sgarlato et al. ........... 435/6 |
| 2006/0165659 A1 | 7/2006 | Croce et al. ............ 424/93.2 |
| 2006/0183128 A1 | 8/2006 | Berlin et al. ............. 435/6 |
| 2006/0185026 A1 | 8/2006 | Sacktor et al. ........... 800/12 |
| 2006/0185027 A1 | 8/2006 | Bartel et al. ............. 800/14 |
| 2006/0189557 A1 | 8/2006 | Slack et al. .............. 514/44 |
| 2006/0195269 A1 | 8/2006 | Yeatman et al. ............ 702/20 |
| 2006/0210979 A1 | 9/2006 | Yang et al. ............... 435/6 |
| 2006/0247193 A1 | 11/2006 | Taira et al. .............. 514/44 |
| 2006/0252057 A1 | 11/2006 | Raponi et al. ............. 435/6 |
| 2006/0258566 A1 | 11/2006 | Von Wronski et al. ........ 514/7 |
| 2006/0271309 A1 | 11/2006 | Showe et al. ............. 702/20 |
| 2006/0292616 A1 | 12/2006 | Neely et al. .............. 435/6 |
| 2007/0003960 A1 | 1/2007 | Tuschl et al. ............. 435/6 |
| 2007/0003961 A1 | 1/2007 | Tuschl et al. ............. 435/6 |
| 2007/0003962 A1 | 1/2007 | Tuschl et al. ............. 435/6 |
| 2007/0003963 A1 | 1/2007 | Tuschl et al. ............. 435/6 |
| 2007/0009484 A1 | 1/2007 | Hunt et al. ............... 424/450 |
| 2007/0025997 A1 | 2/2007 | Nagavarapu et al. ...... 424/155.1 |
| 2007/0031840 A1 | 2/2007 | Klussmann et al. .......... 435/6 |
| 2007/0031873 A1 | 2/2007 | Wang et al. .............. 435/6 |
| 2007/0041934 A1 | 2/2007 | William et al. ............ 424/78.3 |
| 2007/0048758 A1 | 3/2007 | Lokhov et al. ............. 435/6 |
| 2007/0050146 A1 | 3/2007 | Bentwich et al. ........... 702/19 |
| 2007/0054287 A1 | 3/2007 | Bloch .................... 435/6 |
| 2007/0065844 A1 | 3/2007 | Golub et al. .............. 435/6 |
| 2007/0072204 A1 | 3/2007 | Hannon et al. ............. 435/6 |
| 2007/0093445 A1 | 4/2007 | Tuschl et al. ............. 514/44 |
| 2007/0099196 A1 | 5/2007 | Kauppinen et al. .......... 435/6 |
| 2007/0213292 A1 | 9/2007 | Stoffel et al. ............ 514/44 |
| 2007/0259827 A1 | 11/2007 | Aronin et al. ............. 514/44 |
| 2007/0287179 A1 | 12/2007 | Tuschl et al. ............. 435/455 |
| 2007/0299030 A1 | 12/2007 | Dmitrovsky et al. ......... 514/44 |
| 2008/0026951 A1 | 1/2008 | Brown et al. .............. 435/6 |
| 2008/0050744 A1 | 2/2008 | Brown et al. ............. 536/24.5 |
| 2008/0076674 A1 | 3/2008 | Litman et al. ............. 506/9 |
| 2008/0131878 A1 | 6/2008 | Latham et al. ............. 435/200 |
| 2008/0132461 A1 | 6/2008 | Tuschi et al. ............. 514/44 |
| 2008/0171667 A1 | 7/2008 | Brown et al. ............. 536/24.5 |
| 2008/0171715 A1 | 7/2008 | Brown et al. .............. 514/44 |
| 2008/0176766 A1 | 7/2008 | Brown et al. .............. 435/6 |
| 2008/0182237 A1 | 7/2008 | Bentwich et al. ............ 435/6 |
| 2008/0182245 A1 | 7/2008 | Brown et al. .............. 435/6 |
| 2008/0261908 A1 | 10/2008 | Croce et al. .............. 514/44 |
| 2008/0269147 A1 | 10/2008 | Tuschl et al. ............. 514/44 |
| 2008/0306006 A1 | 12/2008 | Croce .................... 514/12 |
| 2008/0306018 A1 | 12/2008 | Croce et al. .............. 514/44 |
| 2009/0029932 A1 | 1/2009 | Voinnet et al. ............ 514/44 |
| 2009/0092974 A1 | 4/2009 | Davison et al. ............ 435/91.1 |
| 2009/0131348 A1 | 5/2009 | Labourier et al. ........... 435/6 |
| 2009/0131354 A1 | 5/2009 | Bader et al. .............. 514/44 |
| 2009/0131356 A1 | 5/2009 | Bader et al. .............. 514/44 |
| 2009/0186353 A1 | 7/2009 | Aharonov et al. ........... 435/6 |
| 2009/0186843 A1 | 7/2009 | Tuschl et al. ............. 514/44 |
| 2010/0144850 A1 | 6/2010 | Croce .................... 514/44 |
| 2010/0203544 A1 | 8/2010 | Croce et al. .............. 435/6 |
| 2010/0234241 A1 | 9/2010 | Croce et al. .............. 506/9 |

FOREIGN PATENT DOCUMENTS

| | | |
|---|---|---|
| EP | 0870842 | 10/1998 |
| EP | 0921195 | 6/1999 |
| EP | 1352061 | 5/2006 |
| FR | 2877350 | 5/2006 |
| WO | WO 93/21329 | 10/1993 |
| WO | WO 97/27317 | 7/1997 |
| WO | WO 97/43450 | 11/1997 |
| WO | WO 97/45539 | 12/1997 |
| WO | WO 98/08973 | 3/1998 |
| WO | WO 99/21881 | 5/1999 |
| WO | WO 99/23256 | 5/1999 |
| WO | WO 99/36760 | 7/1999 |
| WO | WO 00/05409 | 2/2000 |
| WO | WO 00/24939 | 5/2000 |
| WO | WO 00/44895 | 8/2000 |
| WO | WO 00/56748 | 9/2000 |
| WO | WO 00/66604 | 11/2000 |
| WO | WO 00/75356 | 12/2000 |
| WO | WO 01/68255 | 9/2001 |
| WO | WO 01/75164 | 10/2001 |
| WO | WO 02/00169 | 1/2002 |
| WO | WO 02/64835 | 1/2002 |
| WO | WO 02/44321 | 6/2002 |
| WO | WO 03/020898 | 3/2003 |
| WO | WO 03/022421 | 3/2003 |
| WO | WO 03/023058 | 3/2003 |
| WO | WO 03/029459 | 4/2003 |
| WO | WO 03/029485 | 4/2003 |
| WO | WO 03/040410 | 5/2003 |
| WO | WO 03/053586 | 7/2003 |
| WO | WO 03/066906 | 8/2003 |
| WO | WO 03/067217 | 8/2003 |
| WO | WO 03/076928 | 9/2003 |
| WO | WO 03/087297 | 10/2003 |
| WO | WO 03/091426 | 11/2003 |
| WO | WO 03/093810 | 11/2003 |
| WO | WO 03/100012 | 12/2003 |
| WO | WO 03/100448 | 12/2003 |
| WO | WO 2004/020085 | 3/2004 |
| WO | WO 2004/027093 | 4/2004 |
| WO | WO 2004/029212 | 4/2004 |
| WO | WO 2004/043387 | 5/2004 |
| WO | WO 2004/046324 | 6/2004 |
| WO | WO 2004/050125 | 6/2004 |
| WO | WO 2004/066183 | 8/2004 |
| WO | WO 2004/074509 | 9/2004 |
| WO | WO 2004/076622 | 9/2004 |
| WO | WO 2005/013901 | 2/2005 |
| WO | WO 2005/078139 | 8/2005 |
| WO | WO 2005078139 A2 * | 8/2005 |
| WO | WO 2005/079397 | 9/2005 |
| WO | WO 2005/116261 | 12/2005 |
| WO | WO 2005/118806 | 12/2005 |
| WO | WO 2006/028967 | 3/2006 |
| WO | WO 2006/033928 | 3/2006 |
| WO | WO 2006/101173 | 9/2006 |
| WO | WO 2006/113679 | 10/2006 |
| WO | WO 2006/119365 | 11/2006 |
| WO | WO 2006/128245 | 12/2006 |
| WO | WO 2006/135765 | 12/2006 |
| WO | WO 2006/137941 | 12/2006 |
| WO | WO 2007/016548 | 2/2007 |
| WO | WO 2007/033023 | 3/2007 |
| WO | WO 2007/073737 | 7/2007 |
| WO | WO 2007/081720 | 7/2007 |
| WO | WO 2007/081740 | 7/2007 |
| WO | WO 2007/087113 | 8/2007 |
| WO | WO 2008/014008 | 1/2008 |
| WO | WO 2008/095096 | 9/2008 |
| WO | WO 2008/136971 | 11/2008 |
| WO | WO 2008/137867 | 11/2008 |

OTHER PUBLICATIONS

McManus (2003) "MicroRNAs and cancer" Seminars in Cancer Biology 13:253-258.*

Metzler et al. (2004) "High expression of precursor microRNA-155/BIC RNA in children with Burkitt lymphoma" Genes, Chromosomes & Cancer 39:167-169.*

Michael et al. (2003) "Reduced accumulation of specific MicroRNAs in colorectal neoplasia" Mol. Cancer Res. 1:882-891.*

Lilja et al. (2008) "Prostate-specific antigen and prostate cancer: prediction, detection and monitoring" Nat Rev Cancer Apr;8(4):268-78.*

Tricoli et al. (2007) "MicroRNA: Potential for Cancer Detection, Diagnosis, and Prognosis" Cancer Res 2007; 67 (10): 4553-4555.*

Database EMBL, "Human DNA related to regulating mammalian cells using miRNAs Seq 471," EBI Database Accession No. ADR83569, Dec. 2, 2004.

PCT International Search Report and Written Opinion, issued in International Application No. PCT/US2005/041162, dated Nov. 16, 2007.

Calin et al., "Human microRNA genes are frequently located at fragile sites and genomic regions involved in cancers," PNAS, 101(9):2999-3004, 2004.

Cao et al., "A functional study of miR-124 in the developing neural tube," Genes & Development, 21(5):531-536, 2007.

Conaco et al., "Reciprocal actions of REST and a microRNA promote neuronal identity," PNAS, 103(7):2422-2427, 2006.

Decision on Appeal, Appeal 2008-002253, issued in U.S. Appl. No. 10/880,350, decided May 29, 2009.

Karginov et al., "A biochemical approach to identifying microRNA targets," PNAS, 104(49):19291-19296, 2007.

Lujambio et al., "Genetic unmasking of an epigenetically silenced microRNA in human cancer cells," Cancer Research, 67(4):1424-1429, 2007.

Makeyev et al., "The microRNA miR-124 promotes neuronal differentiation by triggering brain-specific alternative pre-mRNA splicing," Molecular Cell, 27(3):435-448, 2007.

Nakamura et al., "MARCH-II is a syntaxin-6-binding protein involved in endosomal trafficking," Molecular Biology of the Cell, 16(4):1696-1710, 2005.

Office Action issued in U.S. Appl. No. 09154092.2, mailed May 7, 2009.

Office Action issued in U.S. Appl. No. 10/963,415, mailed Mar. 9, 2009.

Office Action issued in U.S. Appl. No. 11/273,640, mailed Jun. 26, 2009.

Office Action issued in U.S. Appl. No. 11/837,487, mailed Mar. 25, 2009.

Office Action issued in U.S. Appl. No. 11/837,498, mailed Apr. 30, 2009.

Office Action issued in U.S. Appl. No. 11/857,948, mailed Jun. 4, 2009.

Office Action issued in U.S. Appl. No. 11/967,639, mailed May 14, 2009.

Office Action issued in U.S. Appl. No. 11/967,639, mailed Mar. 13, 2009.

PCT International Preliminary Report on Patentability, issued in International Application No. PCT/US2007/078894, mailed Apr. 2, 2009.

PCT International Preliminary Report on Patentability, issued in International Application No. PCT/US2007/078936, mailed Apr. 2, 2009.

PCT International Preliminary Report on Patentability, issued in International Application No. PCT/US2007/078859, mailed Apr. 2, 2009.

PCT International Search Report and Written Opinion, issued in International Application No. PCT/US2008/076246, mailed Feb. 27, 2009.

PCT Invitation to Pay Additional Fees and Partial International Search, issued in International Application No. PCT/US2008/085178, mailed May 8, 2009.

Tang et al., "PS 7-2 microrna expression profile in cervical cancer and its derived cell lines," 23$^{rd}$ International Papillomavirus Conference and Clinical Workshop, Prague, Czech Republic, Sep. 1-7, 2006.

Visvanathan et al., "The microRNA miR-124 antagonizes the antineural REST/SCP1pathway during embryonic CNS development," Genes & Development, 21(7):744-749, 2007.

Wang and Wang, "Systematic identification of microRNA functions by combining target prediction and expression profiling," Nucleic Acids Research, 34(5):1646-1652, 2006.

"Poster Abstracts," Annals of Surgical Oncology, 15(Suppl 1):33-64, 2008.

Agrawal and Syngal, "Colon cancer screening strategies," Curr Opin Gastroenterol, 21(1):59-63, 2005.

Aoki et al., "Proteasomal degradation of the FoxO1 transcriptional regulator in cells transformed by the P3k and Akt oncoproteins," Proc Natl Acad Sci U S A, 101(37):13613-13617, 2004.

Austin and Cook, "Increased expression of Mcl-1 is required for protection against serum starvation in phosphatase and tensin homologue on chromosome 10 null mouse embryonic fibroblasts, but repression of Bim is favored in human glioblastomas," J Biol Chem, 280(39):33280-33288, 2005.

Bader and Vogt, "An essential role for protein synthesis in oncogenic cellular transformation," Oncogene, 23(18):3145-3150, 2004.

Bader et al.,"Oncogenic PI3K deregulates transcription and translation," Nat Rev Cancer, 5(12):921-929, 2005.

Baffa et al., "MicroRNA expression profiling of human metastatic cancers identifies cancer gene targets," J. Pathol., Epub Ahead of Print, 2009.

Bai et al., "Downregulation of selective microRNAs in trigeminal ganglion neurons following inflammatory muscle pain," Mol Pain, 3:15, 2007.

Bartel et al., "Alternative and aberrant splicing of MDM2 mRNA in human cancer," Cancer Cell, 2(1):9-15, 2002.

Beeram et al., "Raf: a strategic target for therapeutic development against cancer," J Clin Oncol, 23(27):6771-6790, 2005.

Bell and Dutta, "DNA replication in eukaryotic cells," Annu Rev Biochem, 71:333-374, 2002.

Bello et al., "Androgen responsive adult human prostatic epithelial cell lines immortalized by human papillomavirus 18," Carcinogenesis, 18(6):1215-1223, 1997.

Bertagnolli et al., "Sentinel node staging of resectable colon cancer: results of a multicenter study," Ann. Surg., 240(4):624-630, 2004.

Blobe et al., "Functional roles for the cytoplasmic domain of the type III transforming growth factor beta receptor in regulating transforming growth factor beta signaling," J Biol Chem, 276(27):24627-24637, 2001.

Brothman et al., "Metastatic properties of the human prostatic cell line, PPC-1, in athymic nude mice," J Urol., 145(5):1088-1091, 1991.

Calin et al., "MicroRNA profiling reveals distinct signatures in B cell chronic lymphocytic leukemias," Proc Natl Acad Sci USA, 101(32):11755-11760, 2004.

Carter and Brunet, "FOXO transcription factors," Curr Biol, 17(4):R113-114, 2007.

Caselitz et al., "Malignant melanomas contain only the vimentin type of intermediate filaments," Virchows Arch A Pathol Anat Histopathol, 400(1):43-51, 1983.

Chendrimada et al., "MicroRNA silencing through RISC recruitment of eIF6," Nature, 447(7146):823-828, 2007.

Chieffi et al., "Aurora B expression directly correlates with prostate cancer malignancy and influence prostate cell proliferation," Prostate, 66(3):326-333, 2006.

Chmielarz et al., "Prognostic factors for the time of occurrence and dynamics of distant metastases and local recurrences after radical treatment in patients with rectal cancer," Med Sci Monit., 7(6):1263-1269, 2001.

Churg, "Immunohistochemical staining for vimentin and keratin in malignant mesothelioma," Am J Surg Pathol, 9(5):360-365, 1985.

Cipriano and Chen, "Insensitivity to growth inhibition by TGF-beta1 correlates with a lack of inhibition of the CDK2 activity in prostate carcinoma cells," Oncogene, 17(12):1549-1556, 1998.

Coello et al., "Prognostic significance of micrometastasis in non-small-cell lung cancer," Clin. Lung Cancer, 5:214-225, 2004.

Cohen et al., "Prognosis of node-positive colon cancer," Cancer, 67(7):1859-1861, 1991.

Coll et al., "Molecular cloning of the avian acute transforming retrovirus MH2 reveals a novel cell-derived sequence (v-mil) in addition to the myc oncogene," Embo J, 2(12):2189-2194, 1983.

Costello et al., "Cyclin-dependent kinase 6 (CDK6) amplification in human gliomas identified using two-dimensional separation of genomic DNA," *Cancer Res*, 57(7):1250-1254, 1997.

Cox et al., "Significance of sentinel lymph node micrometastases in human breast cancer," *J. Am. Coll. Surg.*, 206(2):261-268, 2008.

Dahl et al., "Identification of sentinel nodes in patients with colon cancer," *Eur. J. Surg. Oncol.*, 31(4):381-385, 2005.

Davison et al., "Analyzing micro-RNA expression using microarrays," *Meth. Enzymol.*, 411:14-34, 2006.

D'Cunha et al., "Poor correspondence between clinical and pathologic staging in stage 1 non-small cell lung cancer: results from CALGB 9761, a prospective trial," *Lung Cancer*, 48:241-246, 2005.

De Boer et al., "Micrometastases and isolated tumor cells: relevant and robust or rubbish? (MIRROR): preliminary results of the MIRROR study from the Dutch breast cancer trialists' group (BOOG)," *San Antonio Breast Cancer Symposium*, Abstract 23, 2008.

Dillon et al., "An April to remember: novel TNF ligands as therapeutic targets," *Nat Rev Drug Discov*, 5(3):235-246, 2006.

Dittmer, "The biology of the Ets1 proto-oncogene," *Mol Cancer*, 2:29, 2003.

Dyer and Bremner, "The search for the retinoblastoma cell of origin," *Nat Rev Cancer*, 5(2):91-101, 2005.

Egle et al., "Bim is a suppressor of Myc-induced mouse B cell leukemia," *Proc Natl Acad Sci U S A*, 101(16):6164-6169, 2004.

Egloff et al., "Cyclin B1 and other cyclins as tumor antigens in immunosurveillance and immunotherapy of cancer," *Cancer Res*, 66(1):6-9, 2006.

Esser et al., "The role of sentinel lymph node mapping in staging of colon and rectal cancer," *Dis Colon Rectum*, 44(6):850-856, 2001.

European Search Report and Search Opinion issued in European Application No. 09154092.2, mailed Aug. 12, 2009.

Fakharzadeh et al., "Tumorigenic potential associated with enhanced expression of a gene that is amplified in a mouse tumor cell line," *Embo J*, 10(6):1565-1569, 1991.

Ferris et al., "Molecular staging of cervical lymph nodes in squamous cell carcinoma of the head and neck," *Cancer Res.*, 65:2147-2156, 2005.

Gerald and Haber, "The EWS-WT1 gene fusion in desmoplastic small round cell tumor," *Semin Cancer Biol*, 15(3):197-205, 2005.

Gillanders et al., "Molecular detection of micrometastatic breast cancer in histopathology-negative axillary lymph nodes correlates with traditional predictors of prognosis: an interim analysis of a prospective multi-institutional cohort study," *Ann. Surg.*, 239:828-840, 2004.

Gilles et al., "Vimentin expression in cervical carcinomas: association with invasive and migratory potential," *J Pathol*, 180(2):175-180, 1996.

Gipponi et al., "Sentinel lymph node as a new marker for therapeutic planning in breast cancer patients," *J. Surg. Oncol.*, 85(3):102-111, 2004.

Gomez-Bougie et al., "The imbalance between Bim and Mcl-1 expression controls the survival of human myeloma cells," *Eur J Immunol*, 34(11):3156-3164, 2004.

Gonzalez et al., "Oncogenic activity of Cdc6 through repression of the INK4/ARF locus," *Nature*, 440(7084):702-706, 2006.

Goyns et al., "The c-ets-1 proto-oncogene is rearranged in some cases of acute lymphoblastic leukaemia," *Br J Cancer*, 56(5):611-613, 1987.

Hayette et al., "In B-cell chronic lymphocytic leukemias, 7q21 translocations lead to overexpression of the CDK6 gene," *Blood*, 102(4):1549-1550, 2003.

Ho et al., "Quantification of colorectal cancer micrometastases in lymph nodes by nested and real-time reverse transcriptase-PCR analysis for carcinoembryonic antigen," *Clin. Cancer Res.*, 10(17):5777-5784, 2004.

Hodge et al., "The role of IL-6 and STAT3 in inflammation and cancer," *Eur J Cancer*, 41(16):2502-2512, 2005.

Hoeflich et al., "Insulin-like growth factor-binding protein 2 in tumorigenesis: protector or promoter?" *Cancer Res*, 61(24):8601-8610, 2001.

Hofer et al., "The role of metastasis-associated protein 1 in prostate cancer progression," *Cancer Res*, 64(3):825-829, 2004.

Horoszewicz et al., "The LNCaP cell line—a new model for studies on human prostatic carcinoma," *Prog Clin Biol Res.*, 37:115-32, 1980.

Houston and O'Connell, "The Fas signalling pathway and its role in the pathogenesis of cancer," *Curr Opin Pharmacol*, 4(4):321-326, 2004.

Houvenaeghel et al., "Micrometastases in sentinel lymph node in a multicentric study: predictive factors of nonsentinel lymph node involvement—Groupe des Chirurgiens de la Federation des Centres de Lutte Contre le Cancer," *J. Clin. Oncol.*, 24:1814-1822, 2006.

Hsu et al., "BOD (Bcl-2-related ovarian death gene) is an ovarian BH3 domain-containing proapoptotic Bcl-2 protein capable of dimerization with diverse antiapoptotic Bcl-2 members," *Mol Endocrinol*, 12(9):1432-1440, 1998.

Huber et al., "Variance stabilization applied to microarray data calibration and to the quantification of differential expression," *Bioinformatics*,18:Suppl 1:S96-104, 2002.

Hughes et al., "A rapid, fully automated, molecular-based assay accurately analyzes sentinel lymph nodes for the presence of metastatic breast cancer," *Ann. Surg.*, 243:389-398, 2006.

Iorio et al., "MicroRNA gene expression deregulation in human breast cancer," *Cancer Res*, 65(16):7065-7070, 2005.

Islam et al., "Vimentin expression in human squamous carcinoma cells: relationship with phenotypic changes and cadherin-based cell adhesion," *J Cell Biochem*, 78(1):141-150, 2000.

Jackson and Foster, "The enigmatic protein kinase Cdelta: complex roles in cell proliferation and survival," *Faseb J*, 18(6):627-636, 2004.

Jang et al., "MTA1 overexpression correlates significantly with tumor grade and angiogenesis in human breast cancers," *Cancer Sci*, 97(5):374-379, 2006.

Janknecht, "EWS-ETS oncoproteins: the linchpins of Ewing tumors," *Gene*, 363:1-14, 2005.

Jansen et al., "Two unrelated cell-derived sequences in the genome of avian leukemia and carcinoma inducing retrovirus MH2," *Embo J*, 2(11):1969-1975, 1983.

Kalin et al., "Increased levels of the FoxM1 transcription factor accelerate development and progression of prostate carcinomas in both TRAMP and LADY transgenic mice," *Cancer Res*, 66(3):1712-1720, 2006.

Kalinichenko et al., "Foxm1b transcription factor is essential for development of hepatocellular carcinomas and is negatively regulated by the p19ARF tumor suppressor, " *Genes Dev*, 18(7):830-850, 2004.

Kammula et al., "Serial follow-up and the prognostic significance of reverse transcriptase-polymerase chain reaction—staged sentinel lymph nodes from melanoma patients," *J. Clin. Oncol.*, 22:3989-3996, 2004.

Kapsimali et al., "MicroRNAs show a wide diversity of expression profiles in the developing and mature central nervous system," *Genome Biol*, 8(8):R173, 2007.

Karakaidos et al., "Overexpression of the replication licensing regulators hCdt1 and hCdc6 characterizes a subset of non-small-cell lung carcinomas: synergistic effect with mutant p53 on tumor growth and chromosomal instability—evidence of E2F-1 transcriptional control over hCdt1, " *Am J Pathol*, 165(4):1351-1365, 2004.

Karin et al., "NF-kappaB in cancer: from innocent bystander to major culprit," *Nat Rev Cancer*, 2(4):301-310, 2002.

Kastan and Lim, "The many substrates and functions of ATM," *Nat Rev Mol Cell Biol*, 1(3):179-186, 2000.

Kim et al., "The Forkhead Box m1 transcription factor stimulates the proliferation of tumor cells during development of lung cancer," *Cancer Res*, 66(4):2153-2161, 2006.

Kiriakidou et al., "An mRNA m7G cap binding-like motif within human Ago2 represses translation," *Cell*, 129(6):1141-1151, 2007.

Kops et al., "On the road to cancer: aneuploidy and the mitotic checkpoint," *Nat Rev Cancer*, 5(10):773-785. 2005.

Kristjánsdóttir and Rudolph, "Cdc25 phosphatases and cancer," *Chem Biol*, 11(8):1043-1051, 2004.

Kuehbacher et al., "Targeting microRNA expression to regulate angiogenesis," *Tren•ds Pharmacol Sci.*, 29(1):12-15, 2008.

Kuhajda, "Fatty acid synthase and cancer: new application of an old pathway," *Cancer Res*, 66(12):5977-5980, 2006.

Lagos-Quintana et al., "New microRNAs from mouse and human," *RNA*, 9(2):175-179, 2003.

Lam et al., "Expression of p19INK4d, CDK4, CDK6 in glioblastoma multiforme," *Br J Neurosurg*, 14(1):28-32, 2000.

Lee et al, "Altered microRNA expression in cervical carcinomas," *Clin Cancer Res*, 14(9):2535-2542, 2008.

Li et al., "Apoptosis of non-small-cell lung cancer cell lines after paclitaxel treatment involves the BH3-only proapoptotic protein Bim," *Cell Death Differ*, 12(3):292-303, 2005.

Li et al., "PDGF-D is a potent transforming and angiogenic growth factor," *Oncogene*, 22(10):1501-1510, 2003.

Liang et al., "Chacterization of microRNA expression profiles in normal human tissues," *BMC Genomics*, 8:166, 2007.

Liu and Erikson, "Polo-like kinase (Plk)1 depletion induces apoptosis in cancer cells," *Proc Natl Acad Sci U S A*, 100(10):5789-5794, 2003.

Lukiw, "Micro-RNA speciation in fetal, adult and Alzheimer's disease hippocampus," *Neuroreport*, 18(3):297-300, 2007.

Ma et al., "Tumour invasion and metastasis initiated by microRNA-10b in breast cancer," *Nature*, 449(7163):682-688, 2007.

Malumbres and Barbacid, "To cycle or not to cycle: a critical decision in cancer," *Nat Rev Cancer*, 1(3):222-231, 2001.

Marone et al., "Analysis of cyclin E and CDK2 in ovarian cancer: gene amplification and RNA overexpression," *Int J Cancer*,75(1):34-39, 1998.

McInroy and Määttä, "Down-regulation of vimentin expression inhibits carcinoma cell migration and adhesion," *Biochem Biophys Res Commun*, 360(1):109-114, 2007.

Mendrzyk et al., "Genomic and protein expression profiling identifies CDK6 as novel independent prognostic marker in medulloblastoma," *J Clin Oncol*, 23(34):8853-8862, 2005.

Mishima et al., "RT-PCR-based analysis of microRNA (miR-1 and -124) expression in mouse CNS," *Brain Res*, 1131(1):37-43, Epub Dec. 19, 2006. 2007.

Momand et al., "The MDM2 gene amplification database," *Nucleic Acids Res*, 26(15):3453-3459, 1998.

Morton et al., "Sentinel-node biopsy or nodal observation in melanoma," *N. Engl. J. Med.*, 355(13):1307-1317, 2006.

Morton et al., "Technical details of intraoperative lymphatic mapping for early stage melanoma," *Arch Surg*, 127(4):392-399, 1992.

Murphy et al., "p16INK4A, CDC6, and MCM5: predictive biomarkers in cervical preinvasive neoplasia and cervical cancer," *J Clin Pathol*, 58(5):525-534, 2005.

Nauert et al., "Gravin, an autoantigen recognized by serum from myasthenia gravis patients, is a kinase scaffold protein, " *Curr Biol*, 7(1):52-62, 1997.

Nerlov, "C/EBPalpha mutations in acute myeloid leukaemias," *Nat Rev Cancer*, 4(5):394-400, 2004.

Ngan et al., "Quantitative evaluation of vimentin expression in tumour stroma of colorectal cancer," *Br J Cancer*, 96(6):986-992, 2007.

Nordgård et al., "Quantitative RT-PCR detection of tumor cells in sentinel lymph nodes isolated from colon cancer patients with an ex vivo approach," *Annals of Surgery*, 249(4):602-607, 2009.

Öberg et al., "Detection of occult tumour cells in lymph nodes of colorectal cancer patients using real-time quantitative RT-PCR for CEA and CK20 mRNAS," *Int. J. Cancer*, 111(1):101-110, 2004.

O'Connor et al., "Bim: a novel member of the Bcl-2 family that promotes apoptosis," *Embo J*, 17(2):384-395, 1998.

Office Action issued in U.S. Appl. No. 11/837,490, mailed Aug. 18, 2009.

Office Action issued in U.S. Appl. No. 11/953,606, mailed Aug. 10, 2009.

Ohlsson et al., "Biomarker selection for detection of occult tumour cells in lymph nodes of colorectal cancer patients using real-time quantitative RT-PCR," *Br. J. Cancer*, 95(2):218-225, 2006.

Ohsaki et al., "Antitumor activity of magainin analogues against human lung cancer cell lines," *Cancer Res*, 52(13):3534-3538, 1992.

Ollila et al., "Metastatic melanoma cells in the sentinel node cannot be ignored," *J. Am. Coll. Surg.*, 208(5):924-929, 2009.

Paik et al., "FoxOs are lineage-restricted redundant tumor suppressors and regulate endothelial cell homeostasis," *Cell*, 128(2):309-323, 2007.

Paramo et al., "Validation of sentinel node mapping in patients with colon cancer," *Ann Surg Oncol*, 9(6):550-554, 2002.

Payton and Coats, "Cyclin E2, the cycle continues," *Int J Biochem Cell Biol*, 34(4):315-320, 2002.

Payton et al., "Deregulation of cyclin E2 expression and associated kinase activity in primary breast tumors," *Oncogene*, 21(55):8529-8534, 2002.

PCT International Preliminary Report on Patentability and Written Opinion, issued in International Application No. PCT/US2007/087033, mailed Jun. 18, 2009.

PCT International Preliminary Report on Patentability and Written Opinion, issued in International Application No. PCT/US2007/087031, mailed Jun. 18, 2009.

PCT International Preliminary Report on Patentability and Written Opinion, issued in International Application No. PCT/US2007/087029, mailed Jun. 18, 2009.

PCT International Preliminary Report on Patentability and Written Opinion, issued in International Application No. PCT/US2007/087037, mailed Jun. 18, 2009.

PCT International Preliminary Report on Patentability and Written Opinion, issued in International Application No. PCT/US2007/086396, mailed Jun. 18, 2009.

PCT International Preliminary Report on Patentability and Written Opinion, issued in International Application No. PCT/US2007/087021, mailed Jun. 18, 2009.

PCT International Preliminary Report on Patentability and Written Opinion, issued in International Application No. PCT/US2007/089206, mailed Jun. 18, 2009.

PCT International Preliminary Report on Patentability and Written Opinion, issued in International Application No. PCT/US2007/087038, mailed Jun. 18, 2009.

PCT International Search Report and Written Opinion, issued in International Application No. PCT/US2008/085178, mailed Aug. 21, 2009.

PCT International Search Report and Written Opinion, issued in International Application No. PCT/US2009/033556, mailed Aug. 4, 2009.

PCT Invitation to Pay Additional Fees and Partial International Search, issued in International Application No. PCT/US2009/043361, mailed Jul. 22, 2009.

PCT Invitation to Pay Additional Fees and Partial International Search, issued in International Application No. PCT/US2009/036195, mailed Jul. 2, 2009.

PCT Invitation to Pay Additional Fees and Partial International Search, issued in International Application No. PCT/US2009/033556, mailed Jun. 5, 2009.

Pendas et al., "Worldwide experience with lymphatic mapping for invasive breast cancer," *Semin. Oncol.*, 31(3):318-323, 2004.

Phan et al., "Sentinel lymph node biopsy for melanoma: indications and rationale," *Cancer Control*, 16(3):234-239, 2009.

Pietras et al., "PDGF receptors as cancer drug targets," *Cancer Cell*, 3(5):439-443, 2003.

Pretlow et al., "K-ras mutations in putative preneoplastic lesions in human colon," *J. Natl Cancer Inst.*, 85(24):2004-2007, 1993.

Qian et al., "Expression profiling of CD34+ hematopoietic stem/progenitor cells reveals distinct subtypes of therapy-related acute myeloid leukemia," *Proc Natl Acad Sci U S A*, 99(23):14925-14930, 2002.

Quan et al., "The evolution of lymph node assessment in breast cancer," *Journal of Surgical Oncology*, 2008.

Rapp et al., "Structure and biological activity of v-raf, a unique oncogene transduced by a retrovirus," *Proc Natl Acad Sci U S A*, 80(14):4218-4222, 1983.

Redston et al., "Analysis of micrometastatic disease in sentinel lymph nodes from resectable colon cancer: results of Cancer and Leukemia Group B Trial 80001," *J. Clin. Oncol.*, 24(6):878-883, 2006.

Reintgen et al., "Sentinel Node Biopsy in Breast Cancer: An Overview," *Breast J.*, 6(5):299-305, 2000.

Reshmi and Pillai, "Beyond HPV: oncomirs as new players in cervical cancer," *FEBS Letters*, 582:4113-4116, 2008.

Roberts et al., "Interpretive disparity among pathologists in breast sentinel lymph node evaluation," *Am. J. Surg.*, 186:324-329, 2003.

Rous, "A sarcoma of the fowl transmissible by an agent separable from the tumor cells," *J Exp Med*, 13:397-411, 1911.
Ryan et al., "MicroRNAs of the mammalian eye display distinct and overlapping tissue specificity," *Molecular Vision*, 12:1175-1184, 2006.
Saha et al., "Historical review of lymphatic mapping in gastrointestinal malignancies," *Ann Surg Oncol*, 11(3 Suppl):245S-249S, 2004.
Saha et al., "Ultrastaging of colorectal cancer by sentinel lymph node mapping technique—a multicenter trial," *Ann. Surg. Oncol.*, 8(9 Suppl):94S-98S, 2001.
Sasaki et al., "Expression of the MTA1 mRNA in advanced lung cancer," *Lung Cancer*, 35(2):149-154, 2002.
Schepeler et al., "Diagnostic and prognostic microRNAs in stage II colon cancer," *Cancer Research*, 68(15):6416-6424, 2008.
Schetter et al., "MicroRNA expression profiles associated with prognosis and therapeutic outcome in colon adenocarcinoma," *JAMA*, 299(4):425-436, 2008.
Schurr et al., "Lymphatic spread and microinvolvement in adenocarcinoma of the esophago-gastric junction," *J. Surg. Oncol.*, 94:307-315, 2006.
Schuster and Porse, "C/EBPalpha: a tumour suppressor in multiple tissues?" *Biochim Biophys Acta*, 1766(1):88-103, 2006.
Scoggins et al., "Prospective multi-institutional study of reverse transcriptase polymerase chain reaction for molecular staging of melanoma," *J. Clin. Oncol.*, 24:2849-2857, 2006.
Semple and Duncker, "ORC-associated replication factors as biomarkers for cancer," *Biotechnol Adv*, 22(8):621-631, 2004.
Shen et al., "MicroRNAs regulate ocular neovascularization," *Molecular Therapy*, 16(7):1208-1216, 2008.
Shen et al., "Suppression of ocular neovascularization with siRNA targeting VEGF receptor 1," *Gene Therapy*, 13:225-234, 2006.
Sherr and McCormick, "The RB and p53 pathways in cancer," *Cancer Cell*, 2(2):103-112, 2002.
Sherr and Roberts, "CDK inhibitors: positive and negative regulators of G1-phase progression," *Genes Dev*, 13(12):1501-1512, 1999.
Singh et al., "Overexpression of vimentin: role in the invasive phenotype in an androgen-independent model of prostate cancer," *Cancer Res*, 63(9):2306-2311, 2003.
Slaby et al., "Altered expression of miR-21, miR-31, miR-143 and miR-145 is related to clinicopathologic features of colorectal cancer," *Oncology*, 72(5-6):397-402, 2007.
Smirnova et al., "Regulation of miRNA expression during neural cell specification," *Eur J Neurosci*, 21(6):1469-1477, 2005.
Smith et al., "Overexpression of aurora B kinase (AURKB) in primary non-small cell lung carcinoma is frequent, generally driven from one allele, and correlates with the level of genetic instability," *Br J Cancer*, 93(6):719-729, 2005.
Sommers et al., "Loss of epithelial markers and acquisition of vimentin expression in adriamycin- and vinblastine-resistant human breast cancer cell lines," *Cancer Res*, 52(19):5190-5197, 1992.
Stehelin et al., "DNA related to the transforming gene(s) of avian sarcoma viruses is present in normal avian DNA," *Nature*, 260(5547):170-173, 1976.
Swanson et al., "The prognosis of T3N0 colon cancer is dependent on the number of lymph nodes examined," *Ann. Surg. Oncol.*, 10(1):65-71, 2003.
Tagawa et al., "Genome-wide array-based CGH for mantle cell lymphoma: identification of homozygous deletions of the proapoptotic gene BIM," *Oncogene*, 24(8):1348-1358, 2005.
Takeuchi et al., "Prognostic significance of molecular upstaging of paraffin-embedded sentinel lymph nodes in melanoma patients," *J. Clin. Oncol.*, 22:2671-2680, 2004.
Toh et al., "A novel candidate metastasis-associated gene, mta1, differentially expressed in highly metastatic mammary adenocarcinoma cell lines. cDNA cloning, expression, and protein analyses," *J Biol Chem*, 269(37):22958-22963, 1994.
Toh et al., "Overexpression of metastasis-associated MTA1 mRNA in invasive oesophageal carcinomas," *Br J Cancer*, 79(11-12):1723-1726, 1999.
Toh et al., "Overexpression of the MTA1 gene in gastrointestinal carcinomas: correlation with invasion and metastasis," *Int J Cancer*, 74(4):459-463, 1997.
Tsai et al., "Correlation of intrinsic chemoresistance of non-small-cell lung cancer cell lines with HER-2/neu gene expression but not with ras gene mutations," *J Natl Cancer Inst*, 85(11):897-901, 1993.
Turner et al., "Hallmarks of 'BRCAness' in sporadic cancers," *Nat Rev Cancer*, 4(10):814-819, 2004.
Tuveson et al., "BRAF as a potential therapeutic target in melanoma and other malignancies," *Cancer Cell*, 4(2):95-98, 2003.
Upton et al., "Expression of vimentin in surgically resected adenocarcinomas and large cell carcinomas of lung," *Am J Surg Pathol*, 10(8):560-567, 1986.
Vanhaesebroeck et al., "Phosphoinositide 3-kinases: a conserved family of signal transducers," *Trends Biochem Sci*, 22(7):267-272, 1997.
Vogt et al., "Triple layer control: phosphorylation, acetylation and ubiquitination of FOXO proteins," *Cell Cycle*, 4(7):908-913, 2005.
Wagner and Sondak, "The sentinel lymph node: more than just another blue lymph node," *Cancer*, 97(8):1821-1823, 2003.
Wang et al., "Aberrant expression of oncogenic and tumor-suppressive microRNAs in cervical cancer is required for cancer cell growth," *PLoS One*, 3(7):e2557, 2008.
Wang et al., "Increased levels of forkhead box M1B transcription factor in transgenic mouse hepatocytes prevent age-related proliferation defects in regenerating liver," *Proc Natl Acad Sci U S A*, 98(20):11468-11473, 2001.
Wang et al., "Oncogenic HPV infection interrupts the expression of tumor-suppressive miR-34a through viral oncoprotein E6," *RNA*, 15(4):637-647, 2009.
Weil et al., "Targeting the kinesin Eg5 to monitor siRNA transfection in mammalian cells, " *Biotechniques*, 33(6):1244-1248, 2002.
Wiemer, "The role of microRNAs in cancer: no small matter, " *Eur J Cancer*, 43(10):1529-1544, 2007.
Wong et al., "Number of nodes examined and staging accuracy in colorectal carcinoma," *J. Clin. Oncol.*, 17(9):2896-2900, 1999.
Wood et al., "One hundred consecutive cases of sentinel lymph node mapping in early colorectal carcinoma: detection of missed micrometastases," *J. Gastrointest Surg.*, 6(3):322-330, 2002.
Xi et al., "A combination of molecular markers accurately detects lymph node metastasis in non-small cell lung cancer patients," *Clin. Cancer Res.*, 12:2484-2491, 2006.
Xi et al., "Identification of mRNA markers for molecular staging of lymph nodes in colorectal cancer," *Clin. Chem.*, 52(3):520-523, 2006.
Xi et al., "Molecular staging of lymph nodes from patients with esophageal adenocarcinoma," *Clin. Cancer Res.*, 11:1099-1109, 2005.
Yamamoto et al., "Cdk2/cdc2 expression in colon carcinogenesis and effects of cdk2/cdc2 inhibitor in colon cancer cells," *Int J Oncol*, 13(2):233-239, 1998.
Yeatman, "A renaissance for SRC," *Nat Rev Cancer*, 4(6):470-480, 2004.
Yi et al., "The association of the expression of MTA1, nm23H1 with the invasion, metastasis of ovarian carcinoma," *Chin Med Sci J*, 18(2):87-92, 2003.
Yu et al., "Crosstalk between cancer and immune cells: role of STAT3 in the tumour microenvironment," *Nat Rev Immunol*, 7(1):41-51, 2007.
Zhang et al., "Enhancement of hematopoietic stem cell repopulating capacity and self-renewal in the absence of the transcription factor C/EBP alpha," *Immunity*, 21(6):853-863, 2004.
U.S. Appl. No. 10/667,126, filed Sep. 19, 2003, Conrad.
Ambros et al., "A uniform system for microRNA annotation," *RNA*, 9(3):277-279, 2003.
Brennecke et al., "Bantam encodes a developmentally regulated microRNA that controls cell proliferation and regulates the proapoptotic gene hid in Drosophila," *Cell*, 113:25-36, 2003.
Calin et al., "Frequent deletions and down-regulation of micro-RNA genes miR15 and miR16 at 13q14 in chronic lymphocytic leukemia," *Prac Natl Acad Sci*; 99:15524-15529; 2002.
Carrington and Ambros, "Role of MicroRNAs in Plant and Animal Development," *Science*; 301:336-338; 2003.
Caudy et al., "Fragile X-related protein and VIG associate with the RNA interference machinery," *Genes & Development*, 16:2491-2496; 2002.

Chang et al., "MicroRNAs act sequentially and asymmetrically to control chemosensory laterality in the nematode," *Nature*, 430(7001):785-789, 2004.

Chen et al., "MicroRNAs modulate hematopoietic lineage differentiation," *Science*, 303(5654):83-86, 2004.

Denli and Hannon., "RNAi: an ever-growing puzzle," *Trends Biochem. Sci.*, 28:196, 2003.

Doench et al., "siRNAs can function as miRNAs," *Genes & Dev*, 17:438-442, 2003.

Doench and Sharp, "Specificity of microRNA target selection in translational repression," *Genes Dev*, 18(5):504-11, 2004.

Dong et al., "Telomerase: regulation, function and transformation," *Crit Rev Oncol Hematol* 54(2):85-93, 2005.

Dostie et al., "Numerous microRNPs in neuronal cells containing novel microRNAs," *RNA*, 9:180-186; 2003.

Grishok et al., "Genes and mechanisms related to RNA interference regulate expression of the small temporal RNAs that control *C. elegans* developmental timing," *Cell*, 106:23-34, 2001.

Ha et al., "A bulged lin-4/lin-14 RNA duplex is sufficient for *Caenorhabditis elegans* lin-14 temporal gradient formation," *Genes Dev.*, 10, 3041-3050, 1996.

Hutvagner and Zamore, "A microRNA in a multiple-turnover RNAi enzyme complex," *Science*, 297(5589):2056-2060, 2002.

Hutvagner et al., "Sequence-specific inhibition of small RNA function," *PLoS Biol.* 2(4):E98, 2004.

Kiriakidou et al., "A combined computational-experimental approach predicts human microRNA targets," *Genes Dev.* 18(10):1165-78, 2004.

Krichevsky et al., "A microRNA array reveals extensive regulation of microRNAs during brain development," *RNA*, 9(10):1274-1281, 2003.

Lagos-Quintana et al., "Identification of novel genes coding for small expressed RNAs," *Science*, 294(5543):853-858, 2001.

Lau et al., "An abundant class of tiny RNAs with probable regulatory roles in *Caenorhabditis elegans,*" *Science*, 294(5543):858-862, 2001.

Lee and Ambros, "An extensive class of small RNAs in *Caenorhabditis elegans,*" *Science*, 294(5543):862-864, 2001.

Lee et al., "MicroRNA maturation: stepwise processing and subcellular localization," *EMBO J.*, 21(17):4663-4670, 2002.

Lee et al., "The nuclear RNase III Drosha initiates microRNA processing," *Nature*, 425(6956):415-419, 2003.

Lewis et al., "Prediction of mammalian microRNA targets," *Cell*, 115(7):787-798, 2003.

Lim et al., "The microRNAs of *Caenorhabditis elegans,*" *Genes and Development*, 17;991-1008, 2003.

Martin and Keller, "Tailing and 3'-end labeling of RNA with yeast poly(A) polymerase and various nucleotides," *RNA*, 4(2):226-230, 1998.

Meijer et al., Progress in Cell cycle research vol. 5, 219-224. (Meijer, L., Jezequel, A., and Roberge, M. eds), Chapter 22.

Meister et al., "Sequence-specific inhibition of microRNA- and siRNA-induced RNA silencing," *RNA*, 10(3):544-50, 2004.

Meltzer et al., "High Expression of Precursor MicroRNA-155/B/C RNA in Children with Burkitt Lymphoma," *Genes, Chromosomes, & Cancer* 39:167-169; 2004.

Michael et al., "Reduced Accumulation of Specific MicroRNAs in colorectal Neoplasia," *Molecular Cancer Research*; 1:882-891; 2003.

Monhanty and Kushner, "Polynucleotide phosphorylase functions both as a 3'-5' exonuclease and a poly(A) polymerase in *Escherichia coli,*" *PNAS*, 97:11966-11971; 2000.

Olsen and Ambros, "The lin-4 regulatory RNA controls developmental timing in *Caenorhabditis elegans* by blocking LIN-14 protein synthesis after the initiation of translation," *Dev. Biol.*, 216:671, 1999.

Pasquinelli and Ruvkun, "Control of developmental timing by micrornas and their targets," *Ann. Rev. Cell Dev. Biol.*, 18:495-513, 2002.

Reinhart et al. "The 21-nucleotide let-7 RNA regulates developmental timing in *Caenorhabditis elegans,*" *Nature*, 403:901-906, 2000.

Seggerson et al., "Two genetic circuits repress the *Caenorhabditis elegans* heterochronic gene lin-28 after translation initiation," *Dev. Biol.*, 243:215, 2002.

Shingara et al., "An optimized isolation and labeling platform for accurate microRNA expression profiling," *RNA*, 11:1461-1470, 2005.

Xu et al, "The Drosophila microRNA Mir-14 suppresses cell death and is required for normal fat metabolism," *Curr. Biol.*, 13:790-795, 2003.

Zeng et al., "Both natural and designed micro RNAs can inhibit the expression of cognate mRNAs when expressed in human cells," *Mol Cell.* 9, 1327-33, 2002.

Zeng et al, "MicroRNAs and small interfering RNAs can inhibit mRNA expression by similar mechanisms," *Proc. Natl. Acad. Sci.* 100: 9779-9784, 2003.

"Control of developmental timing by microRNAs," believed at the time of the filing of this form to have been presented by Frank Slack at Santa Cruz in Aug. 2004.

"Control of the Development by microRNAs," believed at the time of the filing of this form to have been presented by Frank Slack at IIT Bombay on Jan. 28, 2004.

"Control of the Development by microRNAs," believed at the time of the filing of this form to have been presented by Frank Slack at Keystone miRNAs on Apr. 15, 2005.

"Control of the Development by microRNAs," believed at the time of the filing of this form to have been presented by Frank Slack at UCT on Feb. 17, 2004.

"Control of the Development by microRNAs," believed at the time of the filing of this form to have been presented by Frank Slack at UNMC on Mar. 29, 2004.

"MicroRNA control of oncogene expression," believed at the time of the filing of this form to have been presented by Frank Slack at Slack GTBIO on Nov. 8, 2004.

"MicroRNAs and cancer," believed at the time of the filing of this form to have presented by Frank Slack at University of Puerto Rico Bayamon on Sep. 22, 2004.

"Multiple, dynamic microRNA ribonucleoprotein complexes with select microRNA cargos in *C. elegans,*" believed at the time of the filing of this form to have been presented by Frank Slack at Gordon on Jun. 8, 2004.

"Small RNA genes as potential causes and treatments of cancer," believed at the time of the filing of this form to have been presented by Frank Slack at Jaslok on Feb. 1, 2004.

"Temporal patterning and biological timing," believed at the time of the filing of this form to have been presented by Frank Slack at Dartmouth on Mar. 19, 2004.

Al-Hajj et al., "Prospective identification of tumorigenic breast cancer cells," *Proc. Natl. Acad. Sci. U S A*, 100(7):3983-8, 2003.

Bao et al., "Glioma stem cells promote radioresistance by preferential activation of the DNA damage response," *Nature*, 444(7120):756-60, 2006.

Bartel, "MicroRNAs: genomics, biogenesis, mechanism, and function," *Cell*, 116:281-297, 2004.

Basturk et al., "MicroRNA expression in androgen independent and metastatic prostate cancer," *Modern Pathology*, Abstract No. 669, 21(Suppl. 1):148A, 2008.

Beier et al., "CD133(+) and CD133(−) glioblastoma-derived cancer stem cells show differential growth characteristics and molecular profiles," *Cancer Res.*, 67(9):4010-5, 2007.

Ben-Porath et al., "An embryonic stem cell-like gene expression signature in poorly differentiated aggressive human tumors," *Nat. Genet.*, 40(5):499-507, 2008.

Berman et al., "Medulloblastoma growth inhibition by hedgehog pathway blockade," *Science*, 297(5586):1559-61, 2002.

Birnie et al., "Gene expression profiling of human prostate cancer stem cells reveals a pro-inflammatory phenotype and the importance of extracellular matrix interactions," *Genome Biol.*, 9(5):R83. [Epub ahead of print], 2008.

Blower et al., "MicroRNAs modualte the chemosensitivity of tumor cells," *Mol Cancer Ther*, 7(1):1-9, 2008.

Bonci et al., "The miR-15A/miR-16-1 cluster controls prostate cancer progression by targeting multiple oncogenic activities," *European Urology Supplements*, Abstract No. 802, 7(3):271, 2008.

Bourguignon et al., "Hyaluronan-CD44 interaction activates stem cell marker Nanog, Stat-3-mediated MDR1 gene expression, and ankyrin-regulated multidrug efflux in breast and ovarian tumor cells," *J. Biol. Chem.*, 283(25): 17635-51, 2008.

Büssing et al., "*let-7* microRNAs in development, stem cells and cancer," *Trends in Molecular Medicine*, 14(9):400-409, 2008.

Clement et al., "HEDGEHOG-GLI1 signaling regulates human glioma growth, cancer stem cell self-renewal, and tumorigenicity," *Curr. Biol.*, 17(2): 165-72, 2007.

Collins et al., "Prospective identification of tumorigenic prostate cancer stem cells," *Cancer Res.*, 65(23):10946-51, 2005.

Cummins et al., "The colorectal microRNAome," *Proc. Natl. Acad. Sci. U S A*, 103(10):3687-3692, 2006.

Dai et al., "Prostate cancer induces bone metastasis through Wnt-induced bone morphogenetic protein-dependent and independent mechanisms," *Cancer Res.*, 68(14): 5785-94, 2008.

Declaration of Dr. David P. Bartel under 37 C.F.R. 1.132, submitted in U.S. Appl. No. 10/913,288, 2009.

Dontu et al., "In vitro propagation and transcriptional profiling of human mammary stem/progenitor cells," Genes Dev., 17:1253-70, 2003.

Doyle and Ross, "Multidrug resistance mediated by the breast cancer resistance protein BCRP (ABCG2)," *Oncogene*, 22(47):7340-58, 2003.

Dröge and Davey, "Do cells *let-7* determine sternness?" *Cell Stem Cell*, 2(1):8-9, 2008.

Dylla et al., "Colorectal cancer stem cells are enriched in xenogeneic tumors following chemotherapy," *PLoS One*, 3(6):e2428, 13 pages, 2008.

Engelmann et al., "MCF7 side population cells with characteristics of cancer stem/progenitor cells express the tumor antigen MUC1," *Cancer Res.*, 68(7):2419-26, 2008.

Esquela-Kerscher et al., "The *let-7* microRNA reduces tumor growth in mouse models of lung cancer," *Cell Cycle*, 7(6):759-764, 2008.

Fan et al., "Hedgehog signaling promotes prostate xenograft tumor growth," *Endocrinology*, 145: 3961-3970, 2004.

Fan et al., "Notch pathway inhibition depletes stem-like cells and blocks engraftment in embryonal brain tumors," *Cancer Res.*, 66(15): 7445-52, 2006.

Francipane et al., "Crucial role of interleukin-4 in the survival of colon cancer stem cells," *Cancer Res.*, 68 (11):4022-4025, 2008.

Ginestier et al., "ALDH1 is a marker of normal and malignant human mammary stem cells and a predictor of poor clinical outcome," *Cell Stem Cell*, 1(5):555-567, 2007.

Goodell et al., "Isolation and functional properties of murine hematopoietic stem cells that are replicating in vivo," *J. Exp. Med.*, 183(4):1797-806, 1996.

Gu et al., "Prostate cancer cells with stem cell characteristics reconstitute the original human tumor in vivo," *Cancer Res.*, 67(10):4807-15, 2007.

Hambardzumyan et al., "PI3K pathway regulates survival of cancer stem cells residing in the perivascular niche following radiation in medulloblastoma in vivo," *Genes Dev.*, 22(4):436-48, 2008.

Hermann et al., "Distinct populations of cancer stem cells determine tumor growth and metastatic activity in human pancreatic cancer," *Cell Stem Cell*, 1(3):313-23, 2007.

Hirschmann-Jax et al., "A distinct "side population" of cells with high drug efflux capacity in human tumor cells," *Proc. Natl. Acad. Sci. U S A*, 101:14228-33, 2004.

Ho et al., "MDR1 and BCRP1 expression in leukemic progenitors correlates with chemotherapy response in acute myeloid leukemia," *Exp. Hematol.*, 36(4): 433-42, 2008.

Hurt et al., "CD44+ CD24(−) prostate cells are early cancer progenitor/stem cells that provide a model for patients with poor prognosis," *Br. J. Cancer*, 98(4):756-65, 2008.

Ibarra et al., "A role for microRNAs in maintenance of mouse mammary epithelial progenitor cells", *Genes Dev.*, 21(24):3238-3243, 2007.

Isbarn et al., "Association of numerous micro-RNAs (μRNAs) with prostate cancer initiation and progression," *European Urology Supplements*, Abstract No. 429, 6(2):130, 2007.

Jamieson et al., "Granulocyte-macrophage progenitors as candidate leukemic stem cells in blast-crisis CML," *N. Engl. J. Med.*, 351(7):657-67, 2004.

Jiang et al., "Real-time expression profiling of microRNA precursors in human cancer cell lines," *Nucleic Acids Research*, 33(17):5394-5403, 2005.

Johnson et al., "The *let-7* microRNA represses cell proliferation pathways in human cells," *Cancer Res*, 67(16):7713-7722, 2007.

Karhadkar et al., "Hedgehog signalling in prostate regeneration, neoplasia and metastasis," *Nature*, 431(7009):707-12, 2004.

Keshet et al., "MDR1 expression identifies human melanoma stem cells," *Biochem. Biophys. Res. Commun.*, 368(4):930-6, 2008.

Konopleva et al., "Mechanisms of apoptosis sensitivity and resistance to the BH3 mimetic ABT-737 in acute myeloid leukemia," *Cancer Cell*, 10(5):375-88, 2006.

Kumar et al., "Suppression of non-small cell lung tumor development by the *let-7* microRNA family," *PNAS*, 105(10):3903-3908, 2008.

Lanza et al., "mRNA/microRNA gene expression profile in microsatellite unstable colorectal cancer," *Molec Cancer*, 6:54, 2007.

Lechner et al., "Nestin-positive progenitor cells derived from adult human pancreatic islets of Langerhans contain side population (SP) cells defined by expression of the ABCG2 (BCRP1) ATP-binding cassette transporter," *Biochem. Biophys. Res. Commun.*, 293(2):670-674, 2002.

Leong and Gao, "The Notch pathway in prostate development and cancer," *Differentiation*, 76(6): 699-716, 2008.

Lessard and Sauvageau, "Bmi-1 determines the proliferative capacity of normal and leukaemic stem cells," *Nature*, 423(6937):255-60, 2003.

Li et al., "Evidence that transgenes encoding components of the Wnt signaling pathway preferentially induce mammary cancers from progenitor cells," *Proc Natl Acad Sci USA*, 100(26):15853-8, 2003.

Li et al., "Intrinsic resistance of tumorigenic breast cancer cells to chemotherapy," *J. Natl. Cancer Inst.*, 100(9):672-9, 2008.

Li et al., "Mutant TNFalpha negatively regulates human breast cancer stem cells from MCF7 in vitro," *Cancer Biol. Ther.*, 6(9):1480-9, 2007.

Liu et al., "Functional studies of BCL11A: characterization of the conserved BCL11A-XL splice variant and its interaction with BCL6 in nuclear paraspeckles of germinal center B cells," *Mol. Cancer*, 5:18, 2006.

Liu et al., "Hedgehog signaling and Bmi-1 regulate self-renewal of normal and malignant human mammary stem cells," *Cancer Res.*, 66(12):6063-71, 2006.

Liu et al., "Sex-determining region Y box 4 is a transforming oncogene in human prostate cancer cells," *Cancer Res.*, 66(8):4011-9, 2006.

Liu et al., "The prognostic role of a gene signature from tumorigenic breast-cancer cells," *N. Engl. J. Med.*, 356(3):217-26, 2007.

Lu et al., "Defined culture conditions of human embryonic stem cells,"*Proc. Natl. Acad. Sci. USA*, 103(15): 5688-93, 2006.

Maitland & Collins, "Prostate cancer stem cells: a new target for therapy", *J Clin Oncol.*, 26(17):2862-70, 2008. (Abstract).

Malanchi et al., "Cutaneous cancer stem cell maintenance is dependent on beta-catenin signalling," *Nature*, 452(7187):650-3, 2008.

Miki & Rhim, "Prostate cell cultures as in vitro models for the study of normal stem cells and cancer stem cells", *Prost. Can. Prost. Dis.*, 11:32-39, 2008.

Miki et al., "Identification of putative stem cell markers, CD133 and CXCR4, in hTERT-immortalized primary nonmalignant and malignant tumor-derived human prostate epithelial cell lines and in prostate cancer specimens," *Cancer Res.*, 67(7):3153-61, 2007.

Nykänen et al., "ATP requirements and small interfering RNA structure in the RNA interference pathway," *Cell*, 107:309-321, 2001.

Office Action issued in European Application No. 05858321.2., mailed Apr. 16, 2010.

Office Action issued in European Application No. 09154092.2, mailed Apr. 1, 2010.

Office Action issued in U.S. Appl. No. 11/141,707, mailed Mar. 11, 2010.

Office Action issued in U.S. Appl. No. 11/273,640, mailed May 5, 2010.

Office Action issued in U.S. Appl. No. 11/837,487, mailed May 28, 2010.
Office Action issued in U.S. Appl. No. 11/837,490, mailed Apr. 9, 2010.
Office Action issued in U.S. Appl. No. 11/837,498, mailed May 7, 2010.
Office Action issued in U.S. Appl. No. 11/857,948, mailed May 25, 2010.
Office Action issued in U.S. Appl. No. 11/967,639, mailed May 14, 2010.
Office Action issued in U.S. Appl. No. 11/967,639, mailed Mar. 24, 2010.
Office Action issued in U.S. Appl. No. 12/112,291, mailed Mar. 1, 2010.
Office Action issued in U.S. Appl. No. 12/125,675, mailed Apr. 22, 2010.
Office Action issued in U.S. Appl. No. 12/134,932, mailed Mar. 24, 2010.
Office Action issued in U.S. Appl. No. 12/325,917, mailed May 3, 2010.
Office Action issued in U.S. Appl. No. 12/420,634, mailed May 26, 2010.
Patrawala et al., "Hierarchical organization of prostate cancer cells in xenograft tumors: the CD44+alpha2beta1+ cell population is enriched in tumor-initiating cells," *Cancer Res.*, 67(14):6796-805, 2007.
Patrawala et al., "Highly purified CD44+ prostate cancer cells from xenograft human tumors are enriched in tumorigenic and metastatic progenitor cells," *Oncogene*, 25(12):1696-708, 2006.
Patrawala et al., "MicroRNAs in prostate cancer stem cells", AACR Cancer Stem Cell Special Conference—Los Angeles, Feb. 12-15, 2008.
Patrawala et al., "Side population is enriched in tumorigenic, stem-like cancer cells, whereas ABCG2+ and ABCG2- cancer cells are similarly tumorigenic," *Cancer Res.*, 65(14):6207-19, 2005.
PCT International Preliminary Report on Patentability issued in International Application No. PCT/US2008/076246, mailed Mar. 16, 2010.
PCT International Search Report and Written Opinion issued in International Application No. PCT/US2008/087762, mailed Mar. 16, 2010.
PCT International Search Report and Written Opinion issued in International Application No. PCT/US2009/038399, mailed Mar. 3, 2010.
PCT International Search Report and Written Opinion issued in International Application No. PCT/US2009/064015, mailed May 11, 2010.
Peacock et al., "Hedgehog signaling maintains a tumor stem cell compartment in multiple myeloma," *Proc. Natl. Acad. Sci. USA*, 104(10):4048-53, 2007.
Peng et al., "Overexpression of microRNA let-7c in prostate cancer," *Modern Pathology*, Abstract No. 788, 20 (Suppl. 2):169A, 2007.
Reiter and Sawyers, "Xenograft models and the molecular biology of human prostate cancer," In :*Prostate Cancer: Biology, Genetics, and the New Therapeutics*, Totowa, NJ, 163-173, 2001.
Richardson et al., "CD133, a novel marker for human prostatic epithelial stem cells," *J. Cell Sci.*, 117(Pt 16):3539-45, 2004.
Schwarz et al., "Asymmetry in the assembly of the RNAi enzyme complex," *Cell*, 115:199-208, 2003.
Shepherd et al., "Expression profiling of CD133+ and CD133– epithelial cells from human prostate," *Prostate*, 68(9):1007-1024, 2008.
Shipitsin et al., "Molecular definition of breast tumor heterogeneity," *Cancer Cell*, 11(3):259-73, 2007.
Singh et al., "Identification of a cancer stem cell in human brain tumors," *Cancer Res.*, 63(18):5821-8, 2003.
Sinner et al., "Sox17 and Sox4 differentially regulate beta-catenin/T-cell factor activity and proliferation of colon carcinoma cells," *Mol. Cell Biol.*, 27(22):7802-15, 2007.
Takeshita et al., "Systemic delivery of synthetic microRNA-16 inhibits the growth of metastatic prostate tumors via downregulation of multiple cell-cycle genes," *Molecular Therapy*, 18(1):181-187, 2010.

Tang et al., "Prostate cancer stem/progenitor cells: identification, characterization, and implications," *Mol. Carcinog.*, 46(1):1-14, 2007.
Tang et al., "Transforming growth factor-beta can suppress tumorigenesis through effects on the putative cancer stem or early progenitor cell and committed progeny in a breast cancer xenograft model," Cancer Res., 67(18):8643-52, 2007.
Thiyagarajan et al., "Role of GLI2 transcription factor in growth and tumorigenicity of prostate cells," *Cancer Res.*, 67(22):10642-6, 2007.
Tijsterman and Plasterk, "Dicers at RISC: the mechanism of RNAi," *Cell*, 117:1-4, 2004.
Tockman et al., "Considerations in bringing a cancer biomarker to clinical application," *Cancer Research*, 52:2711s-2718s, 1992.
Trang et al., "Regression of murine lung tumors by the *let-7* microRNA," *Oncogene*, 29(11):1580-1587, Epub 2009.
U.S. Appl. No. 10/778,908, entitled "Anti-microRNA oligonucleotide molecules," by Thomas Tuschl et al., filed Feb. 13, 2004.
U.S. Appl. No. 60/869,295 entitled "MicroRNAs Differentially Expressed in Leukemia and Uses Thereof"by Tim Davison, et al., submitted Dec. 8, 2006.
Vermeulen et al., "Single-cell cloning of colon cancer stem cells reveals a multi-lineage differentiation capacity," *PNAS*, 105(360):13427-13432, 2008.
Vezina & Bushman, "Hedgehog signaling in prostate growth and benign prostate hyperplasia," *Curr. Urol. Rep.*, 8(4): 275-80, 2007.
Wang & Dick, "Cancer stem cells:lessons from leukemia", *Trends Cell Biol.*, 15(9):494-501, 2005.
Wang et al., "Pten deletion leads to the expansion of a prostatic stem/progenitor cell subpopulation and tumor initiation," *Proc. Natl. Acad. Sci. USA*, 103(5):1480-1485, 2006.
Watabe et al., "Growth, regeneration, and tumorigenesis of the prostate activates the PSCA promoter," *Proc Natl Acad Sci USA*, 99(1):401-6, 2002.
Weidhaas et al., "MicroRNAs as potential agents to alter resistance to cytotoxic anticancer therapy," *Cancer Res*, 67(23):11111-11116, 2007.
Willert et al., "Wnt proteins are lipid-modified and can act as stem cell growth factors," *Nature*, 423(6938):448-52, 2003.
Xi et al., "Differentially regulated micro-RNAs and actively translated messenger RNA transcripts by tumor suppressor p53 in colon cancer," *Clin Cancer Res.*, 12:2014-2024, 2006b.
Xi et al., "Prognostic Values of microRNAs in Colorectal Cancer," *Biomark Insights*, 2:113-121, 2006a.
Yang et al., "Significance of CD90+ cancer stem cells in human liver cancer," *Cancer Cell*, 13(2):153-66, 2008.
Yu et al., "*let-7* regulates self renewal and tumorigenicity of breast cancer cells," *Cell*, 131:1109-1123, 2007.
Zhang et al., "Identification and characterization of ovarian cancer-initiating cells from primary human tumors," *Cancer Res.*, 68(11):4311-20, 2008.
Zhang et al., "NANOGP8 is a retrogene expressed in cancers," *FEBS J.*, 273(8):1723-30, 2006.
Zhou et al., "Activation of the PTEN/mTOR/STAT3 pathway in breast cancer stem-like cells is required for viability and maintenance," *Proc. Natl. Acad. Sci. USA*, 104(41):16158-63, 2007.
Zhou et al., "The ABC transporter Bcrp1/ABCG2 is expressed in a wide variety of stem cells and is a molecular determinant of the side-population phenotype," *Nat. Med.*, 7(9):1028-1034, 2001.
Agrawal and Kandimalla, "Antisense therapeutics: is it as simple as complementary base recognition," *Molecular Medicine Today*, 6:72-81, 2000.
Benlloch et al., "Role of CEA, PLUNC and CK19 mRNA expression in lymph nodes from resected stage I non-small cell lung cancer (NSCLC) patients as markers of occult micrometastasis: A pilot study," *Lung Cancer*, Abstract No. P-649, 49(1):S289, 2005.
Chirila et al., "The use of synthetic polymers for delivery of therapeutic antisense oligodeoxynucleotides," *Biomaterials*, 23:321-342, 2002.
Crooke, "Progress in antisense technology," *Annu. Rev. Med.*, 55:61-95, 2004.

Jang et al., "Gene delivery from polymer scaffolds for tissue engineering," *Expert Rev. Medical Devices*, 1(1):127-138, 2004.

Logsdon et al., "Molecular profiling of pancreatic adenocarcinoma and chronic pancreatitis identifies multiple genes differentially regulated in pancreatic cancer," *Cancer Research*, 63:2649-2657, 2003.

Office Action issued in European Application No. 07871756.8, mailed Jun. 30, 2010.

Office Action issued in European Application No. 08770269.2, mailed Jul. 30, 2010.

Office Action issued in U.S. Appl. No. 11/857,948, mailed Aug. 24, 2010.

Office Action issued in U.S. Appl. No. 11/953,606, mailed Jul. 1, 2010.

Office Action issued in U.S. Appl. No. 12/120,388, mailed Jul. 21, 2010.

Office Action issued in U.S. Appl. No. 12/167,492, mailed Aug. 12, 2010.

Office Action issued in U.S. Appl. No. 12/253,718, mailed Jun. 11, 2010.

Office Action issued in U.S. Appl. No. 12/325,917, mailed Jul. 28, 2010.

Office Action issued in U.S. Appl. No. 12/368,053, mailed Aug. 19, 2010.

Office Action issued in U.S. Appl. No. 12/420,634, mailed Aug. 30, 2010.

Office Action issued in U.S. Appl. No. 12/616,616, mailed Aug. 13, 2010.

Opalinska and Gewirtz, "Nucleic-acid therapeutics: basic principles and recent applications," *Nature Reviews*, 1:503-514, 2002.

PCT International Preliminary Report on Patentability and Written Opinion issued in International Application No. PCT/US2008/080318, mailed Apr. 29, 2010.

PCT International Preliminary Report on Patentability and Written Opinion issued in International Application No. PCT/US2008/085178, mailed Jun. 10, 2010.

PCT International Preliminary Report on Patentability and Written Opinion issued in International Application No. PCT/US2008/087762, mailed Jul. 1, 2010.

PCT International Search Report and Written Opinion issued in International Application No. PCT/US2009/064015, mailed Jul. 26, 2010.

Peracchi, "Prospects for antiviral ribozymes and deoxyribozymes," *Rev. Med. Virol.*, 14:47-64, 2004.

Doench and Sharp, "Specificity of microRNA target selection in translational repression," *Genes Dev*, 18(5):504-11, 2004.

Dong et al., "Telomerase: regulation, function and transformation," *Crit Rev Onco! Hematol.* 54(2):85-93, 2005.

Dostie et al., "Numerous microRNPs in neuronal cells containing novel microRNAs," *RNA*, 9:180-186; 2003.

Grishok et al., "Genes and mechanisms related to RNA interference regulate expression of the small temporal RNAs that control *C. elegans* developmental timing," *Cell*, 106:23-34, 2001.

Ha et al., "A bulged lin-4/lin-14 RNA duplex is sufficient for *Caenorhabditis elegans* lin-14 temporal gradient formation," *Genes Dev.*, 10, 3041-3050, 1996.

Hutvagner and Zamore, "A microRNA in a multiple-turnover RNAi enzyme complex," *Science*, 297(5589):2056-2060, 2002.

Hutvagner et al., "Sequence-specific inhibition of small RNA function," *PLoS Biol.* 2(4):E98, 2004.

Kiriakidou et al., "A combined computational-experimental approach predicts human microRNA targets," *Genes Dev.* 18(10):1165-78, 2004.

Krichevsky et al., "A microRNA array reveals extensive regulation of microRNAs during brain development," *RNA*, 9(10):1274-1281, 2003.

Lagos-Quintana et al., "Identification of novel genes coding for small expressed RNAs," *Science*, 294(5543):853-858, 2001.

Lau et al., "An abundant class of tiny RNAs with probable regulatory roles in *Caenorhabditis elegans*," *Science*, 294(5543):858-862, 2001.

Lee and Ambros, "An extensive class of small RNAs in *Caenorhabditis elegans*," *Science*, 294(5543):862-864, 2001.

Lee et al., "MicroRNA maturation: stepwise processing and subcellular localization," *EMBO J.*, 21(17):4663-4670, 2002.

Lee et al., "The nuclear RNase III Drosha initiates microRNA processing," *Nature*, 425(6956):415-419, 2003.

Lewis et al., "Prediction of mammalian microRNA targets," *Cell*, 115(7):787-798, 2003.

Lim et al., "The microRNAs of *Caenorhabditis elegans*," *Genes and Development*, 17;991-1008, 2003.

Martin and Keller, "Tailing and 3'-end labeling of RNA with yeast poly(A) polymerase and various nucleotides," *RNA*, 4(2):226-230, 1998.

Meijer et al,, Progress in Cell cycle research vol. 5, 219-224. (Meijer, L., Jezequel, A., and Roberge, M. eds), Chapter 22, 2003

Meister et al., "Sequence-specific inhibition of microRNA- and siRNA-induced RNA silencing," *RNA*, 10(3):544-50, 2004.

Meltzer et al., "High Expression of Precursor MicroRNA-155/B/C RNA in Children with Burkitt Lymphoma," *Genes, Chromosomes, & Cancer* 39:167-169; 2004.

Michael et al., "Reduced Accumulation of Specific MicroRNAs in colorectal Neoplasia," *Molecular Cancer Research*; 1:882-891; 2003.

Monhanty and Kushner, "Polynucleotide phosphorylase functions both as a 340 -5' exonuclease and a poly(A) polymerase in *Escherichia coli*," *Pnas*, 97:11966-11971; 2000.

Olsen and Ambros, "The lin-4 regulatory RNA controls developmental timing in *Caenorhabditis elegans* by blocking LIN-14 protein synthesis after the initiation of translation," *Dev. Biol.*, 216:671, 1999.

Pasquinelli and Ruvkun, "Control of developmental timing by micrornas and their targets," *Ann. Rev. Cell Dev. Biol.*, 18:495-513, 2002.

Reinhart et al. "The 21-nucleotide let-7 RNA regulates developmental timing in *Caenorhabditis elegans*," *Nature*, 403:901-906, 2000.

Seggerson et al., "Two genetic circuits repress the *Caenorhabditis elegans* heterochronic gene lin-28 after translation initiation," *Dev. Biol.*, 243:215, 2002.

Shingara et al., "An optimized isolation and labeling platform for accurate microRNA expression profiling," *RNA*, 11:1461-1470, 2005.

Xu et al, "The Drosophila microRNA Mir-14 suppresses cell death and is required for normal fat metabolism," *Curr. Biol.*, 13:790-795, 2003.

Zeng et al., "Both natural and designed micro RNAs can inhibit the expression of cognate mRNAs when expressed in human cells," *Mol Cell.* 9, 1327-33, 2002.

Zeng et al, "MicroRNAs and small interfering RNAs can inhibit mRNA expression by similar mechanisms," *Proc. Natl. Acad. Sci.* 100: 9779-9784, 2003.

"Control of developmental timing by microRNAs," believed at the time of the filing of this form to have been presented by Frank Slack at Santa Cruz in Aug. 2004.

"Control of the Development by microRNAs," believed at the time of the filing of this form to have been presented by Frank Slack at IIT Bombay on Jan. 28, 2004.

"Control of the Development by microRNAs," believed at the time of the filing of this form to have been presented by Frank Slack at Keystone miRNAs on Apr. 15, 2005.

"Control of the Development by microRNAs," believed at the time of the filing of this form to have been presented by Frank Slack at UCT on Feb. 17, 2004.

"Control of the Development by microRNAs," believed at the time of the filing of this form to have been presented by Frank Slack at UNMC on Mar. 29, 2004.

"MicroRNA control of oncogene expression," believed at the time of the filing of this form to have been presented by Frank Slack at Slack GTBIO on Nov. 8, 2004.

"MicroRNAs and cancer," believed at the time of the filing of this form to have presented by Frank Slack at University of Puerto Rico Bayamon on Sep. 22, 2004.

"Multiple, dynamic microRNA ribonucleoprotein complexes with select microRNA cargos in C. elegans," believed at the time of the filing of this form to have been presented by Frank Slack at Gordon on Jun. 8, 2004.

"Small RNA genes as potential causes and treatments of cancer," believed at the time of the filing of this form to have been presented by Frank Slack at Jaslok on Feb. 1, 2004.

"Temporal patterning and biological timing," believed at the time of the filing of this form to have been presented by Frank Slack at Dartmouth on Mar. 19, 2004.

Aaboe et al., "Vitronectin in human breast carcinomas," Biochem. Biophys. Acta., 1638 (1): 72-82, 2003.

Aagaard et al., "An inflammatory role for the mammalian carboxypeptidase inhibitor latexin: relationship to cystatins and the tumor suppressor TIG1," Structure (Camb), 13: 309-317, 2005.

Abuharbeid et al., "The fibroblast growth factor-binding protein FGF-BP," Int. J. Biochem. Cell Biol., 38(9):1463-1468, 2006.

Adams et al., "Infrequent mutation of TRAIL receptor 2 (TRAIL-R2/DR5) in transitional cell carcinoma of the bladder with 8p21 loss of heterozygosity," Cancer Lett. 220 (2): 137-144, 2005.

Akao et al., "let-7 microRNA functions as a potential growth suppressor in human colon cancer cells," Biol. Pharm. Bull, 29(5):903-906, 2006.

Akao et al., "MicroRNAs 143 and 145 are possible common onco-microRNAs in human cancers," Oncology Reports, 16:845-850, 2006.

Akiba et al., "Expression and function of interleukin-8 in human hepatocellular carcinoma," Int. J. Oncol., 18 (2): 257-264, 2001.

Alevizos et al., "Oral cancer in vivo gene expression profiling assisted by laser capture microdissection and microarray analysis," Oncogene, 20(43):6196-6204, 2001.

Allawi et al., "Quantitation of MicroRNAs using a modified Invader assay," RNA, 10:1153-1161, 2004.

Altucci and Gronemeyer, "The promise of retinoids to fight against cancer," Nat. Rev. Cancer, 1:181-193, 2001.

Altucci and Gronemeyer, "Retinoids and TRAIL: two cooperating actors to fight against cancer," Vitam. Horm., 67:319-345, 2004.

Ambros, "microRNAs: tiny regulators with great potential," Cell, 107(7):823-826, 2001.

Anatharaman and Aravind, "Evolutionary history, structural features and biochemical diversity of the N1pC/P60 superfamily of enzymes," Genome Biol., 4: R11, 2003.

Ando et al., "Polo-like kinase 1 (Plk1) inhibits p53 function by physical interaction and phosphorylation," J. Biol. Chem., 279 (24): 25549-25561, 2004.

Armour et al., "Measurement of locus copy number by hybridisation with amplifiable probes," Nucleic Acids Research, 28(2):605-609, 2000.

Association of Directors of Anatomic and Surgical Pathology, "Recommendations for the reporting of resected large intestinal carcinomas. Association of directors of anatomic and surgical pathology," Am. J. Clin. Pathol., 106 (1): 12-15, 1996.

Astler and Coller, "The prognostic significance of direct extension of carcinoma of the colon and rectum," Ann. Surg., 139: 846-852, 1954.

Asuragen, Inc. website, "Asuragen's DiscovArray miRNA Expression Profiling Service," located at http://www.asuragen.com/Services/solutions/discovarray.aspx, printed Mar. 6, 2009.

Baba et al., "Involvement of deregulated epiregulin expression in tumorigenesis in vivo through activated Ki-Ras signaling pathway in human colon cancer cells," Cancer Res, 60(24):6886-6889, 2000.

Bae et al., "MCL-1S, a splicing variant of the antiapoptotic BCL-2 family member Mcl-1, encodes a proapoptotic protein possessing only the BH3 domain," J. Biol. Chem., 275(33):25255-61, 2000.

Bagga et al., "Regulation by let-7 and lin-4 miRNAs results in target mRNA degradation," Cell, 122(4):553-563, 2005.

Bandres et al., "Identification by Real-time PCR of 13 mature microRNAs differentially expressed in colorectal cancer and non-tumoral tissues," Mol. Cancer, 5:29, 2006.

Bangoura et al., "Expression of HIF-2alpha/EPAS1 in hepatocellular carcinoma," World J. Gastroenterol., 10(4):525-530, 2004.

Bartlett and Davis, "Effect of siRNA nuclease stability on the in vitro and in vivo kinetics of siRNA-mediated gene silencing," Biotechnol. Bioeng., 97(4): 909-921, 2007.

Bartlett et al., "Impact of tumor-specific targeting on the biodistribution and efficacy of siRNA nanoparticles measured by multimodality in vivo imaging," 104(39):15549-15554, 2007.

Bartlett et al., "Insights into the kinetics of siRNA-mediated gene silencing from live-cell and live-animal bioluminescent imaging," Nucleic Acids Research, 34(1):322-333, 2006.

Barton et al., "Angiogenic protein expression in advanced epithelial ovarian cancer," Clin. Cancer Res., 3 (9): 1579-1586, 1997.

Bellovin et al., "Reciprocal regulation of RhoA and RhoC characterizes the EMT and identifies RhoC as a prognostic marker of colon carcinoma," Oncogene, 25 (52): 6959-6967, 2006.

Bendtsen et al., "Feature-based prediction of non-classical and leaderless protein secretion," Protein Eng. Des. Sel., 17: 349-356, 2004.

Bentwich et al., "Identification of hundreds of conserved and nonconserved human microRNAs," Nat Genet., 37(7):766-770, 2005.

Berezikov et al, Cell, "Phylogenetic shadowing and computational identification of human microRNA genes," 120(1):21-24, 2005.

Billottet et al., "A selective inhibitor of the p110delta isoform of PI 3-kinase inhibits AML cell proliferation and survival and increases the cytotoxic effects of VP16," Oncogene, 25 (50): 6648-6659, 2006.

Birchmeier et al., "Met, metastasis, motility and more," Nat Rev Mol Cell Biol, 4(12):915-925, 2003.

Biswas et al., "Transforming growth factor beta receptor type II inactivation promotes the establishment and progression of colon cancer," Cancer Res., 64 (14): 4687-4692, 2004.

Bitomsky et al., "Transformation suppressor protein Pdcd4 interferes with JNK-mediated phosphorylation of c-Jun and recruitment of the coactivator p300 by c-Jun," Oncogene, 23(45):7484-93, 2004.

Black et al., "Expression of cyclin D1, cyclin E, EGFR, UBE1L and K167 in paired benign and malignant lung tissues," Lung Cancer, 49:S289, Abstract P-650, 2005.

Blanc et al., "Wnt-5a gene expression in malignant human neuroblasts," Cancer Lett., 228 (1-2): 117-123, 2005.

Boccaccio and Comoglio, "Invasive growth: a MET-driven genetic programme for cancer and stem cells," Nat Rev Cancer, 6(8):637-645, 2006.

Bodner-Adler et al., "Serum levels of angiogenin (ANG) in invasive cervical cancer and in cervical intraepithelial neoplasia (CIN)," Anticancer Res., 21 (1B): 809-812, 2001.

Bostwick et al., "Amphiregulin expression in prostatic intraepithelial neoplasia and adenocarcinoma: a study of 93 cases," Prostate, 58(2):164-168, 2004.

Bottoni et al., "miR-15a and miR-16-1 Down-Regulation in Pituitary Adenomas," J. Cell. Physiol., 204:280-285, 2005.

Boultwood et al., "Low expression of the putative tumour suppressor gene gravin in chronic myeloid leukaemia, myelodysplastic syndromes and acute myeloid leukaemia," Br J Haematol, 126(4):508-511, 2004.

Brazma and Vilo, "Gene expression data analysis," FEBS Letters, 480:17-24, 2000.

Bustin et al., "Real-time reverse transcription PCR (qRT-PCR) and its potential use in clinical diagnosis," Clinical Science, 109:365-379, 2005.

Byrd et al., "Pretreatment cytogenetic abnormalities are predictive of induction success, cumulative incidence of relapse, and overall survival in adult patients with de novo acute myeloid leukemia: results from Cancer and Leukemia Group B (CALGB 8461)" Blood, 100:4325-4336, 2002.

Calin and Croce, "Genomics of chronic lymphocytic leukemia microRNAs as new players with clinical significance," Seminars in Oncology, 33(2):167-173, 2006.

Calin and Croce, "MicroRNA signatures in human cancers," Nat Rev Cancer, 6(11):857-866, 2006.

Calin and Croce, "MicroRNA-cancer connection: the beginning of a new tale," Cancer Res., 66 (15):7390-7394, 2006.

Calin and Croce, "MicroRNAs and chromosomal abnormalities in cancer cells," Oncogene, 25 (46):6202-6210, 2006.

Calin et al., "A MicroRNA signature associated with prognosis and progression in chronic lymphocytic leukemia," New England Journal of Medicine, 353(17):1793-1801, 2005.

Carrano et al., "SKP2 is required for ubiquitin-mediated degradation of the CDK inhibitor p27," Nat. Cell. Biol., 1 (4): 193-199, 1999.

Carreiras et al., "Expression and localization of alpha v integrins and their ligand vitronectin in normal ovarian carcinoma," Gynecol. Oncol., 62 (2): 260-267, 1996.

Carreiras et al., "Human ovarian adenocarcinoma cells synthesize vitronectin and use It to organize their adhesion," *Gynecol. Oncol.*, 72 (3): 312-322, 1999.

Casanova et al., "The class II tumor-suppressor gene RARRES3 is expressed in B cell lymphocytic leukemias and down-regulated with disease progression," *Leukemia*, 15 (10): 1521-1526, 2001.

Castillo et al., "Amphiregulin contributes to the transformed phenotype of human hepatocellular carcinoma cells," *Cancer Res.*, 66(12):6129-6138, 2006.

Chan et al., "Downregulation of ID4 by promoter hypermethylation in gastric adenocarcinoma," *Oncogene*, 22 (44): 6946-6953, 2003.

Chan et al., "MicroRNA-21 is an antiapoptotic factor in human glioblastoma cells," *Cancer Res.*, 65(14):6029-6033, 2005.

Chandler et al., "Prevalent expression of fibroblast growth factor (FGF) receptors and FGF2 in human tumor cell lines," *Int. J. Cancer*, 81(3):451-458, 1999.

Chang et al., "Elevated circulating level of osteopontin is associated with advanced disease state of non-small cell lung cancer," *Lung Cancer*, 57(3):373-380, 2007.

Chang et al., "Transactivation of miR-34a by p53 broadly influences gene expression and promotes apoptosis," *Mol. Cell.*, 26(5):745-752, 2007.

Chen et al., "Identification of trophinin as an enhancer for cell invasion and a prognostic factor for early stage lung cancer," *European Journal of Cancer*, 43(4):782-790, 2007.

Chen et al., "Loss of PDCD4 expression in human lung cancer correlates with tumour progression and prognosis," *J. Pathol.*, 200(5):640-646, 2003.

Chen et al., "Real-time quanitfication of microRNAs by stem-loop RT-PCR," *Nucleic Acids Research*, 33(20): e179 (13 printed pages), 2005.

Cheng et al., "Antisense inhibition of human miRNAs and indications for an involvement of miRNA in cell growth and apoptosis," *Nucleic Acids Res.*, 33(4):1290-1297, 2005.

Choi et al., "AKAP12/Gravin is inactivated by epigenetic mechanism in human gastric carcinoma and shows growth suppressor activity," *Oncogene*, 23(42):7095-7103, 2004.

Ciafre et al., "Extensive modulation of a set of microRNAs in primary glioblastoma," *Biochem. Biophys. Res. Commun.*, 334(4):1351-1358, 2005.

Cimmino et al., "miR-15 and miR-16 induce apoptosis by targeting BCL2," *Proceedings of the National Academy of Sciences of the USA*, 102(39):13944-13949, 2005.

Ciocca et al., "Heat shock portein hsp70 in patients with axillary lymph node-negative breast cancer: Prognostic implications," *Journal of the National Cancer Institute*, 85(7):570-574, 1993.

Claudio et al., "Expression of cell-cycle-regulated proteins pRb2/p130, p107, p27(kip1), p53, mdm-2, and Ki-67 (MIB-1) in prostatic gland adenocarcinoma," *Clin Cancer Res*, 8(6):1808-1815, 2002.

Cohen et al., "Expression of a down-regulated target, SSeCKS, reverses v-Jun-induced transformation of 10T1/2 murine fibroblasts," *Oncogene*, 20(2):141-146, 2001.

Coleman et al., "Superior 5' homogeneity of RNA from ATP-initiated transcription under T7 Φ2.5 promoter," *Nucleic Acids Research*, 32(1):e14, 2004.

Cooper et al., "Molecular cloning of a new transforming gene from a chemically transformed human cell line," *Nature*, 311(5981):29-33, 1984.

Croci et al., "Inhibition of connective tissue growth factor (CTGF/CCN2) expression decreases the survival and myogenic differentiation of human rhabdomyosarcoma cells," *Cancer Res.*, 64(5):1730-1736, 2004.

Cross et al., "25-Hydroxyvitamin D (3)-1alpha-hydroxylase and vitamin D receptor gene expression in human colonic mucosa is elevated during early cancerogenesis," *Steroids*, 66: 287-292, 2001.

Cully et al., "Transforming acidic coiled coil 1 promotes transformation and mammary tumorigenesis," *Cancer Res.*, 65(22):10363-10370, 2005.

Danilkovitch-Miagkova and Zbar, "Dysregulation of Met receptor tyrosine kinase activity in invasive tumors," *J Clin Invest*, 109(7):863-867, 2002.

D'Antonio et al., "Transforming growth factor alpha, amphiregulin and cripto-1 are frequently expressed in advanced human ovarian carcinomas," *Int. J. Oncol.*, 21(5):941-948, 2002.

Davalos et al., "High EPHB2 mutation rate in gastric but not endometrial tumors with microsatellite instability," *Oncogene*, 26 (2): 308-311, 2006.

Davis et al., "Modeling of repeated-batch transcription for production of RNA," *Journal of Biotechnology*, 71:25-37, 1999.

De Candia et al., "Id4 messenger RNA and estrogen receptor expression: inverse correlation in human normal breast epithelium and carcinoma," *Hum. Pathol.*, 37 (8): 1032-1041, 2006.

De Nigris et al., "Induction of ETS-1 and ETS-2 transcription factors is required for thyroid cell transformation," *Cancer Res.*, 61 (5): 2267-2275, 2001.

Dean et al., "The human met oncogene is related to the tyrosine kinase oncogenes," *Nature*, 318(6044):385-388, 1985.

Devine et al., "Serum markers CASA, CEA, CYFRA, TPS, and NSE in lung cancer," *Lung Cancer*, Abstract, 11:37, 1994.

Diederichs and Haber, "Sequence variations of microRNAs in human cancer: Alterations in predicted secondary structure do not affect processing," *Cancer Res.*, 66(12):6097-6104, 2006.

DiSepio et al., "Identification and characterization of a retinoid-induced class II tumor suppressor/growth regulatory gene," *Proc. Natl. Acad. Sci. USA*, 95: 14811-14815, 1998.

Donnellan and Chetty, "Cyclin D1 and human neoplasia," *Mol Pathol*, 51(1):1-7, 1998.

Duvic et al., "Expression of a retinoid-inducible tumor suppressor, tazarotene-inducible gene-3 is decreased in psoriasis and skin cancer," *Clin. Cancer Res.*, 6 (8): 3249-3259, 2000.

Duvic et al., "Tazarotene-induced gene 3 is suppressed in basal cell carcinomas and reversed in vivo by tazarotene application," *J. Invest. Dermatol.*, 121: 902-909, 2003.

Ebert et al., "Induction and expression of amphiregulin in human pancreatic cancer," *Cancer Res.*, 54(15):3959-3962, 1994.

Eferl et al., "Liver tumor development. c-Jun antagonizes the proapoptotic activity of p53," *Cell*, 112 (2): 181-192, 2003.

Einama et al., "High-level Skp2 expression in pancreatic ductal adenocarcinoma: correlation with the extent of lymph node metastasis, higher histological grade, and poorer patient outcome," *Pancreas*, 32(4):376-381, 2006.

Esau et al., "MicroRNA-143 regulates adipocyte differentiation," *Journal of Biological Chemistry*, 279(50):52361-52365, 2004.

Esquela-Kerscher and Slack, "Oncomirs—microRNAs with a role in cancer," *Nat Rev Cancer*, 6(4):259-269, 2006.

Ezzat et al., "Dual inhibition of RET and FGFR4 restrains medullary thyroid cancer cell growth," *Clin. Cancer Res.*, 11 (3): 1336-1341, 2005.

Faried et al., "RhoA and RhoC proteins promote both cell proliferation and cell invasion of human oesophageal squamous cell carcinoma cell lines in vitro and in vivo," *Eur. J. Cancer*, 42 (10): 1455-1465, 2006.

Fay et al., "Analysis of CUL-5 expression in breast epithelial cells, breast cancer cell lines, normal tissues and tumor tissues," *Mol. Cancer*, 2:40, 2003.

Feldman and Feldman, "The development of androgen-independent prostate cancer," *Nat. Rev. Cancer*, 1(1):34-45, 2001.

Fernandez et al., "The matrix metalloproteinase-9/neutrophil gelatinase-associated lipocalin complex plays a role in breast tumor growth and is present in the urine of breast cancer patients," *Clin. Cancer Res.*, 11(15):5390-5395, 2005.

Fesik, "Promoting apoptosis as a strategy for cancer drug discovery," *Nat Rev Cancer*, 5(11):876-885, 2005.

Firth and Baxter, "Cellular actions of the insulin-like growth factor binding proteins," *Endocrin. Rev.*, 23 (6): 824-854, 2002.

Fontana et al., "MicroRNA's 17-5p-20a-106a control monocytopeiesis through AML1 targeting and M-CSF receptor upregulation," *Nature Cell Biology*, 9(7):775-787, 2007.

Freelove and Walling, "Pancreatic cancer: diagnosis and management," *Am. Fam. Physician*, 73(3):485-492, 2006.

Fujiwara et al., "Isolation of a candidate tumor suppressor gene on chromosome 8p21.3-p22 that is homologous to an extracellular domain of the PDGF receptor beta gene," *Oncogene*, 10(5):891-895, 1995.

Galardi et al., "miR-221 and miR-222 expression affects the proliferation potential of human prostate carcinoma cell lines by targeting p27Kip1," *J. Biol. Chem*, 282(32):23716-23724, 2007.

Gao et al., "Frequent loss of PDCD4 expression in human glioma: possible role in the tumorigenesis of glioma," *Oncol. Rep.*, 17(1):123-128, 2007.

Garzon et al., "MicroRNA fingerprints during human megakaryocytopoiesis," *Proc. Natl. Acad. Sci. USA*, 103(13):5078-5083, 2006.

Garzon et al., "MicroRNA signatures associated with cytogenetics and outcome in acute myeloid leukemia. Session Type: Oral Session," *Blood*, 108(11): 49A, Abstract #151, 2006.

Giannakakis et al., "miRNA genetic alterations in human cacners," *Expert opinion on biological therapy*, 7(9):1375-1386, 2007.

Goke et al., "Programmed cell death protein 4 suppresses CDK1/cdc2 via induction of p21(Waf1/Cip1)," *Am. J. Physiol. Cell Physiol*, 287(6):C1541-6, 2004.

Grandori et al., "The Myc/Max/Mad network and the transcriptional control of cell behavior," *Annu. Rev. Cell. Dev. Biol.*, 16: 653-699, 2000.

Grenier et al., "Cyfra 21-1, a new marker for lung cancer," *Nucl. Med. Biol.*, 21(3):471-476, 1994.

Griffiths-Jones et al., "miRBase: microRNA sequences, targets and gene nomenclature," *Nucleic Acids Res.*, 34 (Database Issue):D140-D144, 2006.

Grimwade, "The clinical significance of cytogenetic abnormalities in acute myeloid leukaemia," *Best. Pract. Res. Clin.Haematol.*, 14:497-529, 2001.

Grosshans et al., "The temporal patterning microRNA let-7 regulates several transcription factors at the larval to adult transition in *C. elegans*," *Dev. Cell*, 8(3):321-330, 2005.

Gstaiger et al., "Skp2 is oncogenic and overexpressed in human cancers," *Proc. Natl. Acad. Sci. USA*, 98(9):5043-5048, 2001.

Guda and Subramaniam, "TARGET: a new method for predicting protein subcellular localization in eukaryotes," *Bioinformatics*, 21: 3963-3969, 2005.

Guo et al., "Reduced expression of EphB2 that parallels invasion and metastasis in colorectal tumours," *Carcinogenesis*, 27(3):454-464, 2006.

Gurevich, "Preparative in vitro mRNA synthesis using SP6 and T7 RNA polymerases," *Anal Biochem.*, 195(2):207-213, 1991.

Hajnal et al., "Subtaction cloning of H-rev107, a gene specifically expressed in H-ras resistant fibroblasts," *Oncogene*, 9: 479-490, 1994.

Hamamura et al., "Ganglioside GD3 promotes cell growth and invasion through p130Cas and paxillin in malignant melanoma cells," *Proc Natl Acad Sci U S A*, 102(31):11041-11046, 2005.

Hanahan and Weinberg, "The hallmarks of cancer," *Cell*, 100(1):57-70, 2000.

Hannigan et al., "Integrin-linked kinase: a cancer therapeutic target unique among its ILK," *Nat Rev Cancer*, 5(1):51-63, 2005.

Hardenbol et at," Multiplexed genotyping with sequence-tagged molecular inversion probes," *Nat Biotechnol*, 21(6):673-678, 2003.

Hartmann et al., "Hypoxia-induced up-regulation of angiogenin in human malignant melanoma," *Cancer Res.*, 59 (7): 1578-1583, 1999.

He et al., "A microRNA polycistron as a potential human oncogene," *Nature*, 435(7043):828-833, 2005.

He et al., "The role of microRNA genes in papillary thyroid carcinoma," *Proc. Natl. Acad. Sci. USA*, 102(52):19075-19080, 2005.

Hishikawa et al., "Connective tissue growth factor induces apoptosis in human breast cancer cell line MCF-7," *J. Biol. Chem.*, 274(52):37461-37466, 1999.

Holmquist-Mengelbier et al., "Recruitment of HIF-1alpha and HIF-2alpha to common target genes is differentially regulated in neuroblastoma: HIF-2alpha promotes an aggressive phenotype," *Cancer Cell*, 10(5):413-423, 2006.

Huang et al., "Cloning and characterization of a novel retinoid-inducible gene 1 (RIG1) deriving from human gastric cancer cells," *Mol. Cell. Endocrinol.*, 159: 15-24, 2000.

Huang et al., "Skp2 inhibits FOXO1 in tumor suppression through ubiquitin-mediated degradation," *Proc. Natl. Acad. Sci. USA*, 102(5):1649-1654, 2005.

Huang et al., "Skp2 overexpression is highly representative of intrinsic biological aggressiveness and independently associated with poor prognosis in primary localized myxofibrosarcomas," *Clin. Cancer Res.*, 12 (2): 487-498, 2006.

Huang et al., "The retinoid-inducible gene I: effect on apoptosis and mitogen-activated kinase signal pathways," *Anticancer Res.*, 22: 799-804, 2002.

Huang et al., "Wnt5a expression is associated with the tumor proliferation and the stromal vascular endothelial growth factor—an expression in non-small-cell lung cancer," *J. Clin. Oncol.*, 23 (34): 8765-8773, 2005.

Huusko et al, "Nonsense-mediated decay microarray analysis identifies mutations of EPHB2 in human prostate cancer," *Nat. Genet.*, 36 (9): 979-983, 2004.

Hynes and Lane, "ERBB receptors and cancer: the complexity of targeted inhibitors," *Nat Rev Cancer*, 5(5):341-354, 2005.

Illmer et al., "MiRNA expression signatures in actue myeloid leukemia are predictors for patient outcome. Session Type: Oral Session," *Blood*, 108(11): 49A, Abstract #152, 2006.

Ishikawa et al., "Increases of amphiregulin and transforming growth factor-alpha in serum as predictors of poor response to gefitinib among patients with advanced non-small cell lung cancers," *Cancer Res.*, 65(20):9176-9184, 2005.

Ito et al., "Decreased expression of cyclin G2 is significantly linked to the malignant transformation of papillary carcinoma of the thyroid," *Anticancer Res.*, 23(3B):2335-2338, 2003.

Ito et al., "Decreased expression of p107 is correlated with anaplastic transformation in papillary carcinoma of the thyroid," *Anticancer Res.*, 23(5A):3819-3824, 2003.

Ito et al., "Expression of ets-1 and ets-2 in colonic neoplasms," *Anticancer Res.*, 22 (3): 15811584, 2002.

Ito et al., "Expression of p8 protein in medullary thyroid carcinoma," *Anticancer Res.*, 25 (5): 3419-3423, 2005.

Jaakkola et al., "Amplification of fgfr4 gene in human breast and gynecological cancers," *Int. J. Cancer*, 54 (3): 378-382, 1993.

Jaattela, "Over-expression of hsp70 confers tumorigenicity to mouse fibrosarcoma cells," *Int. J. Cancer*, 60(5):689-693, 1995.

Jansen et al., "Characterization of programmed cell death 4 in multiple human cancers reveals a novel enhancer of drug sensitivity," *Mol. Cancer Ther.*, 3(2):103-110, 2004.

Jansen et al., "Epidermal expression of the translation inhibitor programmed cell death 4 suppresses tumorigenesis," *Cancer Res.*, 65(14):6034-41, 2005.

Jemal et al., "Cancer statistics, 2007," *CA Cancer J. Clin.*, 57:43-66, 2007.

Jemielity et al., "Novel 'anti-reverse' cap analogs with superior translational properties," *RNA*, 9(9):1108-1122, 2003.

Jiang et al., "Decreased expression of type II tumor suppressor gene RARRES3 in tissues of hepatocellular carcinoma and cholangiocarcinoma," *World J. Gastroenterol.*, 11: 948-953, 2005.

Jiang et al., "RNA silencing of S-phase kinase-interacting protein 2 inhibits proliferation and centrosome amplification in lung cancer cells," *Oncogene*, 24(21):3409-3418, 2005.

Jin et al., "Tumorigenic transformation by CPI-17 through inhibition of a merlin phosphatase," *Nature*, 442 (7102): 576-579, 2006.

Jing et al., "Tazarotene-induced gene 1 (TIG1) expression in prostate carcinomas and its relationship to tumorigenicity," *J. Natl. Cancer Inst.*, 94: 482-490, 2002.

Johnson et al., "RAS is regulated by the let-7 microRNA family," *Cell*, 120:635-647, 2005.

Jonsson et al., "Loss of Wnt-5a protein is associated with early relapse in invasive ductal breast carcinomas," *Cancer Res.*, 62 (2): 409-416, 2002.

Jubb et al., "EphB2 is a prognostic factor in colorectal cancer," *Clin. Cancer Res.*, 11 (14): 5181-5187, 2005.

Kallay et al., "Vitamin D receptor activity and prevention of colonic hyperproliferation and oxidative stress," *Food Chem. Toxicol.*, 40: 1191-1196, 2002.

Kamata et al., "High expression of skp2 correlates with poor prognosis in endometrial endometrioid adenocarcinoma," *J. Cancer Res. Clin. Oncol.*, 131(9):591-596, 2005.

Kato, "Adaptor-tagged competitive PCR: a novel method for measuring relative gene expression," *Nucleic Acids Research*, Oxford University Press, Surrey, GB, 25(22):4694-4696, 1997.

Kaufmann et al., "Elevated expression of the apoptotic regulator Mcl-1 at the time of leukemic relapse," *Blood*, 91(3):991-1000, 1998.

Keen and Taylor, "Aurora-kinase inhibitors as anticancer agents," *Nat. Rev. Cancer*, 4(12):927-936, 2004.

Kern et al., "Application of a fed-batch system to produce RNA by in vitro transcription," *Biotechnol. Prog.*, 15:174-184, 1999.

Kern et al., "Application of solution equilibrium analysis to in vitro RNA transcription," *Biotechnol. Prog.*, 13:747-756, 1997.

Kim et al., "Genomics of microRNA," *Trends in Genetics*, 22:165-173, 2006.

Kim et al., "Identification of many microRNAs that copurify with polyribosomes in mammalian neurons," *Proc. Natl. Acad. Sci.*, USA, 101:360-365, 2004.

Kirikoshi et al., "Up-regulation of Frizzled-7 (FZD7) in human gastric cancer," *Int. J. Oncol.*, 19 (1): 111-115, 2001.

Kita et al., "Modulation of polygulutamine-induced cell death by genes identified by expression profiling," Human Molecular Genetics, 11(19):2279-2287, 2002.

Kitadai et al., "Expression of amphiregulin, a novel gene of the epidermal growth factor family, in human gastric carcinomas," *Jpn. J. Cancer Res.*, 84(8):879-884, 1993.

Kleer et al., "RhoC GTPase expression as a potential marker of lymph node metastasis in squamous cell carcinomas of the head and neck," *Clin. Cancer Res.*, 12 (15): 4485-4490, 2006.

Koivunen et al., "Protein kinase C (PKC) family in cancer progression," *Cancer Lett*, 235(1):1-10, 2006.

Koivunen et al., "Protein kinase C alpha/beta inhibitor Go6976 promotes formation of cell junctions and inhibits invasion of urinary bladder carcinoma cells," *Cancer Res*, 64(16):5693-5701, 2004.

Kokko et al., "EPHB2 germline variants in patients with colorectal cancer or hyperplastic polyposis," *BMC Cancer*, 6: 145, 2006.

Komatsu et al., "Increased expression of S100A6 (Calcyclin), a calcium-binding protein of the S100 family, in human colorectal adenocarcinomas," *Clin. Cancer Res.*, 6: 172-177, 2000.

Komiya et al., "PRLTS gene alterations in human prostate cancer," *Jpn. J. Cancer Res.*, 88(4):389-393, 1997.

Krek et al., "Combinatorial microRNA target predictions," *Nature Genet.*, 37:495-500, 2005.

Kubista et al., "Light-up probe based real-time Q-PCR," *SPIE*, 4264:53-58, 2001.

Kwong et al., "Silencing of the retinoid response gene TIG1 by promoter hypermethylation in nasopharyngeal carcinoma," *Int. J. Cancer*, 113 (3): 386-392, 2005.

L'hote and Knowles, "Cell responses to FGFR3 signalling: growth, differentiation and apoptosis," *Exp. Cell. Res.*, 304 (2): 417-431, 2005.

Labourier et al., "Improving in vitro transcription for large scale sytnthesis of human quality capped RNA," *Ambion Diagnostics, RNA Healthcare Solutions*, Eukaryotic mRNA Processing meeting, Cold Spring Harbor Laboratory, Cold Spring Harbor, NY, Aug. 2003.

Lao et al., "Multiplexing RT-PCR for the detection of multiple miRNA species in small samples," *Biochemical and Biophysical Research Communications*, 343:85-89, 2006.

Lee et al., "A protein reacted with anti-vitronectin antibody accumulates in tumors derived from B16F10 melanoma cells," *Cell Struct. Funct.*, 23 (4): 193-199, 1998.

Lee et al., "Ectopic expression of neutrophil gelatinase-associated lipocalin suppresses the invasion and liver metastasis of colon cancer cells," *Int. J. Cancer*, 118(10):2490-2497, 2006.

Lee et al., "Expression profiling identifies stroma- and tumor-related microRNAs in pancreatic cancer," 97th Annual AACR, Washington D.C., Abstract No. 5725, 2006.

Leprince et al., "A putative second cell-derived oncogene of the avian leukaemia retrovirus E26," *Nature*, 306 (5941): 395-397, 1983.

Leris et al., "WNT5A expression in human breast cancer," *Anticancer Res.*, 25 (2a): 731-734, 2005.

Li et al., "Overexpression of ETS2 in human esophageal squamous cell carcinoma," *World J. Gastroenterol.*, 9 (2): 205-208, 2003.

Lim et al., "Microarray analysis shows that some microRNAs downregulate large numbers of target mRNAs," *Nature*, 433(7027):769-773, 2005.

Lin and Gelman, "Reexpression of the major protein kinase C substrate, SSeCKS, suppresses v-src-induced morphological transformation and tumorigenesis," *Cancer Res*, 57(11):2304-2312, 1997.

Lin et al., "Connective tissue growth factor inhibits metastasis and acts as an independent prognostic marker in colorectal cancer," *Gastroenterology*, 128(1):9-23, 2005.

Lin et al., "The C. elegans hunchback homolog, hbl-1, controls temporal patterning and is a probable microRNA target," *Dev. Cell*, 4(5):639-650, 2003.

Linsley et al., "Transcripts targeted by the microRNA-16 family cooperatively regulate cell cycle progression," *Molecular and Cellular Biology*, 27(6):2240-2252, 2007.

Liu and Matsuura, "Inhibition of Smad antiproliferative function by CDK phosphorylation," *Cell Cycle*, 4(1):63-66, 2005.

Liu et al., "CpG island methylation and expression of the secreted frizzled-related protein gene family in chronic lymphocytic leukemia," *Cancer Res.*, 66 (2): 653-658, 2006.

Liu et al., "An oligonucleotide microchip for genome-wide micronRNA profiling in human and mouse tissue," *Proc. Nat. Acad. Sci. USA*, 101:9740-9744, 2004.

Liu et al., "FoxMlB is overexpressed in human glioblastomas and critically regulates the tumorigenicity of glioma cells," *Cancer Res.*, 66 (7): 3593-3602, 2006.

Lo et al., "High resolution allelotype of microdissected primary nasopharyngeal carcinoma," *Cancer Res.*, 60: 3348-3353, 2000.

Lo Vasco et al., "Inositide-specific phospholipase c beta1 gene deletion in the progression of myelodysplastic syndrome to acute myeloid leukemia," *Leukemia*, 18 (6): 1122-1126, 2004.

Lu et al., "MicroRNA expression profiles classify human cancers," *Nature*, 435(7043):834-838, 2005.

Lucke et al., "Inhibiting mutations in the transforming growth factor beta type 2 receptor in recurrent human breast cancer," *Cancer Res*, 61(2):482-485, 2001.

Maki et al., "Avian sarcoma virus 17 carries the jun oncogene," *Proc. Natl. Acad. Sci. USA*, 84 (9): 2848-2852, 1987.

Manion and Hockenbery, "Targeting Bcl-2-related proteins in cancer therapy," *Cancer Biol Ther*, 2(4 Suppl 1):S105-114, 2003.

Marcucci et al., "Prognostic factors and outcome of core binding factor acute myeloid leukemia patients with t(8;21) differ from those of patients with inv(16): a Cancer and Leukemia Group B study," *J.Clin.Oncol.*, 23:5705-5717, 2005.

Markowitz et al., "Inactivation of the type II TGF-beta receptor in colon cancer cells with microsatellite instability," *Science*, 268(5215):1336-1338, 1995.

Markowitz, "TGF-beta receptors and DNA repair genes, coupled targets in a pathway of human colon carcinogenesis," *Biochim. Biophys. Acta.*, 1470 (1): M13-20, 2000.

Marks, "Thioredoxin in cancer—role of histone deacetylase inhibitors," *Semin. Cancer Biol.*, 16(6):436-443, 2006.

Martello et al., "MicroRNA control of nodal signaling," *Nature*, 449(7159):183-188, 2007.

Martin et al., "Molecular profiling of cervical neoplasia," *Expert Review of Molecular Diagnostics*, 6(2):217-229, 2006.

Martinez, "Identification of differentially expressed genes in HPV associated cancers using gene expression, tissue, and microRNA microarrays," Dissertation Abstract, University of Pittsburg, 2007.

Massague et al., "TGFbeta signaling in growth control, cancer, and heritable disorders," *Cell*, 103 (2): 295-309, 2000.

Matoba et al., "Gene expression in mouse cerebellum during its development," *Gene*, 241:125-131, 2000.

Matoba et al., "Gene expression profiling of mouse postnatal cerebellar development," *Physiol.Genomics*, 4:155-164, 2000.

Meng et al., "Involvement of human micro-rna in growth and response to chemotherapy in human cholangiocarcinoma cell lines," *Gastroenterology*, 130(7):2113-2129, 2006.

Merle et al., "Functional consequences of frizzled-7 receptor overexpression in human hepatocellular carcinoma," *Gastroenterology*, 127 (4): 110-1122, 2004.

Miyake et al., "Increased angiogenin expression in the tumor tissue and serum of urothelial carcinoma patients is related to disease progression and recurrence," *Cancer*, 86 (2): 316-324, 1999.

Mizunuma et al., "The LIM-only protein, LMO4, and the LIM domain-binding protein, LDB1, expression in squamous cell carcinomas of the oral cavity," *Br J Cancer*, 88(10):1543-1548, 2003.

Moller et al., "Expression of APO-1 (CD95), a member of the NGF/TNF receptor superfamily, in normal and neoplastic colon epithelium," *Int J Cancer*, 57(3):371-377, 1994.

Montero et al., "Angiogenin expression and prognosis in primary breast carcinoma," *Clin. Cancer Res.*, 4 (9): 2161-2168, 1998.

Mori et al., "A genome-wide search identifies epigenetic silencing of somatostatin, tachykinin-1, and 5 other genes in colon cancer," *Gastroenterology*, 131(3):797-808, 2006.

Mrozek et al., "Clinical relevance of mutations and gene-expression changes in adult acute myeloid leukemia with normal cytogenetics: are we ready for a prognostically prioritized molecular classification?," *Blood*, 109:431-448, 2007.

Mundt et al., "On the regulation and function of human polo-like kinase 1 (PLK1): effects of overexpression on cell cycle progression," *Biochem Biophys Res Commun*, 239(2):377-385, 1997.

Muralidhar et al., "Global microRNA profiles in cervical squamous cell carcinoma depend on Drosha expression levels," *J. Pathol.*, 212:368-377, 2007.

Nagpal et al., "Tazaratone-induced gen 1 (TIG1), a novel retinoic acid receptor-responsive gene in skin," *J. Invest. Dermatol.*, 106 (2): 269-274, 1996.

Nakada et al., "The phosphorylation of EphB2 receptor regulates migration and invasion of human glioma cells," *Cancer Res.*, 64 (9): 3179-3185, 2004.

Nelson et al., "Microarray-based, high-throughput gene expression profiling of microRNAs," *Nature Methods*, 1(2):1-7, 2004.

Nesbit et al., "MYC oncogenes and human neoplastic disease," *Oncogene*, 18 (19): 3004-3016, 1999.

O'Donnel et al., "c-Myc-regulated microRNA's modulcate E2F1 expression," *Nature*, 435(7043):839-4843, 2005.

Office Action issued in European Application No. 02720894.1, mailed Jul. 11, 2007.

Office Action issued in European Application No. 05804851.3, mailed Jul. 30, 2008.

Office Action issued in European Application No. 05804851.3, mailed Dec. 21, 2007.

Office Action issued in European Application No. 05815286.9, mailed Apr. 3, 2008.

Office Action issued in European Application No. 05858321.2, mailed Apr. 11, 2008.

Office Action issued in U.S. Appl. No. 10/632,534, mailed Jul. 11, 2006.

Office Action issued in U.S. Appl. No. 10/632,534, mailed Mar. 29, 2007.

Office Action issued in U.S. Appl. No. 10/632,534, mailed Mar. 24, 2006.

Office Action issued in U.S. Appl. No. 10/632,539, mailed Apr. 17, 2007.

Office Action issued in U.S. Appl. No. 10/632,539, mailed Jul. 27, 2006.

Office Action issued in U.S. Appl. No. 10/632,539, mailed Mar. 27, 2006.

Office Action issued in U.S. Appl. No. 10/880,350, mailed Feb. 21, 2006.

Office Action issued in U.S. Appl. No. 10/880,350, mailed Oct. 4, 2006.

Office Action issued in U.S. Appl. No. 10/880,350, mailed Sep. 10, 2007.

Office Action issued in U.S. Appl. No. 10/963,415, mailed Aug. 2, 2007.

Office Action issued in U.S. Appl. No. 10/963,415, mailed Apr. 13, 2007.

Office Action issued in U.S. Appl. No. 10/963,415, mailed Mar. 17, 2008.

Office Action issued in U.S. Appl. No. 11/567,082, mailed Jan. 27, 2009.

Office Action issued in U.S. Appl. No. 11/567,082, mailed Jul. 21, 2008.

Office Action issued in U.S. Appl. No. 11/567,082, mailed Jul. 3, 2007.

Office Action issued in U.S. Appl. No. 11/567,082, mailed Nov. 13, 2007.

Office Action issued in U.S. Appl. No. 11/837,490, mailed Aug. 6, 2008.

Office Action issued in U.S. Appl. No. 11/837,490, mailed Jan. 13, 2009.

Office Action issued in U.S. Appl. No. 11/837,494, mailed Jan. 15, 2009.

Office Action issued in U.S. Appl. No. 11/837,494, mailed Mar. 5, 2009.

Office Action issued in U.S. Appl. No. 11/837,494, mailed Oct. 30, 2008.

Office Action issued in U.S. Appl. No. 11/837,495, mailed Mar. 5, 2009.

Office Action issued in U.S. Appl. No. 11/837,495, mailed Oct. 30, 2008.

Office Action issued in U.S. Appl. No. 11/837,498, mailed Jan. 15, 2009.

Office Action issued in U.S. Appl. No. 11/837,498, mailed Oct. 29, 2008.

Ovcharenko et al., "High-throughput RNAi screening in vitro: from cell lines to primary cells," *RNA*, 11(6):985-93, 2005.

Palleres et al., "Structure of human carboxypeptidase A4: with its endogenous protein inhibitor, latexin," *Proc. Natl. Acad. Sci. USA*, 102: 3978-3983, 2005.

Parkin et al., "Global cancer statistics, 2002," *CA Cancer J. Clin.*, 55(2):74-108, 2005.

Pasquinelli et al., "Reverse 5' caps in RNAs made in vitro by phage RNA polymerases," *RNA*, 1:957-967, 1995.

PCT International Preliminary Report on Patentability and Written Opinion, issued in International Application No. PCT/US2005/018826, mailed Dec. 7, 2006.

PCT International Preliminary Report on Patentability and Written Opinion, issued in International Application No. PCT/US2005/022710, mailed Jan. 18, 2007.

PCT International Preliminary Report on Patentability and Written Opinion, issued in International Application No. PCT/US2005/036799, mailed Apr. 26, 2007.

PCT International Preliminary Report on Patentability and Written Opinion, issued in International Application No. PCT/US2005/041162, mailed Dec. 6, 2007.

PCT International Search Report and Written Opinion, issued in International Application No. PCT/US2005/036799, mailed Jun. 22, 2006.

PCT International Search Report and Written Opinion, issued in International Application No. PCT/US2005/022710, mailed Oct. 7, 2005.

PCT International Search Report and Written Opinion, issued in International Application No. PCT/US2007/078859, mailed Mar. 25, 2008.

PCT International Search Report and Written Opinion, issued in International Application No. PCT/US2007/078894, mailed Apr. 14, 2008.

PCT International Search Report and Written Opinion, issued in International Application No. PCT/US2007/078936, mailed Apr. 14, 2008.

PCT International Search Report and Written Opinion, issued in International Application No. PCT/US2007/086396, mailed May 30, 2008.

PCT International Search Report and Written Opinion, issued in International Application No. PCT/US2007/087021, mailed Sep. 3, 2008.

PCT International Search Report and Written Opinion, issued in International Application No. PCT/US2007/087037, mailed Jan. 12, 2009.

PCT International Search Report and Written Opinion, issued in International Application No. PCT/US2007/087038, mailed Oct. 17, 2008.

PCT International Search Report and Written Opinion, issued in International Application No. PCT/US2007/089206, mailed Aug. 26, 2008.
PCT International Search Report and Written Opinion, issued in International Application No. PCT/US2007/087029, mailed Jan. 13, 2009.
PCT International Search Report and Written Opinion, issued in International Application No. PCT/US2007/087031, mailed Jan. 13, 2009.
PCT International Search Report and Written Opinion, issued in International Application No. PCT/US2007/087033, mailed Jan. 13, 2009.
PCT International Search Report and Written Opinion, issued in International Application No. PCT/US2008/080318, mailed Feb. 9, 2009.
PCT International Search Report, issued in International Application No. PCT/US2002/003169, mailed Feb. 17, 2003.
PCT Invitation to Pay Additional Fees and Partial International Search, issued in International Application No. PCT/US2005/018826, mailed Mar. 20, 2006.
PCT Invitation to Pay Additional Fees and Partial International Search, issued in International Application No. PCT/US2005/041162, mailed Aug. 31, 2007.
PCT Invitation to Pay Additional Fees and Partial International Search, issued in International Application No. PCT/US2007/087031, mailed Sep. 10, 2008.
PCT Invitation to Pay Additional Fees and Partial International Search, issued in International Application No. PCT/US2007/087033, mailed Sep. 5, 2008.
PCT Invitation to Pay Additional Fees and Partial International Search, issued in International Application No. PCT/US2007/087029, mailed Sep. 10, 2008.
PCT Invitation to Pay Additional Fees and Partial International Search, issued in International Application No. PCT/US2007/078859, mailed Jan. 28, 2008.
PCT Invitation to Pay Additional Fees and Partial International Search, issued in International Application No. PCT/US2007/078894, mailed Feb. 11, 2008.
PCT Invitation to Pay Additional Fees and Partial International Search, issued in International Application No. PCT/US2007/078936, mailed Feb. 5, 2008.
PCT Invitation to Pay Additional Fees and Partial International Search, issued in International Application No. PCT/US2007/087021, mailed Jul. 10, 2008.
PCT Invitation to Pay Additional Fees and Partial International Search, issued in International Application No. PCT/US2007/087037, mailed Aug. 25, 2008..
PCT Invitation to Pay Additional Fees and Partial International Search, issued in International Application No. PCT/US2007/087038, mailed Jul. 16, 2008.
PCT Invitation to Pay Additional Fees and Partial International Search, issued in International Application No. PCT/US2007/089206, mailed Jul. 7, 2008.
PCT Invitation to Pay Additional Fees and Partial International Search, issued in International Application No. PCT/US2008/076246, mailed Dec. 30, 2008.
Petit et al., "LHFP, a novel translocation partner gene of HMGIC in a lipoma, is a member of a new family of LHFP-like genes," *Genomics*, 57 (3): 438-441, 1999.
Phillips et al., "Antisense RNA amplification: A linear amplification method for analyzing the mRNA populaion," *Methods, a Companion to Methods in Enzymology*, 10(3):283-288, 1996.
Ree et al., "Expression of a novel factor in human breast cancer cells with metastatic potential," *Cancer Res.*, 59 (18): 4675-4680, 1999.
Reimer et al., "Altered regulation of cyclin G in human breast cancer and its specific localization at replication foci in response to DNA damage in p53+/+ cells," *J. Biol. Chem.*, 274 (16): 11022-11029, 1999.
Rickert et al., "Multiplexed Real-Time PCR Using Universal Reporters," *Clin. Chem.*, 50(9):1680-1683, 2004.
Rosenkilde and Schwartz, "The chemokine system—a major regulator of angiogenesis in health and disease," *Apmis*, 112(7-8):481-495, 2004.
Rossi et al., "Identification of inactivating mutations in the JAK1, SYNJ2, and CLPTM1 genes in prostate cancer cells using inhibition of nonsense-mediated decay and microarray analysis," *Cancer Genet. Cytogenet.*, 161 (2): 97-103, 2005.
Rubin and Gutmann, "Neurofibromatosis type 1—a model for nervous system tumour formation?," *Nat Rev Cancer*, 5(7):557-564, 2005.
Ruth et al., "RhoC promotes human melanoma invasion in a PI3K/Akt-dependent pathway," *J. Invest. Dermatol.*, 126 (4): 862-868, 2006.
Sacchi et al., "Hu-ets-1 and Hu-ets-2 genes are transposed in acute leukemias with (4;11) and (8;21) translocations," *Science*, 231 (4736): 379-382, 1986.
Saigusa et al., "Overexpressed Skp2 within 5p amplification detected by array-based comparative genomic hybridization is associated with poor prognosis of glioblastomas," *Cancer Sci*, 96(10):676-683, 2005.
Saitoh et al., "Frequent up-regulation of WNT5A mRNA in primary gastric cancer," *Int. J. Mol. Med.*, 9 (5): 515-519, 2002.
Sakai et al., "Microarray hybridization with fractionated cDNA: enhanced identification of differentially expressed genes," *Analytical Biochemistry*, 287(1):32-37, 2000.
Sampson and Uhlenbeck, "Bichemical and physical characterization of an unmodified yeast phenylalanine transfer RNA transcribed in vitro," *Proc. Natl. Acad. Sci.*, USA, 85(4):10331037, 1988.
Sanger Institute, miRBase::Sequences—Stem-loop sequence MI0000268, Sep. 2008, located at http://microRNA.sanger.ac.ukm, printed on Dec. 23, 2008.
Sanger Institute, "miRBase" *miRBase Sequence Database*, located at http://microrna.sanger.ac.uk/, printed Jan. 21, 2009.
Schenborn and Stecha, "Ribo m$^7$G cap analog: A reagent for preparing in vitro capped transcripts", *Promega Notes*, 74:18-20, 2000.
Scherr et al., "Lentrivirus-mediated antagomir expression for specific inhibition of miRNA function," *Nucleic Acids Research*, 35(22):e149, 2007.
Schouten et al., "Relative quantification of 40 nucleic acid sequences by multiplex ligation-dependent probe amplification," *Nucleic Acids Research*, 30(12):e57, 2002.
Schulze-Bergkamen et al., "Suppression of Mcl-1 via RNA interference sensitizes human hepatocellular carcinoma cells towards apoptosis induction," *BMC Cancerp*, 6:232, 2006.
Sementchenko et al, "ETS2 function is required to maintain the transformed state of human prostate cancer cells," *Oncogene*, 17 (22): 2883-2888, 1998.
Shah et al., "FGFR4 overexpression in pancreatic cancer is mediated by an intronic enhancer activated by HNF1alpha," *Oncogene*, 21 (54): 8251-8261, 2002.
Shelly et al., "Epiregulin is a potent pan-ErbB ligand that preferentially activates heterodimeric receptor complexes," *J. Biol. Chem.*, 273 (17): 10496-10505, 1998.
Shelton et al., "MicroRNAs and Human Cancer," Abstract submitted for a Cold Spring Symposium in early Jun., 2006—71$^{st}$ Symposium: Regulatory RNAs.
Shi et al., "Facile means for quantifying microRNA expression by real-time PCR," *BioTechniques*, 39(4):519-524, 2005.
Shibahara et al., "Down-regulation of Skp2 is correlated with p27-associated cell cycle arrest induced by phenylacetate in human prostate cancer cells," *Anticancer Res.*, 25 (3b): 1881-1888, 2005.
Shigemasa et al., "Increased MCL-1 expression is associated with poor prognosis in ovarian carcinomas," *Jpn. J. Cancer Res.*, 93(5):542-550, 2002.
Shimo et al., "Connective tissue growth factor as a major angiogenic agent that is induced by hypoxia in a human breast cancer cell line," *Cancer Lett.*, 174(1):57-64, 2001.
Shimoyama et al., "Increased serum angiogenin concentration in colorectal cancer is correlated with cancer progression," *Clin. Cancer Res.*, 5 (5): 1125-1130, 1999.
Shuldiner et al., "RNA template-specific polymerase chain reaction RS-PCR a novel strategy to reduce dramatically false positives," *Gene*, 91(1):139-142, 1990.
Shyu et al., "RARRES3 expression positively correlated to tumour differentiation in tissues of colorectal adenocarcinoma," *Br. J. Cancer*, 89 (1): 146-151, 2003.
Si et al., "miR-21-mediated tumor growth," *Oncogene*, 1-5, 2006.

Simpson et al., "Altered expression of Erg and Ets-2 transcription factors is associated with genetic changes at 21q22.2-22.3 in immortal and cervical carcinoma cell lines," *Oncogene*, 14 (18): 2149-2157, 1997.

Sirera et al., "The analysis of serum DNA concentration by means of hTERT quantification: A useful prognostic factor in advanced non-small cell lung cancer (NSCLC)," *Lung Cancer*, 49:S74, Abstract PD-026, 2005.

Skotzko et al., "Retroviral vector-mediated gene transfer of antisense cyclin G1 (CYCG1) inhibits proliferation of human osteogenic sarcoma cells," *Cancer Res.*, 55 (23): 5493-5498, 1995.

Slack et al., "The lin-41 RBCC gene acts in the *C. elegans* heterochronic pathway between the let-7 regulatory RNA and the LIN-29 transcription factor," *Molec. Cell*, 5(4):659-669, 2000.

Smith et al., "Exclusive amplification of cDNA template (EXACT) RT-PCR to avoid amplifying contaminating genomic pseudogenes," *BioTechniques*, 31(4): 776-778, 780, 782, 2001.

Smith et al., "Malignant transformation of mammalian cells initiated by constitutive expression of the polo-like kinase," *Biochem Biophys Res Commun*, 234(2):397-405, 1997.

Sparmann and Bar-Sagi, "Ras-induced interleukin-8 expression plays a critical role in tumor growth and angiogenesis," *Cancer Cell*, 6(5):447-458, 2004.

Stepinski et al., "Synthesis and properties of mRNAs containing the novel 'anti-reverse' cap analogs 7-methyl(3'O-methyl)GpppG and 7-methyl(e'-deoxy)GpppG," *RNA*, 7:1486-1495, 2001.

Stone et al., "Isolation of a human prostate carcinoma cell line (DU 145)," *Int. J. Cancer*, 21 (3): 274-281, 1978.

Strebhardt and Ullrich, "Targeting polo-like kinase 1 for cancer therapy," *Nat. Rev. Cancer*, 6 (4): 321-330, 2006.

Sturniolo et al., "A novel tumor suppressor protein promotes keratinocyte terminal differentiation via activation of type I transglutaminase," *J. Biol. Chem.*, 278 (48): 48066-48073, 2003.

Su et al,. "Overexpression of p8 is inversely correlated with apoptosis in pancreatic cancer," *Clin. Cancer Res.*, 7 (5): 1320-1324, 2001.

Sueoka et al., "Detection of plasma hnRNP B1 mRNA, a new cancer biomarker, in lung cancer patients by quantitative real-time polymerase chain reaction," *Lung Cancer*, 48(1):77-83, 2005.

Sui et al., "Clinical significance of Skp2 expression, alone and combined with Jab1 and p27 in epithelial ovarian tumors," *Oncol. Rep.*, 15 (4): 765-771, 2006.

Sum et al., "Overexpression of LMO4 induces mammary hyperplasia, promotes cell invasion, and is a predictor of poor outcome in breast cancer," *Proc Natl Acad Sci USA*, 102(21):76597664, 2005.

Sum et al., "The LIM domain protein LMO4 interacts with the cofactor CtIP and the tumor suppressor BRCA1 and inhibits BRCA1 activity," *J Biol Chem*, 277(10):7849-7856, 2002.

Sunpaweravong et al., "Epidermal growth factor receptor and cyclin D1 are independently amplified and overexpressed in esophageal squamous cell carcinoma," *J Cancer Res Clin Oncol*, 131(2):111-119, 2005.

Szafranska et al., "A unique microRNA molecular signature for pancreatic carcinoma," AACRP-Pancreatic Cancer: Early Detection and Novel Therapeutics, Chapel Hill, NC, Jun. 26-27, 2006.

Takamizawa et al., "Reduced expression of the let-7 microRNAs in human lung cancers in association with shortened postoperative survival," *Cancer Research*, 64:3753-3756, 2004.

Takanami, "The prognostic value of overexpression of Skp2 mRNA in non-small cell lung cancer.," *Oncol. Rep.*, 13 (4): 727-731, 2005.

Takimoto et al., "Genetic alterations in the retinoblastoma protein-related p107 gene in human hematologic malignancies," *Biochem Biophys Res Commun*, 251(1):264-268, 1998.

Tanaka et al., "A novel frizzled gene identified in human esophageal carcinoma mediates APC/beta-catenin signals," *Proc. Natl. Acad. Sci. USA*, 95 (17): 10164-10169, 1998.

Taniwaki et al., "Gene expression profiles of small-cell lung cancers: molecular signatures of lung cancer," *Int J Oncol*, 29(3):567-575, 2006.

Tassi et al., "Enhancement of fibroblast growth factor (FGF) activity by an FGF-binding protein," *J. Biol. Chem.*, 276(43):40247-40253, 2001.

Tazawa et al., "Tumor-suppressive *miR-34a* induces senescence-like growth arrest through modulation of the E2F pathway in human colon cancer cells," *PNAS*, 104(39):15472-15477, 2007.

Thøgersen et al., "A subclass of HER1 ligands are prognostic markers for survival in bladder cancer patients," *Cancer Res.*, 61 (16): 6227-6233, 2001.

Tomasini-Johansson et al., "Vitronectin in colorectal adenocarcinoma—synthesis by stromal cells in culture," *Exp. Cell. Res.*, 214 (1): 303-312, 1994.

Toning et al., "Increased expression of heparin binding EGF (HB-EGF), amphiregulin, TGF alpha and epiregulin in androgen-independent prostate cancer cell lines," *Anticancer Res.*, 20 (1a): 91-95, 2000.

Toyoda et al., "Distribution of mRNA for human epiregulin, a differentially expressed member of the epidermal growth factor family," *Biochem J*, 326 (Pt 1):69-75, 1997.

Traub et al., "Prognostic impact of Skp2 and p27 in human breast cancer.," *Breast Cancer Res. Treat.*, 99 (2): 185-191, 2006.

Tsai et al., "RIG1 inhibits the Ras/mitogen-activated protein kinase pathway by suppressing the activation of Ras.," *Cell Signal*, 18 (3): 349-358, 2006.

U.S. Appl. No. 11/273,640, entitled "Methods and compositions involving miRNA and miRNA inhibitors molecules," by David Brown et al., filed Nov. 14, 2005.

U.S. Appl. No. 11/855,792, entitled "Methods of normalization in microRNA detection assays," by Gary Latham et al., filed Sep. 14, 2007.

U.S. Appl. No. 11/967,639, entitled "Functions and targets of LET-7 micro RNAs," by Charles Johnson et al., filed Dec. 31, 2007.

U.S. Appl. No. 11/967,663, entitled "miR-16 regulated genes and pathways as targets for therapeutic intervention," by Mike Byrom et al., filed Dec. 31, 2007.

U.S. Appl. No. 12/112,291, entitled "miR-20 Regulated Genes and Pathways as Targets for Therapeutic Intervention ," by Andreas Bader et al., filed Apr. 30, 2008.

U.S. Appl. No. 12/120,388, entitled "miR-21 regulated genes and pathways as targets for therapeutic intervention," by Andreas Bader et al., filed May 14, 2008.

U.S. Appl. No. 12/124,394, entitled "miR-200 Regulated Genes and Pathways as Targets for Therapeutic Intervention," by Andreas Bader et al., filed May 21, 2008.

U.S. Appl. No. 12/125,412, entitled "miR-143 regulated genes and pathways as targets for therapeutic intervention," by Andreas Bader et al., filed May 22, 2008.

U.S. Appl. No. 12/134,932, entitled "miR-134 Regulated Genes and Pathways as Targets for Therapeutic Intervention," by Andreas Bader et al., filed Jun. 6, 2008.

U.S. Appl. No. 12/209,822, entitled "MicroRNAs idfferentially expressed in cervical cancer and uses thereof," by Sylvie Beaudenon et al., filed Sep. 12, 2008.

U.S. Appl. No. 12/253,718, entitled "MicroRNAs differentially expressed in lung diseases and uses thereof," by Gary J. Lathan et al., filed Oct. 17, 2008.

U.S. Appl. No. 12/325,917, entitled "miR-124 Regulated Genes and Pathways as Targets for Therapeutic Intervention," by Andreas Bader et al., filed Dec. 1, 2008.

U.S. Appl. No. 12/340,329, entitled "miR-10 Regulated Genes and Pathways as Targets for Therapeutic Intervention," by Ovcharenko et al., filed Dec. 19, 2008.

U.S. Appl. No. 12/368,053, entitled "miRNAs Differentially Expressed in Lymph Nodes from Cancer Patients," by Sylvie Beaudenon et al., filed Feb. 9, 2009.

U.S. Appl. No. 12/398,852, entitled "MicroRNA markers for recurrence of colorectal cancer," by Elizabeth Mambo et al., filed Mar. 5, 2009..

U.S. Appl. No. 12/412,087, entitled "Compositions and methods related to miR-16 and therapy of prostate cancer," by Fumitaka Takeshita et al., filed Mar. 26, 2009.

U.S. Appl. No. 12/420,634, entitled "Methods and compositions for diagnosing and modulating human papillomavirus (HPV)," by Sylvie Beaudenon-Huibregtse, filed Apr. 8, 2009.

U.S. Appl. No. 12/437,899, entitled "Compositions and methods related to miRNA modulation of neovascularization or angiogenesis," by Jikui Shen et al., filed May 8, 2009.

U.S. Appl. No. 60/575,743, entitled "Methods and compositions involving MicroRNA," by David Brown et al., filed May 28, 2004.

U.S. Appl. No. 60/649,584, entitled "Methods and compositions involving MicroRNA," by David Brown et al., filed Feb. 3, 2005.

U.S. Appl. No. 60/650,807, entitled "Compositions and methods involving MDA-7 and COX-2 inhibitors for the treatment of cancer," by Sunil Chada et al., filed Feb. 8, 2005.

U.S. Appl. No. 60/906,028, entitled "Prostate cancer specific miRNAs," by David Brown, filed Mar. 9, 2007.

U.S. Appl. No. 61/113,385, entitled "Methods and compositions involving miRNAs in cancer stem cells," by Lubna Patrawala et aL, filed Nov. 11, 2008.

Uhm et al., "Vitronectin, a glioma-derived extracellular matrix protein, protects tumor cells from apoptotic death," *Clin. Cancer Res.*, 5 (6): 1587-1594, 1999.

Ulisse et al., "Expression of Aurora kinases in human thyroid carcinoma cell lines and tissues," *Int. J. Cancer*, 119 (2): 275-282, 2006.

Vargas-Roig et al., "Heat shock protein expression and drug resistance in breast cancer patients treated with induction chemotherapy," *Cancer Detection and Prevention*, 21(5):441-451, 1997.

Vella et al., "Architecture of a validated microRNA::target interaction," *Chem. Biol.*, 11(12):1619-1623, 2004.

Vella et al., "The *C. elegans* microRNA *let-7* binds to imperfect *let-7* complementary sites from the *lin-41* 3'UTR," *Genes Dev.*, 18(2):132-7, 2004.

Visvader et al., "The LIM domain gene LMO4 inhibits differentiation of mammary epithelial cells in vitro and is overexpressed in breast cancer," *Proc Natl Acad Sci U S A*, 98(25):14452- 14457, 2001.

Volinia et al., "A microRNA expression signature of human solid tumors defines cancer gene targets," *Proc. Natl. Acad. Sci. USA*, 103(7):2257-2261, 2006.

Volloch and Sherman, "Oncogenic potential of Hsp72," *Oncogene*, 18(24):3648-3651, 1999.

Vos et al., "RASSF2 is a novel K-Ras-specific effector and potential tumor suppressor," *J Biol Chem*, 278(30):28045-28051, 2003.

Wade, "Transcriptional control at regulatory checkpoints by histone deacetylases: molecular connections between cancer and chromatin," *Hum. Mol. Genet.*, 10(7):693-698, 2001.

Wang et al., "Identification of rat lung-specific microRNAs by micoRNA microarray: valuable discoveries for the facilitation of lung research," *BMC Genomics*, 8:29-42, 2007.

Weeraratna et al., "Wnt5a signaling directly affects cell motility and invasion of metastatic melanoma," *Cancer Cell*, 1 (3): 279-288, 2002.

Weinstein, "Disorders in cell circuitry during multistage carcinogenesis, the role of homeostasis," *Carcinogenesis*, 21 (5): 857-864, 2000.

Weiss and Bohmann, "Deregulated repression of c-Jun provides a potential link to its role in tumorigenesis," *Cell Cycle*, 3 (2): 111-113, 2004.

Welsh et al., "Fingerprinting genomes using PCR with arbitrary primers," *Nucleic Acids Research*, Oxford University Press, Surrey, GB, 18(24):7213-7218, 1990.

Welsh et al., "Nucleic acid fingerprinting by PCR-based methods: applications to problems in aging and mutagenesis," *Mutation Research*, 338(1-6):215-229, 1995.

Wheeler and Ridley, "Why three Rho proteins? RhoA, RhoB, RhoC, and cell motility," *Exp. Cell. Res.*, 301 (1): 43-49, 2004.

Whitcombe et al., "A homogeneous fluorescence assay for PCR amplicons: its application to real-time, single-tube genotyping," *Clin. Chem.*, 44(5):918-923, 1998.

Whitcombe et al., "Advances in approaches to DNA-based diagnostics," *Curr. Opin. Biotechnol.*, 9(6):602-608, 1998.

Wikman et al., "Identification of differentially expressed genes in pulmonary adenocarcinoma by using cDNA array," *Oncogene*, 21(37):5804-5813, 2002.

Wood et al., "DNA microarray analysis of vitamin D-induced gene expression in a human colon carcinoma cell line," *Physiol. Genomics*, 17 (2): 122-129, 2004.

Wooster and Weber, "Breast and ovarian cancer," *N. Engl. J. Med.*, 348(23):2339-2347, 2003.

Wu et al., "Expression of Ephb2 and Ephb4 in breast carcinoma," *Pathol. Oncol. Res.*, 10 (1): 26-33, 2004.

Wu et al., "MicroRNA and cancer: current status and prospective," *International Journal of Cancer*, 120:953-960, 2006.

Wu et al., "p107 Expression in colorectal tumours rises during carcinogenesis and falls during invasion," *Eur J Cancer*, 38(14):1838-1848, 2002.

Wu et al., "RARRES1 expression is significantly related to tumour differentiation and staging in colorectal adenocarcinoma," *Eur. J. Cancer*, 42(4):557-565, 2006.

Wu et al., "RhoC induces differential expression of genes involved in invasion and metastasis in MCF10A breast cells," *Breast Cancer Res., Treat.*, 84 (1); 3-12, 2004.

Wu et al., "The prognostic impact of EphB2/B4 expression on patients with advanced ovarian carcinoma," *Gynecol. Oncol.*, 102 (1): 15-21, 2006.

Wyatt et al., "Synthesis and purification of large amounts of RNA oligonucleotides," *Biotechniques*, 11(6):764-769, 1991.

Wyttenbach et al., "Polyglutamine expansions cause decreased CRE-mediated transcription and early gene expression changes prior to cell death in an inducible cell model of Huntington's disease," *Human Molecular Genetics*, 10(17):1829-1845, 2001.

Xia et al., "Positive expression of HIF-2alpha/EPAS1 in invasive bladder cancer," *Urology*, 59(5):774-778, 2002.

Xia et al., "Regulation of vascular endothelial growth factor transcription by endothelial PAS domain protein 1 (EPAS1) and possible involvement of EPAS1 in the angiogenesis of renal cell carcinoma," *Cancer*, 91(8):1429-1436, 2001.

Xia et al., "The Src-suppressed C kinase substrate, SSeCKS, is a potential metastasis inhibitor in prostate cancer," *Cancer Res*, 61(14):5644-5651, 2001.

Xie et al., "Negative feedback regulation of Dicer-Like1 in Arabidopsis by microRNA-guided mRNA degradation," *Current Biology*, 13:784-789, 2003.

Xie, et al., "Systematic discovery of regulatory motifs in human promoters and 3' UTRs by comparison of several mammals," *Nature*, 434(7031):338-345, 2005.

Yanaihara et al., "Unique microRNA molecular profiles in lung cancer diagnosis and prognosis," *Cancer Cell*, 9:189-198, 2006.

Yang et al., "Differential expression of CCAAT/enhancer-binding protein-delta (c/EBPdelta) in rat androgen-dependent tissues and human prostate cancer," *J. Androl.*, 22 (3): 471-480, 2001.

Yang et al., "Smad3 reduces susceptibility to hepatocarcinoma by sensitizing hepatocytes to apoptosis through downregulation of Bcl-2," *Cancer Cell*, 9(6):445-457, 2006.

Yang et al., "Stromal expression of connective tissue growth factor promotes angiogenesis and prostate cancer tumorigenesis," *Cancer Res.*, 65(19):8887-8895, 2005.

Yang et al., "The transformation suppressor Pdcd4 is a novel eukaryotic translation initiation factor 4A binding protein that inhibits translation," *Mol. Cell Biol.*, 23(1):26-37, 2003.

Yang et al., "Tumorigenesis suppressor Pdcd4 down-regulates mitogen-activated protein kinase kinase kinase kinase 1 expression to suppress colon carcinoma cell invasion," *Mol Cell Biol*, 26(4):1297-1306, 2006.

Yao et al., "RhoC GTPase is required for PC-3 prostate cancer cell invasion but not motility," *Oncogene*, 25 (16): 2285-2296, 2006.

Yoon and De Micheli, "Prediction of regulatory modules comprising microRNAs and target genes," *Bioinformatics*, 21(Suppl.2):ii93-ii100, 2005.

Yoshida et al., "The clinical significance of Cyclin B1 and Wee1 expression in non-small-cell lung cancer," *Ann Oncol*, 15(2):252-256, 2004.

Yoshimura et al., "Prognostic impact of hypoxia-inducible factors 1alpha and 2alpha in colorectal cancer patients: correlation with tumor angiogenesis and cyclooxygenase-2 expression," *Clin. Cancer Res.*, 10(24):8554-8560, 2004.

Yoshioka et al,. "A role for LIM kinase in cancer invasion," *Proc. Natl. Acad. Sci. USA*, 100 (12): 7247-7252, 2003.

Youssef et al., "Hypermethylation and silencing of the putative tumor suppressor, Tazarotene-induced gene 1 in human cancers," *Cancer Res.*, 64 (7): 2411-2417, 2004.

Yu et al,. "Global assessment of promoter methylation in a mouse model of cancer identifies ID4 as a putative tumor-suppressor gene in human leukemia," *Nat. Genet.*, 37 (3): 265-274, 2005.

Zangemeister-Wittke and Huwiler, "Antisense targeting of Mcl-1 has therapeutic potential in gastric cancer," *Cancer Biol. Ther.*, 5(10):1355-1356, 2006.

Zhang et al., "Involvement of programmed cell death 4 in transforming growth factor-beta1-1-induced apoptosis in human hepatocellular carcinoma," *Oncogene*, 25(45):6101-6112, 2006.

Zhang et al., "Methylation of the retinoid response gene TIG1 in prostate cancer correlates with methylation of the retinoic acid receptor beta gene," *Oncogene*, 23 (12): 2241-2249, 2004.

Zhao et al., "Cyclin G1 has growth inhibitory activity linked to the ARF-Mdm2-p53 and pRb tumor suppressor pathways," *Mol Cancer Res*, 1(3):195-206, 2003.

Zhu et al., "MicroRNA-21 targets the tumor suppressor gene tropomyosin 1 (TIPM1)" *The Journal of Biological Chemistry*, 282(19):14328-14336, 2007.

Zhu et al., "Epiregulin is Up-regulated in pancreatic cancer and stimulates pancreatic cancer cell growth," *Biochem. Biophys. Res. Commun.*, 273 (3): 1019-1024, 2000.

Zimmerman et al., "Technical aspects of quantitative competitive PCR," *Biotechniques*, 21(2):268-270, 1996.

"Human miRNA targets," for "mmu-miR-126-3p" Apr. 2005 version, accessed and retrieved from miRanda webserver at www.microma.org and http://cbio.mskcc.org/cgi-bin/mirnaviewer, on Dec. 31, 2009. p. 1 of the 23 print-out pp. included.

Aiello et al., "Suppression of retinal neovascularization in vivo by inhibition of vascular endothelial growth factor (VEGF) using soluble VEGF-receptor chimeric proteins," *Proc. Natl. Acad. Sci. USA*. 92(23):10457-10461, 1995.

Bedell et al., "Amplification of human papillomavirus genomes in vitro is dependent on epithelial differentiation," *J Virol.*, 65(5):2254-60, 1991.

Bommer et al., "p53-mediated activation of miRNA34 candidate tumor-suppressor genes," *Current Biology*, 17:1298-1307, mailed 2007.

Bonci et al., "The *miR-15a-miR-16-1* cluster controls prostate cancer by targeting multiple oncogenic activities," *Nature Medicine*, 14(11):1271-1277, 2008.

Bosch and de Sanjosé, "The epidemiology of human papillomavirus infection and cervical cancer," *Dis Markers.*, 23(4):213-27, 2007.

Brown and Regillo, "Anti-VEGF agents in the treatment of neovascular age-related macular degeneration: applying clinical trial results to the treatment of everyday patients," *Am. J. Ophthalmol.*, 144(4):627-637, 2007.

Bullinger et al., "Gene expression profiling in acute myeloid leukemia," *Journal of Clinical Oncology*, 23(26):6296-6305, 2005.

Cai et al., "Human papillomavirus genotype 31 does not express detectable microRNA levels during latent or productive virus replication," *J. Virol.*, 80(21):10890-3, 2006.

Campochiaro and Hackett, "Ocular neovascularization: a valuable model system," *Oncogene*, 22(42):6537-6548, 2003.

Clifford et al., "Human papillomavirus types in invasive cervical cancer worldwide: a meta-analysis," *Br. J. Cancer*, 88(1):63-73, 2003.

Cogliano et al., "Carcinogenicity of human papillomaviruses," *Lancet Oncol.*, 6(4):204, 2005.

Costinean et al., "Pre-B cell proliferation and lymphoblastic leukemia/high-grade lymphoma in Eµ-miR155 transgenic mice," *Proc. Natl. Acad. Sci. USA*, 103(18):7024-7029, 2006.

Cox, "Epidemiology and natural history of HPV," *J. Fam. Pract.*, Suppl:3-9, 2006.

Cmogorac-Jurcevic et al., "Proteomic analysis of chronic pancreatitis and pancreatic adenocarcinoma," *Gastroenterology*, 129:1454-1463, 2005.

Cummins and Velculescu, "Implications of micro-RNA profiling for cancer diagnosis," *Oncogene*, 25(46):6220-6227, 2006.

Dews et al., "Augmentation of tumor angiogenesis by a Myc-activated microRNA cluster," *Nat. Genet.*, 38(9):1060-1065, 2006.

D'Souza et al., "Case-control study of human papillomavirus and oropharyngeal cancer," *New Engl. J. Med.*, 356:1944-1956, 2007.

European Search Report issued in European Application No. 09154092.2, mailed Aug. 12, 2009.

Fazi et al., "A minicircuitry comprised of microRNA-223 and transcription factors NFI-A and C/EBPβ regulates human granulopoiesis," *Cell*, 123:819-831, 2005.

Folkman, "Successful treatment of an angiogenic disease," *N Engl J Med* 320:1211-1212, 1989.

Griffiths-Jones et al., "miRBase: tools for microRNA genomics," *Nucl. Acids Res.*, 36 (Database Issue):D154-D158, 2008.

Han et al., "Cyclin D 1 expression in human prostate carcinoma cell lines and primary tumors," *The Prostate*, 35:95-101, 1998.

Harfe, "MicroRNAs in vertebrate development," *Curr. Opin. Genet Dev.*, 15(4):410-5, 2005.

Hayashita et al., "A polycistronic microRNA cluster, miR-17-92, is overexpressed in human lung cancers and enhances cell proliferation," *Cancer Res.*, 65(21):9628-9632, 2005.

He et al., "A microRNA component of the p53 tumour suppressor network," *Nature*, 447(7148):1130-1134,2007.

Hermeking, "p53 enters the microRNA world," *Cancer Cell*, 12(5):414-418, 2007.

Hornstein et al., "The microRNA *mir-196* acts upstream of Hoxb8 and Shh in limb development," *Nature*, 438:671-674, 2005.

Houbaviy et al., "Embryonic stem cell-specific micro-RNAs," *Developmental Cell*, 5:351-358, 2003.

Hummel et al., "Differentiation-induced and constitutive transcription of human papillomavirus type 31b in cell lines containing viral episomes," *J. Virol.*, 66(10):6070-80, 1992.

Ji et al., "Restoration of tumor suppressor miR-34 inhibits human p53-mutant gastric cancer tumorspheres," *BMC Cancer*, 8:266, 2008.

John et al., "Human microRNA targets," *PLOS Biology*, 2(11):1862-1879, 2004.

Jopling et al., "Modulation of hepatitis C virus RNA abundance by a liver-specific MicroRNA," *Science*, 309(5740):1577-81, 2005.

Kayed et al., "Hedgehog signaling in the normal and diseased pancreas," *Pancreas*, 32(2):119-129, 2006.

Kwak et al., "VEGF is major stimulator in model of choroidal neovascularization," *Invest. Ophthalmol. Vis. Sci.*, 41(10):3158-3164, 2000.

Lagos-Quintana et al., "Identification of tissue-specific microRNAs from mouse," *Current Biology*, 12:735-739, 2002.

Lecellier et al., "A cellular microRNA mediates antiviral defense in human cells," *Science*, 308(5720):557-60, 2005.

Lee et al., "The *C. elegans* heterochronic gene lin-4 encodes small RNAs with antisense complementarity to *lin-14*," *Cell*, 75(5):843-854, 1993.

Lewis et al., "Conserved seed pairing, often flanked by adenosines, indicates that thousands of human genes are microRNA targets," *Cell*, 120:15-20, 2005.

Lima e Silva et al., "The SDF-1/CXCR4 ligand/receptor pair is an important contributor to several types of ocular neovascularization," *FASEB J.*,21(12):3219-3230, 2007.

Lui et al., "Patterns of known and novel small RNAs in human cervical cancer," *Cancer Res.*, 67(13):6031-6043, 2007.

Mahato et al., "Modulation of gene expression by antisense and antigene oligodeoxynucleotides and small interfering RNA," *Expert Opinion on Drug Delivery*, 2(1):3-28, 2005.

Mammalian Gene Collection (MGC) Program Team, "Generation and initial analysis of more than 15,000 full-length human and mouse cDNA sequences," *PNAS*, 99(26):16899-16903, 2002.

Martinez et al., "Human papillomavirus type 16 reduces the expression of microRNA-218 in cervical carcinoma cells," *Oncogene*, 27:2575-2582, 2008.

Mattie et al., "Optimized high-throughput microRNA expression profiling provides novel biomarker assessment of clinical prostate and breast cancer biopsies," *Mol. Cancer*, 5:24, 2006.

Michael and Oren, "The p53-Mdm2 module and the ubiquitin system," *Semin.Cancer Biol.* 13:49-58, 2003.

Miller et al., "Vascular endothelial growth factor/vascular permeability factor is temporally and spatially correlated with ocular angiogenesis in a primate mode," *Am. J. Pathol.*, 145(3):574-584, 1994.

Minakuchi et al., "Atelocollagen-mediated synthetic small interfering RNA delivery for effective gene silencing in vitro and in vivo," *Nucleic Acids Research*, 32(13):e109, 2004.

Office Action issued in Australian Application No. 2005250432, mailed Dec. 1, 2009.

Office Action issued in European Application No. 07871689.1, mailed Dec. 15, 2009.

Office Action issued in European Application No. 07871690.9, mailed Dec. 14, 2009.

Office Action issued in European Application No. 07871691.7, mailed Dec. 14, 2009.

Office Action issued in European Application No. 07871693.3, mailed Dec. 9, 2009.

Office Action issued in European Application No. 07871694.1, mailed Dec. 10, 2009.

Office Action issued in European Application No. 07871756.8, mailed Oct. 20, 2009.

Office Action issued in U.S. Appl. No. 11/273,640, mailed Nov. 20, 2009.

Office Action issued in U.S. Appl. No. 11/567,082, mailed Sep. 30, 2009.

Office Action issued in U.S. Appl. No. 11/837,487, mailed Sep. 15, 2009.

Office Action issued in U.S. Appl. No. 11/837,488, mailed Feb. 19, 2010.

Office Action issued in U.S. Appl. No. 11/837,494, mailed Jan. 5, 2010.

Office Action issued in U.S. Appl. No. 11/837,495, mailed Jan. 5, 2010.

Office Action issued in U.S. Appl. No. 11/837,498, mailed Nov. 20, 2009.

Office Action issued in U.S. Appl. No. 11/857,948, mailed Nov. 3, 2009.

Office Action issued in U.S. Appl. No. 11/953,606, mailed Jan. 8, 2010.

Office Action issued in U.S. Appl. No. 11/967,663, mailed Feb. 12, 2010.

Office Action issued in U.S. Appl. No. 11/967,663, mailed Oct. 1, 2009.

Office Action issued in U.S. Appl. No. 12/112,291, mailed Nov. 16, 2009.

Office Action issued in U.S. Appl. No. 12/120,388, mailed Feb. 19, 2010.

Office Action issued in U.S. Appl. No. 12/124,394, mailed Feb. 5, 2010.

Office Action issued in U.S. Appl. No. 12/124,394, mailed Nov. 6, 2009.

Office Action issued in U.S. Appl. No. 12/125,412, mailed Feb. 16, 2010.

Office Action issued in U.S. Appl. No. 12/125,412, mailed Nov. 12, 2009.

Office Action issued in U.S. Appl. No. 12/125,675, mailed Sep. 10, 2009.

Office Action issued in U.S. Appl. No. 12/134,932, mailed Nov. 12, 2009.

Office Action issued in U.S. Appl. No. 12/167,492, mailed Feb. 12, 2010.

Ozaki et al., "Blockade of vascular endothelial cell growth factor receptor signaling is sufficient to completely prevent retinal neovascularization," *Am. J. Pathol.*, 156(2):697-707, 2000.

PCT International Preliminary Report on Patentability issued in International Application No. PCT/US2007/078952, mailed Feb. 11, 2010.

PCT International Preliminary Report on Patentability issued in International Application No. PCT/US2008/066025, mailed Dec. 23, 2009.

PCT International Search Report and Written Opinion issued in International Application No. PCT/US2009/036195, mailed Sep. 4, 2009.

PCT International Search Report and Written Opinion issued in International Application No. PCT/US2009/039935, mailed Sep. 17, 2009.

PCT International Search Report and Written Opinion issued in International Application No. PCT/US2008/066025, mailed Sep. 16, 2009.

PCT International Search Report and Written Opinion issued in International Application No. PCT/US2007/078952, mailed Jan. 26, 2010.

PCT International Search Report and Written Opinion issued in International Application No. PCT/US2009/043361, mailed Nov. 4, 2009.

PCT Invitation to Pay Additional Fees issued in International Application No. PCT/US2007/078952, mailed Sep. 22, 2009.

PCT Invitation to Pay Additional Fees issued in International Application No. PCT/US2008/087762, mailed Nov. 9, 2009.

Poliseno et al., "MicroRNAs modulate the angiogenic properties of HUVECs," *Blood* 108(9):3068-3071, 2006.

Porkka et al., "MicroRNA expression profiling in prostate cancer," *Cancer Res.*, 67(13):6130-6135, 2007.

Rader et al, "In vitro differentiation of epithelial cells from cervical neoplasias resembles in vivo lesions," *Oncogene*, 5(4):571-6, 1990.

Rosenfeld et al., "Ranibizumab: Phase III clinical trial results," *Ophthalmol. Clin. North Am.* 19(3):361-372, 2006.

Saiz et al., "MicroRNA expression profiling in acute myelogenous leukemia," *Blood, ASH Annual Meeting Abstracts*, 104:320a, Abstract No. 1131, Poster board No. session 285-I, 2004.

Scaria et al., "Host-virus genome interactions: macro roles for microRNAs," *Cell Microbiol.*, (12):2784-94 2007.

Scaria et al., "Host-virus interaction: a new role for microRNAs," *Retrovirology*, 3:68, 2006.

Scherer and Rossi, "Approaches for the sequence-specific knockdown of mRNA," *Nat. Biotechnol.*, 21(12):1457-1465, 2003.

Scott et al., "*BCL2* antisense reduces prostate cancer cell survival following irradiation," *Cancer Biotherapy & Radiopharmaceuticals*, 17(6):647-656, 2002.

Segal et al., "A module map showing conditional activity of expression modules in cancer," *Nature Genetics*, 36(10):1090-1098, 2004.

Sellner et al., "Reverse transcriptase inhibits Taq polymerase activity," *Nucleic Acids Research*, 20(7):1487-1490, 1992.

Sevignani et al., "Mammalian microRNAs: a small world for fine-tuning gene expression," *Mamm. Genome*, 17(3):189-202, 2006.

Shen et al., "Oxidative damage in age-related macular degeneration," *Histol. Histopathol.* 22(12):1301-1308, 2007.

Si et al., "miR-21-mediated tumor growth," *Oncogene*, 26(19):2799-2803, 2007.

Smith et al., "Human papillornavirus type distribution in invasive cervical cancer and high-grade cervical lesions: a meta-analysis update," *Int. J. Cancer*, 121(3):621-32, 2007.

Smith et al., "Oxygen-induced retinopathy in the mouse," *Invest. Ophthalmol. Vis. Sci.* 35(1):101-111, 1994.

Sun at al., "Development of a micro-array to detect human and mouse microRNAs and characterization of expression in human organs," *Nucleic Acids Research*, 32(22):e188, 2004.

Sun et al., "Downregulation of CCND1 and CDK6 by miR-34a induces cell cycle arrest," *FEBS Letters*, 582:1564-1568, 2008.

Szafranska et al., "MicroRNA expression alterations are linked to tumorigenesis and nonneoplastic processes in pancreatic ductal adenocarcinoma," *Oncogene*, 26:4442-4452, 2007.

Takei et al., "A small interfering RNA targeting vascular endothelial growth factor as cancer therapeutics," *Cancer Research*, 64:3365-3370, 2004.

Voorhoeve et al., "A genetic screen implicates miRNA-372 and miRNA-373 as oncogenes in testicular germ cell tumors," *Cell*, 124(6):1169-1181, 2006.

Walboomers et al., "Human papillomavirus is a necessary cause of invasive cervical cancer worldwide," *J. Pathol.*, 189(1):12-9, 1999.

White at al., "Treatment of pulmonary hemangiomatosis with recombinant interferon alfa-2a," *N Engl J Med* 320:1197-1200, 1989.

Wiemer, "The role of microRNAs in cancer: no. small matter," *Eur. J. Cancer*, 43(10):1529-44, 2007.

Wilson and Laimins, "Differentiation of HPV-containing cells using organotypic "raft" culture or methylcellulose," *Methods Mol. Med.*, 119:157-69, 2005.

Yamato at al., "New highly potent and specific E6 and E7 siRNAs for treatment of HPV16 positive cervical cancer," *Cancer Gene Therapy*, 15:140-153, 2008.

Yang at al., "Dicer is required for embryonic angiogenesis during mouse development," *J. Biol. Chem*. 280(10):9330-9335, 2005.

Zhang et al., "microRNAs as oncogenes and tumor suppressors," *Dev. Biol.*, 302(1):1-12, 2007.

Office Action issued in Australian Application No. 2005250432, mailed Aug. 25, 2010.

Office Action issued in European Application No. 08 831 073.5, mailed Aug. 16, 2010.

Office Action issued in U.S. Appl. No. 11/837,495, mailed Sep. 2, 2010.

Office Action issued in U.S. Appl. No. 11/953,606, mailed Oct. 1, 2010.

Office Action issued in U.S. Appl. No. 12/125,675, mailed Oct. 14, 2010.

Office Action issued in U.S. Appl. No. 12/253,718, mailed Nov. 1, 2010.

Office Action issued in U.S. Appl. No. 12/340,329, mailed Sep. 28, 2010.

PCT International Preliminary Report on Patentability issued in International Application No. PCT/US2009/033556, mailed Aug. 19, 2010.

PCT International Preliminary Report on Patentability issued in International Application No. PCT/US2009/038399, mailed Oct. 7, 2010.

PCT International Preliminary Report on Patentability issued in International Application No. PCT/US2009/039935, mailed Oct. 21, 2010.

* cited by examiner

FIG. 9
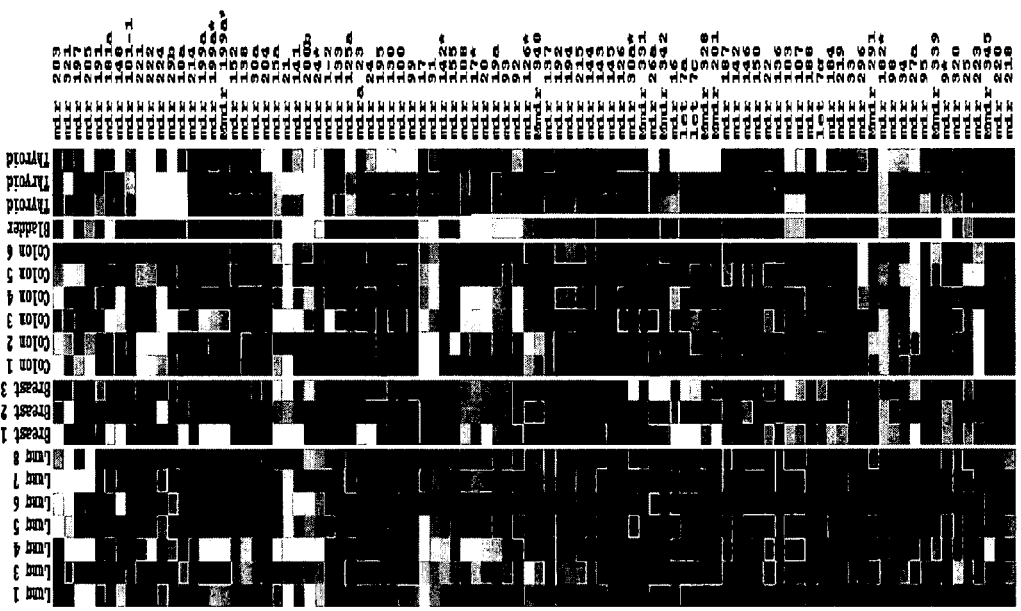

Two samples from the same donor
Correlation: 92%

SEQUENCE LISTING

```
<160> NUMBER OF SEQ ID NOS: 899

<210> SEQ ID NO 1
<211> LENGTH: 85
<212> TYPE: RNA
<213> ORGANISM: Homo sapiens

<400> SEQUENCE: 1
accuacucag aguacauacu ucuuuaugua cccauaugaa cauacaaugc uauggaaugu     60
aaagaaguau guauuuuugg uaggc                                          85

<210> SEQ ID NO 2
<211> LENGTH: 71
<212> TYPE: RNA
<213> ORGANISM: Homo sapiens

<400> SEQUENCE: 2
ugggaaacau acuucuuuau augcccauau ggaccugcua agcuauggaa uguaaagaag     60
uauguaucuc a                                                         71

<210> SEQ ID NO 3
<211> LENGTH: 80
<212> TYPE: RNA
<213> ORGANISM: Homo sapiens
```

```
<400> SEQUENCE: 3
ugggaugagg uaguagguug uauaguuuua gggucacacc caccacuggg agauaacuau    60
acaaucuacu gucuuuccua                                              80

<210> SEQ ID NO 4
<211> LENGTH: 72
<212> TYPE: RNA
<213> ORGANISM: Homo sapiens

<400> SEQUENCE: 4
agguugaggu aguagguugu auaguuuaga auuacaucaa gggagauaac uguacagccu    60
ccuagcuuuc cu                                                      72

<210> SEQ ID NO 5
<211> LENGTH: 74
<212> TYPE: RNA
<213> ORGANISM: Homo sapiens

<400> SEQUENCE: 5
gggugaggua guagguugua uaguuuggggg cucugcccug cuaugggaua acuauacaau    60
cuacugucuu uccu                                                    74

<210> SEQ ID NO 6
<211> LENGTH: 83
<212> TYPE: RNA
<213> ORGANISM: Homo sapiens

<400> SEQUENCE: 6
cggggugagg uaguagguug ugugguuuca gggcagugau guugcccccuc ggaagauaac    60 uauacaaccu acugccuucc cug                                          83

<210> SEQ ID NO 7
<211> LENGTH: 84
<212> TYPE: RNA
<213> ORGANISM: Homo sapiens

<400> SEQUENCE: 7
gcauccgggu ugagguagua gguuguaugg uuuagaguua cacccuggga guuaacugua    60
caaccuucua gcuuuccuug gagc                                         84

<210> SEQ ID NO 8
<211> LENGTH: 87
<212> TYPE: RNA
<213> ORGANISM: Homo sapiens

<400> SEQUENCE: 8
ccuaggaaga gguaguaggu ugcauaguuu uagggcaggg auuuugccca caaggaggua    60 acauauacgac cugcugccuu ucuuagg                                     87

<210> SEQ ID NO 9
<211> LENGTH: 79
<212> TYPE: RNA
<213> ORGANISM: Homo sapiens

<400> SEQUENCE: 9
cccgggcuga gguaggaggu uguauaguug aggaggacac ccaaggagau cacuauacgg    60
ccuccuagcu uuccccagg                                               79
```

```
<210> SEQ ID NO 10
<211> LENGTH: 87
<212> TYPE: RNA
<213> ORGANISM: Homo sapiens

<400> SEQUENCE: 10
ucagagugag guaguagauu guauaguugu gggguaguga uuuuacccug uucaggagau      60
aacuauacaa ucuauugccu ucccuga                                         87

<210> SEQ ID NO 11
<211> LENGTH: 83
<212> TYPE: RNA
<213> ORGANISM: Homo sapiens

<400> SEQUENCE: 11
ugugggauga gguaguagau uguauaguuu uagggucaua ccccaucuug gagauaacua      60
uacagucuac ugucuuuccc acg                                             83

<210> SEQ ID NO 12
<211> LENGTH: 110
<212> TYPE: RNA
<213> ORGANISM: Homo sapiens

<400> SEQUENCE: 12
uuggauguug gccuaguucu guguggaaga cuagugauuu uguuguuuuu agauaacuaa      60
aucgacaaca aaucacaguc ugccauaugg cacaggccau gccucuacag                110

<210> SEQ ID NO 13
<211> LENGTH: 110
<212> TYPE: RNA
<213> ORGANISM: Homo sapiens

<400> SEQUENCE: 13
cuggauacag aguggaccgg cuggccccau cuggaagacu agugauuuug uuguugucuu      60
acugcgcuca acaacaaauc ccagucuacc uaauggugcc agccaucgca                110

<210> SEQ ID NO 14
<211> LENGTH: 110
<212> TYPE: RNA
<213> ORGANISM: Homo sapiens

<400> SEQUENCE: 14
agauuagagu ggcugugguc uagugcugug uggaagacua gugauuuugu uguucugaug      60
uacuacgaca acaagucaca gccggccuca uagcgcagac ucccuucgac                110

<210> SEQ ID NO 15
<211> LENGTH: 84
<212> TYPE: RNA
<213> ORGANISM: Homo sapiens

<400> SEQUENCE: 15
aggcugaggu aguaguuugu acaguuugag ggucuaugau accaccggu acaggagaua       60 acuguacagg ccacugccuu gcca                                            84

<210> SEQ ID NO 16
<211> LENGTH: 84
<212> TYPE: RNA
<213> ORGANISM: Homo sapiens

<400> SEQUENCE: 16
```

-continued cuggcugagg uaguaguuug ugcuguuggu cggguuguga cauugcccgc uguggagaua    60
acugcgcaag cuacugccuu gcua    84

<210> SEQ ID NO 17
<211> LENGTH: 89
<212> TYPE: RNA
<213> ORGANISM: Homo sapiens

<400> SEQUENCE: 17 cggggguuggu uguuaucuuu gguuaucuag cuguaugagu ggguggagu cuucauaaag    60 cuagauaacc gaaaguaaaa auaacccca    89

<210> SEQ ID NO 18
<211> LENGTH: 87
<212> TYPE: RNA
<213> ORGANISM: Homo sapiens

<400> SEQUENCE: 18
ggaagcgagu uguuaucuuu gguuaucuag cuguaugagu guauuggucu ucauaaagcu    60
agauaaccga aaguaaaaac ccuuca    87

<210> SEQ ID NO 19
<211> LENGTH: 90
<212> TYPE: RNA
<213> ORGANISM: Homo sapiens

<400> SEQUENCE: 19
ggaggcccgu uucucucuuu gguuaucuag cuguaugagu gccacagagc cgucauaaag    60
cuagauaacc gaaaguagaa augauucuca    90

<210> SEQ ID NO 20
<211> LENGTH: 110
<212> TYPE: RNA
<213> ORGANISM: Homo sapiens

<400> SEQUENCE: 20
gaucugucug ucuucuguau auacccugua gauccgaauu uguguaagga auuuguggu    60 cacaaauucg uaucuagggg aauauguagu ugacauaaac acuccgcucu    110

<210> SEQ ID NO 21
<211> LENGTH: 110
<212> TYPE: RNA
<213> ORGANISM: Homo sapiens

<400> SEQUENCE: 21
ccagagguug uaacguuguc uauauauacc cuguagaacc gaauugugu gguauccgua    60 uagucacaga uucgauucua ggggaauaua uggucgaugc aaaaacuuca    110

<210> SEQ ID NO 22
<211> LENGTH: 83
<212> TYPE: RNA
<213> ORGANISM: Homo sapiens

<400> SEQUENCE: 22
ccuuggagua aagu agcagc acauaauggu uuguggauuu ugaaaaggug caggccauau    60
ugugcugccu caaaaauaca agg    83

<210> SEQ ID NO 23
<211> LENGTH: 98

```
<212> TYPE: RNA
<213> ORGANISM: Homo sapiens

<400> SEQUENCE: 23
uugaggccuu aaaguacugu agcagcacau caugguuuac augcuacagu caagaugcga     60
aucauuauuu gcugcucuag aaauuuaagg aaauucau                            98

<210> SEQ ID NO 24
<211> LENGTH: 89
<212> TYPE: RNA
<213> ORGANISM: Homo sapiens

<400> SEQUENCE: 24
gucagcagug ccuuagcagc acguaaauau uggcguuaag auucuaaaau uaucuccagu     60
auuaacugug cugcugaagu aagguugac                                     89

<210> SEQ ID NO 25
<211> LENGTH: 81
<212> TYPE: RNA
<213> ORGANISM: Homo sapiens

<400> SEQUENCE: 25
guuccacucu agcagcacgu aaauauuggc guagugaaau auauauuaaa caccaauauu     60
acugugcugc uuuaguguga c                                             81

<210> SEQ ID NO 26
<211> LENGTH: 84
<212> TYPE: RNA
<213> ORGANISM: Homo sapiens

<400> SEQUENCE: 26
gucagaauaa ugucaaagug cuuacagugc agguagugau augugcaucu acugcaguga     60
aggcacuugu agcauuaugg ugac                                          84

<210> SEQ ID NO 27
<211> LENGTH: 71
<212> TYPE: RNA
<213> ORGANISM: Homo sapiens

<400> SEQUENCE: 27
uguucuaagg ugcaucuagu gcagauagug aaguagauua gcaucuacug cccuaagugc     60
uccuucuggc a                                                        71

<210> SEQ ID NO 28
<211> LENGTH: 82
<212> TYPE: RNA
<213> ORGANISM: Homo sapiens

<400> SEQUENCE: 28
gcagccucuc guuaguuuug cauaguugca cuacaagaag aauguaguug ugcaaaucua     60
ugcaaaacug augguggccu gc                                            82

<210> SEQ ID NO 29
<211> LENGTH: 87
<212> TYPE: RNA
<213> ORGANISM: Homo sapiens

<400> SEQUENCE: 29
cacuguucua ugguuaguuu ugcagguuug cauccagcug ugugauauuc ugcugugcaa     60
```
auccaugcaa aacugacugu gguagug                                           87

<210> SEQ ID NO 30
<211> LENGTH: 96
<212> TYPE: RNA
<213> ORGANISM: Homo sapiens

<400> SEQUENCE: 30
acauugcuac uuacaauuag uuuugcaggu uugcauuuca gcguauauau guauaugugg       60
cugugcaaau ccaugcaaaa cugauuguga uaaugu                                96

<210> SEQ ID NO 31
<211> LENGTH: 71
<212> TYPE: RNA
<213> ORGANISM: Homo sapiens

<400> SEQUENCE: 31
guagcacuaa agugcuuaua gugcagguag uguuuaguua cuacugcau uaugagcacu       60 uaaaguacug c                                                           71

<210> SEQ ID NO 32
<211> LENGTH: 72
<212> TYPE: RNA
<213> ORGANISM: Homo sapiens

<400> SEQUENCE: 32
ugucggguag cuuaucagac ugauguugac uguugaaucu cauggcaaca ccagucgaug       60
ggcugucuga ca                                                          72

<210> SEQ ID NO 33
<211> LENGTH: 85
<212> TYPE: RNA
<213> ORGANISM: Homo sapiens

<400> SEQUENCE: 33
ggcugagccg caguaguucu ucagugggcaa gcuuuaugguc cugacccagc uaaagcugcc    60
aguugaagaa cuguugcccu cugcc                                            85

<210> SEQ ID NO 34
<211> LENGTH: 73
<212> TYPE: RNA
<213> ORGANISM: Homo sapiens

<400> SEQUENCE: 34
ggccggcugg gguuccuggg gaugggauuu gcuuccuguc acaaaucaca uugccaggga      60
uuuccaaccg acc                                                         73

<210> SEQ ID NO 35
<211> LENGTH: 97
<212> TYPE: RNA
<213> ORGANISM: Homo sapiens

<400> SEQUENCE: 35
cucaggugcu cuggcugcuu ggguuccugg caugcugauu ugugacuuaa gauuaaaauc      60
acauugccag ggauuaccac gcaaccacga ccuuggc                               97

<210> SEQ ID NO 36
<211> LENGTH: 68
<212> TYPE: RNA
<213> ORGANISM: Homo sapiens

```
<400> SEQUENCE: 36
cuccggugcc uacugagcug auaucaguuc ucauuuuaca cacuggcuca guucagcagg    60
aacaggag                                                            68

<210> SEQ ID NO 37
<211> LENGTH: 73
<212> TYPE: RNA
<213> ORGANISM: Homo sapiens

<400> SEQUENCE: 37
cucugccucc cgugccuacu gagcugaaac acaguugguu uguguacacu ggcucaguuc    60
agcaggaaca ggg                                                      73

<210> SEQ ID NO 38
<211> LENGTH: 84
<212> TYPE: RNA
<213> ORGANISM: Homo sapiens

<400> SEQUENCE: 38
ggccaguguu gagaggcgga gacuugggca auugcuggac gcugcccugg gcauugcacu    60
ugucucgguc ugacagugcc ggcc                                          84

<210> SEQ ID NO 39
<211> LENGTH: 77
<212> TYPE: RNA
<213> ORGANISM: Homo sapiens

<400> SEQUENCE: 39
guggccucgu ucaaguaauc caggauaggc ugugcagguc ccaaugggcc uauucuuggu    60
uacuugcacg gggacgc                                                  77

<210> SEQ ID NO 40
<211> LENGTH: 77
<212> TYPE: RNA
<213> ORGANISM: Homo sapiens

<400> SEQUENCE: 40
ccgggaccca guucaaguaa uucaggauag guugugugcu guccagccug uucuccauua    60
cuuggcucgg ggaccgg                                                  77

<210> SEQ ID NO 41
<211> LENGTH: 84
<212> TYPE: RNA
<213> ORGANISM: Homo sapiens

<400> SEQUENCE: 41
ggcuguggcu ggauucaagu aauccaggau aggcuguuuc caucugugag gccuauucuu    60
gauuacuugu uucuggaggc agcu                                          84

<210> SEQ ID NO 42
<211> LENGTH: 78
<212> TYPE: RNA
<213> ORGANISM: Homo sapiens

<400> SEQUENCE: 42
cugaggagca gggcuuagcu gcuugugagc aggguccaca ccaagucgug uucacagugg    60
cuaaguuccg cccccccag                                                78
```

<210> SEQ ID NO 43
<211> LENGTH: 97
<212> TYPE: RNA
<213> ORGANISM: Homo sapiens

<400> SEQUENCE: 43
accucucuaa caaggugcag agcuuagcug auuggugaac agugauuggu uuccgcuuug    60
uucacagugg cuaaguucug caccugaaga gaaggug                             97

<210> SEQ ID NO 44
<211> LENGTH: 86
<212> TYPE: RNA
<213> ORGANISM: Homo sapiens

<400> SEQUENCE: 44
gguccuugcc cucaaggagc ucacagucua uugaguuacc uuucugacuu ucccacuaga    60
uugugagcuc cuggagggca ggcacu                                         86

<210> SEQ ID NO 45
<211> LENGTH: 64
<212> TYPE: RNA
<213> ORGANISM: Homo sapiens

<400> SEQUENCE: 45
augacugauu ucuuuuggug uucagaguca auauaauuuu cuagcaccau cugaaaucgg    60
uuau                                                                 64

<210> SEQ ID NO 46
<211> LENGTH: 81
<212> TYPE: RNA
<213> ORGANISM: Homo sapiens

<400> SEQUENCE: 46
cuucaggaag cugguuucau augguggutu agauuuaaau agugauuguc uagcaccauu    60
ugaaaucagu guucuugggg g                                              81

<210> SEQ ID NO 47
<211> LENGTH: 81
<212> TYPE: RNA
<213> ORGANISM: Homo sapiens

<400> SEQUENCE: 47
cuucuggaag cugguuucac augguggcuu agauuuuucc aucuuuguau cuagcaccau    60
uugaaaucag uguuuuagga g                                              81

<210> SEQ ID NO 48
<211> LENGTH: 88
<212> TYPE: RNA
<213> ORGANISM: Homo sapiens

<400> SEQUENCE: 48
aucucuuaca caggcugacc gauuucuccu gguguucaga gucuguuuuu gucuagcacc    60
auuugaaauc gguuaugaug uaggggga                                       88

<210> SEQ ID NO 49
<211> LENGTH: 71
<212> TYPE: RNA
<213> ORGANISM: Homo sapiens

<400> SEQUENCE: 49

-continued gcgacuguaa acauccucga cuggaagcug ugaagccaca gaugggcuuu cagucggaug    60
uuugcagcug c    71

<210> SEQ ID NO 50
<211> LENGTH: 72
<212> TYPE: RNA
<213> ORGANISM: Homo sapiens

<400> SEQUENCE: 50
agauacugua aacauccuac acucucagcu guggaaagua agaaagcugg gagaaggcug    60
uuuacucuuu cu    72

<210> SEQ ID NO 51
<211> LENGTH: 70
<212> TYPE: RNA
<213> ORGANISM: Homo sapiens

<400> SEQUENCE: 51
guuguuguaa auccccga cuggaagcug uaagacacag cuaagcuuuc agucagaugu    60
uugcugcuac    70

<210> SEQ ID NO 52
<211> LENGTH: 88
<212> TYPE: RNA
<213> ORGANISM: Homo sapiens

<400> SEQUENCE: 52
accaaguuuc aguucaugua aacauccuac acucagcugu aauacaugga uuggcuggga    60 ggugauguu uacuucagcu gacuugga    88

<210> SEQ ID NO 53
<211> LENGTH: 89
<212> TYPE: RNA
<213> ORGANISM: Homo sapiens

<400> SEQUENCE: 53
accaugcugu agugugugua aacauccuac acucucagcu gugagcucaa gguggcuggg    60
agaggguugu uuacuccuuc ugccaugga    89

<210> SEQ ID NO 54
<211> LENGTH: 64
<212> TYPE: RNA
<213> ORGANISM: Homo sapiens

<400> SEQUENCE: 54
cuguaaacau ccuugacugg aagcuguaag guguucagag gagcuuucag ucggauguuu    60
acag    64

<210> SEQ ID NO 55
<211> LENGTH: 71
<212> TYPE: RNA
<213> ORGANISM: Homo sapiens

<400> SEQUENCE: 55
ggagaggagg caagaugcug gcauagcugu ugaacuggga accugcuaug ccaacauauu    60
gccaucuuuc c    71

<210> SEQ ID NO 56

```
<211> LENGTH: 70
<212> TYPE: RNA
<213> ORGANISM: Homo sapiens

<400> SEQUENCE: 56
ggagauauug cacauuacua aguugcaugu ugucacggcc ucaaugcaau uuagugugug    60
ugauauuuuc                                                          70

<210> SEQ ID NO 57
<211> LENGTH: 69
<212> TYPE: RNA
<213> ORGANISM: Homo sapiens

<400> SEQUENCE: 57
cuguggugca uguaguugc auugcauguu cuggugguac ccaugcaaug uuccacagu     60 gcaucacag                                                           69

<210> SEQ ID NO 58
<211> LENGTH: 110
<212> TYPE: RNA
<213> ORGANISM: Homo sapiens

<400> SEQUENCE: 58
ggccagcugu gaguguuucu uuggcagugu cuuagcuggu uguugugagc aauaguaagg    60
aagcaaucag caaguauacu gcccuagaag ugcugcacgu uguggggccc              110

<210> SEQ ID NO 59
<211> LENGTH: 84
<212> TYPE: RNA
<213> ORGANISM: Homo sapiens

<400> SEQUENCE: 59
gugcucgguu uguaggcagu gucauuagcu gauuguacug uggugguuac aaucacuaac    60
uccacugcca ucaaaacaag gcac                                          84

<210> SEQ ID NO 60
<211> LENGTH: 77
<212> TYPE: RNA
<213> ORGANISM: Homo sapiens

<400> SEQUENCE: 60
agucuaguua cuaggcagug uaguuagcug auugcuaaua guaccaauca cuaccacac    60 ggccagguaa aaagauu                                                  77

<210> SEQ ID NO 61
<211> LENGTH: 78
<212> TYPE: RNA
<213> ORGANISM: Homo sapiens

<400> SEQUENCE: 61
cuuucuacac agguugggau cgguugcaau gcuguguuuc uguaugguau ugcacuugc    60 ccggccuguu gaguuugg                                                 78

<210> SEQ ID NO 62
<211> LENGTH: 75
<212> TYPE: RNA
<213> ORGANISM: Homo sapiens

<400> SEQUENCE: 62
ucaucccugg gugggggauuu guugcauuac uuguguucua uauaaaguau ugcacuugc    60
```

```
ccggccugug gaaga                                              75

<210> SEQ ID NO 63
<211> LENGTH: 80
<212> TYPE: RNA
<213> ORGANISM: Homo sapiens

<400> SEQUENCE: 63 cuggggcuc caaagugcug uucgugcagg uagugugauu acccaaccua cugcugagcu    60
agcacuuccc gagccccgg                                              80

<210> SEQ ID NO 64
<211> LENGTH: 81
<212> TYPE: RNA
<213> ORGANISM: Homo sapiens

<400> SEQUENCE: 64
aacacagugg gcacucaaua aaugucuguu gaauugaaau gcguuacauu caacggguau    60
uuauugagca cccacucugu g                                           81

<210> SEQ ID NO 65
<211> LENGTH: 78
<212> TYPE: RNA
<213> ORGANISM: Homo sapiens

<400> SEQUENCE: 65
uggccgauuu uggcacuagc acauuuuugc uugugucucu ccgcucugag caaucaugug    60
cagugccaau augggaaa                                               78

<210> SEQ ID NO 66
<211> LENGTH: 80
<212> TYPE: RNA
<213> ORGANISM: Homo sapiens

<400> SEQUENCE: 66
gugagguagu aaguuguauu guugugggu agggauauua ggccccaauu agaagauaac    60
uauacaacuu acuacuuucc                                             80

<210> SEQ ID NO 67
<211> LENGTH: 81
<212> TYPE: RNA
<213> ORGANISM: Homo sapiens

<400> SEQUENCE: 67
cccauuggca uaaacccgua gauccgaucu uguggugaag uggaccgcac aagcucgcuu    60
cuaugggucu gugucagugu g                                           81

<210> SEQ ID NO 68
<211> LENGTH: 70
<212> TYPE: RNA
<213> ORGANISM: Homo sapiens

<400> SEQUENCE: 68
ggcacccacc cguagaaccg accuugcggg gccuucgccg cacacaagcu cgugucugug    60
gguccguguc                                                        70

<210> SEQ ID NO 69
<211> LENGTH: 80
<212> TYPE: RNA
```

-continued

<213> ORGANISM: Homo sapiens

<400> SEQUENCE: 69

```
ccuguugcca caaacccgua gauccgaacu ugugguauua guccgcacaa gcuuguaucu    60
auagguaugu gucuguuagg                                                80
```

<210> SEQ ID NO 70
<211> LENGTH: 75
<212> TYPE: RNA
<213> ORGANISM: Homo sapiens

<400> SEQUENCE: 70

```
ugcccuggcu caguuaucac agugcugaug cugucuauuc uaaagguaca guacugugau    60
aacugaagga uggca                                                    75
```

<210> SEQ ID NO 71
<211> LENGTH: 79
<212> TYPE: RNA
<213> ORGANISM: Homo sapiens

<400> SEQUENCE: 71

```
acuguccuuu uucgguuauc auggguaccga ugcuguauau cugaaaggua caguacugug   60
auaacugaag aaugguggu                                                79
```

<210> SEQ ID NO 72
<211> LENGTH: 78
<212> TYPE: RNA
<213> ORGANISM: Homo sapiens

<400> SEQUENCE: 72

```
uugugcuuuc agcuucuuua cagugcugcc uuguagcauu caggucaagc agcauuguac    60
agggcuauga aagaacca                                                 78
```

<210> SEQ ID NO 73
<211> LENGTH: 78
<212> TYPE: RNA
<213> ORGANISM: Homo sapiens

<400> SEQUENCE: 73

```
uacugcccuc ggcuucuuua cagugcugcc uuguugcaua uggaucaagc agcauuguac    60
agggcuauga aggcauug                                                 78
```

<210> SEQ ID NO 74
<211> LENGTH: 81
<212> TYPE: RNA
<213> ORGANISM: Homo sapiens

<400> SEQUENCE: 74

```
ugugcaucgu ggucaaaugc ucagacuccu gugguggcug cucaugcacc acggauguuu    60
gagcaugugc uacggugucu a                                             81
```

<210> SEQ ID NO 75
<211> LENGTH: 81
<212> TYPE: RNA
<213> ORGANISM: Homo sapiens

<400> SEQUENCE: 75

```
ugugcaucgu ggucaaaugc ucagacuccu gugguggcug cuuaugcacc acggauguuu    60
gagcaugugc uauggugucu a                                             81
```

<210> SEQ ID NO 76
<211> LENGTH: 81
<212> TYPE: RNA
<213> ORGANISM: Homo sapiens

<400> SEQUENCE: 76
ccuuggccau guaaaagugc uuacagugca gguagcuuuu ugagaucuac ugcaauguaa    60
gcacuucuua cauuaccaug g                                             81

<210> SEQ ID NO 77
<211> LENGTH: 82
<212> TYPE: RNA
<213> ORGANISM: Homo sapiens

<400> SEQUENCE: 77
ccugccgggg cuaaagugcu gacagugcag auaguggucc ucccgugcu accgcacugu     60 ggguacuugc ugcuccagca gg                                            82

<210> SEQ ID NO 78
<211> LENGTH: 81
<212> TYPE: RNA
<213> ORGANISM: Homo sapiens

<400> SEQUENCE: 78
cucucugcuu ucagcuucuu uacaguguug ccuuguggca uggaguucaa gcagcauugu    60
acagggcuau caaagcacag a                                             81

<210> SEQ ID NO 79
<211> LENGTH: 85
<212> TYPE: RNA
<213> ORGANISM: Homo sapiens

<400> SEQUENCE: 79
ccuuagcaga gcuguggagu gugacaaugg uguuuguguc uaaacuauca aacgccauua    60
ucacacuaaa uagcuacugc uaggc                                         85

<210> SEQ ID NO 80
<211> LENGTH: 85
<212> TYPE: RNA
<213> ORGANISM: Homo sapiens

<400> SEQUENCE: 80
aggccucucu cuccguguuc acagcggacc uugauuuaaa uguccauaca auuaaggcac    60
gcggugaaug ccaagaaugg ggcug                                         85

<210> SEQ ID NO 81
<211> LENGTH: 109
<212> TYPE: RNA
<213> ORGANISM: Homo sapiens

<400> SEQUENCE: 81
aucaagauua gaggcucugc ucuccguguu cacagcggac cuugauuuaa ugucauacaa    60
uuaaggcacg cggugaaugc caagagcgga gccuacggcu gcacuugaa               109

<210> SEQ ID NO 82
<211> LENGTH: 87
<212> TYPE: RNA
<213> ORGANISM: Homo sapiens -continued

<400> SEQUENCE: 82
ugagggcccc ucugcguguu cacagcggac cuugauuuaa ugucuauaca auuaaggcac    60
gcggugaaug ccaagagagg cgccucc                                       87

<210> SEQ ID NO 83
<211> LENGTH: 88
<212> TYPE: RNA
<213> ORGANISM: Homo sapiens

<400> SEQUENCE: 83
ugcgcuccuc ucagucccug agacccuaac uugugauguu uaccguuuaa auccacgggu    60
uaggcucuug ggagcugcga gucgugcu                                      88

<210> SEQ ID NO 84
<211> LENGTH: 86
<212> TYPE: RNA
<213> ORGANISM: Homo sapiens

<400> SEQUENCE: 84
ugccagucuc uaggucccug agacccuuua accugugagg acauccaggg ucacagguga    60
gguucuuggg agccuggcgu cuggcc                                        86

<210> SEQ ID NO 85
<211> LENGTH: 89
<212> TYPE: RNA
<213> ORGANISM: Homo sapiens

<400> SEQUENCE: 85
accagacuuu uccuagcccc ugagacccua acuugugagg uauuuuagua acaucacaag    60
ucaggcucuu gggaccuagg cggagggga                                     89

<210> SEQ ID NO 86
<211> LENGTH: 85
<212> TYPE: RNA
<213> ORGANISM: Homo sapiens

<400> SEQUENCE: 86
cgcuggcgac gggacauuau uacuuuuggu acgcgcugug acacuucaaa cucguaccgu    60
gaguaauaau gcgccgucca cggca                                         85

<210> SEQ ID NO 87
<211> LENGTH: 97
<212> TYPE: RNA
<213> ORGANISM: Homo sapiens

<400> SEQUENCE: 87
ugugaucacu gucuccagcc ugcugaagcu cagagggcuc ugauucagaa agaucaucgg    60
auccgucuga gcuuggcugg ucggaagucu caucauc                            97

<210> SEQ ID NO 88
<211> LENGTH: 82
<212> TYPE: RNA
<213> ORGANISM: Homo sapiens

<400> SEQUENCE: 88
ugagcuguug gauucggggc cguagcacug ucgagaggu uuacauuucu cacagugaac     60
cggucucuuu uucagcugcu uc                                            82

```
<210> SEQ ID NO 89
<211> LENGTH: 84
<212> TYPE: RNA
<213> ORGANISM: Homo sapiens

<400> SEQUENCE: 89
ugugcagugg aagggggggc cgauacacug uacgagagug aguagcaggu cucacaguga    60
accggucucu uucccuacug uguc                                          84

<210> SEQ ID NO 90
<211> LENGTH: 90
<212> TYPE: RNA
<213> ORGANISM: Homo sapiens

<400> SEQUENCE: 90
ugcccuucgc gaaucuuuuu gcggucuggg cuugcuguac auaacucaau agccggaagc    60 ccuuaccccca aaaagcauuu gcggagggcg                                   90

<210> SEQ ID NO 91
<211> LENGTH: 89
<212> TYPE: RNA
<213> ORGANISM: Homo sapiens

<400> SEQUENCE: 91
ugcugcuggc cagagcucuu uucacauugu gcuacugucu gcaccuguca cuagcagugc    60
aauguuaaaa gggcauuggc cguguagug                                     89

<210> SEQ ID NO 92
<211> LENGTH: 82
<212> TYPE: RNA
<213> ORGANISM: Homo sapiens

<400> SEQUENCE: 92
ggccugcccg acacucuuuc ccuguugcac uacuauaggc cgcugggaag cagugcaaug    60
augaaagggc aucggucagg uc                                            82

<210> SEQ ID NO 93
<211> LENGTH: 101
<212> TYPE: RNA
<213> ORGANISM: Homo sapiens

<400> SEQUENCE: 93 ccgccccgc gucuccaggg caaccguggc uuucgauugu uacguggga acuggaggua     60 acagcuaca gccauggucg ccccgcagca cgcccacgcg c                       101

<210> SEQ ID NO 94
<211> LENGTH: 88
<212> TYPE: RNA
<213> ORGANISM: Homo sapiens

<400> SEQUENCE: 94
acaaugcuuu gcuagagcug guaaaaugga accaaaucgc cucuucaaug gauuuggucc    60
ccuucaacca gcuguagcua ugcauuga                                      88

<210> SEQ ID NO 95
<211> LENGTH: 102
<212> TYPE: RNA
<213> ORGANISM: Homo sapiens

<400> SEQUENCE: 95
```

```
gggagccaaa ugcuuugcua gagcugguaa aauggaacca aaucgacugu ccaauggauu        60 uggucccuu caaccagcug uagcugugca uugauggcgc cg                           102

<210> SEQ ID NO 96
<211> LENGTH: 119
<212> TYPE: RNA
<213> ORGANISM: Homo sapiens

<400> SEQUENCE: 96
ccucagaaga aagaugcccc cugcucuggc uggucaaacg gaaccaaguc cgucuuccug        60
agagguuugg uccccuucaa ccagcuacag cagggcuggc aaugcccagu ccuuggaga       119

<210> SEQ ID NO 97
<211> LENGTH: 73
<212> TYPE: RNA
<213> ORGANISM: Homo sapiens

<400> SEQUENCE: 97
cagggugugu gacugguuga ccagaggggc augcacgug uucacccugu gggccaccua         60
gucaccaacc cuc                                                          73

<210> SEQ ID NO 98
<211> LENGTH: 90
<212> TYPE: RNA
<213> ORGANISM: Homo sapiens

<400> SEQUENCE: 98
aggccucgcu guucucuaug gcuuuuuauu ccuaugugau ucuacugcuc acucauauag        60
ggauuggagc cguggcgcac ggcggggaca                                        90

<210> SEQ ID NO 99
<211> LENGTH: 100
<212> TYPE: RNA
<213> ORGANISM: Homo sapiens

<400> SEQUENCE: 99
agauaaauuc acucuagugc uuuauggcuu uuuauuccua ugugauagua auaaagucuc        60
auguagggau ggaagccaug aaauacauug ugaaaaauca                            100

<210> SEQ ID NO 100
<211> LENGTH: 97
<212> TYPE: RNA
<213> ORGANISM: Homo sapiens

<400> SEQUENCE: 100
cacucugcug uggccuaugg cuuuucauuc cuaugugauu gcugucccaa acucauguag        60
ggcuaaaagc caugggcuac agugaggggc gagcucc                                97

<210> SEQ ID NO 101
<211> LENGTH: 82
<212> TYPE: RNA
<213> ORGANISM: Homo sapiens

<400> SEQUENCE: 101
ugagcccucg gaggacucca uuuguuuuga ugauggauuc uuaugcucca ucaucgucuc        60
aaaugagucu ucagagggu cu                                                 82

<210> SEQ ID NO 102
<211> LENGTH: 102
```

```
<212> TYPE: RNA
<213> ORGANISM: Homo sapiens

<400> SEQUENCE: 102
gguccucuga cucucuucgg ugacggguau ucuugggugg auaauacgga uuacguuguu    60
auugcuuaag aauacgcgua gucgaggaga guaccagcgg ca                        102

<210> SEQ ID NO 103
<211> LENGTH: 84
<212> TYPE: RNA
<213> ORGANISM: Homo sapiens

<400> SEQUENCE: 103
cguugcugca gcuggguguug ugaaucaggc cgacgagcag cgcauccucu uacccggcua    60
uuucacgaca ccaggguugc auca                                            84

<210> SEQ ID NO 104
<211> LENGTH: 99
<212> TYPE: RNA
<213> ORGANISM: Homo sapiens

<400> SEQUENCE: 104
cccuggcaug guguggugg gcagcuggug uugugaauca ggccguugcc aaucagagaa     60
cggcuacuuc acaacaccag ggccacacca cacuacagg                            99

<210> SEQ ID NO 105
<211> LENGTH: 68
<212> TYPE: RNA
<213> ORGANISM: Homo sapiens

<400> SEQUENCE: 105
guguauucua cagugcacgu gucuccagug uggcucggag gcuggagacg cggcccuguu    60
ggaguaac                                                              68

<210> SEQ ID NO 106
<211> LENGTH: 100
<212> TYPE: RNA
<213> ORGANISM: Homo sapiens

<400> SEQUENCE: 106 ugugcucuc ucugugucccu gccagugguu uuacccuaug guagguuacg ucaugcuguu    60
cuaccacagg guagaaccac ggacaggaua ccggggcacc                           100

<210> SEQ ID NO 107
<211> LENGTH: 95
<212> TYPE: RNA
<213> ORGANISM: Homo sapiens

<400> SEQUENCE: 107
cggccggccc uggguccauc uuccaguaca guguuggaug gucuaauugu gaagcuccua    60
acacugucug guaaagaugg cucccggguug gguuc                               95

<210> SEQ ID NO 108
<211> LENGTH: 87
<212> TYPE: RNA
<213> ORGANISM: Homo sapiens

<400> SEQUENCE: 108
gacagugcag ucacccauaa aguagaaagc acuacuaaca gcacuggagg guguaguguu    60
```
uccuacuuua uggaugagug uacugug    87

<210> SEQ ID NO 109
<211> LENGTH: 106
<212> TYPE: RNA
<213> ORGANISM: Homo sapiens

<400> SEQUENCE: 109
gcgcagcgcc cugucuccca gccugaggug cagugcugca ucucggucca guugggaguc    60
ugagaugaag cacuguagcu caggaagaga gaaguuguuc ugcagc    106

<210> SEQ ID NO 110
<211> LENGTH: 86
<212> TYPE: RNA
<213> ORGANISM: Homo sapiens

<400> SEQUENCE: 110
uggggcccug gcugggauau caucauauac uguaaguuug cgaugagaca cuacaguaua    60
gaugauguac uaguccgggc accccc    86

<210> SEQ ID NO 111
<211> LENGTH: 88
<212> TYPE: RNA
<213> ORGANISM: Homo sapiens

<400> SEQUENCE: 111
caccuugucc ucacggucca guuucccag gaaucccuua gaugcuaaga uggggauucc    60
uggaaauacu guucuugagg ucaugguu    88

<210> SEQ ID NO 112
<211> LENGTH: 99
<212> TYPE: RNA
<213> ORGANISM: Homo sapiens

<400> SEQUENCE: 112
ccgaugugua uccucagcuu ugagaacuga auuccauggg uugugucagu gucagaccuc    60
ugaaauucag uucuucagcu gggauaucuc ugucaucgu    99

<210> SEQ ID NO 113
<211> LENGTH: 72
<212> TYPE: RNA
<213> ORGANISM: Homo sapiens

<400> SEQUENCE: 113
aaucuaaaga caacauuucu gcacacacac cagacuaugg aagccagugu guggaaaugc    60
uucugcuaga uu    72

<210> SEQ ID NO 114
<211> LENGTH: 68
<212> TYPE: RNA
<213> ORGANISM: Homo sapiens

<400> SEQUENCE: 114
gaggcaaagu ucugagacac uccgacucug aguaugauag aagucagugc acuacagaac    60
uuugucuc    68

<210> SEQ ID NO 115
<211> LENGTH: 99
<212> TYPE: RNA
<213> ORGANISM: Homo sapiens -continued

```
<400> SEQUENCE: 115
caagcacgau uagcauuuga ggugaaguuc uguuauacac ucaggcugug gcucucugaa      60
agucagugca ucacagaacu uugucucgaa agcuuucua                             99

<210> SEQ ID NO 116
<211> LENGTH: 89
<212> TYPE: RNA
<213> ORGANISM: Homo sapiens

<400> SEQUENCE: 116
gccggcgccc gagcucuggc uccgugucuu cacucccgug cuuguccgag gagggaggga      60
gggacggggg cugugcuggg gcagcugga                                        89

<210> SEQ ID NO 117
<211> LENGTH: 84
<212> TYPE: RNA
<213> ORGANISM: Homo sapiens

<400> SEQUENCE: 117
cuccccaugg cccugucucc caacccuugu accagugcug ggcucagacc cugguacagg      60 ccuggggac agggaccugg ggac                                              84

<210> SEQ ID NO 118
<211> LENGTH: 90
<212> TYPE: RNA
<213> ORGANISM: Homo sapiens

<400> SEQUENCE: 118
uuuccugccc ucgaggagcu cacagucuag uaugucucau ccccuacuag acugaagcuc      60
cuugaggaca gggaugguca uacucaccuc                                       90

<210> SEQ ID NO 119
<211> LENGTH: 87
<212> TYPE: RNA
<213> ORGANISM: Homo sapiens

<400> SEQUENCE: 119 ugucccccc ggcccagguu cugugauaca cuccgacucg ggcucuggag cagucagugc       60
augacagaac uugggcccgg aaggacc                                          87

<210> SEQ ID NO 120
<211> LENGTH: 90
<212> TYPE: RNA
<213> ORGANISM: Homo sapiens

<400> SEQUENCE: 120
cucacagcug ccagugucau uuuugugauc ugcagcuagu auucucacuc caguugcaua      60
gucacaaaag ugaucauugg cagguguggc                                       90

<210> SEQ ID NO 121
<211> LENGTH: 87
<212> TYPE: RNA
<213> ORGANISM: Homo sapiens

<400> SEQUENCE: 121
agcgguggcc agugucauuu uugugauguu gcagcuagua auaugagccc aguugcauag      60
ucacaaaagu gaucauugga aacugug                                          87
```

<210> SEQ ID NO 122
<211> LENGTH: 84
<212> TYPE: RNA
<213> ORGANISM: Homo sapiens

<400> SEQUENCE: 122
gugguacuug aagauagguu auccguguug ccuucgcuuu auuugugacg aaucauacac    60
gguugaccua uuuuucagua ccaa                                          84

<210> SEQ ID NO 123
<211> LENGTH: 65
<212> TYPE: RNA
<213> ORGANISM: Homo sapiens

<400> SEQUENCE: 123
cuguuaaugc uaaucgugau aggguuuuu gccuccaacu gacuccuaca uauuagcauu    60
aacag                                                               65

<210> SEQ ID NO 124
<211> LENGTH: 110
<212> TYPE: RNA
<213> ORGANISM: Homo sapiens

<400> SEQUENCE: 124 agaaggcua ucaggccagc cuucagagga cuccaaggaa cauucaacgc ugucggugag    60
uuugggauuu gaaaaaacca cugaccguug acuguaccuu ggggguccuua            110

<210> SEQ ID NO 125
<211> LENGTH: 110
<212> TYPE: RNA
<213> ORGANISM: Homo sapiens

<400> SEQUENCE: 125
ccugugcaga gauuauuuuu uaaaagguca caaucaacau ucauugcugu cgguggguug    60
aacugugugg acaagcucac ugaacaauga augcaacugu ggccccgcuu              110

<210> SEQ ID NO 126
<211> LENGTH: 110
<212> TYPE: RNA
<213> ORGANISM: Homo sapiens

<400> SEQUENCE: 126
cggaaaauuu gccaagggu uggggggaaca uucaaccugu cggugaguuu gggcagcuca    60
ggcaaaccau cgaccguuga guggacccug aggccuggaa uugccauccu              110

<210> SEQ ID NO 127
<211> LENGTH: 89
<212> TYPE: RNA
<213> ORGANISM: Homo sapiens

<400> SEQUENCE: 127
cugauggcug cacucaacau ucauugcugu cgguggguuu gagucugaau caacucacug    60
aucaaugaau gcaaacugcg gaccaaaca                                     89

<210> SEQ ID NO 128
<211> LENGTH: 110
<212> TYPE: RNA
<213> ORGANISM: Homo sapiens

<400> SEQUENCE: 128

```
gagcugcuug ccuccccccg uuuuuggcaa ugguagaacu cacacugguga agguaacagg      60 auccggugguu ucuagacuug ccaacuaugg ggcgaggacu cagccggcac                 110

<210> SEQ ID NO 129
<211> LENGTH: 110
<212> TYPE: RNA
<213> ORGANISM: Homo sapiens

<400> SEQUENCE: 129
ccgcagagug ugacuccugu ucuguguaug gcacugguag aauucacugu gaacagucuc      60
agucagugaa uuaccgaagg gccauaaaca gagcagagac agauccacga                 110

<210> SEQ ID NO 130
<211> LENGTH: 84
<212> TYPE: RNA
<213> ORGANISM: Homo sapiens

<400> SEQUENCE: 130
ccagucacgu ccccuuauca cuuuuccagc ccagcuuugu gacuguaagu guuggacgga      60
gaacugauaa ggguagguga uuga                                              84

<210> SEQ ID NO 131
<211> LENGTH: 82
<212> TYPE: RNA
<213> ORGANISM: Homo sapiens

<400> SEQUENCE: 131
agggggcgag ggauuggaga gaaaggcagu uccgauggu ccccuccccca ggggcuggcu      60 uuccucuggu ccuucccucc ca                                                82

<210> SEQ ID NO 132
<211> LENGTH: 86
<212> TYPE: RNA
<213> ORGANISM: Homo sapiens

<400> SEQUENCE: 132
ugcuuguaac uuuccaaaga auucuccuuu ugggcuuucu gguuuauuuu uaagcccaaa      60
ggugaauuuu uugggaaguu ugagcu                                            86

<210> SEQ ID NO 133
<211> LENGTH: 109
<212> TYPE: RNA
<213> ORGANISM: Homo sapiens

<400> SEQUENCE: 133
ggucgggcuc accaugacac agugugagac cucgggcuac aacacaggac ccgggcgcug      60
cucugacccc ucgugucuug guugcagcc ggagggacgc agguccgca                   109

<210> SEQ ID NO 134
<211> LENGTH: 86
<212> TYPE: RNA
<213> ORGANISM: Homo sapiens

<400> SEQUENCE: 134
ugcucccucu cucacauccc uugcauggug gagggugagc uuucugaaaa ccccucccac      60 augcagggu ugcaggaugg cgagcc                                             86

<210> SEQ ID NO 135
```

```
<211> LENGTH: 85
<212> TYPE: RNA
<213> ORGANISM: Homo sapiens

<400> SEQUENCE: 135
ugcaggccuc ugugugauau guuugauaua uuagguuguu auuuaauccua acuauauauc      60 aaacauauuc cuacaguguc uugcc                                             85

<210> SEQ ID NO 136
<211> LENGTH: 92
<212> TYPE: RNA
<213> ORGANISM: Homo sapiens

<400> SEQUENCE: 136
cggcuggaca gcgggcaacg gaaucccaaa agcagcuguu gucccagag cauuccagcu        60 gcgcuuggau uucguccccu gcucuccugc cu                                     92

<210> SEQ ID NO 137
<211> LENGTH: 110
<212> TYPE: RNA
<213> ORGANISM: Homo sapiens

<400> SEQUENCE: 137
gccgagaccg agugcacagg gcucugaccu augaauugac agccagugcu cucgucuccc       60
cucuggcugc caauuccaua ggucacaggu auguucgccu caaugccagc                  110

<210> SEQ ID NO 138
<211> LENGTH: 88
<212> TYPE: RNA
<213> ORGANISM: Homo sapiens

<400> SEQUENCE: 138
cgaggauggg agcugagggc ugggucuuug cgggcgagau gagggugucg gaucaacugg       60
ccuacaaagu cccaguucuc ggcccccg                                          88

<210> SEQ ID NO 139
<211> LENGTH: 85
<212> TYPE: RNA
<213> ORGANISM: Homo sapiens

<400> SEQUENCE: 139
augguguuau caaguguaac agcaacucca uguggacugu guaccaauuu ccaguggaga       60
ugcuguuacu uuugaugguu accaa                                             85

<210> SEQ ID NO 140
<211> LENGTH: 85
<212> TYPE: RNA
<213> ORGANISM: Homo sapiens

<400> SEQUENCE: 140
ugguucccgc ccccuguaac agcaacucca uguggaagug cccacugguu ccaguggggc      60
ugcuguuauc uggggcgagg gccag                                             85

<210> SEQ ID NO 141
<211> LENGTH: 87
<212> TYPE: RNA
<213> ORGANISM: Homo sapiens

<400> SEQUENCE: 141
agcuucccug gcucuagcag cacagaaaua uuggcacagg gaagcgaguc ugccaauauu       60
```

```
ggcugugcug cuccaggcag gguggug                                           87

<210> SEQ ID NO 142
<211> LENGTH: 70
<212> TYPE: RNA
<213> ORGANISM: Homo sapiens

<400> SEQUENCE: 142
gugaauuagg uaguuucaug uuguugggcc uggguuucug aacacaacaa cauuaaacca      60
cccgauucac                                                             70

<210> SEQ ID NO 143
<211> LENGTH: 110
<212> TYPE: RNA
<213> ORGANISM: Homo sapiens

<400> SEQUENCE: 143
ugcucgcuca gcugaucugu ggcuuaggua guuucauguu guugggauug aguuuugaac      60
ucggcaacaa gaaacugccu gaguuacauc agucgguuuu cgucgagggc                110

<210> SEQ ID NO 144
<211> LENGTH: 75
<212> TYPE: RNA
<213> ORGANISM: Homo sapiens

<400> SEQUENCE: 144
ggcugugccg gguagagagg gcagugggag guaagagcuc ucacccuuc accaccuucu       60 ccacccagca uggcc                                                       75

<210> SEQ ID NO 145
<211> LENGTH: 62
<212> TYPE: RNA
<213> ORGANISM: Homo sapiens

<400> SEQUENCE: 145
ucauuggucc agaggggaga uagguuccug ugauuuuucc uucuucucua agaauaaau       60 ga                                                                     62

<210> SEQ ID NO 146
<211> LENGTH: 71
<212> TYPE: RNA
<213> ORGANISM: Homo sapiens

<400> SEQUENCE: 146
gccaacccag uguucagacu accuguucag gaggcucuca auguguacag uagucugcac      60
auugguuagg c                                                           71

<210> SEQ ID NO 147
<211> LENGTH: 110
<212> TYPE: RNA
<213> ORGANISM: Homo sapiens

<400> SEQUENCE: 147
aggaagcuuc uggagauccu gcuccgucgc cccagguguuc agacuaccug uucaggacaa     60
ugccguugua caguagucug cacauugguu agacugggca agggagagca                110

<210> SEQ ID NO 148
<211> LENGTH: 110
<212> TYPE: RNA
```

<213> ORGANISM: Homo sapiens

<400> SEQUENCE: 148

| ccagaggaca ccuccacucc gucuacccag uguuuagacu aucuguucag gacucccaaa | 60 |
| uuguacagua gucugcacau ugguuaggcu gggcugggu agacccucgg | 110 |

<210> SEQ ID NO 149
<211> LENGTH: 95
<212> TYPE: RNA
<213> ORGANISM: Homo sapiens

<400> SEQUENCE: 149

| ccagcucggg cagccguggc caucuuacug ggcagcauug gauggaguca ggucucuaau | 60 |
| acugccuggu aaugaugacg gcggagcccu gcacg | 95 |

<210> SEQ ID NO 150
<211> LENGTH: 68
<212> TYPE: RNA
<213> ORGANISM: Homo sapiens

<400> SEQUENCE: 150

| cccucgucuu acccagcagu guuugggugc gguugggagu cucuaauacu gccggguaau | 60 |
| gauggagg | 68 |

<210> SEQ ID NO 151
<211> LENGTH: 90
<212> TYPE: RNA
<213> ORGANISM: Homo sapiens

<400> SEQUENCE: 151

| ccgggcccu gugagcaucu uaccggacag ugcuggauuu cccagcuuga cucuaacacu | 60 |
| gucugguaac gauguucaaa ggugacccgc | 90 |

<210> SEQ ID NO 152
<211> LENGTH: 110
<212> TYPE: RNA
<213> ORGANISM: Homo sapiens

<400> SEQUENCE: 152

| guguugggga cucgcgcgcu ggguccagug guucuuaaca guucaacagu ucguagcgc | 60 |
| aauugugaaa uguuuaggac cacuagaccc ggcgggcgcg gcgacagcga | 110 |

<210> SEQ ID NO 153
<211> LENGTH: 110
<212> TYPE: RNA
<213> ORGANISM: Homo sapiens

<400> SEQUENCE: 153

| ggcuacaguc uuucuucaug ugacucgugg acuucccuuu gcauccuau gccugagaau | 60 |
| auaugaagga ggcugggaag gcaaagggac guucaauugu caucacuggc | 110 |

<210> SEQ ID NO 154
<211> LENGTH: 110
<212> TYPE: RNA
<213> ORGANISM: Homo sapiens

<400> SEQUENCE: 154

| aaagauccuc agacaaucca ugugcuucuc uugccuuuca uuccaccgga gucugucuca | 60 |
| uacccaacca gauuucagug gagugaaguu caggaggcau ggagcugaca | 110 |

<210> SEQ ID NO 155
<211> LENGTH: 86
<212> TYPE: RNA
<213> ORGANISM: Homo sapiens

<400> SEQUENCE: 155
ugcuucccga ggccacaugc uucuuuauau ccccauaugg auuacuuugc uauggaaugu    60
aaggaagugu gugguuucgg caagug                                        86

<210> SEQ ID NO 156
<211> LENGTH: 71
<212> TYPE: RNA
<213> ORGANISM: Homo sapiens

<400> SEQUENCE: 156
ugacgggcga gcuuuggcc cggguuauac cugaugcuca cguauaagac gagcaaaaag    60
cuuguugguc a                                                        71

<210> SEQ ID NO 157
<211> LENGTH: 110
<212> TYPE: RNA
<213> ORGANISM: Homo sapiens

<400> SEQUENCE: 157
acccggcagu gccuccaggc gcagggcagc cccugcccac cgcacacugc gcugcccag    60 acccacugug cgugugacag cggcugaucu gugccugggc agcgcgaccc              110

<210> SEQ ID NO 158
<211> LENGTH: 110
<212> TYPE: RNA
<213> ORGANISM: Homo sapiens

<400> SEQUENCE: 158
ucaccuggcc augugacuug ugggcuuccc uuugucaucc uucgccuagg gcucugagca    60
gggcagggac agcaaagggg ugcucaguug ucacuuccca cagcacggag              110

<210> SEQ ID NO 159
<211> LENGTH: 110
<212> TYPE: RNA
<213> ORGANISM: Homo sapiens

<400> SEQUENCE: 159
cggggcaccc cgcccggaca gcgcgccggc accuuggcuc uagacugcuu acugcccggg    60
ccgcccucag uaacagucuc cagucacggc caccgacgcc uggccccgcc              110

<210> SEQ ID NO 160
<211> LENGTH: 110
<212> TYPE: RNA
<213> ORGANISM: Homo sapiens

<400> SEQUENCE: 160
ugaguuuuga gguugcuuca gugaacauuc aacgcgucg gugaguuugg aauuaaaauc    60
aaaaccaucg accguugauu guacccuaug gcuaaccauc aucuacucca              110

<210> SEQ ID NO 161
<211> LENGTH: 110
<212> TYPE: RNA
<213> ORGANISM: Homo sapiens

<400> SEQUENCE: 161
ggccuggcug acagaguug ucaugugucu gccugucuac acuugcugug cagaacaucc    60
gcucaccugu acagcaggca cagacaggca gucacaugac aacccagccu              110

<210> SEQ ID NO 162
<211> LENGTH: 110
<212> TYPE: RNA
<213> ORGANISM: Homo sapiens

<400> SEQUENCE: 162
aucauucaga aaugguauac aggaaaauga ccuaugaauu gacagacaau auagcugagu    60
uugucuguca uuucuuuagg ccaauauucu guaugacugu gcuacuucaa              110

<210> SEQ ID NO 163
<211> LENGTH: 110
<212> TYPE: RNA
<213> ORGANISM: Homo sapiens

<400> SEQUENCE: 163
gauggcugug aguuggcuua aucucagcug gcaacuguga gauguucaua caaucccuca    60 cagggucuc ugggauuaug cuaaacagag caauuuccua gcccucacga               110

<210> SEQ ID NO 164
<211> LENGTH: 110
<212> TYPE: RNA
<213> ORGANISM: Homo sapiens

<400> SEQUENCE: 164
aguauaauua uuacauaguu uuugaugucg cagauacugc aucaggaacu gauuggauaa    60
gaaucaguca ccaucaguuc cuaaugcauu gccuucagca ucuaaacaag               110

<210> SEQ ID NO 165
<211> LENGTH: 110
<212> TYPE: RNA
<213> ORGANISM: Homo sapiens

<400> SEQUENCE: 165
gugauaaugu agcgagauuu ucuguugugc uugaucuaac caugugguug cgagguauga    60
guaaaacaug guuccgucaa gcaccaugga acgucacgca gcuuucuaca               110

<210> SEQ ID NO 166
<211> LENGTH: 110
<212> TYPE: RNA
<213> ORGANISM: Homo sapiens

<400> SEQUENCE: 166
gaccagucgc ugcggggcuu uccuuugugc uugaucuaac caugguggug aacgauggaa    60
acggaacaug guucugucaa gcaccgcgga aagcaccgug cucuccugca               110

<210> SEQ ID NO 167
<211> LENGTH: 110
<212> TYPE: RNA
<213> ORGANISM: Homo sapiens

<400> SEQUENCE: 167
ccgcccgggg ccgcggcucc ugauugucca aacgcaauuc ucgagucuau ggcuccggcc    60
gagaguugag ucuggacguc ccgagccgcc gcccccaaac cucgagcggg              110

```
<210> SEQ ID NO 168
<211> LENGTH: 97
<212> TYPE: RNA
<213> ORGANISM: Homo sapiens

<400> SEQUENCE: 168
acucaggggc uucgccacug auuguccaaa cgcaauucuu guacgagucu gcggccaacc      60
gagaauugug gcuggacauc uguggcugag cuccggg                              97

<210> SEQ ID NO 169
<211> LENGTH: 110
<212> TYPE: RNA
<213> ORGANISM: Homo sapiens

<400> SEQUENCE: 169
gacagugugg cauuguaggg cuccacaccg uaucugacac uuugggcgag ggcaccaugc      60
ugaagguguu caugaugcgg ucugggaacu ccucacggau cuuacugaug              110

<210> SEQ ID NO 170
<211> LENGTH: 110
<212> TYPE: RNA
<213> ORGANISM: Homo sapiens

<400> SEQUENCE: 170
ugaacaucca ggucgggggc augaaccugg cauacaaugu agauuucugu guucguuagg      60
caacagcuac auugucugcu ggguuucagg cuaccuggaa acauguucuc              110

<210> SEQ ID NO 171
<211> LENGTH: 110
<212> TYPE: RNA
<213> ORGANISM: Homo sapiens

<400> SEQUENCE: 171
gcugcuggaa gguguaggua cccucaaugg cucaguagcc aguguagauc cugucuuucg      60
uaaucagcag cuacaucugg cuacuggguc ucgauggca ucuucuagcu              110

<210> SEQ ID NO 172
<211> LENGTH: 110
<212> TYPE: RNA
<213> ORGANISM: Homo sapiens

<400> SEQUENCE: 172
ccuggccucc ugcagugcca cgcuccgugu auuugacaag cugaguugga cacuccaugu      60
gguagagugu caguuuguca aauacccccaa gugcggcaca ugcuuaccag              110

<210> SEQ ID NO 173
<211> LENGTH: 81
<212> TYPE: RNA
<213> ORGANISM: Homo sapiens

<400> SEQUENCE: 173
gggcuuucaa gucacuagug guuccguuua guagaugauu ugcauuguu ucaaaauggu      60 gcccuaguga cuacaaagcc c                                              81

<210> SEQ ID NO 174
<211> LENGTH: 80
<212> TYPE: RNA
<213> ORGANISM: Homo sapiens

<400> SEQUENCE: 174
```

```
aggacccuuc cagagggccc ccccucaauc cuguugugcc uaauucagag gguuggguggg    60 aggcucuccu gaagggcucu                                                 80

<210> SEQ ID NO 175
<211> LENGTH: 63
<212> TYPE: RNA
<213> ORGANISM: Homo sapiens

<400> SEQUENCE: 175
aagaaauggu uuaccgucccc acauacauuu ugaauaugua ugugggaugg uaaaccgcuu    60
cuu                                                                   63

<210> SEQ ID NO 176
<211> LENGTH: 86
<212> TYPE: RNA
<213> ORGANISM: Homo sapiens

<400> SEQUENCE: 176
acugcuaacg aaugcucuga cuuuauugca cuacuguacu uuacagcuag cagugcaaua    60
guauugucaa agcaucugaa agcagg                                          86

<210> SEQ ID NO 177
<211> LENGTH: 69
<212> TYPE: RNA
<213> ORGANISM: Homo sapiens

<400> SEQUENCE: 177
ccaccacuua aacguggaug uacuugcuuu gaaacuaaag aaguaagugc uuccauguuu    60
uggugaugg                                                             69

<210> SEQ ID NO 178
<211> LENGTH: 82
<212> TYPE: RNA
<213> ORGANISM: Homo sapiens

<400> SEQUENCE: 178
gcuucgcucc ccuccgccuu cucuucccgg uucuucccgg agucgggaaa agcugggu ug    60 agagggcgaa aaaggaugag gu                                              82

<210> SEQ ID NO 179
<211> LENGTH: 59
<212> TYPE: RNA
<213> ORGANISM: Homo sapiens

<400> SEQUENCE: 179
uuggccuccu aagccaggga uugugggguc gagucccacc cgggguaaag aaaggccga     59

<210> SEQ ID NO 180
<211> LENGTH: 86
<212> TYPE: RNA
<213> ORGANISM: Homo sapiens

<400> SEQUENCE: 180
uugguacuug gagagaggug guccguggcg cguucgcuuu auuuauggcg cacauuacac    60
ggucgaccuc uuugcaguau cuaauc                                          86

<210> SEQ ID NO 181
<211> LENGTH: 83
<212> TYPE: RNA
<213> ORGANISM: Homo sapiens
```

<400> SEQUENCE: 181
cugacuaugc cuccccgcau ccccuagggc auugguguaa agcuggagac ccacugcccc      60
aggugcugcu ggggguugua guc      83

<210> SEQ ID NO 182
<211> LENGTH: 95
<212> TYPE: RNA
<213> ORGANISM: Homo sapiens

<400> SEQUENCE: 182
cucaucuguc uguugggcug gaggcagggc cuuugugaag gcgggguggug cucagaucgc      60 cucugggccc uuccuccagc cccgaggcgg auuca      95

<210> SEQ ID NO 183
<211> LENGTH: 75
<212> TYPE: RNA
<213> ORGANISM: Homo sapiens

<400> SEQUENCE: 183
uggagugggg gggcaggagg ggcucaggga gaaagugcau acagcccug gcccucucug      60 cccuuccguc cccug      75

<210> SEQ ID NO 184
<211> LENGTH: 94
<212> TYPE: RNA
<213> ORGANISM: Homo sapiens

<400> SEQUENCE: 184
cuuuggcgau cacugccucu cugggccugu gucuuaggcu cugcaagauc aaccgagcaa      60
agcacacggc cugcagagag gcagcgcucu gccc      94

<210> SEQ ID NO 185
<211> LENGTH: 94
<212> TYPE: RNA
<213> ORGANISM: Homo sapiens

<400> SEQUENCE: 185
gaguuugguu uuguuugggu uuguucuagg uauggucccag gggaucccag aucaaaccag      60
gccccugggc cuauccuaga accaaccuaa gcuc      94

<210> SEQ ID NO 186
<211> LENGTH: 94
<212> TYPE: RNA
<213> ORGANISM: Homo sapiens

<400> SEQUENCE: 186
uguuuugagc gggggucaag agcaauaacg aaaaauguuu gucauaaacc guuuucauu      60 auugcuccug accuccucuc auuugcuaua uuca      94

<210> SEQ ID NO 187
<211> LENGTH: 93
<212> TYPE: RNA
<213> ORGANISM: Homo sapiens

<400> SEQUENCE: 187
guagucagua guuggggggu gggaacggcu ucauacagga guugaugcac aguuauccag      60
cuccuauaug augccuuucu ucaucccuu caa      93

```
<210> SEQ ID NO 188
<211> LENGTH: 67
<212> TYPE: RNA
<213> ORGANISM: Homo sapiens

<400> SEQUENCE: 188
ucuccaacaa uauccuggug cugagugaug acucaggcga cuccagcauc agugauuuug      60
uugaaga                                                                67

<210> SEQ ID NO 189
<211> LENGTH: 94
<212> TYPE: RNA
<213> ORGANISM: Homo sapiens

<400> SEQUENCE: 189
cggggcggcc gcucucccug uccuccagga gcucacgugu gccugccugu gagcgccucg      60
acgacagagc cggcgccugc cccagugucu gcgc                                  94

<210> SEQ ID NO 190
<211> LENGTH: 95
<212> TYPE: RNA
<213> ORGANISM: Homo sapiens

<400> SEQUENCE: 190
uuguaccugg ugugauuaua aagcaaugag acugauuguc auaugucguu guggganucc      60
gucucaguua cuuuauagcc auaccuggua ucuua                                 95

<210> SEQ ID NO 191
<211> LENGTH: 99
<212> TYPE: RNA
<213> ORGANISM: Homo sapiens

<400> SEQUENCE: 191
gaaacugggc ucaaggugag gggugcuauc ugugauugag ggacaugguu aauggaauug      60
ucucacacag aaaucgcacc cgucaccuug gccuacuua                             99

<210> SEQ ID NO 192
<211> LENGTH: 77
<212> TYPE: RNA
<213> ORGANISM: Homo sapiens

<400> SEQUENCE: 192
gcuugggaca cauacuucuu uauaugccca uaugaaccug cuaagcuaug gaauguaaag      60
aaguauguau uucaggc                                                     77

<210> SEQ ID NO 193
<211> LENGTH: 72
<212> TYPE: RNA
<213> ORGANISM: Homo sapiens

<400> SEQUENCE: 193
ucagagcaca uacuucuuua uguacccaua ugaacauuca gugcuaugga auguaaagaa      60
guauguauuu ug                                                          72

<210> SEQ ID NO 194
<211> LENGTH: 88
<212> TYPE: RNA
<213> ORGANISM: Homo sapiens

<400> SEQUENCE: 194
```
ccaggcugag guaguaguuu guacaguuug agggucuaug auaccacccg guacaggaga    60
uaacuguaca ggccacugcc uugccagg    88

<210> SEQ ID NO 195
<211> LENGTH: 85
<212> TYPE: RNA
<213> ORGANISM: Homo sapiens

<400> SEQUENCE: 195
cuggcugagg uaguaguuug ugcuguuggu cggguuguga cauugcccgc uguggagaua    60
acugcgcaag cuacugccuu gcuag    85

<210> SEQ ID NO 196
<211> LENGTH: 103
<212> TYPE: RNA
<213> ORGANISM: Homo sapiens

<400> SEQUENCE: 196 aaugggpuucc uaggaagagg uaguaggpuug cauaguuuua gggcagagau uuugcccaca    60
aggaguuaac uauacgaccu gcugccuuuc uuagggccuu auu    103

<210> SEQ ID NO 197
<211> LENGTH: 94
<212> TYPE: RNA
<213> ORGANISM: Homo sapiens

<400> SEQUENCE: 197
uucacugugg gaugaggguag uagguuguau aguuuuaggg ucacacccac cacugggaga    60
uaacuauaca aucuacuguc uuuccuaagg ugau    94

<210> SEQ ID NO 198
<211> LENGTH: 96
<212> TYPE: RNA
<213> ORGANISM: Homo sapiens

<400> SEQUENCE: 198
cugcauguuc ccagguugag guaguaggu guauaguuua gaguuacauc aaggagaua    60 acuguacagc cuccuagcuu uccuugggac uugcac    96

<210> SEQ ID NO 199
<211> LENGTH: 85
<212> TYPE: RNA
<213> ORGANISM: Homo sapiens

<400> SEQUENCE: 199
gcagggugag guaguagguu gugugguuuc agggcaguga uguugccccu ccgaagauaa    60
cuauacaacc uacugccuuc ccuga    85

<210> SEQ ID NO 200
<211> LENGTH: 94
<212> TYPE: RNA
<213> ORGANISM: Homo sapiens

<400> SEQUENCE: 200
ugugugcauc cggguugagg uaguagguug uaugguuuag aguuacaccc ugggaguuaa    60
cuguacaacc uucuagcuuu ccuuggagca cacu    94

<210> SEQ ID NO 201

```
<211> LENGTH: 95
<212> TYPE: RNA
<213> ORGANISM: Homo sapiens

<400> SEQUENCE: 201
acggccuuug gggugaggua guagguugua ugguuuuggg cucugccccg cucugcggua    60
acuauacaau cuacugucuu uccugaagug gccgc                              95

<210> SEQ ID NO 202
<211> LENGTH: 93
<212> TYPE: RNA
<213> ORGANISM: Homo sapiens

<400> SEQUENCE: 202 cgcgccccc gggcugaggu aggagguugu auaguugagg aagacacccg aggagaucac     60
uauacggccu ccuagcuuuc cccaggcugc gcc                                93

<210> SEQ ID NO 203
<211> LENGTH: 89
<212> TYPE: RNA
<213> ORGANISM: Homo sapiens

<400> SEQUENCE: 203
aucagaguga gguaguagau uguauaguug uggggguagug auuuuacccu guuuaggaga   60
uaacuauaca aucuauugcc uucccugag                                     89

<210> SEQ ID NO 204
<211> LENGTH: 83
<212> TYPE: RNA
<213> ORGANISM: Homo sapiens

<400> SEQUENCE: 204
ugugggauga gguaguagau uguauaguuu uagggucaua ccccaucuug gagauaacua    60
uacagucuac ugucuuuccc acg                                           83

<210> SEQ ID NO 205
<211> LENGTH: 108
<212> TYPE: RNA
<213> ORGANISM: Homo sapiens

<400> SEQUENCE: 205
uuggauguug gccuaguucu guguggaaga cuagugauuu uguuguuuuu agauaacuaa    60
aacgacaaca aaucacaguc ugccauaugg cacaggccac cucuacag               108

<210> SEQ ID NO 206
<211> LENGTH: 97
<212> TYPE: RNA
<213> ORGANISM: Homo sapiens

<400> SEQUENCE: 206
ggucgggcca gccccguuug gaagacuagu gauuuuguug uugugucucu guauccaaca    60
acaagcccca gucugccaca uggugcuggu cauuuca                            97

<210> SEQ ID NO 207
<211> LENGTH: 111
<212> TYPE: RNA
<213> ORGANISM: Homo sapiens

<400> SEQUENCE: 207
aggagcggag uacgugagcc agugcuaugu ggaagacuug ugauuuuguu guucugauau    60
```

```
gauaugacaa caagucacag ccagccucau agcguggacu ccuaucaccu u            111

<210> SEQ ID NO 208
<211> LENGTH: 72
<212> TYPE: RNA
<213> ORGANISM: Homo sapiens

<400> SEQUENCE: 208
guuguuaucu uugguuaucu agcuguauga guguauuggu cuucauaaag cuagauaacc   60
gaaaguaaaa ac                                                      72

<210> SEQ ID NO 209
<211> LENGTH: 89
<212> TYPE: RNA
<213> ORGANISM: Homo sapiens

<400> SEQUENCE: 209
cggggunggu uguuaucuuu gguuaucuag cuguaugagu ggugnggagu cuucauaaag   60
cuagauaacc gaaaguaaaa auaacccca                                    89

<210> SEQ ID NO 210
<211> LENGTH: 90
<212> TYPE: RNA
<213> ORGANISM: Homo sapiens

<400> SEQUENCE: 210
ggaggcccgu uucucucuuu gguuaucuag cuguaugagu gccacagagc cgucauaaag   60
cuagauaacc gaaaguagaa augacucuca                                   90

<210> SEQ ID NO 211
<211> LENGTH: 68
<212> TYPE: RNA
<213> ORGANISM: Homo sapiens

<400> SEQUENCE: 211
uauauacccu guagaaccga auuugugugg uacccacaua gucacagauu cgauucuagg   60
ggaauaua                                                           68

<210> SEQ ID NO 212
<211> LENGTH: 110
<212> TYPE: RNA
<213> ORGANISM: Homo sapiens

<400> SEQUENCE: 212
gaucugucug ucuucuguau uacccuguag auccgaauu uguguaagga auuuguggu     60 cacaaauucg uaucuagggg aauauguagu ugacauaaac acuccgcuca              110

<210> SEQ ID NO 213
<211> LENGTH: 110
<212> TYPE: RNA
<213> ORGANISM: Homo sapiens

<400> SEQUENCE: 213
gaccugucug ucuucuguau uacccuguag auccgaauu uguguaagga auuuguggu     60 cacaaauucg uaucuagggg aauauguagu ugacauaaac acuccgcuca              110

<210> SEQ ID NO 214
<211> LENGTH: 64
<212> TYPE: RNA
```

<213> ORGANISM: Homo sapiens

<400> SEQUENCE: 214 cguagcagc acaucauggu uuacauacua cagucaagau gcgaaucauu auuugcugcu    60
cuag                                                               64

<210> SEQ ID NO 215
<211> LENGTH: 84
<212> TYPE: RNA
<213> ORGANISM: Homo sapiens

<400> SEQUENCE: 215
cccuuggagu aaaguagcag cacauaaugg uuuguggaug uugaaaaggu gcaggccaua    60
cugugcugcc ucaaaauaca agga                                          84

<210> SEQ ID NO 216
<211> LENGTH: 93
<212> TYPE: RNA
<213> ORGANISM: Homo sapiens

<400> SEQUENCE: 216
augucagcgg ugccuuagca gcacguaaau auuggcguua agauucugaa auuaccucca    60
guauugacug ugcugcugaa guaagguugg caa                                93

<210> SEQ ID NO 217
<211> LENGTH: 95
<212> TYPE: RNA
<213> ORGANISM: Homo sapiens

<400> SEQUENCE: 217
caugcuuguu ccacucuagc agcacguaaa uauuggcgua gugaaauaaa uauuaaacac    60
caauauuauu gugcugcuuu agugugacag ggaua                              95

<210> SEQ ID NO 218
<211> LENGTH: 84
<212> TYPE: RNA
<213> ORGANISM: Homo sapiens

<400> SEQUENCE: 218
gucagaauaa ugucaaagug cuuacagugc agguagugau gugugcaucu acugcaguga    60
gggcacuugu agcauuaugc ugac                                          84

<210> SEQ ID NO 219
<211> LENGTH: 96
<212> TYPE: RNA
<213> ORGANISM: Homo sapiens

<400> SEQUENCE: 219
ugcgugcuuu uuguucuaag gugcaucuag ugcagauagu gaaguagacu agcaucuacu    60
gcccuaagug cuccuucugg cauaagaagu uauguc                             96

<210> SEQ ID NO 220
<211> LENGTH: 84
<212> TYPE: RNA
<213> ORGANISM: Homo sapiens

<400> SEQUENCE: 220
acuuacgauu aguuugcag auuugcaguu cagcguauau gugaauauau ggcugugcaa    60
auccaugcaa aacugauugu ggga                                          84

<210> SEQ ID NO 221
<211> LENGTH: 82
<212> TYPE: RNA
<213> ORGANISM: Homo sapiens

<400> SEQUENCE: 221
gcagcccucu guuaguuuug cauaguugca cuacaagaag aauguaguug ugcaaaucua    60
ugcaaaacug augguggccu gc                                            82

<210> SEQ ID NO 222
<211> LENGTH: 87
<212> TYPE: RNA
<213> ORGANISM: Homo sapiens

<400> SEQUENCE: 222 cacuggucua igguuaguuu ugcagguuug cauccagcug uauaauauuc ugcugugcaa    60
auccaugcaa aacugacugu gguggug                                       87

<210> SEQ ID NO 223
<211> LENGTH: 107
<212> TYPE: RNA
<213> ORGANISM: Homo sapiens

<400> SEQUENCE: 223
gugugaugug acagcuucug uagcacuaaa gugcuuauag ugcagguagu guguagccau    60
cuacugcauu acgagcacuu aaaguacugc cagcuguaga acuccag                 107

<210> SEQ ID NO 224
<211> LENGTH: 92
<212> TYPE: RNA
<213> ORGANISM: Homo sapiens

<400> SEQUENCE: 224
uguaccaccu ugucggauag cuuaucagac ugauguugac uguugaaucu cauggcaaca    60
gcagucgaug ggcugucuga cauuuuggua uc                                 92

<210> SEQ ID NO 225
<211> LENGTH: 95
<212> TYPE: RNA
<213> ORGANISM: Homo sapiens

<400> SEQUENCE: 225
accuggcuga gccgcaguag uucuucagug gcaagcuuua ugccugacc cagcuaaagc     60 ugccaguuga agaacuguug cccucugccc cuggc                              95

<210> SEQ ID NO 226
<211> LENGTH: 74
<212> TYPE: RNA
<213> ORGANISM: Homo sapiens

<400> SEQUENCE: 226
ggcugcuugg guuccuggca ugcugauuug ugacuugaga uuaaaaucac auugccaggg    60
auuaccacgc aacc                                                     74

<210> SEQ ID NO 227
<211> LENGTH: 75
<212> TYPE: RNA
<213> ORGANISM: Homo sapiens

<400> SEQUENCE: 227
cggacggcug ggguccuggg ggaugggauu ugaugccagu cacaaaucac auugccaggg    60
auuuccaacu gaccc                                                    75

<210> SEQ ID NO 228
<211> LENGTH: 68
<212> TYPE: RNA
<213> ORGANISM: Homo sapiens

<400> SEQUENCE: 228
cuccggugcc uacugagcug auaucaguuc ucauuucaca cacuggcuca guucagcagg    60
aacaggag                                                            68

<210> SEQ ID NO 229
<211> LENGTH: 107
<212> TYPE: RNA
<213> ORGANISM: Homo sapiens

<400> SEQUENCE: 229
gccucucucc gggcuccgcc ucccgugccu acugagcuga aacaguugau uccagugcac    60
uggcucaguu cagcaggaac aggaguccag cccccuagga gcuggca                 107

<210> SEQ ID NO 230
<211> LENGTH: 84
<212> TYPE: RNA
<213> ORGANISM: Homo sapiens

<400> SEQUENCE: 230
ggccaguguu gagaggcgga gacuugggca auugcuggac gcugcccugg gcauugcacu    60
ugucucgguc ugacagugcc ggcc                                          84

<210> SEQ ID NO 231
<211> LENGTH: 90
<212> TYPE: RNA
<213> ORGANISM: Homo sapiens

<400> SEQUENCE: 231
aaggccgugg ccucguucaa guaauccagg auaggcugug cagucccaa ggggccuauu    60 cuugguuacu ugcacgggga cgcgggccug                                    90

<210> SEQ ID NO 232
<211> LENGTH: 85
<212> TYPE: RNA
<213> ORGANISM: Homo sapiens

<400> SEQUENCE: 232
ugcccgggac ccaguucaag uaauucagga uagguugugg ugcugaccag ccuguucucc    60
auuacuuggc ucggggccg gugcc                                          85

<210> SEQ ID NO 233
<211> LENGTH: 84
<212> TYPE: RNA
<213> ORGANISM: Homo sapiens

<400> SEQUENCE: 233
ggcugcggcu ggauucaagu aauccaggau aggcuguguc cguccaugag gccguucuu    60 gauuacuugu uucuggaggc agcg                                          84

```
<210> SEQ ID NO 234
<211> LENGTH: 73
<212> TYPE: RNA
<213> ORGANISM: Homo sapiens

<400> SEQUENCE: 234
aggugcagag cuuagcugau uggugaacag ugauuggunu ccgcuuuguu cacagugggcu      60 aaguucugca ccu                                                          73

<210> SEQ ID NO 235
<211> LENGTH: 87
<212> TYPE: RNA
<213> ORGANISM: Homo sapiens

<400> SEQUENCE: 235
uggccugagg agcagggcuu agcugcuugu gagcaagguc cacagcaaag ucguguucac      60
aguggcuaag uuccgccccc uggaccc                                          87

<210> SEQ ID NO 236
<211> LENGTH: 86
<212> TYPE: RNA
<213> ORGANISM: Homo sapiens

<400> SEQUENCE: 236
ggucccuacc uucaaggagc ucacagucua uugaguugcc uuucugauuc ucccacuaga      60
uugugagcug cuggagggca ggcacu                                           86

<210> SEQ ID NO 237
<211> LENGTH: 71
<212> TYPE: RNA
<213> ORGANISM: Homo sapiens

<400> SEQUENCE: 237
aggaagcugg uuucauaugg ugguuuagau uuaaauagug auugucuagc accauuugaa      60
aucaguguuc u                                                           71

<210> SEQ ID NO 238
<211> LENGTH: 88
<212> TYPE: RNA
<213> ORGANISM: Homo sapiens

<400> SEQUENCE: 238
accccuuaga ggaugacuga uuucuuuugg uguucagagu caauagaauu uucuagcacc      60
aucugaaauc gguuauaaug auugggga                                         88

<210> SEQ ID NO 239
<211> LENGTH: 88
<212> TYPE: RNA
<213> ORGANISM: Homo sapiens

<400> SEQUENCE: 239
aucucuuaca caggcugacc gauuucuccu ggguucagag gucuguuuuu gucuagcacc      60
auuugaaauc gguuaugaug uaggggga                                         88

<210> SEQ ID NO 240
<211> LENGTH: 81
<212> TYPE: RNA
<213> ORGANISM: Homo sapiens

<400> SEQUENCE: 240
```

```
cuucuggaag cugguuucac augguggcuu agauuuuucc aucuuuguau cuagcaccau    60
uugaaaucag uguuuagga g                                              81
```

<210> SEQ ID NO 241
<211> LENGTH: 71
<212> TYPE: RNA
<213> ORGANISM: Homo sapiens

<400> SEQUENCE: 241

```
gcgacuguaa acauccucga cuggaagcug ugaagccaca aaugggcuuu cagucggaug    60
uuugcagcug c                                                        71
```

<210> SEQ ID NO 242
<211> LENGTH: 60
<212> TYPE: RNA
<213> ORGANISM: Homo sapiens

<400> SEQUENCE: 242

```
auguaaacau ccuacacuca gcugucauac augcguuggc ugggaugugg auguuuacgu    60
```

<210> SEQ ID NO 243
<211> LENGTH: 64
<212> TYPE: RNA
<213> ORGANISM: Homo sapiens

<400> SEQUENCE: 243

```
cuguaaacau ccuugacugg aagcuguaag guguugagag gagcuuucag ucggauguuu    60
acag                                                                64
```

<210> SEQ ID NO 244
<211> LENGTH: 89
<212> TYPE: RNA
<213> ORGANISM: Homo sapiens

<400> SEQUENCE: 244

```
accauguugu agugugugua aacauccuac acucucagcu gugagcucaa gguggcuggg    60
agaggguugu uuacuccuuc ugccaugga                                     89
```

<210> SEQ ID NO 245
<211> LENGTH: 84
<212> TYPE: RNA
<213> ORGANISM: Homo sapiens

<400> SEQUENCE: 245

```
gagugacaga uauuguaaac auccuacacu cucagcugug aaaaguaaga aagcugggag    60
aaggcuguuu acucucucug ccuu                                          84
```

<210> SEQ ID NO 246
<211> LENGTH: 82
<212> TYPE: RNA
<213> ORGANISM: Homo sapiens

<400> SEQUENCE: 246

```
aagucugugu cuguaaacau ccccgacugg aagcuguaag ccacagccaa gcuuucaguc    60
agauguuugc ugcuacuggc uc                                            82
```

<210> SEQ ID NO 247
<211> LENGTH: 106
<212> TYPE: RNA
<213> ORGANISM: Homo sapiens

<400> SEQUENCE: 247
ugcuccugua acucggaacu ggagaggagg caagaugcug gcauagcugu ugaacugaga    60
accugcuaug ccaacauauu gccaucuuuc cugucugaca gcagcu                   106

<210> SEQ ID NO 248
<211> LENGTH: 70
<212> TYPE: RNA
<213> ORGANISM: Homo sapiens

<400> SEQUENCE: 248
ggagauauug cacauuacua aguugcaugu ugucacggcc ucaaugcaau uuagugugug    60
ugauauuuuc                                                           70

<210> SEQ ID NO 249
<211> LENGTH: 69
<212> TYPE: RNA
<213> ORGANISM: Homo sapiens

<400> SEQUENCE: 249
cuguggugca uuguaguugc auugcauguu cuggcaauac cugugcaaug uuccacagu     60 gcaucacgg                                                            69

<210> SEQ ID NO 250
<211> LENGTH: 77
<212> TYPE: RNA
<213> ORGANISM: Homo sapiens

<400> SEQUENCE: 250
agucuaguua cuaggcagug uaguuagcug auugcuaaua guaccaauca cuaccacac     60 agccagguaa aaagacu                                                   77

<210> SEQ ID NO 251
<211> LENGTH: 84
<212> TYPE: RNA
<213> ORGANISM: Homo sapiens

<400> SEQUENCE: 251
gugcucgguu uguaggcagu guaauuagcu gauuguagug cggugcugac aaucacuaac    60
uccacugcca ucaaaacaag gcac                                           84

<210> SEQ ID NO 252
<211> LENGTH: 102
<212> TYPE: RNA
<213> ORGANISM: Homo sapiens

<400> SEQUENCE: 252
ccagcuguga guaauucuuu ggcagugucu uagcugguug uugugaguau uagcuaagga    60
agcaaucagc aaguauacug cccuagaagu gcugcacauu gu                       102

<210> SEQ ID NO 253
<211> LENGTH: 91
<212> TYPE: RNA
<213> ORGANISM: Homo sapiens

<400> SEQUENCE: 253
ugcccauuca uccacaggug gggauuggug gcauuacuug guuagauau aaaguauugc     60 acuugcccg gccugaggaa gaaagagggu u                                    91

```
<210> SEQ ID NO 254
<211> LENGTH: 80
<212> TYPE: RNA
<213> ORGANISM: Homo sapiens

<400> SEQUENCE: 254
cuuucuacac agguugggau uugucgcaau gcuguguuuc ucuguauggu auugcacuug    60
ucccggccug uugaguuugg                                                80

<210> SEQ ID NO 255
<211> LENGTH: 88
<212> TYPE: RNA
<213> ORGANISM: Homo sapiens

<400> SEQUENCE: 255 agucauggggg gcuccaaagu gcuguucgug cagguagugu aauuaccuga ccuacugcug    60
agcuagcacu ucccgagccc ccaggaca                                       88

<210> SEQ ID NO 256
<211> LENGTH: 106
<212> TYPE: RNA
<213> ORGANISM: Homo sapiens

<400> SEQUENCE: 256
ccaguaccau cugcuuggcc gauuuuggca cuagcacauu uuugcuugug ucucuccgcu    60
gugagcaauc auguguagug ccaauauggg aaaagcgggc ugcugc                  106

<210> SEQ ID NO 257
<211> LENGTH: 80
<212> TYPE: RNA
<213> ORGANISM: Homo sapiens

<400> SEQUENCE: 257
gugagguagu aaguuguauu guugugggu agggauuuua ggccccagua agaagauaac    60
uauacaacuu acuacuuucc                                                80

<210> SEQ ID NO 258
<211> LENGTH: 65
<212> TYPE: RNA
<213> ORGANISM: Homo sapiens

<400> SEQUENCE: 258
cauaaacccg uagauccgau cuuguggugg agggaccgc gcaagcucgu uucuaugggu    60
cugug                                                                65

<210> SEQ ID NO 259
<211> LENGTH: 70
<212> TYPE: RNA
<213> ORGANISM: Homo sapiens

<400> SEQUENCE: 259
ggcacccacc cguagaaccg accuugcggg gccuucgccg cacacaagcu cgucucugug    60
gguccguguc                                                           70

<210> SEQ ID NO 260
<211> LENGTH: 80
<212> TYPE: RNA
<213> ORGANISM: Homo sapiens

<400> SEQUENCE: 260
```

```
ccuguugcca caaacccgua gauccgaacu ugugcugauu cugcacacaa gcuugugucu    60
auagguaugu gucuguuagg                                                80

<210> SEQ ID NO 261
<211> LENGTH: 57
<212> TYPE: RNA
<213> ORGANISM: Homo sapiens

<400> SEQUENCE: 261
ucaguuauca cagugcugau gcuguccauu cuaaagguac aguacuguga uaacuga       57

<210> SEQ ID NO 262
<211> LENGTH: 97
<212> TYPE: RNA
<213> ORGANISM: Homo sapiens

<400> SEQUENCE: 262
aucugagacu gaacugcccu uuuucgguua ucaugguacc gaugcuguag cucugaaagg    60
uacaguacug ugauagcuga agaauggcgg ugccauc                             97

<210> SEQ ID NO 263
<211> LENGTH: 86
<212> TYPE: RNA
<213> ORGANISM: Homo sapiens

<400> SEQUENCE: 263
uucuuacugc ccucggcuuc uuuacagugc ugccuuguug cauauggauc aagcagcauu    60
guacagggcu augaaggcau ugagac                                         86

<210> SEQ ID NO 264
<211> LENGTH: 86
<212> TYPE: RNA
<213> ORGANISM: Homo sapiens

<400> SEQUENCE: 264
gucuucgugc uuucagcuuc uuuacagugc ugccuuguag cauucagguc aagcagcauu    60
guacagggcu augaaagaac caagaa                                         86

<210> SEQ ID NO 265
<211> LENGTH: 65
<212> TYPE: RNA
<213> ORGANISM: Homo sapiens

<400> SEQUENCE: 265
augucaaagu gcuaacagug cagguagcuu uuugaguucu acugcagugc cagcacuucu    60
uacau                                                                65

<210> SEQ ID NO 266
<211> LENGTH: 82
<212> TYPE: RNA
<213> ORGANISM: Homo sapiens

<400> SEQUENCE: 266
ccugcuggga cuaaagugcu gacagugcag auaguggucc ucucugugcu accgcacugu    60
ggguacuugc ugcuccagca gg                                             82

<210> SEQ ID NO 267
<211> LENGTH: 87
<212> TYPE: RNA
```

<213> ORGANISM: Homo sapiens

<400> SEQUENCE: 267
uucucugugc uuucagcuuc uuuacagugu ugccuugugg cauggaguuc aagcagcauu    60
guacagggcu aucaaagcac agagagc    87

<210> SEQ ID NO 268
<211> LENGTH: 66
<212> TYPE: RNA
<213> ORGANISM: Homo sapiens

<400> SEQUENCE: 268
agcuguggag ugugacaaug guguuugugu ccaaaccauc aaacgccauu aucacacuaa    60
auagcu    66

<210> SEQ ID NO 269
<211> LENGTH: 68
<212> TYPE: RNA
<213> ORGANISM: Homo sapiens

<400> SEQUENCE: 269
cucugcgugu ucacagcgga ccuugauuua augucuauac aauuaaggca cgcggugaau    60
gccaagag    68

<210> SEQ ID NO 270
<211> LENGTH: 85
<212> TYPE: RNA
<213> ORGANISM: Homo sapiens

<400> SEQUENCE: 270
aggccucucu cuccguguuc acagcggacc uugauuuaaa uguccauaca auuaaggcac    60
gcggugaaug ccaagaaugg ggcug    85

<210> SEQ ID NO 271
<211> LENGTH: 109
<212> TYPE: RNA
<213> ORGANISM: Homo sapiens

<400> SEQUENCE: 271
aucaagauca gagacucugc ucuccguguu cacagcggac cuugauuuaa ugucauacaa    60
uuaaggcacg cggugaaugc caagagcgga ccuacggcu gcacuugaa    109

<210> SEQ ID NO 272
<211> LENGTH: 68
<212> TYPE: RNA
<213> ORGANISM: Homo sapiens

<400> SEQUENCE: 272
cugggucccu gagacccuuu aaccugugag gacguccagg ucacaggug agguucuugg    60 gagccugg    68

<210> SEQ ID NO 273
<211> LENGTH: 71
<212> TYPE: RNA
<213> ORGANISM: Homo sapiens

<400> SEQUENCE: 273
gccuagcccc ugagacccua acugugagg uauuuuagua acaucacaag ucagguucuu    60
gggaccuagg c    71

<210> SEQ ID NO 274
<211> LENGTH: 77
<212> TYPE: RNA
<213> ORGANISM: Homo sapiens

<400> SEQUENCE: 274
ugcgcucccc ucagcccug agacccuaac uugugauguu uaccguuuaa auccacgggu     60
uaggcucuug ggagcug                                                  77

<210> SEQ ID NO 275
<211> LENGTH: 73
<212> TYPE: RNA
<213> ORGANISM: Homo sapiens

<400> SEQUENCE: 275
ugacagcaca uuauuacuuu ugguacgcgc ugugacacuu caaacucgua ccgugaguaa    60
uaaugcgcgg uca                                                      73

<210> SEQ ID NO 276
<211> LENGTH: 70
<212> TYPE: RNA
<213> ORGANISM: Homo sapiens

<400> SEQUENCE: 276
ccagccugcu gaagcucaga gggcucugau ucagaaagau caucggaucc gucugagcuu    60
ggcuggucgg                                                          70

<210> SEQ ID NO 277
<211> LENGTH: 70
<212> TYPE: RNA
<213> ORGANISM: Homo sapiens

<400> SEQUENCE: 277
guuggauucg gggccguagc acugucugag agguuuacau uucucacagu gaaccggucu    60
cuuuuucagc                                                          70

<210> SEQ ID NO 278
<211> LENGTH: 76
<212> TYPE: RNA
<213> ORGANISM: Homo sapiens

<400> SEQUENCE: 278
cagugggaag gggggccgau gcacuguaag agagugagua gcaggucuca cagugaaccg    60
gucucuuucc cuacug                                                   76

<210> SEQ ID NO 279
<211> LENGTH: 73
<212> TYPE: RNA
<213> ORGANISM: Homo sapiens

<400> SEQUENCE: 279
uggaucuuuu ugcggucugg gcuugcuguu cucucgacag uagucaggaa gcccuuaccc    60
caaaaaguau cua                                                      73

<210> SEQ ID NO 280
<211> LENGTH: 90
<212> TYPE: RNA
<213> ORGANISM: Homo sapiens -continued

<400> SEQUENCE: 280
ugccuuucgc gaaucuuuuu gcggucuggg cuugcuguac auaacucaau agccggaagc    60
ccuuacccca aaaagcauuc gcggagggcg                                     90

<210> SEQ ID NO 281
<211> LENGTH: 64
<212> TYPE: RNA
<213> ORGANISM: Homo sapiens

<400> SEQUENCE: 281
gagcucuuuu cacauugugc uacugucuaa cguguaccga gcagugcaau guuaaaaggg    60
cauc                                                                 64

<210> SEQ ID NO 282
<211> LENGTH: 82
<212> TYPE: RNA
<213> ORGANISM: Homo sapiens

<400> SEQUENCE: 282
ggcuuguugg acacucuuuc ccuguugcac uacuguggc cucugggaag cagugcaaug    60
augaaagggc aucugucggg cc                                             82

<210> SEQ ID NO 283
<211> LENGTH: 66
<212> TYPE: RNA
<213> ORGANISM: Homo sapiens

<400> SEQUENCE: 283
gggcaaccgu ggcuuucgau uguuacugug ggaaccggag guaacagucu acagccaugg    60
ucgccc                                                               66

<210> SEQ ID NO 284
<211> LENGTH: 68
<212> TYPE: RNA
<213> ORGANISM: Homo sapiens

<400> SEQUENCE: 284
gcuaaagcug guaaaaugga accaaaucgc cucuucaaug gauuuggucc ccuucaacca    60
gcuguagc                                                             68

<210> SEQ ID NO 285
<211> LENGTH: 104
<212> TYPE: RNA
<213> ORGANISM: Homo sapiens

<400> SEQUENCE: 285
agaagccaaa ugcuuugcug aagcugguaa aauggaacca aaucagcugu uggauggauu    60
ugguccccuu caaccagcug uagcugcgca uugaucacgc cgca                    104

<210> SEQ ID NO 286
<211> LENGTH: 119
<212> TYPE: RNA
<213> ORGANISM: Homo sapiens

<400> SEQUENCE: 286
ccuccaaagg gaguggcccc cugcucuggc uggucaaacg gaaccaaguc cgucuuccug    60
agagguuugg uccccuucaa ccagcuacag cagggcuggc aaagcucaau auuuggaga   119

```
<210> SEQ ID NO 287
<211> LENGTH: 71
<212> TYPE: RNA
<213> ORGANISM: Homo sapiens

<400> SEQUENCE: 287
agggugugug acugguugac cagaggggcg ugcacucugu ucacccugug ggccaccag      60 ucaccaaccc u                                                         71

<210> SEQ ID NO 288
<211> LENGTH: 90
<212> TYPE: RNA
<213> ORGANISM: Homo sapiens

<400> SEQUENCE: 288
aggccucacu guucucuaug gcuuuuauu ccuaugugau ucuauugcuc gcucauaug       60 ggauuggagc cguggcguac ggugaggaua                                     90

<210> SEQ ID NO 289
<211> LENGTH: 97
<212> TYPE: RNA
<213> ORGANISM: Homo sapiens

<400> SEQUENCE: 289
cgcucugcug uggccuaugg cuuucauuc cuaugugauu gcuguccga acucauguag       60 ggcuaaaagc caugggcuac agugaggggc aagcucc                             97

<210> SEQ ID NO 290
<211> LENGTH: 100
<212> TYPE: RNA
<213> ORGANISM: Homo sapiens

<400> SEQUENCE: 290
agauaaauuc acucuagugc uuuauggcuu uuuauuccua ugugaucgua auaaagucuc     60
auguagggau ggaagccaug aaauacauug ugaaaauuca                          100

<210> SEQ ID NO 291
<211> LENGTH: 62
<212> TYPE: RNA
<213> ORGANISM: Homo sapiens

<400> SEQUENCE: 291
gaggacucca uuuguuuga ugauggauuc uuaagcucca ucaucgucuc aaaugagucu      60
uc                                                                   62

<210> SEQ ID NO 292
<211> LENGTH: 73
<212> TYPE: RNA
<213> ORGANISM: Homo sapiens

<400> SEQUENCE: 292
cuucggugac ggguauucuu gggugauaaa uacggauuac guuguauug cuuaagaaua      60 cgcguagucg agg                                                       73

<210> SEQ ID NO 293
<211> LENGTH: 71
<212> TYPE: RNA
<213> ORGANISM: Homo sapiens

<400> SEQUENCE: 293
```

```
cagcuggugu ugugaaucag gccgacgagc agcgcauccu cuuacccggc uauuucacga    60 caccagggu g                                                         71
```

```
<210> SEQ ID NO 294
<211> LENGTH: 99
<212> TYPE: RNA
<213> ORGANISM: Homo sapiens

<400> SEQUENCE: 294
```

```
cucuagcaug guguugggg acagcuggug uugugaauca ggccguugcc aaucagagaa    60
cggcuacuuc acaaccagg ggccacacug cacugcaag                           99
```

```
<210> SEQ ID NO 295
<211> LENGTH: 68
<212> TYPE: RNA
<213> ORGANISM: Homo sapiens

<400> SEQUENCE: 295
```

```
guguauucua cagugcacgu gucuccagug uggcucggag gcuggagacg cggcccuguu    60
ggaguaac                                                            68
```

```
<210> SEQ ID NO 296
<211> LENGTH: 70
<212> TYPE: RNA
<213> ORGANISM: Homo sapiens

<400> SEQUENCE: 296
```

```
ccugccagug guuuacccu augguagguu acgucaugcu guucuaccac aggguagaac     60
cacggacagg                                                          70
```

```
<210> SEQ ID NO 297
<211> LENGTH: 72
<212> TYPE: RNA
<213> ORGANISM: Homo sapiens

<400> SEQUENCE: 297
```

```
ggguccaucu uccagugcag uguuggaugg uugaaguaug aagcuccuaa cacugucugg    60
uaaagauggc cc                                                       72
```

```
<210> SEQ ID NO 298
<211> LENGTH: 64
<212> TYPE: RNA
<213> ORGANISM: Homo sapiens

<400> SEQUENCE: 298
```

```
acccauaaag uagaaagcac uacuaacagc acuggagggu guaguguuuc cuacuuuaug    60
gaug                                                                64
```

```
<210> SEQ ID NO 299
<211> LENGTH: 63
<212> TYPE: RNA
<213> ORGANISM: Homo sapiens

<400> SEQUENCE: 299
```

```
ccugaggugc agugcugcau cucuggucag uugggagucu gagaugaagc acuguagcuc    60
agg                                                                 63
```

```
<210> SEQ ID NO 300
<211> LENGTH: 66
```

```
<212> TYPE: RNA
<213> ORGANISM: Homo sapiens

<400> SEQUENCE: 300
ggcugggaua ucaucauaua cuguaaguuu gugaugagac acuacaguau agaugaugua      60
cuaguc                                                                66

<210> SEQ ID NO 301
<211> LENGTH: 70
<212> TYPE: RNA
<213> ORGANISM: Homo sapiens

<400> SEQUENCE: 301
cucacggucc aguuucccca ggaaucccuu ggaugcuaag auggggauuc cuggaaauac      60
uguucuugag                                                            70

<210> SEQ ID NO 302
<211> LENGTH: 65
<212> TYPE: RNA
<213> ORGANISM: Homo sapiens

<400> SEQUENCE: 302
agcucugaga acugaauucc augguuaua ucaaugucag accugugaaa uucaguucuu       60
cagcu                                                                 65

<210> SEQ ID NO 303
<211> LENGTH: 99
<212> TYPE: RNA
<213> ORGANISM: Homo sapiens

<400> SEQUENCE: 303
agccaguuug gucuuugag acaaaguucu gagacacucc gacucugagu augauagaag       60
ucagugcacu acagaacuuu gucucuagag gcugugguc                            99

<210> SEQ ID NO 304
<211> LENGTH: 66
<212> TYPE: RNA
<213> ORGANISM: Homo sapiens

<400> SEQUENCE: 304
ggcucuggcu ccgugucuuc acucccgugu uuguccgagg agggagggag ggacgggggc      60
ggugcu                                                                66

<210> SEQ ID NO 305
<211> LENGTH: 65
<212> TYPE: RNA
<213> ORGANISM: Homo sapiens

<400> SEQUENCE: 305
cccugucucc caacccuugu accagugcug ugccucagac ccugguacag gccuggggga     60
uaggg                                                                 65

<210> SEQ ID NO 306
<211> LENGTH: 68
<212> TYPE: RNA
<213> ORGANISM: Homo sapiens

<400> SEQUENCE: 306
ccugcccucg aggagcucac agucuaguau gucuccuccc uacuagacug aggcuccuug     60
```

-continued

| aggacagg | 68 |

<210> SEQ ID NO 307
<211> LENGTH: 73
<212> TYPE: RNA
<213> ORGANISM: Homo sapiens

<400> SEQUENCE: 307

| ccgggccuag guucugugau acacuccgac ucgggcucug gagcagucag ugcaugacag | 60 |
| aacuugggcc cgg | 73 |

<210> SEQ ID NO 308
<211> LENGTH: 69
<212> TYPE: RNA
<213> ORGANISM: Homo sapiens

<400> SEQUENCE: 308

| cggugucauu uuugugacgu ugcagcuagu aauaugagcc caguugcaua gucacaaaag | 60 |
| ugaucauug | 69 |

<210> SEQ ID NO 309
<211> LENGTH: 66
<212> TYPE: RNA
<213> ORGANISM: Homo sapiens

<400> SEQUENCE: 309

| gaagauaggu uauccguguu gccuucgcuu uauucgugac gaaucauaca cgguugaccu | 60 |
| auuuuu | 66 |

<210> SEQ ID NO 310
<211> LENGTH: 65
<212> TYPE: RNA
<213> ORGANISM: Homo sapiens

<400> SEQUENCE: 310

| cuguuaaugc uaauugugau aggggguuuug gccucugacu gacuccuacc uguuagcauu | 60 |
| aacag | 65 |

<210> SEQ ID NO 311
<211> LENGTH: 76
<212> TYPE: RNA
<213> ORGANISM: Homo sapiens

<400> SEQUENCE: 311

| ccauggaaca uucaacgcug ucggugaguu ugggauucaa aaacaaaaaa accaccgacc | 60 |
| guugacugua ccuugg | 76 |

<210> SEQ ID NO 312
<211> LENGTH: 80
<212> TYPE: RNA
<213> ORGANISM: Homo sapiens

<400> SEQUENCE: 312

| aggucacaau caacauucau ugcugucggu ggguugaacu guguagaaaa gcucacugaa | 60 |
| caaugaaugc aacuguggcc | 80 |

<210> SEQ ID NO 313
<211> LENGTH: 89
<212> TYPE: RNA
<213> ORGANISM: Homo sapiens

```
<400> SEQUENCE: 313
gccaaggguu uggggggaaca uucaaccugu cggugaguuu gggcagcuca gacaaaccau    60
cgaccguuga guggacccccg aggccugga                                      89

<210> SEQ ID NO 314
<211> LENGTH: 89
<212> TYPE: RNA
<213> ORGANISM: Homo sapiens

<400> SEQUENCE: 314
uugauggcug cacucaacau ucauugcugu cgguggguuu gaaugucaac caacucacug    60
aucaaugaau gcaaacugcg ggccaaaaa                                       89

<210> SEQ ID NO 315
<211> LENGTH: 75
<212> TYPE: RNA
<213> ORGANISM: Homo sapiens

<400> SEQUENCE: 315
accauuuuug gcaaugguag aacucacacc gguaagguaa ugggacccgg ugguucuaga    60
cuugccaacu auggu                                                      75

<210> SEQ ID NO 316
<211> LENGTH: 70
<212> TYPE: RNA
<213> ORGANISM: Homo sapiens

<400> SEQUENCE: 316
cuguguaugg cacugguaga auucacugug aacagucuca gucagugaau uaccgaaggg    60
ccauaaacag                                                            70

<210> SEQ ID NO 317
<211> LENGTH: 69
<212> TYPE: RNA
<213> ORGANISM: Homo sapiens

<400> SEQUENCE: 317
ccuuuccuua ucacuuuucc agccagcuuu gugacucuaa guguuggacg gagaacugau    60
aaggguagg                                                             69

<210> SEQ ID NO 318
<211> LENGTH: 65
<212> TYPE: RNA
<213> ORGANISM: Homo sapiens

<400> SEQUENCE: 318
agggauugga gagaaaggca guuccugaug gucccucccc aggggcuggc uuuccucugg    60
uccuu                                                                 65

<210> SEQ ID NO 319
<211> LENGTH: 71
<212> TYPE: RNA
<213> ORGANISM: Homo sapiens

<400> SEQUENCE: 319
acuuuccaaa gaauucuccu uuugggcuuu cucauuuuau uuuaagcccu aaggugaauu    60
uuuugggaag u                                                          71
```

```
<210> SEQ ID NO 320
<211> LENGTH: 61
<212> TYPE: RNA
<213> ORGANISM: Homo sapiens

<400> SEQUENCE: 320
ucaggcuaca acacaggacc cgggcgcugc ucugaccccu cgugucuugu guugcagccg    60
g                                                                   61

<210> SEQ ID NO 321
<211> LENGTH: 68
<212> TYPE: RNA
<213> ORGANISM: Homo sapiens

<400> SEQUENCE: 321
ucucacaucc cuugcauggu ggagggugag cucucugaaa accccuccca caugcagggu    60
uugcagga                                                            68

<210> SEQ ID NO 322
<211> LENGTH: 67
<212> TYPE: RNA
<213> ORGANISM: Homo sapiens

<400> SEQUENCE: 322
cugugugaua uguuugauau auuagguugu uauuuaaucc aacuauauau caagcauauu    60
ccuacag                                                             67

<210> SEQ ID NO 323
<211> LENGTH: 74
<212> TYPE: RNA
<213> ORGANISM: Homo sapiens

<400> SEQUENCE: 323
agcgggcaac ggaaucccaa aagcagcugu ugucuccaga gcauccagc ugcacuugga     60 uuucguuccc ugcu                                                     74

<210> SEQ ID NO 324
<211> LENGTH: 89
<212> TYPE: RNA
<213> ORGANISM: Homo sapiens

<400> SEQUENCE: 324
cgugcacagg gcucugaccu augaauugac agccaguacu cuuuucucuc cucuggcugc    60
caauuccaua ggucacaggu auguucacc                                     89

<210> SEQ ID NO 325
<211> LENGTH: 66
<212> TYPE: RNA
<213> ORGANISM: Homo sapiens

<400> SEQUENCE: 325
gagagcuggg ucuuugcggg caagaugaga gugucaguuc aacuggccua caaaguccca    60
guccuc                                                              66

<210> SEQ ID NO 326
<211> LENGTH: 67
<212> TYPE: RNA
<213> ORGANISM: Homo sapiens

<400> SEQUENCE: 326
```

```
aucgggugua acagcaacuc cauguggacu gugcucggau uccaguggag cugcuguuac    60
uucugau                                                              67
```

```
<210> SEQ ID NO 327
<211> LENGTH: 86
<212> TYPE: RNA
<213> ORGANISM: Homo sapiens

<400> SEQUENCE: 327 guggcucccca cccucuguaa cagcaacucc auguggaagu gcccacuggu uccaguggg    60 cugcuguuau cugggguggc ggcuag                                         86
```

```
<210> SEQ ID NO 328
<211> LENGTH: 58
<212> TYPE: RNA
<213> ORGANISM: Homo sapiens

<400> SEQUENCE: 328
uagcagcaca gaaauauugg caugggaag ugagucugcc aauauuggcu gugcugcu       58
```

```
<210> SEQ ID NO 329
<211> LENGTH: 102
<212> TYPE: RNA
<213> ORGANISM: Homo sapiens

<400> SEQUENCE: 329
ugagccggga cguugagug aaguagguag uuucauguug uugggccugg cuuucugaac    60
acaacgacau caaaccaccu gauucauggc aguuacugcu uc                     102
```

```
<210> SEQ ID NO 330
<211> LENGTH: 85
<212> TYPE: RNA
<213> ORGANISM: Homo sapiens

<400> SEQUENCE: 330
agcugaucug uggcuuaggu aguuucaugu uguugggauu gaguuugaa cucggcaaca    60 agaaacugcc ugaguuacau caguc                                         85
```

```
<210> SEQ ID NO 331
<211> LENGTH: 70
<212> TYPE: RNA
<213> ORGANISM: Homo sapiens

<400> SEQUENCE: 331
gccaucccag uguucagacu accuguucag gaggcuggga cauguacagu agucugcaca    60
uugguuaggc                                                           70
```

```
<210> SEQ ID NO 332
<211> LENGTH: 110
<212> TYPE: RNA
<213> ORGANISM: Homo sapiens

<400> SEQUENCE: 332
uggaagcuuc aggagauccu gcuccgucgc cccagguuc agacuaccug uucaggacaa    60
ugccguugua caguagucug cacauugguu agacugggca agggccagca              110
```

```
<210> SEQ ID NO 333
<211> LENGTH: 110
<212> TYPE: RNA
```

-continued

<213> ORGANISM: Homo sapiens

<400> SEQUENCE: 333
ccagaggaua ccuccacucc gucuacccag uguuuagacu accguucag gacucccaaa        60 uuguacagua gucugcacau ugguuaggcu gggcuggguu agacccucgg                  110

<210> SEQ ID NO 334
<211> LENGTH: 70
<212> TYPE: RNA
<213> ORGANISM: Homo sapiens

<400> SEQUENCE: 334
gccguggcca ucuuacuggg cagcauugga uagugucuga ucucuaauac ugccugguaa        60
ugaugacggc                                                              70

<210> SEQ ID NO 335
<211> LENGTH: 90
<212> TYPE: RNA
<213> ORGANISM: Homo sapiens

<400> SEQUENCE: 335
cugggccucu gugggcaucu uaccggacag ugcuggauuu cuuggcuuga cucuaacacu        60
gucugguaac gauguucaaa ggugacccac                                        90

<210> SEQ ID NO 336
<211> LENGTH: 69
<212> TYPE: RNA
<213> ORGANISM: Homo sapiens

<400> SEQUENCE: 336
cccucgucuu acccagcagu guuggguguc ugguugggag ucucuaauac ugccggguaa        60
ugauggagg                                                               69

<210> SEQ ID NO 337
<211> LENGTH: 66
<212> TYPE: RNA
<213> ORGANISM: Homo sapiens

<400> SEQUENCE: 337
uaccuuacuc aguaaggcau uguucuucua uauuaauaaa ugaacagugc cuuucugugu        60
agggua                                                                  66

<210> SEQ ID NO 338
<211> LENGTH: 72
<212> TYPE: RNA
<213> ORGANISM: Homo sapiens

<400> SEQUENCE: 338
guuccuuuuu ccuaugcaua uacuucuuug uggaucuggu cuaaagaggu auagcgcaug        60
ggaagaugga gc                                                           72

<210> SEQ ID NO 339
<211> LENGTH: 76
<212> TYPE: RNA
<213> ORGANISM: Homo sapiens

<400> SEQUENCE: 339
gccuggucca gugguucuug acaguucaac aguucuguag cacaauugug aaauguuuag        60
gaccacuaga cccggc                                                       76

<210> SEQ ID NO 340
<211> LENGTH: 68
<212> TYPE: RNA
<213> ORGANISM: Homo sapiens

<400> SEQUENCE: 340
uggacuuccc uuugucaucc uaugccugag aauauaugaa ggaggcuggg aaggcaaagg        60
gacguuca                                                                68

<210> SEQ ID NO 341
<211> LENGTH: 68
<212> TYPE: RNA
<213> ORGANISM: Homo sapiens

<400> SEQUENCE: 341 cucuugccu ucauuccacc ggagucuguc uuaugccaac cagauuucag uggagugaag         60
cucaggag                                                                68

<210> SEQ ID NO 342
<211> LENGTH: 73
<212> TYPE: RNA
<213> ORGANISM: Homo sapiens

<400> SEQUENCE: 342
ccaggccaca ugcuucuuua uauccucaua gauaucucag cacuauggaa uguaaggaag        60
ugugugguuu ugg                                                          73

<210> SEQ ID NO 343
<211> LENGTH: 79
<212> TYPE: RNA
<213> ORGANISM: Homo sapiens

<400> SEQUENCE: 343
aaggcagggg ugaggggcug cgggaggagc cgggcggagg cugcggcuug cgcuucuccu        60
ggcucuccuc ccucucuuu                                                    79

<210> SEQ ID NO 344
<211> LENGTH: 83
<212> TYPE: RNA
<213> ORGANISM: Homo sapiens

<400> SEQUENCE: 344
uuccuuugac ggguagcuu uuggcccggg uuauaccuga cacucacgua uaagacgagc         60
aaaaagcuug uuggucagag gag                                               83

<210> SEQ ID NO 345
<211> LENGTH: 110
<212> TYPE: RNA
<213> ORGANISM: Homo sapiens

<400> SEQUENCE: 345
ccggggcagu cccuccaggc ucaggacagc cacugcccac cgcacacugc guugcuccgg       60
acccacugug cgugugacag cggcugaucu gucccugggc agcgcgaacc                  110

<210> SEQ ID NO 346
<211> LENGTH: 106
<212> TYPE: RNA
<213> ORGANISM: Homo sapiens

<400> SEQUENCE: 346
cugcuuggac cugugaccug ugggcuuccc uuugucaucc uuugccuagg ccucugagug    60
aggcaaggac agcaaagggg ggcucagugg ucaccucuac ugcaga                 106

<210> SEQ ID NO 347
<211> LENGTH: 91
<212> TYPE: RNA
<213> ORGANISM: Homo sapiens

<400> SEQUENCE: 347
gggcagcgcg ccggcaccuu ggcucuagac ugcuuacugc ccgggccgcc uucaguaaca    60
gucuccaguc acggccaccg acgccuggcc c                                  91

<210> SEQ ID NO 348
<211> LENGTH: 87
<212> TYPE: RNA
<213> ORGANISM: Homo sapiens

<400> SEQUENCE: 348
gguugcuuca gugaacauuc aacgcugucg gugaguuugg aauucaaaua aaaaccaucg    60
accguugauu guacccuaua gcuaacc                                       87

<210> SEQ ID NO 349
<211> LENGTH: 110
<212> TYPE: RNA
<213> ORGANISM: Homo sapiens

<400> SEQUENCE: 349
ggccuggcug gacagaguug ucaugugucu gccugucuac acuugcugug cagaacaucc    60
gcucaccugu acagcaggca cagacaggca gucacaugac aacccagccu              110

<210> SEQ ID NO 350
<211> LENGTH: 112
<212> TYPE: RNA
<213> ORGANISM: Homo sapiens

<400> SEQUENCE: 350
agcucucagc aucaacggug uacaggagaa ugaccauga uuugacagac cgugcagcug     60
uguaugucug ucauucugua ggccaauauu cuguauguca cugcuacuua aa            112

<210> SEQ ID NO 351
<211> LENGTH: 72
<212> TYPE: RNA
<213> ORGANISM: Homo sapiens

<400> SEQUENCE: 351
uugguuuaau cucagcuggc aacugugaga ugucccuauc auuccucaca gggucucug     60 ggauuaugcu aa                                                       72

<210> SEQ ID NO 352
<211> LENGTH: 108
<212> TYPE: RNA
<213> ORGANISM: Homo sapiens

<400> SEQUENCE: 352
aaacauaguc auuacaguuu uugauguugc agauacugca ucaggaacug acuggauaag    60
acuuaauccc caucaguucc uaaugcauug ccuucagcau cuaaacaa                108

```
<210> SEQ ID NO 353
<211> LENGTH: 110
<212> TYPE: RNA
<213> ORGANISM: Homo sapiens

<400> SEQUENCE: 353
gaccaguugc cgcggggcuu uccuugugc uugaucuaac caugugguggaacgauggaa      60 acggaacaug guucugucaa gcaccgcgga aagcaucgcu cucuccugca              110

<210> SEQ ID NO 354
<211> LENGTH: 110
<212> TYPE: RNA
<213> ORGANISM: Homo sapiens

<400> SEQUENCE: 354
ccgucccggg ccgcggcucc ugauugucca aacgcaauuc ucgagcucu ggcuccggcc     60 gagaguugcg ucuggacguc ccgagccgcc gcccccaaac cucgaggggg              110

<210> SEQ ID NO 355
<211> LENGTH: 97
<212> TYPE: RNA
<213> ORGANISM: Homo sapiens

<400> SEQUENCE: 355
acucaggggc uucgccacug auuguccaaa cgcaauucuu guacgagucu gcggccaacc    60
gagaauugug gcuggacauc ugugguugag cuccggg                            97

<210> SEQ ID NO 356
<211> LENGTH: 95
<212> TYPE: RNA
<213> ORGANISM: Homo sapiens

<400> SEQUENCE: 356
auccaggucu ggggcaugaa ccuggcauac aauguagauu ucuguguuug uuaggcaaca    60
gcuacauugu cugcugggu ucaggcuacc uggaa                               95

<210> SEQ ID NO 357
<211> LENGTH: 79
<212> TYPE: RNA
<213> ORGANISM: Homo sapiens

<400> SEQUENCE: 357
cccucagugg ucaguagcc aguguagauc cugucuuugg uaaucagcag cuacaucugg     60
cuacuggguc ucggguggc                                                79

<210> SEQ ID NO 358
<211> LENGTH: 110
<212> TYPE: RNA
<213> ORGANISM: Homo sapiens

<400> SEQUENCE: 358
ucuggccauc ugcaguguca cgcuccgugu auuugacaag cugaguugga cacucugugu    60
gguagagugu caguuuguca aauaccccaa guguggcuca ugccuaucag              110

<210> SEQ ID NO 359
<211> LENGTH: 82
<212> TYPE: RNA
<213> ORGANISM: Homo sapiens

<400> SEQUENCE: 359
```

```
gggcuuuuaa gucacuagug guuccguuua guagaugguu ugugcauugu uucaaaaugg    60
ugcccuagug acuacaaagc cc                                            82

<210> SEQ ID NO 360
<211> LENGTH: 83
<212> TYPE: RNA
<213> ORGANISM: Homo sapiens

<400> SEQUENCE: 360
cucaucuugc gguacucaaa cuaugggggc acuuuuuuu uucuuuaaaa agugccgccu     60
aguuuuaagc cccgccgguu gag                                           83

<210> SEQ ID NO 361
<211> LENGTH: 82
<212> TYPE: RNA
<213> ORGANISM: Homo sapiens

<400> SEQUENCE: 361
ccuauguagc ggccaucaaa guggaggccc ucucuugagc cugaaugaga aagugcuucc    60
acuuugugug ccacugcaug gg                                            82

<210> SEQ ID NO 362
<211> LENGTH: 82
<212> TYPE: RNA
<213> ORGANISM: Homo sapiens

<400> SEQUENCE: 362
cagccuguga uacucaaacu gggggcucuu uuggauuuuc aucggaagaa aagugccgcc    60
agguuuugag ugucaccggu ug                                            82

<210> SEQ ID NO 363
<211> LENGTH: 80
<212> TYPE: RNA
<213> ORGANISM: Homo sapiens

<400> SEQUENCE: 363
uucaaucugu gguacucaaa cugugugaca uuuuguucuu uguaagaagu gccgcagagu    60
uuguaguguu gccgauugag                                               80

<210> SEQ ID NO 364
<211> LENGTH: 84
<212> TYPE: RNA
<213> ORGANISM: Homo sapiens

<400> SEQUENCE: 364
uuccauauag ccauacucaa aauggaggcc cuaucuaagc uuuuaagugg aaagugcuuc    60
ccuuuugugu guugccaugu ggag                                          84

<210> SEQ ID NO 365
<211> LENGTH: 69
<212> TYPE: RNA
<213> ORGANISM: Homo sapiens

<400> SEQUENCE: 365
ggugagacuc aaaugugggg cacacuucug gacuguacau agaaagugcu acuacuuuug    60
agucucucc                                                           69

<210> SEQ ID NO 366
<211> LENGTH: 79
```

<212> TYPE: RNA
<213> ORGANISM: Homo sapiens

<400> SEQUENCE: 366
gggccuuucu ggagggcccc cccucaaucc uguugugcuc gcucagagg guugggugga    60 ggcucuccug aaggugucc                                                79

<210> SEQ ID NO 367
<211> LENGTH: 76
<212> TYPE: RNA
<213> ORGANISM: Homo sapiens

<400> SEQUENCE: 367
auauguaugu auguauguau gugugcaugu gcaugugcau guaugcauau uguauguaua    60
uauuaugcau acaugu                                                   76

<210> SEQ ID NO 368
<211> LENGTH: 64
<212> TYPE: RNA
<213> ORGANISM: Homo sapiens

<400> SEQUENCE: 368
uguaugugca ugcauaugug cucaugugug uguacaugua ugugugcaug ugcauguaua    60
uaug                                                                64

<210> SEQ ID NO 369
<211> LENGTH: 82
<212> TYPE: RNA
<213> ORGANISM: Homo sapiens

<400> SEQUENCE: 369
ccaggccuuu ggcagaggag ggcuguucuu cccuugaguu uuaugacugg gaggaacuag    60
ccuucucuca gcuuaggagu gg                                            82

<210> SEQ ID NO 370
<211> LENGTH: 63
<212> TYPE: RNA
<213> ORGANISM: Homo sapiens

<400> SEQUENCE: 370
aagaaauggu uuaccgucc acauacauuu ugaguaugua uggggacgg uaaaccgcuu     60 cuu                                                                 63

<210> SEQ ID NO 371
<211> LENGTH: 79
<212> TYPE: RNA
<213> ORGANISM: Homo sapiens

<400> SEQUENCE: 371
gcuacuugaa gagagguuau ccuuugugug uuugcuuuac gcgaaaugaa uaugcaaggg    60
caagcucucu ucgaggagc                                                79

<210> SEQ ID NO 372
<211> LENGTH: 86
<212> TYPE: RNA
<213> ORGANISM: Homo sapiens

<400> SEQUENCE: 372
ccugcuaacg gcugcucuga cuuuauugca cuacuguacu uuacagcgag cagugcaaua    60

-continued

| | |
|---|---|
| guauugucaa agcauccgcg agcagg | 86 |

<210> SEQ ID NO 373
<211> LENGTH: 69
<212> TYPE: RNA
<213> ORGANISM: Homo sapiens

<400> SEQUENCE: 373

| | |
|---|---|
| ccaccacuua aacgugguug uacuugcuuu agaccuaaga aaguaagugc uuccauguuu | 60 |
| uggugaugg | 69 |

<210> SEQ ID NO 374
<211> LENGTH: 82
<212> TYPE: RNA
<213> ORGANISM: Homo sapiens

<400> SEQUENCE: 374

| | |
|---|---|
| gccucgccgc ccuccgccuu cucuucccgg uucuucccgg agucgggaaa agcugggbuug | 60 |
| agagggcgaa aaaggaugug gg | 82 |

<210> SEQ ID NO 375
<211> LENGTH: 59
<212> TYPE: RNA
<213> ORGANISM: Homo sapiens

<400> SEQUENCE: 375

| | |
|---|---|
| uuggccuccu aagccaggga uugugggbuuc gagucccacc cggggugauaug agguguuuu | 59 |

<210> SEQ ID NO 376
<211> LENGTH: 86
<212> TYPE: RNA
<213> ORGANISM: Homo sapiens

<400> SEQUENCE: 376

| | |
|---|---|
| uugguacuug gagagaggug guccguggcg cguucgcuuc auuuauggcg cacauuacac | 60 |
| ggucgaccuc uuugcgguau cuaauc | 86 |

<210> SEQ ID NO 377
<211> LENGTH: 89
<212> TYPE: RNA
<213> ORGANISM: Homo sapiens

<400> SEQUENCE: 377

| | |
|---|---|
| aacugacuau gccuccucgc auccccuagg gcauuggugu aaagcuggag acccacugcc | 60 |
| ccaggugcug cuggggguug uagucugac | 89 |

<210> SEQ ID NO 378
<211> LENGTH: 98
<212> TYPE: RNA
<213> ORGANISM: Homo sapiens

<400> SEQUENCE: 378

| | |
|---|---|
| auauagugcu ugguuccuag uaggugcuca guaaguguuu gugacauaau ucguuuauug | 60 |
| agcaccuccu aucaaucaag cacugugcua ggcucugg | 98 |

<210> SEQ ID NO 379
<211> LENGTH: 95
<212> TYPE: RNA
<213> ORGANISM: Homo sapiens

<400> SEQUENCE: 379

```
cucaucuguc uguugggcug ggggcagggc cuuugugaag gcggguuaug cucagaucgc    60
cucugggccc uuccuccagu cccgaggcag auuua                              95

<210> SEQ ID NO 380
<211> LENGTH: 97
<212> TYPE: RNA
<213> ORGANISM: Homo sapiens

<400> SEQUENCE: 380
cugucucgga gccuggggca gggggggcagg aggggcucag ggagaaagua ucuacagccc   60
cuggcccucu cugcccuucc gucccguc cccaagu                               97

<210> SEQ ID NO 381
<211> LENGTH: 97
<212> TYPE: RNA
<213> ORGANISM: Homo sapiens

<400> SEQUENCE: 381
uguucgcuuc ugguaccgga agagagguuu ucgggucuc uguuucuuug augagaauga    60
aacacaccca gcuaaccuuu uuucaguau caaaucc                              97

<210> SEQ ID NO 382
<211> LENGTH: 98
<212> TYPE: RNA
<213> ORGANISM: Homo sapiens

<400> SEQUENCE: 382
gacccuuugg cgaucucugc cucucugggc cuguguccuua ggcucuucaa gauccaacga  60
gcaaagcaca gggccugcag agagguagcg cucugcuc                            98

<210> SEQ ID NO 383
<211> LENGTH: 96
<212> TYPE: RNA
<213> ORGANISM: Homo sapiens

<400> SEQUENCE: 383
gagucugguu uuguuggggu uuguucuagg uauggcccca gggaucccag aucaaaccag    60
gccccugggc cuauccuaga accaaccuaa acccgu                              96

<210> SEQ ID NO 384
<211> LENGTH: 97
<212> TYPE: RNA
<213> ORGANISM: Homo sapiens

<400> SEQUENCE: 384
caguguagug agaaguuggg ggguggggaac ggcgucaugc aggaguugau ugcacagcca   60
uucagcuccu auaugaugcc uuucuucacc cccuuca                             97

<210> SEQ ID NO 385
<211> LENGTH: 98
<212> TYPE: RNA
<213> ORGANISM: Homo sapiens

<400> SEQUENCE: 385
caacgcugca caggccgucc uccccaacaa uauccuggug cugaguggu gcacagugac     60 uccagcauca gugauuuugu ugaagagggc agcugcca                            98

<210> SEQ ID NO 386
```

```
<211> LENGTH: 96
<212> TYPE: RNA
<213> ORGANISM: Homo sapiens

<400> SEQUENCE: 386
acggggugcc cacuaucccu guccuccagg agcucacgua ugccugccug ugagcgccuc    60
ggcgacagag ccggugucca ccccugcacu guccac                              96

<210> SEQ ID NO 387
<211> LENGTH: 98
<212> TYPE: RNA
<213> ORGANISM: Homo sapiens

<400> SEQUENCE: 387
caauuguacu uggugugauu auaaagcaau gagacugauu gcauaugc guuugggga       60 uccgucucag uuacuuuaua gccauaccug guaucuua                            98

<210> SEQ ID NO 388
<211> LENGTH: 96
<212> TYPE: RNA
<213> ORGANISM: Homo sapiens

<400> SEQUENCE: 388
aaaaugauga ugucaguugg ccggucggcc gaucgcucgg ucgucaguc agucggucgg    60 ucgaucgguc ggucggucag ucggcuuccu gucuuc                              96

<210> SEQ ID NO 389
<211> LENGTH: 99
<212> TYPE: RNA
<213> ORGANISM: Homo sapiens

<400> SEQUENCE: 389
gaaaaugggc ucaaggugag gggugcuauc ugugauugag ggacauggc aauggaauug    60 ucucacacag aaaucgcacc cgucaccuug gccugcuga                           99

<210> SEQ ID NO 390
<211> LENGTH: 95
<212> TYPE: RNA
<213> ORGANISM: Homo sapiens

<400> SEQUENCE: 390
cugcagccag gguuuuuacc agucaggcuc cuggcuagau uccagguacc agcugguacc    60
ugaucuagcc aaagccugac uguaagcccu gaaca                               95

<210> SEQ ID NO 391
<211> LENGTH: 96
<212> TYPE: RNA
<213> ORGANISM: Homo sapiens

<400> SEQUENCE: 391
acccaagucc aggccugcug accccuaguc cagucuugu gguggcuacu gggcccugaa    60
cuaggggucu ggagaccugg guuugaucuc cacagg                              96

<210> SEQ ID NO 392
<211> LENGTH: 98
<212> TYPE: RNA
<213> ORGANISM: Homo sapiens

<400> SEQUENCE: 392
ucuguguugg gcgucugucu gcccgagugc cugccucucu guugcucuga aggaggcagg    60
```

```
ggcugggccu gcagcugccu gggcagagcu gcuccuuc                              98

<210> SEQ ID NO 393
<211> LENGTH: 99
<212> TYPE: RNA
<213> ORGANISM: Homo sapiens

<400> SEQUENCE: 393
agaugccuug cuccuacaag aguaaagugc augcgcuuug ggacagugag gaaaauaaug      60
uucacaaagc ccauacacuu ucacccuuua ggagaguug                             99

<210> SEQ ID NO 394
<211> LENGTH: 98
<212> TYPE: RNA
<213> ORGANISM: Rattus norvegicus

<400> SEQUENCE: 394
ugggcuccua ggaagaggua guagguugca uaguuuuagg gcagagauuu ugcccacaag      60
gaguuaacua uacgaccugc ugccuuucuu agggccuu                              98

<210> SEQ ID NO 395
<211> LENGTH: 97
<212> TYPE: RNA
<213> ORGANISM: Rattus norvegicus

<400> SEQUENCE: 395
uguuggccua guucugugug gaagacuagu gauuuuguug uuuuuagaua acuaagacga      60
caacaaauca cagucugcca uaggcacag gccaccu                                97

<210> SEQ ID NO 396
<211> LENGTH: 94
<212> TYPE: RNA
<213> ORGANISM: Rattus norvegicus

<400> SEQUENCE: 396
uucacugugg gaugagguag uagguuguau aguuuuaggg ucacacccac cacugggaga      60
uaacuauaca aucuacuguc uuuccuaagg ugau                                  94

<210> SEQ ID NO 397
<211> LENGTH: 96
<212> TYPE: RNA
<213> ORGANISM: Rattus norvegicus

<400> SEQUENCE: 397
cggcaugcuc ccaggcugag guaguagguu guauaguuua gaguuacaac aagggagaua      60
acuguacagc cuccuagcuu uccuugggac uugcac                                96

<210> SEQ ID NO 398
<211> LENGTH: 85
<212> TYPE: RNA
<213> ORGANISM: Rattus norvegicus

<400> SEQUENCE: 398
gcggggugag guaguagguu guguggguuc agggcaguga ugucgccccu ccgaagauaa      60
cuauacaacc uacugccuuc ccuga                                            85

<210> SEQ ID NO 399
<211> LENGTH: 94
<212> TYPE: RNA
```

-continued

<213> ORGANISM: Rattus norvegicus

<400> SEQUENCE: 399
ugugugcauc cggguugagg uaguagguug uaugguuuag aguuacaccc ugggaguuaa    60 cguacaacc uucuagcuuu ccuuggagca cacu    94

<210> SEQ ID NO 400
<211> LENGTH: 95
<212> TYPE: RNA
<213> ORGANISM: Rattus norvegicus

<400> SEQUENCE: 400
acggccuuug gggugaggua guagguugua ugguuuggg cucugccccg cucugcggua    60
acuauacaau cuacugucuu uccgaagug gccgc    95

<210> SEQ ID NO 401
<211> LENGTH: 93
<212> TYPE: RNA
<213> ORGANISM: Rattus norvegicus

<400> SEQUENCE: 401 cgcgccccc gggcugaggu aggagguugu auaguugagg aagacacccg aggagaucac    60
uauacggccu ccuagcuuuc cccaggcugc gcc    93

<210> SEQ ID NO 402
<211> LENGTH: 89
<212> TYPE: RNA
<213> ORGANISM: Rattus norvegicus

<400> SEQUENCE: 402
aucagaguga gguaguagau uguauaguug uggggaugu auuuuacccu guuuaggaga    60
uaacuauaca aucuauugcc uucccugag    89

<210> SEQ ID NO 403
<211> LENGTH: 83
<212> TYPE: RNA
<213> ORGANISM: Rattus norvegicus

<400> SEQUENCE: 403
ugugggauga gguaguagau uguauaguuu uagggucaua ccccaucuug gagauaacua    60
uacagucuac ugucuuuccc acg    83

<210> SEQ ID NO 404
<211> LENGTH: 85
<212> TYPE: RNA
<213> ORGANISM: Rattus norvegicus

<400> SEQUENCE: 404
cuggcugagg uaguaguuug ugcuguuggu cgguuguga cauugcccgc uguggagaua    60
acugcgcaag cuacugccuu gcuag    85

<210> SEQ ID NO 405
<211> LENGTH: 95
<212> TYPE: RNA
<213> ORGANISM: Rattus norvegicus

<400> SEQUENCE: 405
ggacagacca gcccugucug gaagacuagu gauuuuguug uugugucugu guccaacaac    60
aagucccagu cugccacaug guguugguca cauca    95

<210> SEQ ID NO 406
<211> LENGTH: 110
<212> TYPE: RNA
<213> ORGANISM: Rattus norvegicus

<400> SEQUENCE: 406
aggccagaac acaugagcca augcuaugug gaagacuugu gauuuguug uucugauaug      60 auaugacaac aagucacagc cagccucaua gaguggacuc ccaucaccuu               110

<210> SEQ ID NO 407
<211> LENGTH: 89
<212> TYPE: RNA
<213> ORGANISM: Rattus norvegicus

<400> SEQUENCE: 407 cggggiuggu uguuaucuuu gguuaucuag cuguaugagu ggugguggagu cuucauaaag    60 cuagauaacc gaaaguaaaa auaacccca                                      89

<210> SEQ ID NO 408
<211> LENGTH: 90
<212> TYPE: RNA
<213> ORGANISM: Rattus norvegicus

<400> SEQUENCE: 408
ggaggcccgu uucucucuuu gguuaucuag cuguaugagu gccacagagc cgucauaaag    60
cuagauaacc gaaaguagaa augacucuaa                                     90

<210> SEQ ID NO 409
<211> LENGTH: 87
<212> TYPE: RNA
<213> ORGANISM: Rattus norvegicus

<400> SEQUENCE: 409
ggaagcgagu uguuaucuuu gguuaucuag cuguaugagu guauuggucu ucauaaagcu    60
agauaaccga aaguaaaaac uccuuca                                        87

<210> SEQ ID NO 410
<211> LENGTH: 110
<212> TYPE: RNA
<213> ORGANISM: Rattus norvegicus

<400> SEQUENCE: 410
gaccugucug ucuucuguau auacccugua gauccgaauu uguguaagga auuuguggu     60 cacaaauucg uaucuagggg aauauguagu ugacauaaac acuccgcuca               110

<210> SEQ ID NO 411
<211> LENGTH: 109
<212> TYPE: RNA
<213> ORGANISM: Rattus norvegicus

<400> SEQUENCE: 411
ccaaaguugu aacguugucu auauauaccc uguagaaccg aauuguguug guacccacau    60
agucacagau ucgauucuag gggaauauau ggucgaugca aaaacuuca                109

<210> SEQ ID NO 412
<211> LENGTH: 98
<212> TYPE: RNA
<213> ORGANISM: Rattus norvegicus

<400> SEQUENCE: 412
uuggaaccuu aaaguacugu agcagcacau caugguuuac auacuacagu caagaugcga    60
aucauuauuu gcugcucuag aaauuuaagg aaauucau    98

<210> SEQ ID NO 413
<211> LENGTH: 95
<212> TYPE: RNA
<213> ORGANISM: Rattus norvegicus

<400> SEQUENCE: 413
cauacuuguu ccgcucuagc agcacguaaa uauuggcgua gugaaauaaa uauuaaacac    60
caauauuauu gugcugcuuu agugugacag ggaua    95

<210> SEQ ID NO 414
<211> LENGTH: 84
<212> TYPE: RNA
<213> ORGANISM: Rattus norvegicus

<400> SEQUENCE: 414
gucaggauaa ugucaaagug cuuacagugc agguaguggu gugugcaucu acugcaguga    60
aggcacuugu ggcauugugc ugac    84

<210> SEQ ID NO 415
<211> LENGTH: 96
<212> TYPE: RNA
<213> ORGANISM: Rattus norvegicus

<400> SEQUENCE: 415
ugcgugcuuu uuguucuaag gugcaucuag ugcagauagu gaaguagacu agcaucuacu    60
gcccuaagug cuccuucugg cauaagaagu uauguc    96

<210> SEQ ID NO 416
<211> LENGTH: 87
<212> TYPE: RNA
<213> ORGANISM: Rattus norvegicus

<400> SEQUENCE: 416
cacuggucua ugguuaguuu ugcagguuug cauccagcug uauaauauuc ugcugugcaa    60
auccaugcaa aacugacugu gguggug    87

<210> SEQ ID NO 417
<211> LENGTH: 96
<212> TYPE: RNA
<213> ORGANISM: Rattus norvegicus

<400> SEQUENCE: 417
acauugcuac uuacgguuag uuuugcagau uugcaguuca gcguauaugu ggauauaugg    60
cugugcaaau ccaugcaaaa cugauuguga ugaugu    96

<210> SEQ ID NO 418
<211> LENGTH: 82
<212> TYPE: RNA
<213> ORGANISM: Rattus norvegicus

<400> SEQUENCE: 418
gcagcccucu guucguuuug cauaguugca cuacaagaag aauguaguug ugcaaaucua    60
ugcaaaacug augugggccu gc    82

```
<210> SEQ ID NO 419
<211> LENGTH: 85
<212> TYPE: RNA
<213> ORGANISM: Rattus norvegicus

<400> SEQUENCE: 419
cagcuucugu agcacuaaag ugcuuauagu gcagguagug ugucgucauc uacugcauua    60
cgagcacuua caguacugcc agcug                                         85

<210> SEQ ID NO 420
<211> LENGTH: 92
<212> TYPE: RNA
<213> ORGANISM: Rattus norvegicus

<400> SEQUENCE: 420
uguaccaccu ugucggguag cuuaucagac ugauguugac uguugaaucu cauggcaaca    60
gcagucgaug ggcugucuga cauuuuggua uc                                 92

<210> SEQ ID NO 421
<211> LENGTH: 95
<212> TYPE: RNA
<213> ORGANISM: Rattus norvegicus

<400> SEQUENCE: 421
accuggcuga gccgcaguag uucuucagug gcaagcuuua ugccugacc cagcuaaagc     60 ugccaguuga agaacuguug cccucugcca cuggc                              95

<210> SEQ ID NO 422
<211> LENGTH: 75
<212> TYPE: RNA
<213> ORGANISM: Rattus norvegicus

<400> SEQUENCE: 422
cggccggcug gggguuccugg ggaugggauu ugaugccagu cacaaaucac auugccaggg   60
auuuccaacu gaccc                                                    75

<210> SEQ ID NO 423
<211> LENGTH: 97
<212> TYPE: RNA
<213> ORGANISM: Rattus norvegicus

<400> SEQUENCE: 423
cucaccugcu cuggcugcuu gggguuccugg caugcugauu ugugacuuga gauuaaaauc   60
acauugccag ggauuaccac gcaaccauga ccuuggc                            97

<210> SEQ ID NO 424
<211> LENGTH: 68
<212> TYPE: RNA
<213> ORGANISM: Rattus norvegicus

<400> SEQUENCE: 424
cuccggugcc uacugagcug auaucaguuc ucauuucaca cacuggcuca guucagcagg    60
aacaggag                                                            68

<210> SEQ ID NO 425
<211> LENGTH: 108
<212> TYPE: RNA
<213> ORGANISM: Rattus norvegicus

<400> SEQUENCE: 425
```

```
gccucucccu gggcuccgcc uccugugccu acugagcuga aacaguugau uccagugcac    60
uggcucaguu cagcaggaac aggaguccag cccccauagg agcuggca               108

<210> SEQ ID NO 426
<211> LENGTH: 84
<212> TYPE: RNA
<213> ORGANISM: Rattus norvegicus

<400> SEQUENCE: 426
ggccaguguu gagaggcgga gacacgggca auugcuggac gcugcccugg gcauugcacu    60
ugucucgguc ugacagugcc ggcc                                         84

<210> SEQ ID NO 427
<211> LENGTH: 90
<212> TYPE: RNA
<213> ORGANISM: Rattus norvegicus

<400> SEQUENCE: 427
aaggccgugg ccuuguucaa guaauccagg auaggcugug caggucccaa ggggccuauu    60
cuugguuacu ugcacgggga cgcgggccug                                   90

<210> SEQ ID NO 428
<211> LENGTH: 85
<212> TYPE: RNA
<213> ORGANISM: Rattus norvegicus

<400> SEQUENCE: 428
ugcccgggac ccaguucaag uaauucagga uagguguggg ugcuggccag ccuguucucc    60
auuacuuggc ucgggggccg gugcc                                        85

<210> SEQ ID NO 429
<211> LENGTH: 97
<212> TYPE: RNA
<213> ORGANISM: Rattus norvegicus

<400> SEQUENCE: 429
accucucuaa caaggugcag agcuuagcug auuggugaac agugauuggu uccgcuuug     60 uucacagugg cuaaguucug caccugaaga gaaggug                           97

<210> SEQ ID NO 430
<211> LENGTH: 87
<212> TYPE: RNA
<213> ORGANISM: Rattus norvegicus

<400> SEQUENCE: 430
uggccugugg agcagggcuu agcugcuugu gagcaagguc uacagcaaag ucguguucac    60
aguggcuaag uuccgccccc uggaccc                                      87

<210> SEQ ID NO 431
<211> LENGTH: 86
<212> TYPE: RNA
<213> ORGANISM: Rattus norvegicus

<400> SEQUENCE: 431
ggucccuacc cgcaaggagc ucacagucua uugaguuccu uuucugauuc ucccacuaga    60
uugugagcuc cuggagggca ggcacu                                       86

<210> SEQ ID NO 432
<211> LENGTH: 81
```

```
<212> TYPE: RNA
<213> ORGANISM: Rattus norvegicus

<400> SEQUENCE: 432
cuucuggaag cugguuucac auggugggcuu agauuuuucc aucuuuguau cuagcaccau    60
uugaaaucag uguuuuagga g                                              81

<210> SEQ ID NO 433
<211> LENGTH: 88
<212> TYPE: RNA
<213> ORGANISM: Rattus norvegicus

<400> SEQUENCE: 433
accccuuaga ggaugacuga uuucuuuugg uguucagagu caauagaaauu uucuagcacc   60 aucugaaauc gguuauaaug auuggga                                        88

<210> SEQ ID NO 434
<211> LENGTH: 81
<212> TYPE: RNA
<213> ORGANISM: Rattus norvegicus

<400> SEQUENCE: 434
cuucaggaag cugguuucau auggugguuu agauuuaaau agugauuguc uagcaccauu    60
ugaaaucagu guucuuggug g                                              81

<210> SEQ ID NO 435
<211> LENGTH: 88
<212> TYPE: RNA
<213> ORGANISM: Rattus norvegicus

<400> SEQUENCE: 435
aucucuuaca caggcugacc gauuucuccu gguguucaga gucuguuuuu gucuagcacc    60
auuugaaauc gguuaugaug uaggggga                                       88

<210> SEQ ID NO 436
<211> LENGTH: 89
<212> TYPE: RNA
<213> ORGANISM: Rattus norvegicus

<400> SEQUENCE: 436
accauguugu agugugugua aacauccuac acucucagcu gugagcucaa gguggcuggg    60 agagggguugu uuacuccuuc ugccaugga                                     89

<210> SEQ ID NO 437
<211> LENGTH: 64
<212> TYPE: RNA
<213> ORGANISM: Rattus norvegicus

<400> SEQUENCE: 437
cuguaaacau ccuugacugg aagcuguaag guguugagag gagcuuucag ucggauguuu    60
acag                                                                 64

<210> SEQ ID NO 438
<211> LENGTH: 87
<212> TYPE: RNA
<213> ORGANISM: Rattus norvegicus

<400> SEQUENCE: 438
ccgaguuuca guucauguaa acauccuaca cucagcuguc auacaugagu uggcugggau    60
```
guggauguuu acgucagcug ucuugga    87

<210> SEQ ID NO 439
<211> LENGTH: 82
<212> TYPE: RNA
<213> ORGANISM: Rattus norvegicus

<400> SEQUENCE: 439
aagucugugu cuguaaacau ccccgacugg aagcuguaag ccacagccaa gcuuucaguc    60
agauguuugc ugcuacuggc uc    82

<210> SEQ ID NO 440
<211> LENGTH: 71
<212> TYPE: RNA
<213> ORGANISM: Rattus norvegicus

<400> SEQUENCE: 440
gcaacuguaa acauccucga cuggaagcug ugaagccaca aaugggcuuu cagucggaug    60
uuugcagcug c    71

<210> SEQ ID NO 441
<211> LENGTH: 84
<212> TYPE: RNA
<213> ORGANISM: Rattus norvegicus

<400> SEQUENCE: 441
gagugacaga uacuguaaac auccuacacu cucagcugug aaaaguaaga aagcugggag    60
aaggcuguuu acucucucug ccuu    84

<210> SEQ ID NO 442
<211> LENGTH: 106
<212> TYPE: RNA
<213> ORGANISM: Rattus norvegicus

<400> SEQUENCE: 442
ugcuccugaa acuuggaacu ggagaggagg caagaugcug gcauagcugu ugaacugaga    60
accugcuaug ccaacauauu gccaucuuuc cgucugaca gcagcu    106

<210> SEQ ID NO 443
<211> LENGTH: 70
<212> TYPE: RNA
<213> ORGANISM: Rattus norvegicus

<400> SEQUENCE: 443
ggggauauug cacauuacua aguugcaugu ugcacggcc ucaaugcaau uuagugugug    60
ugauauucuc    70

<210> SEQ ID NO 444
<211> LENGTH: 69
<212> TYPE: RNA
<213> ORGANISM: Rattus norvegicus

<400> SEQUENCE: 444
ccguggugca uuguaguugc auugcauguu cuggcaguac cugugcaaug uuuccacagu    60
gcaucacgg    69

<210> SEQ ID NO 445
<211> LENGTH: 84
<212> TYPE: RNA
<213> ORGANISM: Rattus norvegicus

<400> SEQUENCE: 445
gugcucgguu uguaggcagu guaauuagcu gauuguagug cggugcugac aaucacuaac    60
uccacugcca ucaaaacaag gcac    84

<210> SEQ ID NO 446
<211> LENGTH: 77
<212> TYPE: RNA
<213> ORGANISM: Rattus norvegicus

<400> SEQUENCE: 446
agucuaguua cuaggcagug uaguuagcug auugcuaaua guaccaauca cuaccacac    60 agccagguaa aaagacu    77

<210> SEQ ID NO 447
<211> LENGTH: 102
<212> TYPE: RNA
<213> ORGANISM: Rattus norvegicus

<400> SEQUENCE: 447
ccggcuguga guaauucuuu ggcagugucu uagcugguug uugugaguau uagcuaagga    60
agcaaucagc aaguauacug cccuagaagu gcugcacguu gu    102

<210> SEQ ID NO 448
<211> LENGTH: 78
<212> TYPE: RNA
<213> ORGANISM: Rattus norvegicus

<400> SEQUENCE: 448
cuuucuacac agguugggau uugcgcaau gcuguguuuc uguauaguau ugcacuuguc    60
ccggccuguu gaguuugg    78

<210> SEQ ID NO 449
<211> LENGTH: 92
<212> TYPE: RNA
<213> ORGANISM: Rattus norvegicus

<400> SEQUENCE: 449
ugcccauuca uccacaggug gggauuagug ccauuacuug uguuagauaa aaaguauugc    60
acuguccccg gccugaggaa gaaaagaggg uu    92

<210> SEQ ID NO 450
<211> LENGTH: 87
<212> TYPE: RNA
<213> ORGANISM: Rattus norvegicus

<400> SEQUENCE: 450
agucaugggg gcuccaaagu gcuguucgug cagguagugc auugccugac cuacugcuga    60
gcuagcacuu cccgagcccc caggaca    87

<210> SEQ ID NO 451
<211> LENGTH: 106
<212> TYPE: RNA
<213> ORGANISM: Rattus norvegicus

<400> SEQUENCE: 451
ccaguaccau cugcuuggcc gauuuuggca cuagcacauu uuugcuugug ucucuccgcu    60
cugagcaauc augugcagug ccaauauggg aaaagcgggc ugcugc    106

```
<210> SEQ ID NO 452
<211> LENGTH: 80
<212> TYPE: RNA
<213> ORGANISM: Rattus norvegicus

<400> SEQUENCE: 452
gugagguagu aaguuguauu guugugggu agggauuuua ggccccaaua agaagauaac      60
uauacaacuu acuacuuucc                                                80

<210> SEQ ID NO 453
<211> LENGTH: 81
<212> TYPE: RNA
<213> ORGANISM: Rattus norvegicus

<400> SEQUENCE: 453
cccauuggca uaaacccgua gauccgaucu guggugaag uggaccgcac aagcucguuu      60
cuaugggucu guggcagugu g                                              81

<210> SEQ ID NO 454
<211> LENGTH: 70
<212> TYPE: RNA
<213> ORGANISM: Rattus norvegicus

<400> SEQUENCE: 454
ggcacccacc cguagaaccg accuugcggg gccuucgccg cacacaagcu cgugucugug    60
gguccguguc                                                           70

<210> SEQ ID NO 455
<211> LENGTH: 80
<212> TYPE: RNA
<213> ORGANISM: Rattus norvegicus

<400> SEQUENCE: 455
ccuguugcca caaacccgua gauccgaacu gugcugacc augcacacaa gcuugugucu     60
auagguaugu gucuguuagg                                                80

<210> SEQ ID NO 456
<211> LENGTH: 97
<212> TYPE: RNA
<213> ORGANISM: Rattus norvegicus

<400> SEQUENCE: 456
aucugagacu gaacuguccu uuucgguua ucaugguacc gaugcuguag aucugaaagg     60
uacaguacug ugauagcuga agaauggugg ugccauc                             97

<210> SEQ ID NO 457
<211> LENGTH: 75
<212> TYPE: RNA
<213> ORGANISM: Rattus norvegicus

<400> SEQUENCE: 457
ugcccuggcu caguuaucac agugcugaug cuguccauuc uaaagguaca guacugau      60 aacugaagga uggca                                                     75

<210> SEQ ID NO 458
<211> LENGTH: 86
<212> TYPE: RNA
<213> ORGANISM: Rattus norvegicus

<400> SEQUENCE: 458
```

```
gucuucgugc uuucagcuuc uuuacagugc ugccuuguag cauucagguc aagcagcauu    60
guacagggcu augaaagaac caagaa                                         86

<210> SEQ ID NO 459
<211> LENGTH: 86
<212> TYPE: RNA
<213> ORGANISM: Rattus norvegicus

<400> SEQUENCE: 459
uucuuacugc ccucggcuuc uuuacagugc ugccuuguug cauauggauc aagcagcauu    60
guacagggcu augaaggcau ugagac                                         86

<210> SEQ ID NO 460
<211> LENGTH: 82
<212> TYPE: RNA
<213> ORGANISM: Rattus norvegicus

<400> SEQUENCE: 460
ccugcuggga cuaaagugcu gacagugcag auaguggucc ucucugugcu accgcacugu    60
ggguacuugc ugcuccagca gg                                             82

<210> SEQ ID NO 461
<211> LENGTH: 87
<212> TYPE: RNA
<213> ORGANISM: Rattus norvegicus

<400> SEQUENCE: 461
uucucucugc uuuaagcuuc uuuacagugu ugccuugugg cauggaguuc aagcagcauu    60
guacagggcu aucaaagcac agagagc                                        87

<210> SEQ ID NO 462
<211> LENGTH: 85
<212> TYPE: RNA
<213> ORGANISM: Rattus norvegicus

<400> SEQUENCE: 462
ccuuagcaga gcucuggagu gugacaaugg uguuugeguc caaaacauca aacgccauca    60
ucacacuaaa cagcuacugc uaggc                                          85

<210> SEQ ID NO 463
<211> LENGTH: 87
<212> TYPE: RNA
<213> ORGANISM: Rattus norvegicus

<400> SEQUENCE: 463
ugagggcccc ucugcguguu cacagcggac cuugauuuaa ugucuauaca auuaaggcac    60
gcggugaaug ccaagagagg cgccucc                                        87

<210> SEQ ID NO 464
<211> LENGTH: 85
<212> TYPE: RNA
<213> ORGANISM: Rattus norvegicus

<400> SEQUENCE: 464
aggccucucu cuccguguuc acagcggacc uugauuuaaa ugccauaca auuaaggcac     60 gcggugaaug ccaagaaugg ggcug                                          85

<210> SEQ ID NO 465
```

```
<211> LENGTH: 109
<212> TYPE: RNA
<213> ORGANISM: Rattus norvegicus

<400> SEQUENCE: 465
aucaagauca gagacucugc ucuccguguu cacagcggac cuugauuuaa ugucauacaa    60
uuaaggcacg cggugaaugc caagagcgga gccuacggcu gcacuugaa               109

<210> SEQ ID NO 466
<211> LENGTH: 85
<212> TYPE: RNA
<213> ORGANISM: Rattus norvegicus

<400> SEQUENCE: 466
ugccggccuc ugggucccug agacccuuua accugugagg acguccaggg ucacagguga    60
gguucuuggg agccuggcgc cuggc                                         85

<210> SEQ ID NO 467
<211> LENGTH: 87
<212> TYPE: RNA
<213> ORGANISM: Rattus norvegicus

<400> SEQUENCE: 467
ugcgcuccuc ucagucccug agacccuaac uugugauguu uaccguuuaa auccacgggu    60
uaggcucuug ggagcugcga gucgugc                                       87

<210> SEQ ID NO 468
<211> LENGTH: 88
<212> TYPE: RNA
<213> ORGANISM: Rattus norvegicus

<400> SEQUENCE: 468
accagacuuu uccuagucccc ugagacccua acuugugagg uauuuuagua acaucacaag    60
ucaggcucuu gggaccuagg cggagagg                                      88

<210> SEQ ID NO 469
<211> LENGTH: 73
<212> TYPE: RNA
<213> ORGANISM: Rattus norvegicus

<400> SEQUENCE: 469
ugacagcaca uuauuacuuu ugguacgcgc ugugacacuu caaacucgua ccgugaguaa    60
uaaugcgugg uca                                                      73

<210> SEQ ID NO 470
<211> LENGTH: 97
<212> TYPE: RNA
<213> ORGANISM: Rattus norvegicus

<400> SEQUENCE: 470
uuugaucacu gucuccagcc ugcugaagcu cagagggcuc ugauucagaa agaucaucgg    60
auccgucuga gcuuggcugg ucggaagucu caucauc                            97

<210> SEQ ID NO 471
<211> LENGTH: 82
<212> TYPE: RNA
<213> ORGANISM: Rattus norvegicus

<400> SEQUENCE: 471
ugagcuguug gauucggggc cguagcacug ucugagaggu uuacauuucu cacagugaac    60
```
cggucucuuu uucagcugcu uc                                             82

<210> SEQ ID NO 472
<211> LENGTH: 84
<212> TYPE: RNA
<213> ORGANISM: Rattus norvegicus

<400> SEQUENCE: 472
ugugcagugg aagggggggc cgaugcacug uaagagagug aguagcaggu cucacaguga    60
accggucucu uucccuacug uguc                                           84

<210> SEQ ID NO 473
<211> LENGTH: 97
<212> TYPE: RNA
<213> ORGANISM: Rattus norvegicus

<400> SEQUENCE: 473
agacugcccu ucgcgaaucu uuugcgguc ugggcuugcu guacauaacu caauagccgg     60
aagcccuuac cccaaaaagc auucgcggag ggcgcgc                             97

<210> SEQ ID NO 474
<211> LENGTH: 72
<212> TYPE: RNA
<213> ORGANISM: Rattus norvegicus

<400> SEQUENCE: 474
ugggucuuuu ugcggucugg gcuugcuguu cucuccacag uagucaggaa gcccuuaccc    60
caaaaaguau cu                                                        72

<210> SEQ ID NO 475
<211> LENGTH: 88
<212> TYPE: RNA
<213> ORGANISM: Rattus norvegicus

<400> SEQUENCE: 475
ugcugcuggc cggagcucuu uucacauugu gcuacugucu acacguguac cgagcagugc    60
aauguuaaaa gggcaucggc cuuguagu                                       88

<210> SEQ ID NO 476
<211> LENGTH: 82
<212> TYPE: RNA
<213> ORGANISM: Rattus norvegicus

<400> SEQUENCE: 476
ggcuugcugg acacucuuuc ccuguugcac uacugugggc cucugggaag cagugcaaug    60
augaaagggc auccgucagg cc                                             82

<210> SEQ ID NO 477
<211> LENGTH: 101
<212> TYPE: RNA
<213> ORGANISM: Rattus norvegicus

<400> SEQUENCE: 477
ccgcccccgc gucuccaggg caaccguggc uuucgauugu uacuguggga accggaggua    60
acagucuaca gccauggucg ccccgcagca cgcccacgcu c                        101

<210> SEQ ID NO 478
<211> LENGTH: 87
<212> TYPE: RNA

<213> ORGANISM: Rattus norvegicus

<400> SEQUENCE: 478
caaugcuuug cuaaagcugg uaaaauggaa ccaaaucgcc ucuucaaugg auuuggcccc    60
cuucaaccag cuguagcuau gcauuga                                       87

<210> SEQ ID NO 479
<211> LENGTH: 73
<212> TYPE: RNA
<213> ORGANISM: Rattus norvegicus

<400> SEQUENCE: 479
cagggugugu gacugguuga ccagaggggc gugcacuuug uucacccugu gggccaccua    60
gucaccaacc cuc                                                      73

<210> SEQ ID NO 480
<211> LENGTH: 97
<212> TYPE: RNA
<213> ORGANISM: Rattus norvegicus

<400> SEQUENCE: 480
cgcucugcug uggccuaugg cuuuucauuc cuaugugauu gcguuccga acucauguag     60 ggcuaaaagc caugggcuac agugaggggc aagcucc                            97

<210> SEQ ID NO 481
<211> LENGTH: 100
<212> TYPE: RNA
<213> ORGANISM: Rattus norvegicus

<400> SEQUENCE: 481
agauaaauuc acucuagugc uuuauggcuu uuuauuccua ugugaucgua auaaagucuc    60
auguagggau ggaagccaug aaauacauug ugaaaauuca                         100

<210> SEQ ID NO 482
<211> LENGTH: 82
<212> TYPE: RNA
<213> ORGANISM: Rattus norvegicus

<400> SEQUENCE: 482
ugagcccucg gaggacucca uuuguuuuga ugauggauuc uuaagcucca ucaucgucuc    60
aaaugagucu ucagagggu cu                                             82

<210> SEQ ID NO 483
<211> LENGTH: 102
<212> TYPE: RNA
<213> ORGANISM: Rattus norvegicus

<400> SEQUENCE: 483
ggcccucuga cucucuucgg ugacggguau ucuuggugg auaauacgga uuacguugu      60 auugcuuaag aauacgcgua gucgaggaga guaccagcgg ca                      102

<210> SEQ ID NO 484
<211> LENGTH: 82
<212> TYPE: RNA
<213> ORGANISM: Rattus norvegicus

<400> SEQUENCE: 484
guugcugcag cugguguugu gaaucaggcc gacgagcaac gcauccucuu acccggcuau    60
uucacgacac cagggugca cc                                             82

<210> SEQ ID NO 485
<211> LENGTH: 99
<212> TYPE: RNA
<213> ORGANISM: Rattus norvegicus

<400> SEQUENCE: 485
cucuggcaug guguugugggg acagcuggug uugugaauca ggccguugcc aaucagagaa    60
cggcuacuuc acaacaccag ggucucacug cacugcagg                            99

<210> SEQ ID NO 486
<211> LENGTH: 68
<212> TYPE: RNA
<213> ORGANISM: Rattus norvegicus

<400> SEQUENCE: 486
guguauucua cagugcacgu gucuccagug uggcucggag gcuggagacg cggcccuguu    60
ggaguaac                                                              68

<210> SEQ ID NO 487
<211> LENGTH: 99
<212> TYPE: RNA
<213> ORGANISM: Rattus norvegicus

<400> SEQUENCE: 487
gugucucucu cuguguccug ccaguggguuu uacccuaugg uagguuacau caugcuguuc    60
uaccacaggg uagaaccacg gacaggauac uggagcacc                            99

<210> SEQ ID NO 488
<211> LENGTH: 94
<212> TYPE: RNA
<213> ORGANISM: Rattus norvegicus

<400> SEQUENCE: 488
ggcugacucu gaguccaucu uccagugcag uguuggaugg uugaaguacg aagcuccuaa    60
cacugucugg uaaagauggc ccccgggucag guuc                                94

<210> SEQ ID NO 489
<211> LENGTH: 87
<212> TYPE: RNA
<213> ORGANISM: Rattus norvegicus

<400> SEQUENCE: 489
gacagugcag ucacccauaa aguagaaagc acuacuaaca gcacuggagg guguaguguu    60
uccuacuuua uggaugagug uacugug                                         87

<210> SEQ ID NO 490
<211> LENGTH: 105
<212> TYPE: RNA
<213> ORGANISM: Rattus norvegicus

<400> SEQUENCE: 490
gcggagcgcc ugucucccag ccugagguge agugcugcau cucuggucag uugggagucu    60
gagaugaagc acuguagcuc aggaagggag aagauguucu gcagc                    105

<210> SEQ ID NO 491
<211> LENGTH: 83
<212> TYPE: RNA
<213> ORGANISM: Rattus norvegicus

<400> SEQUENCE: 491
gggccuuggc ugggauauca ucauauacug uaaguuugug augagacacu acaguauaga    60
ugauguacua gucuggguac ccc                                            83

<210> SEQ ID NO 492
<211> LENGTH: 88
<212> TYPE: RNA
<213> ORGANISM: Rattus norvegicus

<400> SEQUENCE: 492
caccuugucc ucacggucca guuucccag gaaucccuug gaugcuaaga uggggauucc     60
uggaaauacu guucuugagg ucauggcu                                       88

<210> SEQ ID NO 493
<211> LENGTH: 95
<212> TYPE: RNA
<213> ORGANISM: Rattus norvegicus

<400> SEQUENCE: 493
uguguauccu cagcucugag aacugaauuc caugggauau agcaauguca gaccugugaa    60
guucaguucu uuagcuggga uagcucuauc gucau                               95

<210> SEQ ID NO 494
<211> LENGTH: 97
<212> TYPE: RNA
<213> ORGANISM: Rattus norvegicus

<400> SEQUENCE: 494
caggcacucu uagcauuuga ggugaaguuc uguuauacac ucaggcugug gcucugaaag    60
ucagugcauc acagaacuuu gucucgaaag cuuucua                             97

<210> SEQ ID NO 495
<211> LENGTH: 85
<212> TYPE: RNA
<213> ORGANISM: Rattus norvegicus

<400> SEQUENCE: 495
cuucucaagg cccugucucc caacccuugu accagugcug ugccucagac ccuguacag     60 gccuggggga cagggacuug gggac                                          85

<210> SEQ ID NO 496
<211> LENGTH: 97
<212> TYPE: RNA
<213> ORGANISM: Rattus norvegicus

<400> SEQUENCE: 496
agcgcuuucc ugcccucgag gagcucacag ucuaguaugu cuccucccua cuagacugag    60
gcuccuugag gacagggauc gucauacuca ccucccg                             97

<210> SEQ ID NO 497
<211> LENGTH: 85
<212> TYPE: RNA
<213> ORGANISM: Rattus norvegicus

<400> SEQUENCE: 497
uguuccccgg gcccagguuc ugugauacac uccgacucgg gcucuggagc agucagugca    60
ugacagaacu ugggcccggu aggac                                          85

```
<210> SEQ ID NO 498
<211> LENGTH: 87
<212> TYPE: RNA
<213> ORGANISM: Rattus norvegicus

<400> SEQUENCE: 498 agcggug gcc agugucauuu uugugauguu gcagcuagua auaugagccc aguugcauag      60
ucacaaaagu gaucauugga aacugug                                           87

<210> SEQ ID NO 499
<211> LENGTH: 84
<212> TYPE: RNA
<213> ORGANISM: Rattus norvegicus

<400> SEQUENCE: 499
gcggugcuug aagauagguu auccguguug ccuucgcuuu auucgugacg aaucauacac      60
gguugaccua uuuuucagua ccaa                                              84

<210> SEQ ID NO 500
<211> LENGTH: 106
<212> TYPE: RNA
<213> ORGANISM: Rattus norvegicus

<400> SEQUENCE: 500
agaacuugcc aaggguuugg gggaacauuc aaccugucgg ugaguuuggg cagcucagac      60
aaaccaucga ccguugagug daccccgagg ccuggaacug ccaccc                    106

<210> SEQ ID NO 501
<211> LENGTH: 117
<212> TYPE: RNA
<213> ORGANISM: Rattus norvegicus

<400> SEQUENCE: 501
agaugggcaa ccaaggcagc cuuaagagga cuccauggaa cauucaacgc ugucggugag      60
uuugggauuc aaaaacaaaa aaaaccacca accguugacu guaccuuggg auucuua       117

<210> SEQ ID NO 502
<211> LENGTH: 110
<212> TYPE: RNA
<213> ORGANISM: Rattus norvegicus

<400> SEQUENCE: 502
ccugugcaga gaugauguuu acaaaagguca caaucaacau ucauugcugu cgguggguug      60
aacuguguag aaaagcucac ugaacaauga augcaacugu ggccccgcuu                110

<210> SEQ ID NO 503
<211> LENGTH: 88
<212> TYPE: RNA
<213> ORGANISM: Rattus norvegicus

<400> SEQUENCE: 503
ugauggcugc acucaacauu cauugcuguc ggugg guuug aaugucaacc aacucacugg      60
ucaaugaaug caaacugcgg gccaaaaa                                          88

<210> SEQ ID NO 504
<211> LENGTH: 110
<212> TYPE: RNA
<213> ORGANISM: Rattus norvegicus

<400> SEQUENCE: 504
```

```
ccagagagug ugacuccugu ccuguguaug gcacugguag aaucacugu gaacagucuc      60 ggucagugaa uuaccgaagg gccauaaaca gagcagagac agauccgcga               110

<210> SEQ ID NO 505
<211> LENGTH: 77
<212> TYPE: RNA
<213> ORGANISM: Rattus norvegicus

<400> SEQUENCE: 505
cacuuccccu uaucaguuuu ccagccagcu uugugacugu aaauguugga cggagaacug     60
auaaggguaa gugacug                                                   77

<210> SEQ ID NO 506
<211> LENGTH: 80
<212> TYPE: RNA
<213> ORGANISM: Rattus norvegicus

<400> SEQUENCE: 506
gggggugagg gauuggagag aaaggcaguu ccgaugguc cccucccagg ggcuggcuuu      60
ccucuggucc uucucuccca                                                80

<210> SEQ ID NO 507
<211> LENGTH: 86
<212> TYPE: RNA
<213> ORGANISM: Rattus norvegicus

<400> SEQUENCE: 507
ugcuuacaac uuccaaaga auucuccuuu ugggcuuucu cauuuauuu uaagcccaaa       60 ggugaauuuu uugggaaguu ugagcu                                         86

<210> SEQ ID NO 508
<211> LENGTH: 104
<212> TYPE: RNA
<213> ORGANISM: Rattus norvegicus

<400> SEQUENCE: 508
gggcucacag gacacaaugc ggauccucag gcuacaacac aggacccggg cgcugcucug     60
accccucgug ucuuguguug cagccggagg gacgcagguc ugca                    104

<210> SEQ ID NO 509
<211> LENGTH: 85
<212> TYPE: RNA
<213> ORGANISM: Rattus norvegicus

<400> SEQUENCE: 509
ugcaggccuc ugugugauau guuugauaua uuagguuguu auuuaaucca acuauauauc     60
aagcauauuc cuacaguguc uugcc                                          85

<210> SEQ ID NO 510
<211> LENGTH: 91
<212> TYPE: RNA
<213> ORGANISM: Rattus norvegicus

<400> SEQUENCE: 510
ggcuggacag cgggcaacgg aaucccaaaa gcagcuguug ucuccagagc auccagcug      60 cacuuggauu ucguucccug cucuccugcc u                                   91

<210> SEQ ID NO 511
<211> LENGTH: 110
```

<212> TYPE: RNA
<213> ORGANISM: Rattus norvegicus

<400> SEQUENCE: 511
gucaagaugg agugcacagg gcucugaccu augaauugac agccaguacu cugaucucgc        60
cucuggcugc caguuccaua ggucacaggu auguucgccu caaugccagc                   110

<210> SEQ ID NO 512
<211> LENGTH: 86
<212> TYPE: RNA
<213> ORGANISM: Rattus norvegicus

<400> SEQUENCE: 512
gcggacggga gcugagagcu ggucuuugc gggcaagaug agggugucag uucaacuggc         60
cuacaaaguc ccaguccucg gcuccc                                             86

<210> SEQ ID NO 513
<211> LENGTH: 83
<212> TYPE: RNA
<213> ORGANISM: Rattus norvegicus

<400> SEQUENCE: 513
auggagucau cacguguaac agcaacucca uguggacugu gcacagaucc caguggagcu        60
gcuguuacuu uugauggccu cca                                                83

<210> SEQ ID NO 514
<211> LENGTH: 85
<212> TYPE: RNA
<213> ORGANISM: Rattus norvegicus

<400> SEQUENCE: 514
uggcucccac ccccuguaac agcaacucca uguggaagug cccacugauu ccaguggggc        60
ugcuguuauc uggggguggag gcugg                                             85

<210> SEQ ID NO 515
<211> LENGTH: 87
<212> TYPE: RNA
<213> ORGANISM: Rattus norvegicus

<400> SEQUENCE: 515
aacucuccug gcucuagcag cacagaaaua uuggcacggg uaagugaguc ugccaauauu        60
ggcugugcug cuccaggcag gguggug                                            87

<210> SEQ ID NO 516
<211> LENGTH: 110
<212> TYPE: RNA
<213> ORGANISM: Rattus norvegicus

<400> SEQUENCE: 516
uguuugcuca gcugaucugu ggcuuaggua guuucauguu guggauug aguuugaac           60 ucggcaacaa gaaacugccu gaguuacauc agucgguuuu cgucgagggc                   110

<210> SEQ ID NO 517
<211> LENGTH: 110
<212> TYPE: RNA
<213> ORGANISM: Rattus norvegicus

<400> SEQUENCE: 517
uggaagcuuc uggagauccu gcuccgucgc cccagyuguuc agacuaccug uucaggacaa       60

-continued ugccguugua caguagucug cacauugguu agacugggca agggccagca 110

<210> SEQ ID NO 518
<211> LENGTH: 69
<212> TYPE: RNA
<213> ORGANISM: Rattus norvegicus

<400> SEQUENCE: 518
cccucgucuu acccagcagu guuugggugc ugguugggag ucucuaauac ugccggguaa 60
ugauggagg 69

<210> SEQ ID NO 519
<211> LENGTH: 89
<212> TYPE: RNA
<213> ORGANISM: Rattus norvegicus

<400> SEQUENCE: 519
cugggccucu gugggcaucu uaccggacag ugcuggauuu cuuggcuuga cucuaacacu 60
gucugguaac gauguucaaa ggugaccca 89

<210> SEQ ID NO 520
<211> LENGTH: 95
<212> TYPE: RNA
<213> ORGANISM: Rattus norvegicus

<400> SEQUENCE: 520
ccaacuuggg cagccguggc caucuuacug ggcagcauug gauagugucu gaucucuaau 60
acugccuggu aaugaugacg gcggagcccu gcacg 95

<210> SEQ ID NO 521
<211> LENGTH: 97
<212> TYPE: RNA
<213> ORGANISM: Rattus norvegicus

<400> SEQUENCE: 521
gcgcgccugg uccagugguu cuuaacaguu caacaguucu guagcgcaau ugugaaaugu 60
uuaggaccac uagacccggc gcgcacggca gcggcga 97

<210> SEQ ID NO 522
<211> LENGTH: 110
<212> TYPE: RNA
<213> ORGANISM: Rattus norvegicus

<400> SEQUENCE: 522
ggcuacagcc cuucuucaug ugacucgugg acuucccuuu gucauccuau gccugagaau 60
auaugaagga ggcugggaag gcaaagggac guucaauugu caucacuggc 110

<210> SEQ ID NO 523
<211> LENGTH: 108
<212> TYPE: RNA
<213> ORGANISM: Rattus norvegicus

<400> SEQUENCE: 523
aaacagcccc agacaaucca uggguccucc ugccuucau uccaccggag ucugucuuau 60
gccaaccaga uuucagugga gugaagcuca ggaggcaugg agcugcca 108

<210> SEQ ID NO 524
<211> LENGTH: 84
<212> TYPE: RNA
<213> ORGANISM: Rattus norvegicus

<400> SEQUENCE: 524
cuuccccagg ccacaugcuu cuuuauaucc ucauagauau cacugcgcua uggaauguaa    60
ggaagugugu gguuuuggca agug    84

<210> SEQ ID NO 525
<211> LENGTH: 83
<212> TYPE: RNA
<213> ORGANISM: Rattus norvegicus

<400> SEQUENCE: 525
uuccuuugac gggugagcuu uuggcccggg uuauaccuga cucucacgua uaagacgagc    60
aaaaagcuug uuggucagag gag    83

<210> SEQ ID NO 526
<211> LENGTH: 110
<212> TYPE: RNA
<213> ORGANISM: Rattus norvegicus

<400> SEQUENCE: 526
ccggggcagu cccuccaggc ucaggacagc cacugcccac agcacacugc guugcuccgg    60
acccacugug cgugugacag cggcugaucu gucccugggc agcgcgaacc    110

<210> SEQ ID NO 527
<211> LENGTH: 106
<212> TYPE: RNA
<213> ORGANISM: Rattus norvegicus

<400> SEQUENCE: 527
cagcuuggac cugugaccuc ugggcuuccc uuugucaucc uuugccuagg ccucugagug    60
gggcaaggac agcaaagggg ggcucagugg ucaccucuac ugcaga    106

<210> SEQ ID NO 528
<211> LENGTH: 111
<212> TYPE: RNA
<213> ORGANISM: Rattus norvegicus

<400> SEQUENCE: 528
cgggauaucc ccgcccgggc agcgcgccgg caccuuggcu cuagacugcu acugcccgg    60 gccgcccuca guaacagucu ccagucacgg ccaccgacgc cuggccccgc c    111

<210> SEQ ID NO 529
<211> LENGTH: 100
<212> TYPE: RNA
<213> ORGANISM: Rattus norvegicus

<400> SEQUENCE: 529
agguugcuuc agugaacauu caacgcuguc ggugaguuug gaauucaaau aaaaaccauc    60
gaccguugau uguacccuau agcuaaccau uaucuacucc    100

<210> SEQ ID NO 530
<211> LENGTH: 110
<212> TYPE: RNA
<213> ORGANISM: Rattus norvegicus

<400> SEQUENCE: 530
guccuggaug gacagaguug ucauguqucu ccugucuac acuugcugug cagaacaucc    60
gcucaccugu acagcaggca cagacaggca gucacaugac aacccagccu    110

```
<210> SEQ ID NO 531
<211> LENGTH: 106
<212> TYPE: RNA
<213> ORGANISM: Rattus norvegicus

<400> SEQUENCE: 531
guuagcuaug aguuaguuua aucucagcug gcaacuguga gaugucccua ucauuccuca      60
caguggucuc ugggauuaug cuaaacagag caauuuccuu gaccuc                   106

<210> SEQ ID NO 532
<211> LENGTH: 105
<212> TYPE: RNA
<213> ORGANISM: Rattus norvegicus

<400> SEQUENCE: 532
accacaguca uuguaguuuu gaugucgcag auacugcauc aggaacugac uggauaagac      60
ucagucacca ucaguccuau augcauugcc uucagcaucu aaaca                    105

<210> SEQ ID NO 533
<211> LENGTH: 110
<212> TYPE: RNA
<213> ORGANISM: Rattus norvegicus

<400> SEQUENCE: 533
gaccaguugc cgcggggcuu uccuuugugc uugaucuaac cauguggugg aacgauggaa      60
acggaacaug guucugucaa gcaccgcgga aagcaucgcu cucuccugca                110

<210> SEQ ID NO 534
<211> LENGTH: 110
<212> TYPE: RNA
<213> ORGANISM: Rattus norvegicus

<400> SEQUENCE: 534
gugauaacgu agcgagauuu ucuguugugc uugaucuaac caugugcuug cgagguauga      60
guaaaacaug guuccgucaa gcaccaugga acgucacgca gcuuucuaca                110

<210> SEQ ID NO 535
<211> LENGTH: 110
<212> TYPE: RNA
<213> ORGANISM: Rattus norvegicus

<400> SEQUENCE: 535
cugucccggg ccgcggcucc ugauugucca aacgcaauuc ucgagucucu ggcuccggcc      60
gagaguugcg ucuggacguc ccgagccgcc gcccccaaac cucgagggggg              110

<210> SEQ ID NO 536
<211> LENGTH: 96
<212> TYPE: RNA
<213> ORGANISM: Rattus norvegicus

<400> SEQUENCE: 536
acucaggggc uucaccacug auuguccaaa cgcaauucuu guacgagucu gcggccaacc      60
gagaauugug gcuggacauc ugugguugag cuccgg                               96

<210> SEQ ID NO 537
<211> LENGTH: 109
<212> TYPE: RNA
<213> ORGANISM: Rattus norvegicus

<400> SEQUENCE: 537
```

```
ugaauauuccaa ggucuggggc augaaccugg cauacaaugu agauuucugu guuuguuagg    60
caacagcuac auugucugcu ggguuucagg cuaccuggaa gcauuucuc                  109

<210> SEQ ID NO 538
<211> LENGTH: 103
<212> TYPE: RNA
<213> ORGANISM: Rattus norvegicus

<400> SEQUENCE: 538
aaggauuagg gugcccucag uggcucagua gccaguguag auccugucuu ugguaaucag    60
cagcuacauc uggcuacugg gucucugaug gcaucaucua gcu                        103

<210> SEQ ID NO 539
<211> LENGTH: 110
<212> TYPE: RNA
<213> ORGANISM: Rattus norvegicus

<400> SEQUENCE: 539
ucuggccuuc ugcaguguua cgcuccgugu auuugacaag cugaguugga cacucugugu    60
gguagagugu caguuuguca aauaccccaa guguggcuca ugcuuaucag                110

<210> SEQ ID NO 540
<211> LENGTH: 81
<212> TYPE: RNA
<213> ORGANISM: Rattus norvegicus

<400> SEQUENCE: 540
ucaucuugcg guucucaaac uauggggca cuuuuuuuu cuuuaaaaag ugccgccagg      60
uuuuagggcc ugccgguuga g                                                81

<210> SEQ ID NO 541
<211> LENGTH: 82
<212> TYPE: RNA
<213> ORGANISM: Rattus norvegicus

<400> SEQUENCE: 541
ccgguguagu agccaucaaa guggaggccc ucucuugggc ccgagcuaga aagugcuucc    60
acuuugugug ccacugcaug gg                                              82

<210> SEQ ID NO 542
<211> LENGTH: 82
<212> TYPE: RNA
<213> ORGANISM: Rattus norvegicus

<400> SEQUENCE: 542
caaccuguga uacucaaacu gggggcucuu uugggguuuuc uuuggaagaa aagugccgcc    60
agguuuugag uguuaccgau ug                                              82

<210> SEQ ID NO 543
<211> LENGTH: 78
<212> TYPE: RNA
<213> ORGANISM: Rattus norvegicus

<400> SEQUENCE: 543
ggaccuuucu ggagggcccc cccucaaucc uguugugcuc gcuucagagg guugggugga    60
ggcucuccug aaggguguc                                                  78

<210> SEQ ID NO 544
```

```
<211> LENGTH: 68
<212> TYPE: RNA
<213> ORGANISM: Rattus norvegicus

<400> SEQUENCE: 544
uauguaugua uguauguaug uaugcaugua ugugugcaug uaugcaugca ugcauguaug    60
uauguaug                                                             68

<210> SEQ ID NO 545
<211> LENGTH: 82
<212> TYPE: RNA
<213> ORGANISM: Rattus norvegicus

<400> SEQUENCE: 545
ccaggccuuc ggcagaggag ggcuguucuu cccuggguu uuaugacugg gaggaacuag     60
ccuucucucu gcuuaggagu gg                                             82

<210> SEQ ID NO 546
<211> LENGTH: 63
<212> TYPE: RNA
<213> ORGANISM: Rattus norvegicus

<400> SEQUENCE: 546
aagaaauggu uuaccguccc acauacauuu ugaguaugua uguggacgg uaaaccgcuu     60 cuu                                                                  63

<210> SEQ ID NO 547
<211> LENGTH: 79
<212> TYPE: RNA
<213> ORGANISM: Rattus norvegicus

<400> SEQUENCE: 547
gcuacuugaa gagagguuau ccuuugugug uuugcuuuac gcgaaaugaa uaugcaaggg    60
caagcucucu ucgaggagc                                                 79

<210> SEQ ID NO 548
<211> LENGTH: 100
<212> TYPE: RNA
<213> ORGANISM: Rattus norvegicus

<400> SEQUENCE: 548
ccugcuggcu acugcugacg acugcucuga cuuuauugca cuacuguacu guacagcuag    60
cagugcaaua guauugucaa agcauccggg agcaggcuac                          100

<210> SEQ ID NO 549
<211> LENGTH: 82
<212> TYPE: RNA
<213> ORGANISM: Rattus norvegicus

<400> SEQUENCE: 549
gccucgcugu ccuccgccuu cucuucccgg uucuucccgg agucgggaaa agcuggguug    60
agagggcgaa aaggauaug gg                                              82

<210> SEQ ID NO 550
<211> LENGTH: 59
<212> TYPE: RNA
<213> ORGANISM: Rattus norvegicus

<400> SEQUENCE: 550
uuggccuccu aagccaggga uugugggguc gagucccacc cggggunaaga gguuguguu    59
```

<210> SEQ ID NO 551
<211> LENGTH: 95
<212> TYPE: RNA
<213> ORGANISM: Rattus norvegicus

<400> SEQUENCE: 551

```
ccucgcugac uccgaaggga ugcagcagca auucauguuu uggaguauug ccaagguuca    60
aaacaugaag cgcugcaaca ccccuucgug ggaaa                                95
```

<210> SEQ ID NO 552
<211> LENGTH: 86
<212> TYPE: RNA
<213> ORGANISM: Rattus norvegicus

<400> SEQUENCE: 552

```
uugguacuug gagagaggug guccguggcg cguucgcuuc auuuauggcg cacauuacac    60
ggucgaccuc uuugcgguau cuaauc                                          86
```

<210> SEQ ID NO 553
<211> LENGTH: 83
<212> TYPE: RNA
<213> ORGANISM: Rattus norvegicus

<400> SEQUENCE: 553

```
cugacuaugc cuccucgcau ccccuagggc auugguguaa agcuggagac ccacugcccc    60
aggugcugcu gggggguugua guc                                            83
```

<210> SEQ ID NO 554
<211> LENGTH: 98
<212> TYPE: RNA
<213> ORGANISM: Rattus norvegicus

<400> SEQUENCE: 554

```
auauagugcu ugguuccuag uaggugcuca guaaguguuu gugacauaau ucguuuauug    60
agcaccuccu aucaaucaag cacugugcua ggcucugg                             98
```

<210> SEQ ID NO 555
<211> LENGTH: 95
<212> TYPE: RNA
<213> ORGANISM: Rattus norvegicus

<400> SEQUENCE: 555

```
cucaucuguc uguggggcug ggggcagggc cuuugugaag gcggguuaug cucagaucgc    60
cucugggccc uuccuccagu cccgaggcag auuua                                95
```

<210> SEQ ID NO 556
<211> LENGTH: 84
<212> TYPE: RNA
<213> ORGANISM: Rattus norvegicus

<400> SEQUENCE: 556

```
ugggggcaggg gggcaggagg ggcucaggga gaaagcaucu acagccccug gcccucucug    60
cccuuccguc cccugucccc aaau                                            84
```

<210> SEQ ID NO 557
<211> LENGTH: 97
<212> TYPE: RNA
<213> ORGANISM: Rattus norvegicus

```
<400> SEQUENCE: 557
uguucgcuuc ugguaccgga agagagguuu ucuggqucuc uguuucuuug augagaauga     60
aacacaccca gcuaaccuuu uuuucaguau caaaucc                             97

<210> SEQ ID NO 558
<211> LENGTH: 97
<212> TYPE: RNA
<213> ORGANISM: Rattus norvegicus

<400> SEQUENCE: 558
acccuuuggc gaucucugcc ucucugggcc ugugucuuag gcucuucaag aucuaacgag     60
caaagcacag ggccugcaga gagguagcgc ucugcuc                             97

<210> SEQ ID NO 559
<211> LENGTH: 96
<212> TYPE: RNA
<213> ORGANISM: Rattus norvegicus

<400> SEQUENCE: 559
gagucugguc uuguuugggu uuguucuagg uaugguccca gggaucccag aucaaaccag     60
gccccugggc cuauccuaga accaaccuaa acccau                              96

<210> SEQ ID NO 560
<211> LENGTH: 95
<212> TYPE: RNA
<213> ORGANISM: Rattus norvegicus

<400> SEQUENCE: 560
ccccggugga accacguggu gugcuaguua cuuuugggcu ggagagacgg cucagggguu     60
aagagcacag acugcucuuc cagagguccu gaguu                               95

<210> SEQ ID NO 561
<211> LENGTH: 96
<212> TYPE: RNA
<213> ORGANISM: Rattus norvegicus

<400> SEQUENCE: 561
augugaccgu gccucucacc cuuccauauc uagucucuga gaaaaaugaa gacuggauuc     60
caugaaggga ugugaggccu ggaaacugga gcuuua                              96

<210> SEQ ID NO 562
<211> LENGTH: 97
<212> TYPE: RNA
<213> ORGANISM: Rattus norvegicus

<400> SEQUENCE: 562
aguguaguga gaaguugggg gguggggaacg gcgucaugca ggaguugauu gcacagccau    60
ucagcuccua uaugaugccu uucuucaccc ccuucaa                             97

<210> SEQ ID NO 563
<211> LENGTH: 66
<212> TYPE: RNA
<213> ORGANISM: Rattus norvegicus

<400> SEQUENCE: 563
uccccaacaa uauccuggug cugaguggu gcacagugac uccagcauca gugauuuugu     60
ugaaga                                                               66
```

```
<210> SEQ ID NO 564
<211> LENGTH: 96
<212> TYPE: RNA
<213> ORGANISM: Rattus norvegicus

<400> SEQUENCE: 564
acggggugga caccguccccu guccuccagg agcucacgua ugccugccug ugagcgccuc    60
gacgacagag ccagaguccu ccccugcacu gcccaa                              96

<210> SEQ ID NO 565
<211> LENGTH: 96
<212> TYPE: RNA
<213> ORGANISM: Rattus norvegicus

<400> SEQUENCE: 565
aaaaugauga ugucaguugg ccggucggcc gaucgcucgg ucugucaguc agucggucgg    60
ucgaucgguc ggucggucag ucggcuuccu gucuuc                              96

<210> SEQ ID NO 566
<211> LENGTH: 99
<212> TYPE: RNA
<213> ORGANISM: Rattus norvegicus

<400> SEQUENCE: 566
gaaaaugggc ucaaggugag ggguugcuauc ugugauugag ggacaugguc aauggaauug    60
ucucacacag aaaucgcacc cgucaccuug gccugcuga                           99

<210> SEQ ID NO 567
<211> LENGTH: 98
<212> TYPE: RNA
<213> ORGANISM: Rattus norvegicus

<400> SEQUENCE: 567
cugcagccag aguuuuuacc agucaggcuc cuggcuagau uccagguacc aacugguacc    60
ugaucuagcc aaagccugac cguaagcugc aaaagaaa                            98

<210> SEQ ID NO 568
<211> LENGTH: 96
<212> TYPE: RNA
<213> ORGANISM: Rattus norvegicus

<400> SEQUENCE: 568
acccaagucc aggccugcug accccuaguc cagucuugu gguggcuacu gggcccugaa     60
cuaggggucu ggagaccugg guuugaucuc cacagg                              96

<210> SEQ ID NO 569
<211> LENGTH: 98
<212> TYPE: RNA
<213> ORGANISM: Rattus norvegicus

<400> SEQUENCE: 569
ucuguguugg gcaucugucu gccugagugc cugccucucu guugcucuga aggaggcagg    60
ggcugggccu gcagcugccu gggcagagcu gcuccuuc                            98

<210> SEQ ID NO 570
<211> LENGTH: 97
<212> TYPE: RNA
<213> ORGANISM: Rattus norvegicus

<400> SEQUENCE: 570
```

```
gaagacucua gcauguaagg uuggggagg gggcugugu uagcaagucu ucuuccccca    60
cagcccugcu gucuuaaccu cuaggugucc cggcucc                            97
```

<210> SEQ ID NO 571
<211> LENGTH: 99
<212> TYPE: RNA
<213> ORGANISM: Rattus norvegicus

<400> SEQUENCE: 571

```
agaugccuug cuccuacaag aguaaagugc acgucuuug ggacagugag gaaaauaaug    60
uucacaaagc ccauacacuu ucacccuuua ggagaguug                          99
```

<210> SEQ ID NO 572
<211> LENGTH: 81
<212> TYPE: RNA
<213> ORGANISM: Rattus norvegicus
<220> FEATURE:
<223> OTHER INFORMATION: Description of Combined DNA/RNA Molecule:c

<400> SEQUENCE: 572

```
cauggcaccu ccauuuccc gaggagcccu uugagccuga ggugaaaaaa aaacagguca    60
agaggcgccu gggaacugga g                                             81
```

<210> SEQ ID NO 573
<211> LENGTH: 98
<212> TYPE: RNA
<213> ORGANISM: Homo sapiens

<400> SEQUENCE: 573

```
acccaaaccc uaggucugcu gacuccuagu ccagggcucg ugauggcugg ugggcccuga   60 acgaggguc uggaggccug gguugaauua ucgacagc                            98
```

<210> SEQ ID NO 574
<211> LENGTH: 86
<212> TYPE: RNA
<213> ORGANISM: Homo sapiens

<400> SEQUENCE: 574

```
gucugucugc ccgcaugccu gccucucugu ugcucugaag gaggcagggg cugggccugc   60
agcugccugg gcagagcggc uccugc                                        86
```

<210> SEQ ID NO 575
<211> LENGTH: 68
<212> TYPE: RNA
<213> ORGANISM: Homo sapiens

<400> SEQUENCE: 575

```
ccauuacugu ugcuaauaug caacucuguu gaauauaaau uggaauugca cuuuagcaau   60
ggugaugg                                                            68
```

<210> SEQ ID NO 576
<211> LENGTH: 66
<212> TYPE: RNA
<213> ORGANISM: Homo sapiens

<400> SEQUENCE: 576

```
aaaaggugga uauuccuucu auguuuaugu uauuuauggu uaaacauaga ggaaauucca   60
cguuuu                                                              66
```

```
<210> SEQ ID NO 577
<211> LENGTH: 70
<212> TYPE: RNA
<213> ORGANISM: Homo sapiens

<400> SEQUENCE: 577
uugaagggag aucgaccgug uuauauucgc uuuauugacu ucgaauaaua caugguugau    60
cuuucucag                                                           70

<210> SEQ ID NO 578
<211> LENGTH: 75
<212> TYPE: RNA
<213> ORGANISM: Homo sapiens

<400> SEQUENCE: 578
agacagagaa gccaggucac gucucugcag uuacacagcu cacgagugcc ugcuggggug    60
gaaccugguc ugucu                                                    75

<210> SEQ ID NO 579
<211> LENGTH: 67
<212> TYPE: RNA
<213> ORGANISM: Homo sapiens

<400> SEQUENCE: 579
guggcacuca aacugugggg gcacuuucug cucucuggug aaagugccgc caucuuuuga    60
guguuac                                                             67

<210> SEQ ID NO 580
<211> LENGTH: 67
<212> TYPE: RNA
<213> ORGANISM: Homo sapiens

<400> SEQUENCE: 580
gugggccuca aauguggagc acuauucuga uguccaagug gaaagugcug cgacauuuga    60
gcgucac                                                             67

<210> SEQ ID NO 581
<211> LENGTH: 69
<212> TYPE: RNA
<213> ORGANISM: Homo sapiens

<400> SEQUENCE: 581
gggauacuca aaauggggggc gcuuccuuu uugucuguac ugggaagugc uucgauuuug    60
ggguguccc                                                           69

<210> SEQ ID NO 582
<211> LENGTH: 72
<212> TYPE: RNA
<213> ORGANISM: Homo sapiens

<400> SEQUENCE: 582
uacaucggcc auuauaauac aaccugauaa guguuauagc acuuaucaga uuguauugua    60
auugucugug ua                                                       72

<210> SEQ ID NO 583
<211> LENGTH: 99
<212> TYPE: RNA
<213> ORGANISM: Mus musculus

<400> SEQUENCE: 583
```

```
cauggcaccu ccguuucccu gaggagcccu uugagccugg agugaaaaaa aaaaacaggu    60
caagaggcgc cugggaacug gagaagagug uuaaacuuc                          99

<210> SEQ ID NO 584
<211> LENGTH: 79
<212> TYPE: RNA
<213> ORGANISM: Mus musculus

<400> SEQUENCE: 584
agacggagag accaggucac gucucugcag uuacacagcu caugagugcc ugcuggggug    60
gaaccugguu ugucugucu                                                79

<210> SEQ ID NO 585
<211> LENGTH: 68
<212> TYPE: RNA
<213> ORGANISM: Mus musculus

<400> SEQUENCE: 585
uaaaagguag auucuccuuc uaugaguaca auauuaauga cuaaucguag aggaaaaucc    60
acguuuuc                                                            68

<210> SEQ ID NO 586
<211> LENGTH: 82
<212> TYPE: RNA
<213> ORGANISM: Mus musculus

<400> SEQUENCE: 586
ugguauuuaa aagguggaua uuccuucuau gguuacgugc uuccuggaua aucauagagg    60
aacauccacu uuucaguau ca                                             82

<210> SEQ ID NO 587
<211> LENGTH: 61
<212> TYPE: RNA
<213> ORGANISM: Mus musculus

<400> SEQUENCE: 587
aagaugguug accauagaac augcgcuacu ucugugucgu auaguauaug guccacaucu    60
u                                                                   61

<210> SEQ ID NO 588
<211> LENGTH: 79
<212> TYPE: RNA
<213> ORGANISM: Mus musculus

<400> SEQUENCE: 588
ugguacucgg agagagguua cccgagcaac uuugcaucug gaggacgaau guugcucggu    60
gaaccccuuu ucgguauca                                                79

<210> SEQ ID NO 589
<211> LENGTH: 81
<212> TYPE: RNA
<213> ORGANISM: Mus musculus

<400> SEQUENCE: 589
ggguacuuga ggagagguug ucugugauga guucgcuuua uuaaugacga auauaacaca    60
gauggccugu uuucaauacc a                                             81

<210> SEQ ID NO 590
<211> LENGTH: 82
```

```
<212> TYPE: RNA
<213> ORGANISM: Mus musculus

<400> SEQUENCE: 590
ugguacuugg agagauagua gaccguauag cguacgcuuu aucugugacg uauguaacac      60
gguccacuaa cccucaguau ca                                              82

<210> SEQ ID NO 591
<211> LENGTH: 80
<212> TYPE: RNA
<213> ORGANISM: Mus musculus

<400> SEQUENCE: 591
ggguauggga cggauggucg accagcugga aaguaauugu uucuaaugua cuucaccugg      60
uccacuagcc gucggugccc                                                 80

<210> SEQ ID NO 592
<211> LENGTH: 96
<212> TYPE: RNA
<213> ORGANISM: Rattus norvegicus

<400> SEQUENCE: 592
guacauaugu ugaagauuau uaauauauag aguggguguu guggugguag uauguauaugu     60 agaguaguag guugcauagu acgauguagu guauga                               96

<210> SEQ ID NO 593
<211> LENGTH: 79
<212> TYPE: RNA
<213> ORGANISM: Rattus norvegicus
<220> FEATURE:
<223> OTHER INFORMATION: Description of Combined DNA/RNA Molecule:c

<400> SEQUENCE: 593
cacacuguag gccucauuaa auguuuguug aaugaaaaaa ugaaucauca acagacauua      60
auugggcgcc ugcucugug                                                  79

<210> SEQ ID NO 594
<211> LENGTH: 22
<212> TYPE: RNA
<213> ORGANISM: Artificial Sequence
<220> FEATURE:
<223> OTHER INFORMATION: Description of Artificial Sequence:
      Synthetic Primer

<400> SEQUENCE: 594
cauacuucuu uauaugccca ua                                              22

<210> SEQ ID NO 595
<211> LENGTH: 21
<212> TYPE: RNA
<213> ORGANISM: Artificial Sequence
<220> FEATURE:
<223> OTHER INFORMATION: Description of Artificial Sequence:
      Synthetic Primer

<400> SEQUENCE: 595
uggaauguaa agaaguaugu a                                               21

<210> SEQ ID NO 596
<211> LENGTH: 21
<212> TYPE: DNA
<213> ORGANISM: Artificial Sequence
<220> FEATURE:
```

```
<221> NAME/KEY: modified_base
<222> LOCATION: (20)..(21)
<223> OTHER INFORMATION: t = t/u
<220> FEATURE:
<223> OTHER INFORMATION: Description of Artificial Sequence:
      Synthetic Primer

<400> SEQUENCE: 596
cauacuucuu uacauucugt t                                              21

<210> SEQ ID NO 597
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 597
uggaauguaa agaaguaugu a                                              21

<210> SEQ ID NO 598
<211> LENGTH: 21
<212> TYPE: DNA
<213> ORGANISM: Artificial Sequence
<220> FEATURE:
<221> NAME/KEY: modified_base
<222> LOCATION: (20)..(21)
<223> OTHER INFORMATION: t = t/u
<220> FEATURE:
<223> OTHER INFORMATION: Description of Artificial Sequence:
      Synthetic Primer

<400> SEQUENCE: 598
cauacuucuu uacauuccat t                                              21

<210> SEQ ID NO 599
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 599
uggaauguaa agaaguaugu a                                              21

<210> SEQ ID NO 600
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 600
guguucacag cggaccuuga uu                                             22

<210> SEQ ID NO 601
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer
```

```
<400> SEQUENCE: 601
uuaaggcacg cggugaaugc ca                                             22

<210> SEQ ID NO 602
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 602
gcauucaccg cgugccuugg tt                                             22

<210> SEQ ID NO 603
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 603
uuaaggcacg cggugaaugc ca                                             22

<210> SEQ ID NO 604
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 604
gcauucaccg cgugccuuaa tt                                             22

<210> SEQ ID NO 605
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 605
uuaaggcacg cggugaaugc ca                                             22

<210> SEQ ID NO 606
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 606
```
ucuuuucaca uugugcuac                                                   19

<210> SEQ ID NO 607
<211> LENGTH: 20
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 607
cagugcaaug uuaaaagggc                                                  20

<210> SEQ ID NO 608
<211> LENGTH: 20
<212> TYPE: DNA
<213> ORGANISM: Artificial Sequence
<220> FEATURE:
<221> NAME/KEY: modified_base
<222> LOCATION: (19)..(20)
<223> OTHER INFORMATION: t = t/u
<220> FEATURE:
<223> OTHER INFORMATION: Description of Artificial Sequence:
      Synthetic Primer

<400> SEQUENCE: 608
uauuuuaaca uugcacugtt                                                  20

<210> SEQ ID NO 609
<211> LENGTH: 20
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 609
cagugcaaug uuaaaagggc                                                  20

<210> SEQ ID NO 610
<211> LENGTH: 20
<212> TYPE: DNA
<213> ORGANISM: Artificial Sequence
<220> FEATURE:
<221> NAME/KEY: modified_base
<222> LOCATION: (19)..(20)
<223> OTHER INFORMATION: t = t/u
<220> FEATURE:
<223> OTHER INFORMATION: Description of Artificial Sequence:
      Synthetic Primer

<400> SEQUENCE: 610
ccuuuuaaca uugcacugtt                                                  20

<210> SEQ ID NO 611
<211> LENGTH: 20
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 611
cagugcaaug uuaaaagggc                                                  20

```
<210> SEQ ID NO 612
<211> LENGTH: 20
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 612
aguuuugcau aguugcacua                                             20

<210> SEQ ID NO 613
<211> LENGTH: 23
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 613
ugugcaaauc uaugcaaaac uga                                         23

<210> SEQ ID NO 614
<211> LENGTH: 23
<212> TYPE: DNA
<213> ORGANISM: Artificial Sequence
<220> FEATURE:
<221> NAME/KEY: modified_base
<222> LOCATION: (22)..(23)
<223> OTHER INFORMATION: t = t/u
<220> FEATURE:
<223> OTHER INFORMATION: Description of Artificial Sequence:
      Synthetic Primer

<400> SEQUENCE: 614
acauuugcau agauuugcac att                                         23

<210> SEQ ID NO 615
<211> LENGTH: 23
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 615
ugugcaaauc uaugcaaaac uga                                         23

<210> SEQ ID NO 616
<211> LENGTH: 23
<212> TYPE: DNA
<213> ORGANISM: Artificial Sequence
<220> FEATURE:
<221> NAME/KEY: modified_base
<222> LOCATION: (22)..(23)
<223> OTHER INFORMATION: t = t/u
<220> FEATURE:
<223> OTHER INFORMATION: Description of Artificial Sequence:
      Synthetic Primer

<400> SEQUENCE: 616
aguuuugcau agauuugcac att                                         23

<210> SEQ ID NO 617
<211> LENGTH: 23
<212> TYPE: RNA
```

```
<213> ORGANISM: Artificial Sequence
<220> FEATURE:
<220> FEATURE:
<223> OTHER INFORMATION: Description of Artificial Sequence:
      Synthetic Primer

<400> SEQUENCE: 617
ugugcaaauc uaugcaaaac uga                                              23

<210> SEQ ID NO 618
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 618
caaauucgua ucuaggggaa ua                                               22

<210> SEQ ID NO 619
<211> LENGTH: 23
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 619
uacccuguag auccgaauuu gug                                              23

<210> SEQ ID NO 620
<211> LENGTH: 23
<212> TYPE: DNA
<213> ORGANISM: Artificial Sequence
<220> FEATURE:
<221> NAME/KEY: modified_base
<222> LOCATION: (22)..(23)
<223> OTHER INFORMATION: t = t/u
<220> FEATURE:
<223> OTHER INFORMATION: Description of Artificial Sequence:
      Synthetic Primer

<400> SEQUENCE: 620
agaauucgga ucuacagggu att                                              23

<210> SEQ ID NO 621
<211> LENGTH: 23
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 621
uacccuguag auccgaauuu gug                                              23

<210> SEQ ID NO 622
<211> LENGTH: 23
<212> TYPE: DNA
<213> ORGANISM: Artificial Sequence
<220> FEATURE:
<221> NAME/KEY: modified_base
<222> LOCATION: (22)..(23)
<223> OTHER INFORMATION: t = t/u
<220> FEATURE:
```

```
<223> OTHER INFORMATION: Description of Artificial Sequence:
      Synthetic Primer

<400> SEQUENCE: 622
caaauucgga ucuacagggu att                                            23

<210> SEQ ID NO 623
<211> LENGTH: 23
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 623
uacccuguag auccgaauuu gug                                            23

<210> SEQ ID NO 624
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 624 auguuccac agugcauca                                                  19

<210> SEQ ID NO 625
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 625
gugcauugua guugcauug                                                 19

<210> SEQ ID NO 626
<211> LENGTH: 19
<212> TYPE: DNA
<213> ORGANISM: Artificial Sequence
<220> FEATURE:
<221> NAME/KEY: modified_base
<222> LOCATION: (18)..(19)
<223> OTHER INFORMATION: t = t/u
<220> FEATURE:
<223> OTHER INFORMATION: Description of Artificial Sequence:
      Synthetic Primer

<400> SEQUENCE: 626
guccaacuac aaugcactt                                                 19

<210> SEQ ID NO 627
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 627
gugcauugua guugcauug                                                 19
```

```
<210> SEQ ID NO 628
<211> LENGTH: 19
<212> TYPE: DNA
<213> ORGANISM: Artificial Sequence
<220> FEATURE:
<221> NAME/KEY: modified_base
<222> LOCATION: (18)..(19)
<223> OTHER INFORMATION: t = t/u
<220> FEATURE:
<223> OTHER INFORMATION: Description of Artificial Sequence:
      Synthetic Primer

<400> SEQUENCE: 628
augcaacuac aaugcactt                                                    19

<210> SEQ ID NO 629
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 629
gugcauugua guugcauug                                                    19

<210> SEQ ID NO 630
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 630
cuauacaacc uacugccuuc c                                                 21

<210> SEQ ID NO 631
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 631
ugagguagua gguugugugg uu                                                22

<210> SEQ ID NO 632
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 632
ccacacaacc uacuaucuua tt                                                22

<210> SEQ ID NO 633
```

-continued

```
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 633
ugagguagua gguugugugg uu                                              22

<210> SEQ ID NO 634
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 634
ccacacaacc uacuaccuca tt                                              22

<210> SEQ ID NO 635
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 635
ugagguagua gguugugugg uu                                              22

<210> SEQ ID NO 636
<211> LENGTH: 21
<212> TYPE: DNA
<213> ORGANISM: Artificial Sequence
<220> FEATURE:
<221> NAME/KEY: modified_base
<222> LOCATION: (20)..(21)
<223> OTHER INFORMATION: t = t/u
<220> FEATURE:
<223> OTHER INFORMATION: Description of Artificial Sequence:
      Synthetic Primer

<400> SEQUENCE: 636
aacaacauga aacuaccuat t                                               21

<210> SEQ ID NO 637
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 637
uagguaguuu cauguuguug g                                               21

<210> SEQ ID NO 638
<211> LENGTH: 22
<212> TYPE: RNA
<213> ORGANISM: Artificial Sequence
```

```
<220> FEATURE:
<220> FEATURE:
<223> OTHER INFORMATION: Description of Artificial Sequence:
      Synthetic Primer

<400> SEQUENCE: 638
caaauucgua ucuagggaa ua                                                  22

<210> SEQ ID NO 639
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 639
uagguaguuu cauguuguug g                                                  21

<210> SEQ ID NO 640
<211> LENGTH: 21
<212> TYPE: DNA
<213> ORGANISM: Artificial Sequence
<220> FEATURE:
<221> NAME/KEY: modified_base
<222> LOCATION: (20)..(21)
<223> OTHER INFORMATION: t = t/u
<220> FEATURE:
<223> OTHER INFORMATION: Description of Artificial Sequence:
      Synthetic Primer

<400> SEQUENCE: 640
aauaacauga aacuaccuat t                                                  21

<210> SEQ ID NO 641
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 641
uagguaguuu cauguuguug g                                                  21

<210> SEQ ID NO 642
<211> LENGTH: 19
<212> TYPE: DNA
<213> ORGANISM: Artificial Sequence
<220> FEATURE:
<221> NAME/KEY: modified_base
<222> LOCATION: (18)..(19)
<223> OTHER INFORMATION: t = t/u
<220> FEATURE:
<223> OTHER INFORMATION: Description of Artificial Sequence:
      Synthetic Primer

<400> SEQUENCE: 642
augcaacuac aaugcactt                                                     19

<210> SEQ ID NO 643
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
```

-continued

```
      Synthetic Primer

<400> SEQUENCE: 643
gugcauugua guugcauug                                               19

<210> SEQ ID NO 644
<211> LENGTH: 19
<212> TYPE: DNA
<213> ORGANISM: Artificial Sequence
<220> FEATURE:
<221> NAME/KEY: modified_base
<222> LOCATION: (18)..(19)
<223> OTHER INFORMATION: t = t/u
<220> FEATURE:
<223> OTHER INFORMATION: Description of Artificial Sequence:
      Synthetic Primer

<400> SEQUENCE: 644
augcaacuac aaugcactt                                               19

<210> SEQ ID NO 645
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 645
gugcauugua guugcauug                                               19

<210> SEQ ID NO 646
<211> LENGTH: 19
<212> TYPE: DNA
<213> ORGANISM: Artificial Sequence
<220> FEATURE:
<221> NAME/KEY: modified_base
<222> LOCATION: (18)..(19)
<223> OTHER INFORMATION: t = t/u
<220> FEATURE:
<223> OTHER INFORMATION: Description of Artificial Sequence:
      Synthetic Primer

<400> SEQUENCE: 646
augcaacuac aaugcactt                                               19

<210> SEQ ID NO 647
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 647
gugcauugua guugcauug                                               19

<210> SEQ ID NO 648
<211> LENGTH: 19
<212> TYPE: DNA
<213> ORGANISM: Artificial Sequence
<220> FEATURE:
<221> NAME/KEY: modified_base
<222> LOCATION: (18)..(19)
<223> OTHER INFORMATION: t = t/u
<220> FEATURE:
<223> OTHER INFORMATION: Description of Artificial Sequence:
```

-continued

```
      Synthetic Primer

<400> SEQUENCE: 648
augcaacuac aaugcactt                                                    19

<210> SEQ ID NO 649
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 649
gugcauugua guugcauug                                                    19

<210> SEQ ID NO 650
<211> LENGTH: 19
<212> TYPE: DNA
<213> ORGANISM: Artificial Sequence
<220> FEATURE:
<221> NAME/KEY: modified_base
<222> LOCATION: (18)..(19)
<223> OTHER INFORMATION: t = t/u
<220> FEATURE:
<223> OTHER INFORMATION: Description of Artificial Sequence:
      Synthetic Primer

<400> SEQUENCE: 650
augcaacuac aaugcactt                                                    19

<210> SEQ ID NO 651
<211> LENGTH: 19
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 651
gugcauugua guugcauug                                                    19

<210> SEQ ID NO 652
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 652
ccacacaacc uacuaccuca tt                                                22

<210> SEQ ID NO 653
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 653
```
ugagguagua gguugugugg uu                                              22

<210> SEQ ID NO 654
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 654
ccacacaacc uacuaccuca tt                                              22

<210> SEQ ID NO 655
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 655
ugagguagua gguugugugg uu                                              22

<210> SEQ ID NO 656
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 656
ccacacaacc uacuaccuca tt                                              22

<210> SEQ ID NO 657
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 657
ugagguagua gguugugugg uu                                              22

<210> SEQ ID NO 658
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 658
ccacacaacc uacuaccuca tt				22

<210> SEQ ID NO 659
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 659
ugagguagua gguugugugg uu				22

<210> SEQ ID NO 660
<211> LENGTH: 21
<212> TYPE: DNA
<213> ORGANISM: Artificial Sequence
<220> FEATURE:
<221> NAME/KEY: modified_base
<222> LOCATION: (20)..(21)
<223> OTHER INFORMATION: t = t/u
<220> FEATURE:
<223> OTHER INFORMATION: Description of Artificial Sequence:
      Synthetic Primer

<400> SEQUENCE: 660
cauacuucuu uacauuccat t				21

<210> SEQ ID NO 661
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 661
uggaauguaa agaaguaugu a				21

<210> SEQ ID NO 662
<211> LENGTH: 21
<212> TYPE: DNA
<213> ORGANISM: Artificial Sequence
<220> FEATURE:
<221> NAME/KEY: modified_base
<222> LOCATION: (20)..(21)
<223> OTHER INFORMATION: t = t/u
<220> FEATURE:
<223> OTHER INFORMATION: Description of Artificial Sequence:
      Synthetic Primer

<400> SEQUENCE: 662
cauacuucuu uacauuccat t				21

<210> SEQ ID NO 663
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 663
uggaauguaa agaaguaugu a				21

-continued

```
<210> SEQ ID NO 664
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 664
gcauucaccg cgugccuuaa tt                                              22

<210> SEQ ID NO 665
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 665
uuaaggcacg cggugaaugc ca                                              22

<210> SEQ ID NO 666
<211> LENGTH: 22
<212> TYPE: DNA
<213> ORGANISM: Artificial Sequence
<220> FEATURE:
<221> NAME/KEY: modified_base
<222> LOCATION: (21)..(22)
<223> OTHER INFORMATION: t = t/u
<220> FEATURE:
<223> OTHER INFORMATION: Description of Artificial Sequence:
      Synthetic Primer

<400> SEQUENCE: 666
gcauucaccg cgugccuuaa tt                                              22

<210> SEQ ID NO 667
<211> LENGTH: 22
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 667
uuaaggcacg cggugaaugc ca                                              22

<210> SEQ ID NO 668
<211> LENGTH: 20
<212> TYPE: DNA
<213> ORGANISM: Artificial Sequence
<220> FEATURE:
<221> NAME/KEY: modified_base
<222> LOCATION: (19)..(20)
<223> OTHER INFORMATION: t = t/u
<220> FEATURE:
<223> OTHER INFORMATION: Description of Artificial Sequence:
      Synthetic Primer

<400> SEQUENCE: 668
ccuuuuaaca uugcacugtt                                                 20
```

<210> SEQ ID NO 669
<211> LENGTH: 20
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 669
cagugcaaug uuaaaagggc                                                      20

<210> SEQ ID NO 670
<211> LENGTH: 20
<212> TYPE: DNA
<213> ORGANISM: Artificial Sequence
<220> FEATURE:
<221> NAME/KEY: modified_base
<222> LOCATION: (19)..(20)
<223> OTHER INFORMATION: t = t/u
<220> FEATURE:
<223> OTHER INFORMATION: Description of Artificial Sequence:
      Synthetic Primer

<400> SEQUENCE: 670
ccuuuuaaca uugcacugtt                                                      20

<210> SEQ ID NO 671
<211> LENGTH: 20
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 671
cagugcaaug uuaaaagggc                                                      20

<210> SEQ ID NO 672
<211> LENGTH: 23
<212> TYPE: DNA
<213> ORGANISM: Artificial Sequence
<220> FEATURE:
<221> NAME/KEY: modified_base
<222> LOCATION: (22)..(23)
<223> OTHER INFORMATION: t = t/u
<220> FEATURE:
<223> OTHER INFORMATION: Description of Artificial Sequence:
      Synthetic Primer

<400> SEQUENCE: 672
caaauucgga ucuacagggu att                                                  23

<210> SEQ ID NO 673
<211> LENGTH: 23
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 673
uacccuguag auccgaauuu gug                                                  23

<210> SEQ ID NO 674
<211> LENGTH: 23

```
<212> TYPE: DNA
<213> ORGANISM: Artificial Sequence
<220> FEATURE:
<221> NAME/KEY: modified_base
<222> LOCATION: (22)..(23)
<223> OTHER INFORMATION: t = t/u
<220> FEATURE:
<223> OTHER INFORMATION: Description of Artificial Sequence:
      Synthetic Primer

<400> SEQUENCE: 674
caaauucgga ucuacagggu att                                           23

<210> SEQ ID NO 675
<211> LENGTH: 23
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 675
uacccuguag auccgaauuu gug                                           23

<210> SEQ ID NO 676
<211> LENGTH: 21
<212> TYPE: RNA
<213> ORGANISM: Artificial Sequence
<220> FEATURE:
<220> FEATURE:
<223> OTHER INFORMATION: Description of Artificial Sequence:
      Synthetic Primer

<400> SEQUENCE: 676
uauacaagag augaaauccu c                                             21

<210> SEQ ID NO 677
<211> LENGTH: 64
<212> TYPE: RNA
<213> ORGANISM: Homo sapiens

<400> SEQUENCE: 677
ccccgcgacg agccccucgc acaaaccgga ccugagcguu uuguucguuc ggcucgcgug    60
aggc                                                                64

<210> SEQ ID NO 678
<211> LENGTH: 68
<212> TYPE: RNA
<213> ORGANISM: Homo sapiens

<400> SEQUENCE: 678
uaaaagguag auucuccuuc uaugaguaca uuauuuauga uuaaucauag aggaaaaucc    60
acguuuuc                                                            68

<210> SEQ ID NO 679
<211> LENGTH: 69
<212> TYPE: RNA
<213> ORGANISM: Homo sapiens

<400> SEQUENCE: 679
uugagcagag guugcccuug gugaauucgc uuuauuuaug uugaaucaca caaaggcaac    60
uuuuguuug                                                           69
```

```
<210> SEQ ID NO 680
<211> LENGTH: 66
<212> TYPE: RNA
<213> ORGANISM: Homo sapiens

<400> SEQUENCE: 680
agggcuccug acuccaggua cuguguguua ccuagaaaua gcacuggacu uggagucaga    60
aggccu                                                              66

<210> SEQ ID NO 681
<211> LENGTH: 67
<212> TYPE: RNA
<213> ORGANISM: Homo sapiens

<400> SEQUENCE: 681
agagauggua gacuauggaa cguaggcguu augauuucug accauguaa cauguccac     60 uaacucu                                                             67

<210> SEQ ID NO 682
<211> LENGTH: 61
<212> TYPE: RNA
<213> ORGANISM: Homo sapiens

<400> SEQUENCE: 682
aagaugguug accauagaac augcgcuauc ucugugucgu auguaauaug guccacaucu    60
u                                                                   61

<210> SEQ ID NO 683
<211> LENGTH: 75
<212> TYPE: RNA
<213> ORGANISM: Homo sapiens

<400> SEQUENCE: 683
uacuuaaagc gagguugccc uuuguauauu cgguuuauug acauggaaua uacaagggca    60
agcucucugu gagua                                                    75

<210> SEQ ID NO 684
<211> LENGTH: 76
<212> TYPE: RNA
<213> ORGANISM: Homo sapiens

<400> SEQUENCE: 684
uacuugaaga gaaguuguuc gugguggauu cgcuuuacuu augacgaauc auucacggac    60
aacacuuuuu ucagua                                                   76

<210> SEQ ID NO 685
<211> LENGTH: 73
<212> TYPE: RNA
<213> ORGANISM: Homo sapiens

<400> SEQUENCE: 685
cuccucagau cagaagguga uuguggcuuu gggguggauau uaaucagcca cagcacugcc   60
uggucagaaa gag                                                      73

<210> SEQ ID NO 686
<211> LENGTH: 88
<212> TYPE: RNA
<213> ORGANISM: Homo sapiens

<400> SEQUENCE: 686
```

-continued uguuaaauca ggaauuuuaa acaauuccua gacaauaugu auaauguuca uaagucauuc   60
cuagaaauug uucauaaugc cuguaaca                                     88

<210> SEQ ID NO 687
<211> LENGTH: 90
<212> TYPE: RNA
<213> ORGANISM: Homo sapiens

<400> SEQUENCE: 687
gagagaagca cuggacuuag ggucagaagg ccugagucuc ucugcugcag augggcucuc   60
ugucccugag ccaagcuuug uccucccugg                                   90

<210> SEQ ID NO 688
<211> LENGTH: 94
<212> TYPE: RNA
<213> ORGANISM: Homo sapiens

<400> SEQUENCE: 688
auaaaggaag uuaggcugag gggcagagag cgagacuuuu cuauuuucca aaagcucggu   60
cugaggcccc ucagucuugc uuccuaaccc gcgc                              94

<210> SEQ ID NO 689
<211> LENGTH: 98
<212> TYPE: RNA
<213> ORGANISM: Homo sapiens

<400> SEQUENCE: 689 cgagggaua cagcagcaau ucauguuuug aaguguucua aaugguucaa aacgugaggc    60
gcugcuauac ccccucgugg ggaagguaga aggugggg                          98

<210> SEQ ID NO 690
<211> LENGTH: 87
<212> TYPE: RNA
<213> ORGANISM: Homo sapiens

<400> SEQUENCE: 690
gaaagcgcuu uggaaugaca cgaucacucc cguugagugg gcacccgaga agccaucggg   60
aaugucgugu ccgcccagug cucuuuc                                      87

<210> SEQ ID NO 691
<211> LENGTH: 111
<212> TYPE: RNA
<213> ORGANISM: Homo sapiens

<400> SEQUENCE: 691 gccggaggu ugaacauccu gcauagugcu gccaggaaau cccuauuuca uauaagaggg    60
ggcuggcugg uugcauaugu aggaugucc aucucccagc ccacuucguc a             111

<210> SEQ ID NO 692
<211> LENGTH: 83
<212> TYPE: RNA
<213> ORGANISM: Homo sapiens

<400> SEQUENCE: 692
cgccggccga ugggcgucuu accagacaug guuagaccug gcccucuguc uaauacuguc   60
ugguaaaacc guccauccgc ugc                                          83

<210> SEQ ID NO 693
<211> LENGTH: 91

```
<212> TYPE: RNA
<213> ORGANISM: Homo sapiens

<400> SEQUENCE: 693
cuguguguga ugagcuggca guguauuguu agcugguuga auaugugaau ggcaucggcu    60
aacaugcaac ugcugucuua uugcauauac a                                   91

<210> SEQ ID NO 694
<211> LENGTH: 91
<212> TYPE: RNA
<213> ORGANISM: Homo sapiens

<400> SEQUENCE: 694
aaacgauacu aaacuguuuu ugcgaugugu uccuaauaug cacuauaaau auauugggaa    60
cauuuugcau guauaguuuu guaucaauau a                                   91

<210> SEQ ID NO 695
<211> LENGTH: 85
<212> TYPE: RNA
<213> ORGANISM: Mus musculus

<400> SEQUENCE: 695
aaagugcuuu ggaaugacac gaucacuccc guugaguggg cacccaagaa gccaucggga    60
augucguguc cgcccagugc ucuuu                                          85

<210> SEQ ID NO 696
<211> LENGTH: 112
<212> TYPE: RNA
<213> ORGANISM: Mus musculus

<400> SEQUENCE: 696
acgaggaggu ugaacauccu gcauagugcu gccaggaaau cccuacuuca acuaagagg     60 gggcuggcug guugcauaug uaggaugucc caucuccugg cccacuucgu ca            112

<210> SEQ ID NO 697
<211> LENGTH: 83
<212> TYPE: RNA
<213> ORGANISM: Mus musculus

<400> SEQUENCE: 697
ccugcugaug gaugucuuac cagacauggu uagaucugga ugcaucuguc uaauacuguc    60
ugguaaugcc guccauccac ggc                                            83

<210> SEQ ID NO 698
<211> LENGTH: 91
<212> TYPE: RNA
<213> ORGANISM: Mus musculus

<400> SEQUENCE: 698
cuguguguga uggcuuggca guguauuguu agcugguuga guaugugagc ggcaccagcu    60
aacaugcgac ugcucuccua uugcacacac a                                   91

<210> SEQ ID NO 699
<211> LENGTH: 91
<212> TYPE: RNA
<213> ORGANISM: Mus musculus

<400> SEQUENCE: 699
gagagauacu gagcuguuuu ugcgaugugu uccuaauaug ugcuauaauu auauugggaa    60
```
cauuuugcau aaauagcuuu gugucaauac a                                           91

<210> SEQ ID NO 700
<211> LENGTH: 112
<212> TYPE: RNA
<213> ORGANISM: Rattus norvegicus

<400> SEQUENCE: 700
acggggaggu ugaacauccu gcauagugcu gccaggaaau cccuacuuca uacuaagagg            60
gggcuggcug guugcauaug uaggaugucc caucucccgg cccacuucgu ca                   112

<210> SEQ ID NO 701
<211> LENGTH: 85
<212> TYPE: RNA
<213> ORGANISM: Rattus norvegicus

<400> SEQUENCE: 701
ugccugcuga uggaugucuu accagacaug guuagaucug gauguaucug ucuaauacug            60
ucugguaaug ccguccaucc auggc                                                  85

<210> SEQ ID NO 702
<211> LENGTH: 91
<212> TYPE: RNA
<213> ORGANISM: Rattus norvegicus

<400> SEQUENCE: 702
cugugugcga ugqguuqqca gquauuguu agcugguuga guauguaaaa ggcaccagcu             60
aacaugcaac ugcucuccua uugcacauac a                                           91

<210> SEQ ID NO 703
<211> LENGTH: 91
<212> TYPE: RNA
<213> ORGANISM: Rattus norvegicus

<400> SEQUENCE: 703
gagagaugcg gagcuguuuu ugcgaugugu uccuaaugug ugcuacaauu auauugggaa            60
cauuuugcau aaauaguuuu acaucgacac a                                           91

<210> SEQ ID NO 704
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 704
ctaaaactat acaacctact acctcatccc                                             30

<210> SEQ ID NO 705
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 705
ctgaaaccac acaacctact acctcaccc                                              29

<210> SEQ ID NO 706
<211> LENGTH: 30

```
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 706
tctaaaccat acaacctact acctcaaccc                                    30

<210> SEQ ID NO 707
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 707
taaaactatg caacctacta cctcttcct                                     29

<210> SEQ ID NO 708
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 708
cctaagaaag gcagcaggtc gtatagttaa                                    30

<210> SEQ ID NO 709
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 709
ctcaactata caacctccta cctcagccc                                     29

<210> SEQ ID NO 710
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 710
ccacaactat acaatctact acctcactct                                    30

<210> SEQ ID NO 711
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 711
ccacaactat acaatctact acctcactct                                    30

<210> SEQ ID NO 712
<211> LENGTH: 29
<212> TYPE: DNA
```

```
<213> ORGANISM: Artificial Sequence
<220> FEATURE:
<223> OTHER INFORMATION: Description of Artificial Sequence:
      Synthetic Primer

<400> SEQUENCE: 712
tcaaactgta caaactacta cctcagcct                                      29

<210> SEQ ID NO 713
<211> LENGTH: 27
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 713
aaacagcaca aactactacc tcagcca                                        27

<210> SEQ ID NO 714
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 714
ataccacaag ttcggatcta cgggtttgtg                                     30

<210> SEQ ID NO 715
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 715
catccttcag ttatcacagt actgtacctt                                     30

<210> SEQ ID NO 716
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 716
tctttcatag ccctgtacaa tgctgcttga t                                   31

<210> SEQ ID NO 717
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 717
caccacagga gtctgagcat ttgaccac                                       28

<210> SEQ ID NO 718
<211> LENGTH: 32
<212> TYPE: DNA
<213> ORGANISM: Artificial Sequence
```

```
<220> FEATURE:
<223> OTHER INFORMATION: Description of Artificial Sequence:
      Synthetic Primer

<400> SEQUENCE: 718
aaaagctacc tgcactgtaa gcacttttac at                          32

<210> SEQ ID NO 719
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 719
gctttgatag ccctgtacaa tgctgcttga a                           31

<210> SEQ ID NO 720
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 720
cttacacaaa ttcggatcta cagggtatat a                           31

<210> SEQ ID NO 721
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 721
caaaaataca tacttcttta cattccatag c                           31

<210> SEQ ID NO 722
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 722
agacacaaac accattgtca cactccacag c                           31

<210> SEQ ID NO 723
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 723
ttcttggcat tcaccgcgtg ccttaattgt                             30

<210> SEQ ID NO 724
<211> LENGTH: 31
<212> TYPE: DNA
<213> ORGANISM: Artificial Sequence
<220> FEATURE:
```

```
<223> OTHER INFORMATION: Description of Artificial Sequence:
      Synthetic Primer

<400> SEQUENCE: 724
tcctcacagg ttaaagggtc tcagggacct a                                        31

<210> SEQ ID NO 725
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 725
aacatcacaa gttagggtct cagggactga                                          30

<210> SEQ ID NO 726
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 726
cggcgcatta ttactcacgg tacgagttt                                           29

<210> SEQ ID NO 727
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 727
acagcgcgta ccaaaagtaa taatgtccc                                           29

<210> SEQ ID NO 728
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 728
gaccagccaa gctcagacgg atccgatgat                                          30

<210> SEQ ID NO 729
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 729
ctgaaaaaga gaccggttca ctgtgagaaa                                          30

<210> SEQ ID NO 730
<211> LENGTH: 29
<212> TYPE: DNA
<213> ORGANISM: Artificial Sequence
<220> FEATURE:
<223> OTHER INFORMATION: Description of Artificial Sequence:
```

```
                          Synthetic Primer

<400> SEQUENCE: 730
tacagcaagc ccagaccgca aaaagattc                                    29

<210> SEQ ID NO 731
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 731
caatgccctt ttaacattgc actgctag                                     28

<210> SEQ ID NO 732
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 732
accgatgccc tttcatcatt gcactgcttc                                   30

<210> SEQ ID NO 733
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 733
ggggcgacca tggctgtaga ctgttacctc                                   30

<210> SEQ ID NO 734
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 734
agctacagct ggttgaaggg gaccaaatcc                                   30

<210> SEQ ID NO 735
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 735
atgcccctct ggtcaaccag tcacacacc                                    29

<210> SEQ ID NO 736
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer
```

-continued

```
<400> SEQUENCE: 736
agaatcacat aggaataaaa agccatagag a                                    31

<210> SEQ ID NO 737
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 737
agaatccatc atcaaaacaa atggagtcct c                                    31

<210> SEQ ID NO 738
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 738
tcgactacgc gtattcttaa gcaataacaa                                      30

<210> SEQ ID NO 739
<211> LENGTH: 25
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 739
gcctgattca caacaccagc tgccc                                           25

<210> SEQ ID NO 740
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 740
ctggagacac gtgcactgta gaatac                                          26

<210> SEQ ID NO 741
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 741
taacctacca tagggtaaaa ccactggca                                       29

<210> SEQ ID NO 742
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer
```

```
<400> SEQUENCE: 742
ggagccatct ttaccagaca gtgttagga                                      29

<210> SEQ ID NO 743
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 743
ctcatccata aagtaggaaa cactacaccc t                                   31

<210> SEQ ID NO 744
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 744
gttagtagtg ctttctactt tatgggtg                                       28

<210> SEQ ID NO 745
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 745
ttcctgagct acagtgcttc atctcagact                                     30

<210> SEQ ID NO 746
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 746
cggactagta catcatctat actgtagtgt                                     30

<210> SEQ ID NO 747
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 747
atctaaggga ttcctgggaa aactggaccg tg                                  32

<210> SEQ ID NO 748
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 748
```

```
acacaaccca tggaattcag ttctcaaagc                                    30
```

<210> SEQ ID NO 749
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 749

```
tctagcagaa gcatttccac acactggc                                      28
```

<210> SEQ ID NO 750
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 750

```
gagaacaaag ttctgtagtg cactgattct                                    30
```

<210> SEQ ID NO 751
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 751

```
cacgggagtg aagacacgga gccagagctc                                    30
```

<210> SEQ ID NO 752
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 752

```
ccagcactgg tacaagggtt gggagacagg                                    30
```

<210> SEQ ID NO 753
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 753

```
ctgtcctcaa ggagcttcag tctagtaggg                                    30
```

<210> SEQ ID NO 754
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 754
gggcccaagt tctgtcatgc actgactgc                                    29

<210> SEQ ID NO 755
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 755
atgatcactt ttgtgactat gcaactgg                                     28

<210> SEQ ID NO 756
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 756
aaagcgaagg caacacggat aacctatctt                                   30

<210> SEQ ID NO 757
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 757
aaaaacccct atcacgatta gcattaacag                                   30

<210> SEQ ID NO 758
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 758
aatccacaaa ccattatgtg ctgctacttt                                   30

<210> SEQ ID NO 759
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 759
agcatgtaaa ccatgatgtg ctgctacagt                                   30

<210> SEQ ID NO 760
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 760
ttaacgccaa tatttacgtg ctgctaaggc                                   30

<210> SEQ ID NO 761
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 761
tgctacaagt gccttcactg cagtagat                               28

<210> SEQ ID NO 762
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 762
tatcactacc tgcactgtaa gcactttgac at                          32

<210> SEQ ID NO 763
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 763
tcactatctg cactagatgc accttagaac                             30

<210> SEQ ID NO 764
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 764
ccaaactcac cgacagcgtt gaatgttcct t                           31

<210> SEQ ID NO 765
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 765
gttcaaccca ccgacagcaa tgaatgttga tt                          32

<210> SEQ ID NO 766
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 766
ccagtgtgag ttctaccatt gccaaaaacg                             30

<210> SEQ ID NO 767
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 767
cccatagttg gcaagtctag aaccaccgg                               29

<210> SEQ ID NO 768
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 768
ttcacagtga attctaccag tgccatacac a                            31

<210> SEQ ID NO 769
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 769
acctacccTt atcagttctc cgtccaacac                              30

<210> SEQ ID NO 770
<211> LENGTH: 26
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 770
tcaggaactg cctttctctc caatcc                                  26

<210> SEQ ID NO 771
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 771
cagaaagccc aaaaggagaa ttctttggaa a                            31

<210> SEQ ID NO 772
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 772
cctccggctg caacacaaga cacgagggg                               29

```
<210> SEQ ID NO 773
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 773
gctcaccctc caccatgcaa gggatgtgag                                    30

<210> SEQ ID NO 774
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 774
gagaactgat atcagctcag taggcaccgg a                                  31

<210> SEQ ID NO 775
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 775
aacaacctaa tatatcaaac atatcacaca                                    30

<210> SEQ ID NO 776
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 776
caacagctgc ttttgggatt ccgttgcccg                                    30

<210> SEQ ID NO 777
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 777
cactggctgt caattcatag gtcagagcc                                     29

<210> SEQ ID NO 778
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 778
agaactggga ctttgtaggc cagttgatc                                     29

<210> SEQ ID NO 779
```

```
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 779
acagtccaca tggagttgct gttacacttg                                           30

<210> SEQ ID NO 780
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 780
ctgtgccaat atttctgtgc tgctagagc                                            29

<210> SEQ ID NO 781
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 781
aggcccaaca acatgaaact acctaattc                                            29

<210> SEQ ID NO 782
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 782
ccatgctggg tggagaaggt ggtgaagggt                                           30

<210> SEQ ID NO 783
<211> LENGTH: 27
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 783
ggaacctatc tcccctctgg accaatg                                              27

<210> SEQ ID NO 784
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 784
gcctaaccaa tgtgcagact actgtacaca                                           30

<210> SEQ ID NO 785
<211> LENGTH: 30
```

```
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 785
gtctaaccaa tgtgcagact actgtacaac                                    30

<210> SEQ ID NO 786
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 786
tcctgaacag gtagtctgaa cactgggttg g                                  31

<210> SEQ ID NO 787
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 787
tcctgaacag gtagtctgaa cactggggcg a                                  31

<210> SEQ ID NO 788
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 788
accatcagtt ttgcatagat ttgcacaact a                                  31

<210> SEQ ID NO 789
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 789
acactacctg cactataagc actttagtgc                                    30

<210> SEQ ID NO 790
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 790
ttgaacatcg ttaccagaca gtgttagagt                                    30

<210> SEQ ID NO 791
<211> LENGTH: 32
<212> TYPE: DNA
```

<213> ORGANISM: Artificial Sequence
<220> FEATURE:
<223> OTHER INFORMATION: Description of Artificial Sequence:
      Synthetic Primer

<400> SEQUENCE: 791
ccgtcatcat taccaggcag tattagagac ct					32

<210> SEQ ID NO 792
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 792
tagaagaaca atgccttact gagtaaggt						29

<210> SEQ ID NO 793
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 793
tccatcttcc catgcgctat acctctttag					30

<210> SEQ ID NO 794
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 794
gggtctagtg gtcctaaaca tttcacaatt					30

<210> SEQ ID NO 795
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 795
tctcaggcat aggatgacaa agggaagtcc					30

<210> SEQ ID NO 796
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 796
gagacagact ccggtggaat gaaggatctg					30

<210> SEQ ID NO 797
<211> LENGTH: 30
<212> TYPE: DNA
<213> ORGANISM: Artificial Sequence

```
<220> FEATURE:
<223> OTHER INFORMATION: Description of Artificial Sequence:
      Synthetic Primer

<400> SEQUENCE: 797
gaaaccacac acttccttac attccatagc                                      30

<210> SEQ ID NO 798
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 798
aagagaggga ggagagccag gagaagcgca a                                    31

<210> SEQ ID NO 799
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 799
accaacaagc tttttgctcg tcttatacgt                                      30

<210> SEQ ID NO 800
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 800
acagtcaaca tcagtctgat aagctacccg                                      30

<210> SEQ ID NO 801
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 801
agatcagccg ctgtcacacg cacagtggg                                       29

<210> SEQ ID NO 802
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 802
ccctaggcga aggatgacaa agggaagccc                                      30

<210> SEQ ID NO 803
<211> LENGTH: 29
<212> TYPE: DNA
<213> ORGANISM: Artificial Sequence
<220> FEATURE:
```

```
<223> OTHER INFORMATION: Description of Artificial Sequence:
      Synthetic Primer

<400> SEQUENCE: 803
cggtggccgt gactggagac tgttactga                                     29

<210> SEQ ID NO 804
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 804
atagggtaca atcaacggtc gatggttttg                                    30

<210> SEQ ID NO 805
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 805
gtgactgcct gtctgtgcct gctgtacag                                     29

<210> SEQ ID NO 806
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 806
tattgtctgt caattcatag gtcatttttc                                    29

<210> SEQ ID NO 807
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 807
atctcacagt tgccagctga gattaagcc                                     29

<210> SEQ ID NO 808
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 808
tcttatccaa tcagttcctg atgcagtatc tg                                 32

<210> SEQ ID NO 809
<211> LENGTH: 29
<212> TYPE: DNA
<213> ORGANISM: Artificial Sequence
<220> FEATURE:
<223> OTHER INFORMATION: Description of Artificial Sequence:
```

```
                        Synthetic Primer

<400> SEQUENCE: 809
aaccacatgg ttagatcaag cacaacaga                                29

<210> SEQ ID NO 810
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 810
ctcgagaatt gcgtttggac aatcaggag                                29

<210> SEQ ID NO 811
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 811
ggcaacagtt cttcaactgg cagctttagc                               30

<210> SEQ ID NO 812
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 812
gcccaaagtg tcagatacgg tgtggagcc                                29

<210> SEQ ID NO 813
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 813
gcctgaaacc cagcagacaa tgtagctgtt g                             31

<210> SEQ ID NO 814
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 814
atcagagacc cagtagccag atgtagctgc tg                            32

<210> SEQ ID NO 815
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer
```

```
<400> SEQUENCE: 815
acttggggta tttgacaaac tgacactct                                           29

<210> SEQ ID NO 816
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 816
ctactaaacg gaaccactag tgacttgaaa g                                        31

<210> SEQ ID NO 817
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 817
ggttggaaat ccctggcaat gtgatttgt                                           29

<210> SEQ ID NO 818
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 818
ttgcgtggta atccctggca atgtgatttt a                                        31

<210> SEQ ID NO 819
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 819
ctcctgttcc tgctgaactg agccagtgtg                                          30

<210> SEQ ID NO 820
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 820
actgtcagac cgagacaagt gcaatgccca                                          30

<210> SEQ ID NO 821
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer
```

-continued

```
<400> SEQUENCE: 821
gcacagccta tcctggatta cttgaacgag                                30

<210> SEQ ID NO 822
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 822 gggggcgga acttagccac tgtgaacacg                                 30

<210> SEQ ID NO 823
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 823
gtaactcaat agactgtgag ctccttgagg                                30

<210> SEQ ID NO 824
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 824
aaaaaaaaag tgcccccata gtttgagtac c                              31

<210> SEQ ID NO 825
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 825
cagtggcaca caaagtggaa gcactttctc a                              31

<210> SEQ ID NO 826
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 826
ctcaagagag ggcctccact ttgatggccg                                30

<210> SEQ ID NO 827
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 827
```
ggtgacactc aaaacctggc ggcactttc t                          31

<210> SEQ ID NO 828
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 828
aatccaaaag agcccccagt ttgagtatca                           30

<210> SEQ ID NO 829
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 829
ggcaacacta caaactctgc ggcacttctt                           30

<210> SEQ ID NO 830
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 830
ggcaacacac aaaagggaag cactttccac                           30

<210> SEQ ID NO 831
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 831
ggagagactc aaaagtagta gcactttcta t                         31

<210> SEQ ID NO 832
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 832
cacaacagga ttgaggggg gccctctgg                             29

<210> SEQ ID NO 833
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 833
tgcacatgca catgcacaca tacatacat                            29

<210> SEQ ID NO 834
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 834
caagggaaga acagccctcc tctgccaaag                           30

<210> SEQ ID NO 835
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 835
caaaatgtat gtgggacggt aaaccatttc                           30

<210> SEQ ID NO 836
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 836
gaacactgat ttcaaatggt gctagaca                             28

<210> SEQ ID NO 837
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 837
cctcgaagag agcttgccct tgcatattca                           30

<210> SEQ ID NO 838
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 838
agatgctttg acaatactat tgcactgcta g                         31

<210> SEQ ID NO 839
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 839
ccatcaccaa aacatggaag cacttacttc t                         31

```
<210> SEQ ID NO 840
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 840
tcacagaaag cacttccatg ttaaagttga a                               31

<210> SEQ ID NO 841
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 841
cctccactga aacatggaag cacttacttt t                               31

<210> SEQ ID NO 842
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 842
cacacagcag gtaccccat cttaaagcaa                                  30

<210> SEQ ID NO 843
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 843
gcaggctgca aacatccgac tgaaagccat                                 30

<210> SEQ ID NO 844
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 844
cacagcttcc agtcgaggat gtttacagtc g                               31

<210> SEQ ID NO 845
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 845
tacagctgag tgtaggatgt ttacatgaa                                  29
```

```
<210> SEQ ID NO 846
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 846
tcaacagcta tgccagcatc ttgcctcct                                  29

<210> SEQ ID NO 847
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 847
acatgcaact tagtaatgtg caatatctc                                  29

<210> SEQ ID NO 848
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 848 cttttcgcc ctctcaaccc agcttttccc g                                31

<210> SEQ ID NO 849
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 849
ggggtgttgc agcgcttcat gttttgaa                                   28

<210> SEQ ID NO 850
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 850
gcaaagaggt cgaccgtgta atgtgcgcca                                 30

<210> SEQ ID NO 851
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 851
acccccagca gcacctgggg cagtgggtct                                 30
```

```
<210> SEQ ID NO 852
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 852
ctttacacca atgccctagg ggatgcgggg a                               31

<210> SEQ ID NO 853
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 853
aaacacttac tggacaccta ctaggaacc                                  29

<210> SEQ ID NO 854
<211> LENGTH: 28
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 854
ggggctggag gaagggccca gaggcgat                                   28

<210> SEQ ID NO 855
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 855
ggggacggaa gggcagagag ggccaggggc                                 30

<210> SEQ ID NO 856
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 856
tgaaaaaaag gttagctggg tgtgtttcat                                 30

<210> SEQ ID NO 857
<211> LENGTH: 27
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 857
catgcaatgc aactacaatg caccaca                                    27

<210> SEQ ID NO 858
```

-continued

```
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 858
tgcctctctg caggccgtgt gctttgctcg g                                   31

<210> SEQ ID NO 859
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 859
ttggttctag gataggccca ggggcctgg                                      29

<210> SEQ ID NO 860
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 860
gaagaaaggc atcatatagg agctggataa c                                   31

<210> SEQ ID NO 861
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 861
tcttcaacaa aatcactgat gctggagtcg c                                   31

<210> SEQ ID NO 862
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 862
cacgtgagct cctggaggac agggagagc                                      29

<210> SEQ ID NO 863
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 863
gtatggctat aaagtaactg agacggatcc                                     30

<210> SEQ ID NO 864
<211> LENGTH: 29
```

```
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 864
gccgactgac cgaccgaccg atcgaccga                              29

<210> SEQ ID NO 865
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 865
aggtgacggg tgcgatttct gtgtgagaca at                          32

<210> SEQ ID NO 866
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 866
gcttacagtc aggctttggc tagatcaggt a                           31

<210> SEQ ID NO 867
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 867
acgagccctg gactaggagt cagcagacc                              29

<210> SEQ ID NO 868
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 868
aacagagagg caggcatgcg ggcagacaga c                           31

<210> SEQ ID NO 869
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 869
cacaacaacc agctaagaca ctgccaaaga                             30

<210> SEQ ID NO 870
<211> LENGTH: 30
<212> TYPE: DNA
```

-continued

```
<213> ORGANISM: Artificial Sequence
<220> FEATURE:
<223> OTHER INFORMATION: Description of Artificial Sequence:
      Synthetic Primer

<400> SEQUENCE: 870
ttagcaatca gctaactaca ctgcctagta                                        30

<210> SEQ ID NO 871
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 871
aagggtgaaa gtgtatgggc tttgtgaaca tt                                     32

<210> SEQ ID NO 872
<211> LENGTH: 32
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 872
actccaggct caaagggctc ctcagggaaa cg                                     32

<210> SEQ ID NO 873
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 873
ccatcaccat tgctaaagtg caattccaat                                        30

<210> SEQ ID NO 874
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 874
aaaacgtgga atttcctcta tgtttaacca                                        30

<210> SEQ ID NO 875
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 875
gagaaaagat caaccatgta ttattcgaa                                         29

<210> SEQ ID NO 876
<211> LENGTH: 31
<212> TYPE: DNA
<213> ORGANISM: Artificial Sequence
```

```
<220> FEATURE:
<223> OTHER INFORMATION: Description of Artificial Sequence:
      Synthetic Primer

<400> SEQUENCE: 876
cagaccaggt tccaccccag caggcactcc c                                      31

<210> SEQ ID NO 877
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 877
gtaacactca aaagatggcg gcactttcac                                        30

<210> SEQ ID NO 878
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 878
gtgacgctca aatgtcgcag cactttccac t                                      31

<210> SEQ ID NO 879
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 879
gggacacccc aaaatcgaag cacttcccag t                                      31

<210> SEQ ID NO 880
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 880
aaaaggaaag cgcccccatt ttgagtatcc                                        30

<210> SEQ ID NO 881
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 881
ataacactta tcaggttgta ttataatggc                                        30

<210> SEQ ID NO 882
<211> LENGTH: 29
<212> TYPE: DNA
<213> ORGANISM: Artificial Sequence
<220> FEATURE:
```

```
<223> OTHER INFORMATION: Description of Artificial Sequence:
      Synthetic Primer

<400> SEQUENCE: 882
gaaaacgtgg attttcctct acgattagt                                           29

<210> SEQ ID NO 883
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 883
tgaaaaagtg gatgttcctc tatgattat                                           29

<210> SEQ ID NO 884
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 884
aagatgtgga ccatactaca tacgaccca                                           29

<210> SEQ ID NO 885
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 885
cgaaaagggg ttcaccgagc aacattcgt                                           29

<210> SEQ ID NO 886
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 886
tgaaaacagg ccatctgtgt tatattcgtc                                          30

<210> SEQ ID NO 887
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 887
tgatactgag ggttagtgga ccgtgttaca t                                        31

<210> SEQ ID NO 888
<211> LENGTH: 31
<212> TYPE: DNA
<213> ORGANISM: Artificial Sequence
<220> FEATURE:
<223> OTHER INFORMATION: Description of Artificial Sequence:
```

```
            Synthetic Primer

<400> SEQUENCE: 888
accgacggct agtggaccag gtgaagtaca t                              31

<210> SEQ ID NO 889
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 889
aaacaacaaa atcactagtc ttccacaca                                 29

<210> SEQ ID NO 890
<211> LENGTH: 31
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 890
ccactcatac agctagataa ccaaagataa c                              31

<210> SEQ ID NO 891
<211> LENGTH: 29
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 891
ttttactttc ggttatctag ctttatgaa                                 29

<210> SEQ ID NO 892
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 892
ctcaacaggc cgggacaagt gcaataccat                                30

<210> SEQ ID NO 893
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 893
cacactacct gcacgaacag cactttggag                                30

<210> SEQ ID NO 894
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer
```

```
<400> SEQUENCE: 894
tgggtgctca ataaataccc gttgaatgta                                30

<210> SEQ ID NO 895
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 895
acaagcaaaa atgtgctagt gccaaaatcg                                30

<210> SEQ ID NO 896
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 896
accccacaac aatacaactt actacctcac                                30

<210> SEQ ID NO 897
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 897
tcaccacaag atcggatcta cgggtttatg                                30

<210> SEQ ID NO 898
<211> LENGTH: 30
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 898
gccccgcaag gtcggttcta cgggtgggtg                                30

<210> SEQ ID NO 899
<211> LENGTH: 72
<212> TYPE: RNA
<213> ORGANISM: Artificial Sequence
<220> FEATURE:
<223> OTHER INFORMATION: Description of Artificial Sequence:
      Synthetic Primer

<400> SEQUENCE: 899
ggagcuuauc agaaucucca gggguacuuu auaauuucaa aaaguccccc aggugugauu   60
cugauuugcu uc                                                      72
```

METHODS AND COMPOSITIONS INVOLVING MICRORNA

CROSS-REFERENCE TO RELATED APPLICATIONS

This application claims the benefit of U.S. Provisional Patent Application Ser. No. 60/575,743 filed on May 28, 2004 and also of U.S. Provisional Patent Application Ser. No. 60/649,584 filed on Feb. 3, 2005. The entire text of each of the above-referenced disclosures is specifically incorporated herein by reference without disclaimer.

This invention was made with government support under R44 CA088699 awarded by the National Cancer Institute. The government has certain rights in the invention.

INCORPORATION BY REFERENCE OF SEQUENCE LISTING SUBMITTED ON A COMPACT DISC

Pursuant to 37 C.F.R. §1.53(e), the Sequence Listing required under 37 C.F.R. §1.821(c) for SEQ ID NOs: 1-899, as set forth below, is submitted on one compact disc (Copy 1), together with a duplicate thereof (Copy 2). Each of Copy 1 and Copy 2 were created on May 31, 2005, in PC format using MS Windows operating system. Copy 1 and Copy 2 each contain one 196 kb file entitled "AMBI097U.S.APP.txt." The material contained on the compact disc is specifically incorporated herein by reference.

BACKGROUND OF THE INVENTION

1. Field of the Invention

The present invention relates generally to the field of molecular biology. More particularly, it concerns methods and compositions involving microRNA (miRNAs) molecules. Methods and compositions for isolating, labeling, preparing miRNAs for analysis or as a tool for analysis are described, such as miRNA arrays. In addition, there are applications for miRNAs in diagnostics, therapeutics, and prognostics.

2. Description of the Related Art

In 2001, several groups used a novel cloning method to isolate and identify a large variety of "micro RNAs" (miRNAs) from *C. elegans, Drosophila*, and humans (Lagos-Quintana et al., 2001; Lau et al., 2001; Lee and Ambros, 2001). Several hundreds of miRNAs have been identified in plants and animals—including humans—which do not appear to have endogenous siRNAs. Thus, while similar to siRNAs, miRNAs are nonetheless distinct.

miRNAs thus far observed have been approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through imprecise base-pairing with their targets.

The function of most miRNAs is not known. A number of miRNAs, however, seem to be involved in gene regulation. Some of these miRNAs, including lin-4 and let-7, inhibit protein synthesis by binding to partially complementary 3' untranslated regions (3' UTRs) of target mRNAs. Others, including the Scarecrow miRNA found in plants, function like siRNA and bind to perfectly complementary mRNA sequences to destroy the target transcript (Grishok et al., 2001).

Some miRNAs, such as lin-4, let-7, miR-14, miR-23, and bantam, have been shown to play critical roles in cell differentiation and tissue development (Ambros, 2003; Xu et al., 2003). Others are believed to have similarly important roles because of their differential spatial and temporal expression patterns.

Research on microRNAs (miRNAs) is increasing as scientists are beginning to appreciate the broad role that these molecules play in the regulation of eukaryotic gene expression. The two best understood miRNAs, lin-4 and let-7, regulate developmental timing in *C. elegans* by regulating the translation of a family of key mRNAs (reviewed in Pasquinelli, 2002). Several hundred miRNAs have been identified in *C. elegans, Drosophila*, mouse, and humans. As would be expected for molecules that regulate gene expression, miRNA levels have been shown to vary between tissues and developmental states. Characterization of a number of miRNAs indicates that they influence a variety of processes, including early development (Reinhart, 2000), cell proliferation and cell death (Brennecke, 2003), and apoptosis and fat metabolism (Xu, 2003). In addition, one study shows a strong correlation between reduced expression of two miRNAs and chronic lymphocytic leukemia, providing a possible link between miRNAs and cancer (Calin, 2002). Although the field is still young, there is speculation that miRNAs could be as important as transcription factors in regulating gene expression in higher eukaryotes.

Several publications describe labeling miRNAs for analysis. These publications describe appending a radioactive phosphate at the 5' end of the miRNA population using a polynucleotide kinase (Krichevsky, 2003) or a radiolabeled, single nucleotide at the 3' end with RNA ligase (Dostie, 2003). For the purpose of using arrays to estimate the relative abundances of miRNAs in samples, these methods have two significant drawbacks: (1) only a single label is appended per miRNA, limiting the sensitivity that can be achieved and (2) the methods are compatible with radiolabeling only, which has disadvantages as compared to non-isotopic platforms for arrays. Furthermore, while RNA oligonucleotides have been labeled with non-isotopic labels (Martin et al., 1998), there is no evidence that small RNA molecules from a cell lysate can be effectively labeled in a similar manner after they have been enriched or isolated from the lysate.

Because microarrays are typically used to analyze messenger RNAs that are hundreds or thousands of nucleotides in length, we found that the 60-500mer probes typically used in microarrays were not compatible with miRNA analysis.

Therefore, there is a need for information about the function and activity of miRNAs, as well as for methods and compositions that can be used for their characterization and analysis.

SUMMARY OF THE INVENTION

The present invention is based on the inventors' studies regarding the manipulation of miRNA and the use of miRNAs to characterize their role and function in cells. It concerns methods and compositions for isolating miRNA, labeling it, preparing arrays directed to miRNAs (miRNA array or microarray), analyzing miRNAs using an array, and characterizing miRNAs for diagnostic, therapeutic, and prognostic applications.

The term "miRNA" is used according to its ordinary and plain meaning and refers to a microRNA molecule found in eukaryotes that is involved in RNA-based gene regulation. See, e.g., Carrington et al., 2003, which is hereby incorporated by reference. The term will be used to refer to the RNA molecule processed from a precursor. Individual miRNAs have been identified and sequenced in different organisms, and they have been given names. Names of miRNAs and their sequences are provided herein. Additionally, other miRNAs are known to those of skill in the art and can be readily implemented in embodiments of the invention. The methods and compositions should not be limited to miRNAs identified in the application, as they are provided as examples, not necessarily as limitations of the invention.

Some embodiments of the invention concern methods for labeling miRNA. While it is contemplated that miRNA may be labeled with a single label, in many embodiments of the invention, multiple labels (may be the same or different labels) are attached to the miRNA. Consequently, methods for multi-labeling are specifically contemplated as part of the invention. In some embodiments, the miRNA to be labeled is contacted with an enzyme that catalyzes the addition of di- or tri-phosphate nucleotides to the 3' end of the miRNA, effectively adding a nucleotide tail to the miRNA. The miRNA and enzyme will be incubated under conditions to allow catalysis by the enzyme to occur such that a reaction mixture (for tailing) is formed. Moreover, the reaction mixture will contain nucleotides that are labeled or unlabeled, which are added to the 3' end of the miRNA by the enzyme to form a tailed miRNA molecule. The nucleotides may be DNA and/or RNA, though in some embodiments, the nucleotide is a ribonucleotide. The term "nucleotide" refers to both ribonucleotides and deoxyribonucleotides, though it is specifically contemplated that any embodiment discussed in the context of "nucleotides" may be implemented specifically with "ribonucleotides" or "deoxyribonucleotides," unless otherwise specified or limited. The nucleotide used in the reaction may be uridine, adenosine, guanosine, and/or cytosine, including any combination thereof. In specific embodiments, the nucleotide is uridine, which may or may not be modified as discussed below. The tail added to the miRNA is at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 nucleotides or more in length, or any range derivable therein.

The nucleotides added to the miRNA may already have a label attached or the label may be attached after the miRNA is tailed. If unlabeled nucleotides are added to the miRNA, the method further comprises attaching a label to the tailed miRNA molecules. Thereafter, the multi-labeled miRNA molecules may be isolated, which means it may be separated from any or all of the following: unincorporated label or nucleotides, enzyme, nontailed miRNA, and other RNA. In the process of isolating the multi-labeled miRNA molecules, the molecules may be dried down for subsequent use.

miRNA used in the reaction may be obtained by a variety of methods and from a variety of sources. The miRNA may be obtained from a biological sample, such as a cell, tissue, or organ. It may be isolated from a biological sample that contains other RNA molecules as well, such as mRNA, tRNA, and/or rRNA. In certain instances, total RNA is first isolated from the sample and then the miRNA is separated from the other RNA, thereby enriching for miRNA. In some embodiments, the miRNA has been isolated away from other RNA to enrich for the miRNA, such that the miRNA substantially pure, meaning it is at least about 80%, 85%, 90%, 95% pure or more, but less than 100% pure, with respect to other RNA molecules. Alternatively, enrichment of miRNA may be expressed in terms of fold-enrichment. In certain embodiments, miRNA is enriched by about, at least about, or at most about 5×, 10×, 20×, 30×, 40×, 50×, 60×, 70×, 80×, 90×, 100×, 110×, 120×, 130×, 140×, 150×, 160×, 170×, 180×, 190×, 200×, 210×, 220×, 230×, 240×, 250×, 260×, 270×, 280×, 290×, 300×, 310×, 320×, 330×, 340×, 350×, 360×, 370×, 380×, 390×, 400×, 410×, 420×, 430×, 440×, 450×, 460×, 470×, 480×, 490×, 500×, 600×, 700×, 800×, 900×, 1000×, 1100×, 1200×, 1300×, 1400×, 1500×, 1600×, 1700×, 1800×, 1900×, 2000×, 3000×, 4000×, 5000×, 6000×, 7000×, 8000×, 9000×, 10,000× or more, or any range derivable therein, with respect to the concentration of miRNA in an RNA isolate or the total RNA in the sample.

miRNA can be separated from other RNA molecules using methods known to those of ordinary skill in the art. In some embodiments, miRNA are separated from other RNA molecules using chromatography. Gel chromatography can be implemented to isolate miRNA molecules. In certain embodiments, gel chromatography can be performed using a polyacrylamide gel and tube electrophoresis.

The biological sample may be from any organism that has endogenous miRNA. Organisms include, but should not be limited to, arthropods (*Drosophila melanogaster*); nematodes (*Caenorhabditis elegans* and *Caenorhabditis briggsae*); vertebrates (*homo sapiens*, mus musculus, *Rattus norvegicus*); plants (*Arabidopsis thaliana* and *Oryza sativa*), all of which have miRNA that has been sequenced. See the miRNA Registry on the world wide web at sanger.ac.uk/cgi-bin/Rfam/mirna/browse.pl. Alternatively, miRNA may be recombinant, such that it is obtained from a cell-free system or reaction mixture or from a recombinant host cell, which may or may not have endogenous miRNA. Furthermore, miRNA may be evaluated in samples that were previously fixed. In some embodiments of the invention, the sample was fixed in formaldehyde or paraformaldehyde prior to taking steps to evaluate its miRNA. In additional embodiments, samples that can be used according to the invention include those in which RNA in the sample has been degraded. Such samples include those in which about or at least about 50%, 60%, 70%, 80%, 90%, 95% or more, or any range derivable therein, of the mRNA and/or rRNA in the sample is degraded. In particular embodiments, samples in which there has been substantial degradation—that is, at least about 80% degradation of mRNA and/or rRNA in the sample—are analyzed according to methods and compositions of the invention.

In some embodiments, enzymes used in methods and compositions of the invention are selected from the group consisting of poly(A) polymerase, terminal transferase, and polynucleotide phosphorylase. In particular embodiments, the enzyme is poly(A) polymerase. In some cases, poly(A) polymerase is from *E. coli* or yeast. The enzyme may be purified, recombinant, and/or purchased commercially.

Labeling methods of the invention involve, in many embodiments, one or more modified nucleotides. The term "modified nucleotide" refers to a nucleotide—the basic structural unit of nucleic acids, RNA and DNA—that has been chemically modified, but still functions as a nucleotide. Modified nucleotides include nucleotides with covalently-bound detectable moieties, such as a fluorescent or chemi-luminescent label. Modified nucleotides also include nucleotides with reactive groups that can react with a detectable moiety before, during, or after incorporation of the modified nucleotide to create a labeled nucleic acid. In specific embodiments, the modified nucleotide is an amine-modified nucleotide, which means the nucleotide has been modified to have a reactive amine group. Modified nucleotides may be uridine, adenosine, guanosine, and/or cytosine. In specific embodiments, the amine-modified nucleotide is selected from the group consisting of 5-(3-aminoallyl)-UTP; 8-[(4-amino)butyl]-amino-ATP and 8-[(6-amino)butyl]-amino-ATP; $N^6$-(4-amino)butyl-ATP, $N^6$-(6-amino)butyl-ATP, $N^4$-[2,2-oxy-bis-(ethylamine)]-CTP; $N^6$-(6-Amino)hexyl-ATP; 8-[(6-Amino)hexyl]-amino-ATP; 5-propargylamino-CTP, 5-propargylamino-UTP. However, it is contemplated that other nucleotides may be similarly modified, for example, 5-(3-aminoallyl)-GTP instead of 5-(3-aminoallyl)-UTP.

In certain embodiments, a reaction mixture includes modified nucleotides that have a labeled moiety attached ("labeled nucleotides"). In this case, a one-step process (a single enzymatic reaction) is used to generate multi-labeled miRNA, which refers to an miRNA molecule having at least two labels attached to it. Labeled nucleotides are readily available; they can be acquired commercially or they can be synthesized by reactions known to those of skill in the art. When the reaction includes labeled nucleotides, it is contemplated that in other embodiments, both labeled and unlabeled nucleotides are included. The labeled and unlabeled nucleotides may be the same nucleotides (but labeled and unlabeled) or they may be different nucleotides (such as a labeled UTP but an unlabeled CTP, GTP, and/or ATP.

In certain other embodiments, the tailing reaction contains unlabeled but modified nucleotides ("unlabeled/modified nucleotide") that are labeled in a subsequent reaction (two-step process). It is contemplated that a reaction may contain modified and unmodified nucleotides to improve tailing efficiency and avoid dye-quenching induced by having dye molecules to close together. The unmodified and modified nucleotides may be the same nucleotide (but one modified and the other not) or they may be different nucleotides (such as a modified UTP but an unmodified CTP, GTP, and/or ATP.

Thus, in both the one-step and two-step processes of the invention, a reaction mixture for tailing comprises modified and unmodified nucleotides. In some embodiments, the ratio of modified to unmodified nucleotides in the reaction mixture is from about 1:1 to about 10:1, and specifically about 5:1. The ratio may be about 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1 or more, or any range derivable therein. It is understood that the ratio is based on concentrations.

If the reaction mixture contains initially unlabeled/modified nucleotides, the nucleotides are added to the miRNA, which becomes tailed, and one or more labels become subsequently attached to one or more of these nucleotides. The way in which the label becomes attached depends on the label being used, and a person of ordinary skill in the art would know how to attach the label in a subsequent reaction.

Labels that can be attached to miRNA include those that are covalently attached to a nucleic acid. It is contemplated that the label on the labeled nucleotides or the label that becomes attached to the nucleotides in the tailed miRNA is biotin, radioactivity, or a dye. Alternatively, the label may be qualified as positron-emitting, calorimetric, enzymatic, luminescent, fluorescent, or a ligand.

In specific embodiments of the invention, the dye is selected from the group consisting of Alexa Fluor, BODIPY, Cascade Blue, Cascade Yellow, cyanine dye, eosins and erythrosins, fluorescein, HEX, Marina Blue, Oregon Green, Rhodamine, Quantum Dye™, SYPRO, tetramethyl-rhodamine, Texas Red, TOTAB, and derivatives thereof.

It is contemplated that miRNA from a single sample can be labeled with the same label or with different labels.

Tailing reactions may be incubated for at least or at most 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12 hours or more. Typically, reactions are about 1 to 3 hours, such as 2 hours. Incubations may be at temperatures of 15, 16, 17, 18, 19, 20, 21, 22, 23, 24, 25, 26, 27, 28, 29, 30, 31, 32, 33, 34, 35, or 40° C. or more, though it is specifically contemplated that temperatures may be in the range of 30° C. to 40° C., particularly at about 37° C.

In some embodiments of the invention, the reaction mixture in which nucleotides are added to miRNA further comprises a volume exclusion reagent. Examples of such reagents include, but are not limited to, a reagent selected from the group consisting of polyethylene glycol (PEG) and dextran. In some embodiments of the invention, the concentration of the volume exclusion reagent in the reaction is between about 1% and about 20% or about 5% to 10%. The concentration of the volume exclusion reagent in the reaction is about, at least about, or at most about 1, 2, 3, 4, 5, 6, 7, 8, 9, 10, 11, 12, 13, 14, 15, 16, 17, 18, 19, or 20%, or any range derivable therein, in embodiments of the reaction. In certain cases, the concentration of the volume exclusion reagent in the reaction is up to about 10%.

The reaction mixture for tailing miRNA molecules has a pH of about or at most about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, or 7.8, or any range derivable therein. In particular embodiments, the reaction mixture has a pH between about 6.0 and about 7.8, and in certain cases, the pH is about 6.5.

The present invention also concerns arrays for evaluating miRNA molecules. Clearly contemplated is an array that is a microarray. The arrays have one or more probes directed to one or more miRNA molecules ("miRNA array"). In some embodiments, an miRNA array includes one or more miRNA probes immobilized on a solid support. An "miRNA probe" refers to a nucleic acid having a sequence that is complementary or identical to all or part of a miRNA precursor or gene such that it is capable of specifically hybridizing to an miRNA gene, the cognate miRNA precursor, or the processed miRNA. Typically, the probe will contain at least ten contiguous nucleotides complementary to all or part of the miRNA precursor or at least ten contiguous nucleotides complementary or identical to all or part of an miRNA gene. It will be understood that DNA probes with sequences relative to an miRNA gene will be identical in sequence to all or part of the coding sequence of the gene and complementary in sequence to all or part of the noncoding sequence of the gene. In specific embodiments, an miRNA probe contains the sequence encoding an miRNA ("miRNA coding sequence," which refers to sequence encoding processed miRNA). Because the precise length and, consequently, sequence of a particular processed miRNA has been found to vary occasionally, the predominant species will be understood as the sequence and length of the processed miRNA. The predominant species is usually the one observed at least 90% of the time.

In embodiments of the invention, there is an amine attached to the 5' or 3' end of the probe. The amine was a reactive group on the probe that allowed for attachment of the probe to the array.

The number of different probes on the array is variable. It is contemplated that there may be, be at least, or be at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more, or any range derivable therein, different miRNA probes on an array. In specific embodiments, arrays have between 5 and 1000 different miRNA probes, between 20 and 500 different miRNA probes, between 50 and 250 different miRNA probes, or between 100 and 225 different miRNA probes. "Different" probes refers to probes with different sequences. Therefore, it is contemplated that different probes can be used to target the same miRNA. Moreover, multiple and different probes to the same miRNA can be included on an array. For example, one probe may target specifically a precursor miRNA or the miRNA gene (depending on what sample is used to hybridize to the array—i.e, whether the sample contains DNA or RNA), while another probe may be capable of hybridizing to the processed miRNA, its precursor, or the gene. Moreover, miRNA probes targeting the same miRNA may be overlapping, such that they share contiguous sequences. It is also contemplated that a single probe may target multiple miRNAs, particularly miRNAs from the same gene family or related miRNAs (distinguished by a letter). It is understood by those of skill in the art that a "gene family" refers to a group of genes having the same miRNA coding sequence. Typically, members of a gene family are identified by a number following the initial designation. For example, miR-16-1 and miR-16-2 are members of the miR-16 gene family. Also, a probe may have a sequence that allows it to target more than 1 miRNA. It is understood that a 2-base pair mismatch between the probe and an miRNA is sufficient to hybridize with at least 90% of the mismatched miRNA under the conditions described in the Examples. Consequently, it will be understood that unless otherwise indicated, a probe for a particular miRNA will also pick up a related miRNA, such as those designated with the same number but with an added letter designation. For example, an miRNA probe that is fully complementary to miR-15a would also hybridize to miR-15b, unless otherwise noted. Thus, an miRNA probe can target 1, 2, 3, 4, 5, 6 or more different miRNAs.

miRNA probes are contemplated to be made of DNA, though in some embodiments, they may be RNA, nucleotide analogs, PNAs, or any combination of DNA, RNA, nucleotide analogs, and PNAs.

As suggested above, it is contemplated that arrays of the invention may target one or more miRNAs. In embodiments of the invention, an array has probes that target 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more, or any range derivable therein, different miRNAs. Accordingly, it is understood that the array contains one or more probes for these different miRNAs. In specific embodiments, human miRNAs are targeted, though the targeting of multiple organisms or species using a single array or other method or technique is contemplated. In certain other embodiments, miRNAs of a mammal are targeted. Such mammals include, but are not limited to, monkeys, gorilla, chimpanzees, rats, mice, cats, dogs, rabbits, hamsters, ferrets, cows, sheep, pigs, humans, rodents, and goats. Thus, arrays or methods including miRNA probes having human miRNA coding sequences or other mammalian miRNA coding sequences are part of the invention.

miRNA probes of the invention have an miRNA coding sequence that is between 19-34 nucleotides in length. Of course, this is understood to mean that the probes have 19-34 contiguous nucleotides that are identical or nearly identical to the miRNA gene and complementary to the processed miRNA or its precursor. As discussed above, a probe can be used to target an miRNA with which it has a 2-base pair mismatch in hybridization. Thus, it is contemplated that miRNA probes of the invention may be almost fully complementary (2 base-pair mismatches or fewer) or fully complementary to any miRNA sequence or set of sequences (such as related miRNAs or miRNAs from the same gene family) that is targeted. The term "nearly identical" means that any difference in sequence is 2 bases or fewer. When an miRNA has a perfectly complementary stem loop in its precursor, the miRNA coding sequence should be identical to a sequence in the precursor as well. In some embodiments of the invention, a probe has an miRNA coding sequence that includes the entire processed miRNA sequence. It is contemplated that the probe has or has at least 5, 6, 7, 8, 9, 10, 11, 12, 13, 14, 15, 16, 17, 18, 19, 20, 21, 22, 23, 24, 25 or more contiguous nucleotides, or any range derivable therein, from an miRNA coding sequence. In specific embodiments, an miRNA probe has a sequence identical or complementary, or at least 90% or greater identity or complementarity, across the lengths discussed in the previous sentence with respect to any of SEQ ID NOs: 1-593, inclusive, as well as any other sequence discussed herein, including in the appendix. The appendix provides a list of 1) miRNAs that were screened, any one of which can be screened for using any array or method of the present invention; 2) the names of the probe used to screen for that miRNA; and, 3) the sequence of the named probe.

As discussed above, miRNA are processed from a precursor molecule. In certain embodiments, probes have an miRNA coding sequence that also includes at least 2 to 5 nucleotides of coding sequence upstream and/or downstream of the processed miRNA sequence. Probes may have or have up to 1, 2, 3, 4, 5, 6, 7, or more contiguous nucleotides, or any range derivable therein, that flank the sequence encoding the predominant processed miRNA on one or both sides (5' and/or 3' end). In particular embodiments, probes have an miRNA coding sequence that includes 4 nucleotides of coding sequence upstream (5') and/or downstream (3') of the processed miRNA sequence. On other embodiments, miRNA probes also have one or more linkers flanking the miRNA coding sequence. In particular embodiments, there is a linker at the 3' end of the miRNA coding sequence. In some embodiments, a linker has a sequence that is between 3 to 25 nucleotides in length.

In some embodiments of the invention, miRNA probes are attached to the array through an amine attached at the 3' end.

The invention is not limited to arrays constructed with particular materials. Typically, arrays are made with materials that do not interfere with the hybridization between the probe and a sample. In some embodiments, the array is a solid support that is made with glass, plastic, or metal.

The present invention concerns methods for identifying a correlation between miRNA expression and a disease or condition. In certain embodiments, methods involve identifying miRNA differentially expressed in a sample representative of the disease or condition (non-normal sample) compared to a normal sample. A sample representative of the disease or condition will be one that has the disease or condition, is affected by the disease or condition, and/or causes the disease or condition. In certain embodiments, identifying differentially expressed miRNA involves: a) labeling miRNA in the sample; and b) hybridizing the labelled miRNA to an miRNA array. In further embodiments, the miRNA in the sample is isolated before or after labeling.

In certain embodiments, isolating miRNA in a sample involves methods concerning electrophoresis. The present invention provides methods for the isolation of nucleic acids using electrophoresis. These methods may be used to isolate any nucleic acid molecules including, but not limited to, small nucleic acid molecules such as miRNA. In some embodiments the nucleic acid molecules are less than 200 nucleotides in length. In other embodiments, the nucleic acid molecules are less than 100 nucleotides in length. In certain aspects the nucleic acid molecules are between 15-200 nucleotides in length, 15-100 nucleotides in length, 15-40 nucleotides in length, or are ≦40 nucleotides in length.

In one embodiment, the method for isolating nucleic acid molecules from a sample comprises: providing an electrophoresis apparatus comprising a lower buffer collection chamber electrically coupled to a positive electrode, an upper buffer chamber electrically coupled to a negative electrode, and a gel matrix disposed between the lower buffer collection chamber and the upper buffer chamber; adding a running buffer to the lower buffer collection chamber and the upper buffer chamber; applying the sample to a surface of the gel matrix; moving the nucleic acid molecules in the sample through the gel matrix by electrophoresis; and collecting the running buffer from the lower collection buffer chamber, wherein the running buffer in the lower collection buffer chamber comprises nucleic acid molecules that passed through the gel matrix. The electrophoresis apparatus used in the practice of the present invention may be a micro-electrophoresis apparatus, such as the flashPAGE Fractionator (Ambion, Inc.). In some embodiments, the method further comprises purifying the nucleic acid molecules present in the collected running buffer. In certain embodiments, between about 1 μg to about 100 μg of nucleic acid are applied to the gel matrix.

In certain aspects of the invention, the electrophoresis is performed at about 50 to about 100 Volts (V) and about 2 to about 5 milliAmps (mA). In other aspects of the invention, the electrophoresis is performed at about 60-80 V and about 3 mA. In some embodiments, the electrophoresis is performed for about 10, 11, 12, 13, 14, 15, 16, 17. 18, 19, or about 20 minutes.

The nucleic acid molecules may be isolated in one fraction or they may be isolated in more than one fraction. Nucleic acid molecules of a desired size or size range may be isolated by collecting specific fractions as they migrate off of the gel. After the running buffer has been removed from the lower buffer collection chamber to collect a first fraction of nucleic acid molecules that has migrated off the gel, it is necessary to add additional running buffer to the lower buffer collection chamber in order to continue electrophoresis and collect additional fractions of nucleic acid molecules. Where the nucleic acid molecules are isolated in multiple fractions, it may be desirable that they are isolated at regular intervals such as 30 second, 1 minute, 2 minute, or 3 minute intervals. By performing a time course and evaluating the size of nucleic acids collected at each time point in an initial run, any desired size class of nucleic acid molecules can be isolated in subsequent runs because the nucleic acid size fractions will exit the gel at the same timepoint during each run as long as the conditions are kept consistent between runs.

A dye marker may also be applied to the surface of the gel matrix at the same time as the sample comprising nucleic acids is loaded onto the gel. A dye marker that is known to migrate through the gel matrix with a particular size of nucleic acid is useful in identifying an approximate time for elution of nucleic acids of the size or sizes of interest. For example, a dye marker that migrates with 40 nucleotide nucleic acids would be useful in collecting nucleic acid fractions that contain nucleic acids that are smaller or larger than 40 nucleotides. To collect nucleic acid molecules that are less than 40 nucleotides in length, electrophoresis should be stopped just as the dye begins to migrate off of the gel, and the running buffer collected from the lower buffer collection chamber. For nucleic acids larger than 40 nucleotides, collection of the lower running buffer would begin once the dye begins to migrate off of the gel.

Electrophoretic purification of nucleic acids can isolate nucleic acids of a desired size or size range away from nucleic acid molecules of other sizes, such that the nucleic acids of the desired size or size range are substantially pure, meaning they are at least about 80%, 85%, 90%, 95% pure or more, but less than 100% pure, with respect to other nucleic acid molecules in the sample. Alternatively, enrichment of nucleic acids of the desired size or size range may be expressed in terms of fold-enrichment. In certain embodiments, the nucleic acids of the desired size or size range are enriched by about, at least about, or at most about 5×, 10×, 20×, 30×, 40×, 50×, 60×, 70×, 80×, 90×, 100×, 110×, 120×, 130×, 140×, 150×, 160×, 170×, 180×, 190×, 200×, 210×, 220×, 230×, 240×, 250×, 260×, 270×, 280×, 290×, 300×, 310×, 320×, 330×, 340×, 350×, 360×, 370×, 380×, 390×, 400×, 410×, 420×, 430×, 440×, 450×, 460×, 470×, 480×, 490×, 500×, 600×, 700×, 800×, 900×, 1000×, 1100×, 1200×, 1300×, 1400×, 1500×, 1600×, 1700×, 1800×, 1900×, 2000×, 3000×, 4000×, 5000×, 6000×, 7000×, 8000×, 9000×, 10,000× or more, or any range derivable therein, with respect to the concentration of the nucleic acids of the desired size or size range in the nucleic acid sample.

In further embodiments, methods involve identifying an appropriate sample to analyze or evaluate. It is particularly contemplated that in some embodiments, an appropriate sample is one that can provide information about a particular disease or condition or about some other phenotype.

Other methods of the invention concern analyzing miRNA in a sample comprising generating an miRNA profile for the sample and evaluating the miRNA profile to determine whether miRNA in the sample are differentially expressed compared to a normal sample. In specific embodiments, methods of the invention include a method for evaluating miRNA in a biological sample. In certain instances, the biological sample is from a patient. This method is implemented by analyzing one or more miRNAs in a sample using the array compositions and methods of the invention. In specific embodiments, miRNA are evaluated by one or more of the following steps: a) isolating miRNA away from other RNA in the sample; b) labeling the miRNA; c) hybridizing the miRNA to an miRNA array; and, d) determining miRNA hybridization to the array. Whether miRNAs hybridize to the array, what miRNAs hybridize to the array, and/or how much total miRNA or any specific miRNAs hybridize to the array are ways of determining the extent of miRNA hybridization to the array. Methods of detecting, measuring and quantifying hybridization are well known to those of skill in the art. In specific embodiments, miRNA hybridization is quantified.

The present invention also concerns methods of generating an miRNA profile for a sample. The term "miRNA profile" refers to a set of data regarding the expression pattern for a plurality of miRNAs in the sample that was obtained using an miRNA array. In some embodiments of the invention, an miRNA profile is generated by steps that include: a) labeling miRNA in the sample; b) hybridizing the miRNA to an miRNA array; and, c) determining miRNA hybridization to the array, wherein an miRNA profile is generated.

miRNA profiles can be generated to compare differences in miRNA expression between any two or more different samples. miRNA profiles can be compared, for example, between a sample with a particular disease, disorder, or condition and a sample that does not have the particular disease, disorder or condition; between samples that have a particular disease, disorder or condition but a different stage of the disease, disorder or condition; between samples that have a particular disease, disorder or condition but with a different prognosis with respect the disease, disorder or condition; between a sample that has been treated with a particular agent and a sample that has not been treated with that agent; between samples that have responded differently to a particular substance or agent, such as one responsive to the treatment and one not, or one resistant to the treatment and one not; samples that differ by gender of the sources; samples that differ by age or stage of development of the source; samples that differ by tissue type; samples that differ by at least one known polymorphism; between a sample that has a particular mutation and a sample that does not; a sample that is defective in a particular pathway or has a defective protein and a sample that does not; between a sample that is apparently resistant to a particular disease, disorder, or condition and a sample that is not expected to be resistant to that particular disease, disorder, or condition, as well as a comparison involving any samples with a combination of characteristics as described above.

Samples from which miRNA profiles are generated include samples that can be characterized based on one or more of the following: age; developmental stage; prognosis of a disease, condition, or disorder; cell type; tissue type; organ type; race or ethnicity; gender; susceptibility to or risk of a particular disease, condition, or disorder; diet; exposure to or treatment with a particular chemical, agent or substance; diagnosis of a particular a disease, condition, or disorder; organism type; genomic makeup, etc.

Methods of the invention allow differences between two or more biological samples to be determined by generating an miRNA profile for each sample and comparing the profiles, wherein a difference in the profiles identifies differentially expressed miRNA molecules. In specific embodiments, a first sample is treated with a substance prior to generating the miRNA profile and a second sample is untreated. In other embodiments, a first sample exhibits a disease or condition and a second sample exhibits the same disease or condition but at a different stage of progression. In further embodiments, a first sample responds favorably to a therapeutic agent and a second sample is unresponsive to the therapeutic agent. Moreover, in other embodiments, a first sample is from a first subject who responds adversely to a therapeutic agent and a second sample is from a second subject does not respond adversely to the therapeutic agent.

Other methods of the invention concern identifying a correlation between miRNA expression and a disease or condition comprising comparing different miRNA profiles, such as 1) an miRNA profile of a sample with the disease or condition or from a subject with the disease or condition and 2) an miRNA profile of a sample that is normal with respect to that disease or condition or that is from a subject that does not have the disease or condition. In specific embodiments, methods include a) isolating miRNA from a sample exhibiting the disease or condition; b) labeling the miRNA; c) hybridizing the miRNA to an miRNA array; and, d) identifying miRNA differentially expressed in the sample compared to a normal sample. It is contemplated that the miRNA profiles may be generated in the process of performing the method; alternatively, they may be obtained from previously obtained results. Moreover, it is contemplated that comparisons may be done by using a plurality of miRNA profiles (multiple samples from the same source obtained at the same or different times and/or samples from different sources). In this case, a normalized miRNA profile may be generated and used for comparison purposes.

In certain embodiments, methods concern identifying miRNAs indicative of a disease or condition by detecting a correlation between the expression of particular miRNAs and a sample believed to have a disease or condition.

In specific embodiments, there are methods for analyzing a biological sample from a patient for a disease or condition comprising generating an miRNA profile for the sample and evaluating the miRNA profile to determine whether miRNA in the sample are differentially expressed compared to a normal sample. The comparison may involve using an array that has selective miRNA probes that are indicative of a disease or condition. Arrays of the invention include macroarrays and microarrays.

Arrays can contains miRNA sequences from any organism having miRNAs, specifically including, mammals such as humans, mice, and rats. However, unless specifically indicated, the naming of a particular miRNA refers to a human miRNA. Specifically contemplated are arrays having, having at least, or having at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000 or more different miRNA probes (that is, miRNA probes having different sequences targeting the same or different miRNAs, miRNA precursors, or miRNA genes). Specifically contemplated are such arrays described in the previous sentence with probes for any of SEQ ID NOs:1-703 or with any other sequence provided herein, including those identified in SEQ ID NOs:704-899. Moreover, embodiments can specifically include or employ any or all of the probes identified in Table 1C. Probes may be identical or complementary to 5, 6, 7, 8, 9, 10, 11, 12, 13, 14, 15, 16, 17, 18, 19, 20, 21, 22, 23, 24, 25, 26, 27, 28 or more contiguous nucleic acids (or any range derivable therein) of SEQ ID NOs:704-899. Alternatively, any probe used may be, be at least, or be at most 80, 81, 82, 83, 84, 85, 86, 87, 88, 89, 90, 91, 92, 93, 94, 95, 96, 97, 98, 99, or 100% complementary or identical (or any range derivable therein) to any sequence in SEQ ID NOs:1-899. It is specifically contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

In specific embodiments, an array has, has at least, or has at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 probes (or any range derivable therein) for human miRNA selected from the group consisting of let-7, miR-7, let-7F-2, miR-9, miR-10a, miR-16, miR-17, miR-21, miR-22, miR-23, miR-24, miR-26a, miR-28, miR-29b, miR-30a, miR-31, miR-95, miR-105, miR-106, miR-125a, miR-126, miR-130, miR-130a, miR-133, miR-135A, miR-137, miR-138, miR-139, miR-140, miR-143, miR-144, miR-145, miR-181a, miR-182, miR-183, miR-186, miR-188, miR-192, miR-194, miR-195, miR-199a, miR-200b, mu-miR-201, miR-205, miR-211, miR-215, miR-219, miR-223, miR-224, mu-miR-290, mu-miR-291-5P, mu-miR-298, miR-301, miR-328, miR-331, and miR-342. It will be understood that shorthand notations are employed such that a generic description of an miRNA refers to any of its gene family members (distinguished by a number) and related members (distinguished by a letter), unless otherwise indicated. For example, "miR-7" refers to miR-7-1, miR-7-2 and miR-7-3. Similarly, "let-7," for example, refers to let-7a-1, let-7-a-2, let-7b, let-7c, let-7d, let-7e, let-7f-1, and let-7f-2." Exceptions to this shorthand notations will be otherwise identified. A probe with at least 90% complementarity will allow hybridization to an miRNA. It is contemplated that a probe for a non-human miRNA can be used in embodiments of the invention to target human homologs or sequences with sufficient complementarity to allow their detection with the non-human miRNA probe. Such probes may be for miRNA identified in mouse or rat, or any other organism, including other mammals. For example, mu-miR-201 is a mouse miRNA yet when a probe for that sequence was employed with a human sample, the human homolog for mu-miRNA-201 was detected.

It is contemplated that any combination of these probes or the target miRNAs can be used in methods and compositions of the invention. Furthermore, an increase and/or decrease in expression of, of at least, or of at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55 or more of these miRNAs relative to a normal sample, where "normal sample" means the sample does not have or is not afflicted with the disease, condition, or state that is being tested for. It is contemplated that such an array may also include a probe for an miRNA listed in Table 1.

Moreover, in specific embodiments, methods and compositions may involve samples that include cancer or tumor cells or are from a subject diagnosed with cancer. In particular embodiments, the cancer is selected from the group consisting of astrocytoma, bone cancer, bladder cancer, brain cancer, breast cancer, cervical cancer, colon cancer, gastrointestinal cancer, glioblastoma cancer, head cancer, hepatocarcinoma, leukemia, lung cancer, lymphoma, melanoma, mesothelioma, neuroblastoma, neck cancer, non-small cell lung cancer, ovarian cancer, pancreatic cancer, prostate cancer, renal cancer, retinoblastoma, small-cell lung cancer, stomach cancer testicular cancer, thymus cancer, and thyroid cancer.

In specific embodiments, an array has, has at least, or has at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 probes (or any range derivable therein) for human miRNA selected from the group consisting let-7, let-7A, let-7C, let-7F-2, miR-7, miR-9a, miR-9-as, miR-10a, miR-15A, miR-16, miR-17, miR-20, miR-21, miR-22, miR-23a, miR-23b, miR-24, miR-25, miR-26a, miR-28, miR-29b, miR-30a, miR-30a-as, miR-31, miR-92, miR-95, miR-99b, miR-103, miR-105, miR-106a, miR-125a, miR-126, miR-126-as, miR-130a, miR-133, miR-137, miR-138, miR-139, miR-140, miR-141, miR-143, miR-144, miR-145, miR-152, miR-181a, miR-181b, miR-182, miR-183, miR-186, miR-188, miR-192, miR-194, miR-195, miR-199a, miR-199a-as, miR-200b, mu-miR-201, miR-203, miR-205, miR-211, miR-215, miR-219, miR-221, miR-222, miR-223, miR-224, miR-290, miR-291, miR-291-5P, miR-298, miR-301, miR-326, miR-328, mu-mu-miR-329, miR-331, miR-341, miR-342, miR-344, miR-361, and miR-425. In certain embodiments involving such an array, a change in expression compared to a normal sample is indicative of cancer. Moreover, it is contemplated that methods may involve such miRNA probes with or without the array.

In particular embodiments, the array or methods involve at least one probe for one or more of the following miRNAs: miR-21, miR-126, miR-143, miR-145, miR-188, miR-200B, miR-219, and miR-331. In methods of the invention using such an array, an increase in miR-17, miR-21, miR-182, miR-183, miR-200b, miR-205, miR-223, and/or miR-224 expression is indicative of cancer, and/or a decrease in the expression of let-7, miR-10a, miR-16, miR-22, miR-23, miR-24, miR-26a, miR-29b, miR-30a, miR-106, miR-125a, miR-126, miR-130, miR-130a, miR-133, miR-143, miR-144, miR-145, miR-181a, miR-188, miR-219, miR-192, miR-194, miR-195, miR-199a, mu-miR-201, miR-215, miR-328, miR-331, and/or miR-342 is indicative of cancer.

This means that any of the following is indicative of cancer: 1) a decrease in expression of one or more of the identified miRNAs (or human homologs thereof); 2) an increase in expression of one or more of the identified miRNAs (or human homologs thereof); or 3) both an increase and a decrease in expression of one or more of the identified miRNAs (or human homologs thereof). It is contemplated in some embodiments that a difference in expression of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 different miRNAs can be used as indicators of a disease, condition, or other phenotype. Moreover, it is contemplated that in some cases, the indicators provide information about the risk of having or developing a particular disease, condition, or phenotype. These different miRNAs include any of the following: let-7, let-7A, let-7C, let-7D-as, let-7F-2, miR-7, miR-9a, miR-9-as, miR-10a, miR-15a, miR-15b, miR-16, miR-17, miR-20, miR-21, miR-22, miR-23a, miR-23b, miR-24, miR-25, miR-26a, miR-27a, miR-28, miR-29, miR-29b, miR-30a, miR-30a-as, miR-31, miR-32, miR-92, miR-95, miR-99b, miR-103, miR-105, miR-106a, miR-125a, miR-125b, miR-126, miR-126-as, miR-126a, miR-128, miR-130a, miR-133, miR-133a, miR-135a, miR-137, miR-138, miR-139, miR-140, miR-141, miR-143, miR-144, miR-145, miR-150, miR-152, miR-181a, miR-181b, miR-182, miR-183, miR-184, miR-186, miR-188, miR-189, miR-192, miR-194, miR-195, miR-199, miR-199a, miR-199a-as, miR-200b, miR-201, miR-203, miR-204, miR-205, miR-207, miR-211, miR-212, miR-215, miR-219, miR-221, miR-222, miR-223, miR-224, miR-239, miR-290, miR-291, miR-291-5P, miR-298, miR-301, miR-326, miR-328, mu-miR-329, miR-331, miR-338, miR-341, miR-342, miR-344, miR-361, and miR-425.

It is specifically contemplated that any kit, array or other detection technique or tool, or any method can involve profiling for any of these miRNAs.

Cancer includes, but is not limited to, malignant cancers, tumors, metastatic cancers, unresectable cancers, chemo- and/or radiation-resistant cancers, and terminal cancers. It is specifically contemplated that in any embodiments involving a possible decrease or increase in expression of certain miRNAs that only a decrease may be evaluated, only an increase may be evaluated, or that both an increase and decrease in expression of any of the miRNA mentioned in that context (or any other discussed herein) may be evaluated.

In specific embodiments, an miRNA array or methods involving 1, 2, 3, 4, 5, 6, 7, 8, 9, 10, 11, 12, or 13 probes (or any range derivable therein) for miRNA(s) selected from the group consisting of: miR-21, miR-15a, miR-16, miR-24, miR-25, miR-99, miR-100, miR-205, miR-197, miR-126, miR-143, and miR-145, or from the group consisting of miR-15A, miR-21, miR-24, miR-135A, miR-145, miR-200B, miR-205, miR-211, miR-298, and mu-miR-329. In methods of the invention, a difference in expression of, of at least, or of at most 1, 2, 3, 4, 5, 6, 7, 8, 9, 10, 11, 12, or 13 of the miRNA(s) (or any range derivable therein), compared to a normal sample, is indicative of breast cancer. In methods of the invention, an increase in miR-21, miR-15a, miR-16, miR-24, and/or miR-25 expression, and/or a decrease in miR-99, miR-100, miR-205, miR-197, miR-126, miR-143, and/or miR-145 expression, compared to a normal sample, is indicative of breast cancer. In other embodiments, a decrease in expression of miR-135A, miR-145, miR-205, miR-211, miR-298, or mu-miR-329 and/or an increase in expression of miR-15A, miR-21, miR-24, or miR-200B compared to a normal sample is indicative of breast cancer. Arrays may specifically involve any combination of probes for the miRNAs described in this paragraph, as well as any other miRNA probe.

In other embodiments, the miRNA array or methods involving 1, 2, 3, 4, 5, 6, 7, 8, 9, 10, 11, 12, 13, 14, 15, 16, 17, 18, 19, 20, 21, 22, 23, 24, 25, 26 probes (or any range derivable therein) for miRNA(s) selected from the group consisting of: miR-10a, miR-17, miR-21, miR-23, miR-26a, miR-30a, miR-106, miR-125a, miR-126, miR-130, miR-130a, miR-133, miR-143, miR-144, miR-145, miR-188, miR-192, miR-194, miR-195, miR-199a, miR-200b, miR-215, miR-223, miR-224, miR-331, and miR-342 or selected from the group consisting of: miR-21, miR-31, miR-106A, miR-125a, miR-130a, miR-133, miR-135, miR-143, miR-145, miR-200B, miR-203, and miR-223. In methods of the invention, a difference in expression of, of at least, or of at most 1, 2, 3, 4, 5, 6, 7, 8, 9, 10, 11, 12, 13, 14, 15, 16, 17, 18, 19, 20, 21, 22, 23, 24, 25, or 26 of the miRNA(s) (or any range derivable therein), compared to a normal sample, is indicative of colon cancer.

In certain embodiments, a decrease in expression of 1, 2, 3, 4, 5, 6, 7, 8, 9, 10, 11, 12, 13, 14, 15, 16, 17, 18, 19, 20, or 21 (or any range derivable therein) of the following miRNA(s) is indicative of colon cancer: miR-145, miR-143, miR-133, miR-342, miR-125a, miR-195, miR-30a, miR-10a, miR-130, miR-130a, miR-192, miR-194, miR-215, miR-144, miR-23, miR-26a, miR-126, miR-199a, miR-188, miR-331, and/or miR-21; and, an increase in expression of 1, 2, 3, 4, 5, 6, or 7 (or any range derivable therein) of the following miRNA(s) is indicative of colon cancer: miR-21, miR-106, miR-200b, miR-223, miR-224, and/or miR-17. Arrays may specifically involve any combination of probes for the miRNAs described in this paragraph, as well as any other miRNA probe.

In specific embodiments, an miRNA array or methods involving 1, 2, 3, 4, 5, 6, 7, 8, or 9 probes (or any range derivable therein) for miRNA(s) selected from the group consisting of: miR-21, miR-31, miR-106A, miR-125a, miR-130a, miR-133, miR-135A, miR-143, miR-145, miR-200B, miR-203, and miR-223. A difference in expression of, of at least, or of at most 1, 2, 3, 4, 5, 6, 7, 8, or 9 of the miRNA(s) (or any range derivable therein), compared to a normal sample, is indicative of colon cancer. In certain methods of the invention, an increase in miR-17, miR-21, miR-106, and/or miR-223 expression; and/or a decrease in miR-130a, miR-143, miR-145, miR-195, and/or miR-331 expression, compared to a normal sample, is indicative of colon cancer. In other embodiments, a decrease in expression of miR-125a, miR-130a, miR-133, miR-135A, miR-143, or miR-145 and/or an increase in expression of miR-21, miR-31, miR-106A, miR-200B, miR-203, or miR-223 compared to a normal sample is indicative of colon cancer. Arrays may specifically involve any combination of probes for the miRNAs described in this paragraph, as well as any other miRNA probe.

Throughout this application, the term "difference in expression" means that the level of a particular miRNA in a sample is higher or lower than the level of that particular miRNA in a normal sample. "Normal sample" in the context of testing for cancer means a noncancerous sample.

In further embodiments, the miRNA array or methods involving 1, 2, or 3 miRNA(s) (or any range derivable therein) selected from the group consisting of: miR-21, miR-23, and miR-143 or selected from the group consisting of miR-15A, miR-21, miR-29, miR-141, miR-188, miR-290, and miR-331. In methods of the invention, a decrease in miR-21, miR-23, and/or miR-143 expression, compared to a normal sample, is indicative of prostate cancer. In certain embodiments, a decrease in expression of miR-188, miR-290, or miR-331 and/or an increase in expression of miR-15A, miR-21, miR-29, or miR-141 compared to a normal sample is indicative of prostate cancer. Arrays may specifically involve any combination of probes for the miRNAs described in this paragraph, as well as any other miRNA probe.

Moreover, in additional embodiments, the miRNA array or methods involving 1, 2, 3, 4, 5, 6, 7, 8, 9, 10, 1, 12, 13, 14, 15, 16, 17, or 18 probes (or any range derivable therein) for miRNA(s) selected from the group consisting of: miR-21, miR-125, miR-24, miR-200b, miR-29b, miR-221, miR-222, miR-224, miR-10a, miR-183, miR-145, miR-22, miR-331, miR-126, miR-30a, miR-199a, and miR-223 or selected from the group consisting of miR-15A, miR-21, miR-30A-as, miR-31, miR-135A, miR-138, miR-152, miR-199A-as, miR-200B, miR-203, and miR-331. In methods of the invention, an increase in miR-21 miR-125, miR-24, miR-200b, miR-29b, miR-221, miR-222, miR-224, miR-10a, and/or miR-183 expression and/or a decrease in miR-145, miR-22, miR-126, miR-30a, miR-199a, miR-223, and/or miR-331, expression, compared to a normal sample, is indicative of thyroid cancer. In certain embodiments, a decrease in expression of miR-30A-as, miR-31, miR-135A, miR-138, miR-152, miR-199A-as, miR-203, or miR-331 and/or an increase in expression of miR-15A, miR-21, or miR-200B compared to a normal sample is indicative of thyroid cancer. Arrays may specifically involve any combination of probes for the miRNAs described in this paragraph, as well as any other miRNA probe.

In specific embodiments, an miRNA array or methods involving 1, 2, 3, 4, 5, 6, 7, 8, 9, 10, 11, 12, 13, 14, 15, 16, 17, 18, 19, 20, 21, 22, 23, 24, 25, 26, 27, or 28 probes (or any range derivable therein) for miRNA(s) selected from the group consisting of: let-7, miR-16, miR-17, miR-21, miR-22, miR-24, miR-26a, miR-29b, miR-30a, miR-106, miR-125a, miR-126, miR-143, miR-145, miR-181a, miR-182, miR-183, miR-188, miR-195, miR-200b, mu-miR-201, miR-205, miR-223, miR-328, miR-331, and miR-342 or selected from the group consisting of let-7a, let-7c, miR-21, miR-26a, miR-30A-AS, miR-95, miR-125a, miR-126, miR-200b, miR-205, miR-331, and miR-342. In methods of the invention, a difference in expression of, of at least, or of at most 1, 2, 3, 4, 5, 6, 7, 8, 9, 10, 11, 12, 13, 14, 15, 16, 17, 18, 19, 20, 21, 22, 23, 24, 25, 26, 27, or 28 of the miRNA(s) (or any range derivable therein), compared to a normal sample, is indicative of lung cancer. In certain embodiments, a decrease in expression of 1, 2, 3, 4, 5, 6, 7, 8, 9, 10, 11, 12, 13, 14, 15, 16, 17, 18, or 19 (or any range derivable therein) of the following miRNA(s) is indicative of lung cancer: miR-130a, miR-145, miR-126, miR-331, miR-342, miR-143, Let-7, miR-30a, miR-16, miR-26a, miR-125a, miR-29b, miR-24, miR-328, mu-miR-201, miR-195, miR-22, miR-181a, and miR-331; and/or, an increase in expression of 1, 2, 3, 4, 5, 6, 7, 8 or 9 (or any range derivable therein) of the following miRNA(s) is indicative of lung cancer: miR-223, miR-106, miR-21, miR-200b, miR-182, miR-183, miR-17, and miR-205. In other embodiments, a decrease in expression of let-7a, let-7c, miR-26a, miR-30A-AS, miR-95, miR-125a, miR-126, miR-331, or miR-342 and/or an increase in expression of miR-21, miR-200B, or miR-205 compared to a normal sample is indicative of lung cancer. Arrays may specifically involve any combination of probes for the miRNAs described in this paragraph, as well as any other miRNA probe.

In specific embodiments, an miRNA array or methods involving 1, 2, 3, 4, 5, 6, 7, 8, or 9 miRNA probes (or any range derivable therein) for miRNA(s) selected from the group consisting of: miR-21, miR-30a, miR-16, miR-126, miR-143, miR-145, miR-188, miR-200b, and miR-331. In methods of the invention using such an array, a difference in expression of, of at least, or of at most 1, 2, 3, 4, 5, 6, 7, 8, or 9 miRNA(s) (or any range derivable therein), compared to a normal sample, is indicative of lung cancer. In methods of the invention, an increase in miR-21 and/or miR-200b expression; and/or a decrease in miR-30a, miR-126, miR-143, miR-145, miR-188, and/or miR-331 expression, compared to a normal sample, is indicative of lung cancer. Arrays may specifically involve any combination of probes for the miRNAs described in this paragraph, as well as any other miRNA probe.

In specific embodiments, an miRNA array or methods involving 1, 2, 3, 4, 5, 6, 7, 8, 9, 10, or 11 probes (or any range derivable therein) for miRNA(s) selected from the group consisting of: miR-145, miR-143, miR-126, miR-30a, miR-125a, miR-21, miR-195, miR-17, miR-182, and miR-183. In methods of the invention, a difference in expression of, of at least, or of at most 1, 2, 3, 4, 5, 6, 7, 8, 9, 10, or 11 of the miRNA(s) (or any range derivable therein), compared to a normal sample, is indicative of cancer. In certain embodiments, a decrease in expression of 1, 2, 3, 4, 5, 6, 7, 8, or 9 (or any range derivable therein) of the following miRNA(s) is indicative of cancer: miR-145, miR-143, miR-126, miR-30a, miR-125a, miR-21, miR-195, and/or miR-17; and, an increase in expression of 1, 2, 3, 4, 5, 6, or 7 (or any range derivable therein) of the following miRNA(s) is indicative of cancer: miR-125a, miR-21, miR-195, miR-17, miR-182, and/or miR-183. Arrays may specifically involve any combination of probes for the miRNAs described in this paragraph, as well as any other miRNA probe.

In further embodiments, the miRNA array or methods involving 1, 2, 3, 4, 5, 6, or 7 probe(s) (or any range derivable therein) for any miRNA selected from the group consisting of miR-9 as, miR-21, miR-133, miR-143, miR-145, miR-182, and miR-200B. In methods of the invention, a difference in expression of, of at least, or of at most 1, 2, 3, 4, 5, 6, or 7 miRNA(s) (or any range derivable therein), compared to a normal sample, is indicative of bladder cancer. In certain embodiments, wherein a decrease in expression of miR-133, miR-143, or miR-145, and/or a increase in expression of miR-9 as, miR-21, miR-182, or miR-200B compared to a normal sample is indicative of bladder cancer. Arrays or other detection techniques may specifically involve any combination of probes for the miRNAs described in this paragraph, as well as any other miRNA probe. Methods involving arrays or other detection techniques may similarly involve any combination of probes for the miRNAs described in this paragraph, as well as any other miRNA probe.

The present invention also concerns an miRNA array or methods involving 1, 2, 3, or 4 probe(s) (or any range derivable therein) for any miRNA selected from the group consisting of miR-29B, miR-326, miR-361, and miR-425. In methods of the invention, a difference in expression of, of at least, or of at most 1, 2, 3, or 4 of the miRNA(s) (or any range derivable therein), compared to a normal sample, is indicative of cervical cancer. In methods of the invention using such an array, an increase in expression of miR-29B, miR-326, miR-361, or miR-425 is indicative of cervical cancer. Arrays may specifically involve any combination of probes for the miRNAs described in this paragraph, as well as any other miRNA probe.

The present invention also concerns an miRNA array or methods involving 1, 2, 3, 4, 5, 6, 7, 8, 9, 10, 11, 12, 13, 14, 15, 16, 17, 18, 19, 20, 21, 22, 23, 24 25, 26, or 27 probe(s) (or any range derivable therein) for any miRNA selected from the group consisting of let-7, miR-15A, miR-16, miR-20, miR-21, miR-23A, miR-23B, miR-25, miR-26A, miR-92, miR-99B, miR-103, miR-106A, miR-126, miR-126AS, miR-181A, miR-181B, miR-221, miR-222, miR-223, miR-291, miR-341, miR-361, and miR-425, miR-326, miR-361, or miR-425. In methods of the invention, a difference in expression of, of at least, or of at most 1, 2, 3, 4, 5, 6, 7, 8, 9, 10, 11, 12, 13, 14, 15, 16, 17, 18, 19, 20, 21, 22, 23, 24 25, 26, or 27 miRNA(s) (or any range derivable therein), compared to a normal sample, is indicative of leukemia.

In certain embodiments, an miRNA array or method involves 1, 2, 3, 4, 5, 6, 7, 8, or 9 probe(s) (or any range derivable therein) for any miRNA selected from the group consisting of miR-25, miR-126, miR-126AS, miR-181B, miR-221, miR-222, miR-291, miR-361, and miR-425. In methods of the invention, a difference in expression of, of at least, or of at most 1, 2, 3, 4, 5, 6, 7, 8, or 9 miRNA(s) (or any range derivable therein), compared to a normal sample, is indicative of acute myelogenous leukemia. Moreover, in some cases, a decrease in expression of miR-25, miR-291, miR-361, or miR-425 and/or a increase in expression of miR-126, miR-126AS, miR-181B, miR-221, or miR-222 compared to a normal sample is indicative of acute myelogenous leukemia.

In other embodiments, an miRNA array or method involves 1, 2, 3, 4, 5, 6, 7, 8, 9, 10, 11, 12, 13, 14, 15, 16, 17, 18, 19, or 20 probe(s) (or any range derivable therein) for any miRNA selected from the group consisting of let-7, miR-15A, miR-16, miR-20, miR-21, miR-23A, miR-23B, miR-26A, miR-92, miR-99B, miR-103, miR-106A, miR-181A, miR-181B, miR-221, miR-222, miR-223, miR-341, miR-361, and miR-425. In methods of the invention, a difference in expression of, of at least, or of at most 1, 2, 3, 4, 5, 6, 7, 8, or 9 miRNA(s) (or any range derivable therein), compared to a normal sample, is indicative of chronic lymphocytic leukemia. Moreover, in some cases, a decrease in expression of let-7, miR-15A, miR-16, miR-20, miR-21, miR-23A, miR-23B, miR-26A, miR-92, miR-99B, miR-103, miR-106A, miR-181A, miR-181B, miR-221, miR-222, or miR-223 and/or a increase in expression of miR-341, miR-361, or miR-425 compared to a normal sample is indicative of chronic lymphocytic leukemia.

Other embodiments of the invention include an miRNA array that comprises 1, 2, 3, 4, 5, 6, 7, 8, 9, 10, 11, 12, 13, or 14 probes (or any range derivable therein) for miRNA(s) selected from the group consisting of: miR-21, miR-95, miR-105, miR-137, miR-186, miR-188, miR-199, miR-211, miR-215, miR-223, mu-miR-290, miR-301, miR-331, and miR-342 or selected from the group consisting of: let7D-AS, miR-21, miR-32, miR-95, miR-133A, miR-137, miR-141, miR-144, miR-181A, miR-184, miR-186, miR-188, miR-199, miR-201, miR-203, miR-204, miR-211, miR-212, miR-223, miR-224, mu-miR-329, miR-331 and miR-344. In methods of the invention, a difference in expression of, of at least, or of at most 1, 2, 3, 4, 5, 6, 7, 8, 9, 10, 11, 12, 13, or 14 miRNA(s) (or any range derivable therein), compared to a normal sample, is indicative of lupus. In methods of the invention using such an array, an increase in miR-21, miR-223, and/or miR-342 expression; and/or a decrease in miR-95, miR-105, miR-137, miR-186, miR-188, miR-199, miR-211, miR-215, mu-miR-290, miR-301, and/or miR-331 expression, compared to a normal sample, is indicative of systemic lupus erythematosus (SLE). Arrays may specifically involve any combination of probes for the miRNAs described in this paragraph, as well as any other miRNA probe.

The present invention also involves an miRNA array or method that involves 1, 2, 3, 4, 5, 6, 7, 8, 9, or 10 probes (or any range derivable therein) for miRNA(s) selected from the group consisting of: miR-7, miR-9-as, miR-16, miR-24, miR-26A, miR-27A, miR-95, miR-130A, and miR-135A, or selected from the group consisting of miR-7, miR-9-as, miR-16, miR-24, miR-26A, miR-27A, miR-95, miR-130A, miR-135A and miR-239. In methods of the invention, a difference in expression of, of at least, or of at most 1, 2, 3, 4, 5, 6, 7, 8, 9, 10, 11, 12, 13, or 14 miRNA(s) (or any range derivable therein), compared to a normal sample, is indicative of a prion disease or susceptibility to a prion disease. In certain methods of the invention, an increase in miR-7, miR-9-as, miR-16, miR-24, miR-26A, miR-27A, and/or miR-130A expression; and/or a decrease in miR-95 and/or miR-135A expression, compared to a normal sample (uninfected and/or insensitive to prions), is indicative of a prion disease or susceptibility to a prion disease. In other embodiments, a decrease in expression of miR-95 or miR-135A and/or an increase in expression of miR-7, miR-9-as, miR-16, miR-24, miR-26A, miR-27A, miR-130A or miR-239 compared to a normal sample is indicative of prion disease or susceptibility to prion disease.

Arrays may specifically involve any combination of probes for the miRNAs described in this paragraph, as well as any other miRNA probe.

Another miRNA array of the invention is one comprising 1, 2, 3, 4, 5, 6, 7, 8, 9, or 10 probes (or any range derivable therein) for miRNA(s) selected from the group consisting of: Let7F-2, miR-16, miR-28, miR-30A, miR-31, miR-138, miR-139, miR-140, mu-miR-291-5P and mu-miR-298. In methods of the invention, an increase in miR-28, miR-30A, miR-31, miR-138, miR-139, miR-140, mu-miR-291-5P and/or mu-miR-298expression; and/or a decrease in Let7F-2 and/or miR-16 expression, compared to a normal sample, is indicative of ischemia or susceptibility to ischemia. Arrays may specifically involve any combination of probes for the miRNAs described in this paragraph, as well as any other miRNA probe.

The present invention also concerns an miRNA array or method that involves 1, 2, 3, 4, 5, 6, or 7 probes (or any range derivable therein) for miRNA(s) selected from the group consisting of: miR-125B, miR-126a, miR-150, miR-192, miR-194, miR-207, and miR-223. In methods of the invention, a difference in expression of, of at least, or of at most 1, 2, 3, 4, 5, 6, or 7 miRNA(s) (or any range derivable therein), compared to a normal sample, is indicative of Crohn's disease or susceptibility to Crohn's disease. In certain methods of the invention, a decrease in expression of miR-126 as, miR-192, miR-194, or miR-207 and/or an increase in expression of miR-125B, miR-150, or miR-223 compared to a normal sample is indicative of Crohn's disease or susceptibility to Crohn's disease. Arrays may specifically involve any combination of probes for the miRNAs described in this paragraph, as well as any other miRNA probe.

Other embodiments of the invention relate to an miRNA array or method that involves 1, 2, 3, 4, 5, 6, 7, 8, 9, or 10 probes (or any range derivable therein) for miRNA(s) selected from the group consisting of: let-7F2, miR-16, miR-126, miR-143, miR-145, miR-204, miR-223, miR-291, miR-338, and miR-425. In methods of the invention, a difference in expression of, of at least, or of at most 1, 2, 3, 4, 5, 6, 7, 8, 9, or 10 miRNA(s) (or any range derivable therein), compared to a normal sample, is indicative of Alzheimer's disease or susceptibility to Alzheimer's disease. In certain methods of the invention, a decrease in expression of let-7F2, miR-16, miR-126, miR-143, miR-145, or miR-223 and/or an increase in expression miR-204, miR-291, miR-338, or miR-425 compared to a normal sample is indicative of Alzheimer's disease or susceptibility to Alzheimer's disease. In other embodiments a difference in expression of miR-182 is indicative of Alzheimer's disease or susceptibility to Alzheimer's disease. Arrays may specifically involve any combination of probes for the miRNAs described in this paragraph, as well as any other miRNA probe.

The present invention also concerns an miRNA array or method that involves 1, 2, 3, 4, 5, 6, 7, or 8 probes (or any range derivable therein) for miRNA(s) selected from the group consisting of: let-7A, let-7C, miR-15B, miR-16, miR-17, miR-106, miR-128, miR-181A, and miR-326. In methods of the invention, a difference in expression of, of at least, or of at most 1, 2, 3, 4, 5, 6, 7, or 8 miRNA(s) (or any range derivable therein), compared to a normal sample, is indicative of T cell development. In certain methods of the invention, a decrease in expression of miR-326 and/or an increase in expression let-7A, let-7C, miR-15B, miR-16, miR-17, miR-106A, miR-128, or miR-181A compared to a normal sample is indicative of T cell development. Arrays may specifically involve any combination of probes for the miRNAs described in this paragraph, as well as any other miRNA probe.

The present invention also concerns an miRNA array or method that involves 1, 2, 3, 4, 5, or 6 probes (or any range derivable therein) for miRNA(s) selected from the group consisting of: miR-23A, miR-23B, miR-99B, miR-126, miR-133A, and miR-326. In methods of the invention, a difference in expression of, of at least, or of at most 1, 2, 3, 4, 5, or 6 miRNA(s) (or any range derivable therein), compared to a normal sample, is indicative of cardiac hypertrophy or risk of cardiac hypertrophy. In certain methods of the invention, a decrease in expression of miR-23A, miR-23B, miR-99B, miR-126, miR-133A, or miR-326 compared to a normal sample is indicative of cardiac hypertrophy or risk of cardiac hypertrophy. Arrays may specifically involve any combination of probes for the miRNAs described in this paragraph, as well as any other miRNA probe.

It is specifically contemplated that miRNA profiles for patients, particularly those suspected of having a particular disease or condition, can be generated by evaluating any of the miRNAs discussed in this application. The miRNA profile that is generated from the patient will be one that provides information regarding the particular disease or condition. In many embodiments, the miRNA profile is generated using the miRNA array discussed.

The present invention also concerns methods for identifying a candidate diagnostic marker or therapeutic target of a disease or condition comprising: a) generating a miRNA profile for a first sample exhibiting the disease or condition; b) identifying any difference in the first miRNA profile as compared to a second miRNA profile of a normal sample, wherein any difference between the samples identifies differentially expressed miRNAs as a candidate diagnostic marker or therapeutic target for the disease or condition. In some embodiments, the sample exhibiting the disease or condition and the normal sample are identified from a single patient. In other embodiments, methods also include evaluating a second sample exhibiting the same disease or condition as the first sample for a difference in expression of at least one miRNA compared to its expression in a normal sample. Any of the methods or arrays discussed above can involve miRNA profiling.

Moreover, it is specifically contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

In embodiments discussed above, the expression of a "set" of miRNAs may be evaluated for information regarding a particular disease or condition. It is specifically contemplated that the invention can be implemented in which one or more miRNAs identified as part of the set is excluded either in terms of it being probed for or in terms of its expression data being excluded from the analysis or conclusion of the rest of the set. In other words, individual miRNAs may be disclaimed in any set identified herein with respect to the embodiments provided.

Other methods of the invention include methods of screening for a candidate therapeutic agent for a disease or condition comprising: a) contacting a sample exhibiting the disease or condition with a substance; b) generating an miRNA profile for the sample; and, c) comparing the miRNA profile for the sample with an miRNA profile of a sample not contacted with the substance, wherein a difference in the miRNA profiles identifies a candidate therapeutic agent.

In certain methods, one can identify or select a patient for a clinical trial or for a particular drug regimen based on his or her miRNA profile. Therefore, in some embodiments of the invention, a patient is identified as a suitable recipient of a drug or drug regimen based on his miRNA profile. Such methods involve generating an miRNA profile for the patient in which the profile involves one or more miRNAs that are indicative of efficacy or toxicity with respect to the drug or drug regimen in question. In some embodiments, methods involve identifying a patient in need of treatment that can be provided by the drug or drug regimen.

Kits are also included as part of the invention. Kits for implementing methods of the invention described herein are specifically contemplated. In some embodiments, there are kits for preparing miRNA for multi-labeling and kits for preparing miRNA probes and/or miRNA arrays. In these embodiments, kit comprise, in suitable container means, 1, 2, 3, 4, 5, 6, 7, 8, 9, 10, 11, 12 or more of the following: 1) poly(A) polymerase; 2) unmodified nucleotides (G, A, T, C, and/or U); 3) a modified nucleotide (labeled or unlabeled); 4) poly(A) polymerase buffer; and, 5) at least one microfilter; 6) label that can be attached to a nucleotide; 7) at least one miRNA probe; 8) reaction buffer; 9) an miRNA array or components for making such an array; 10) acetic acid; 11) alcohol; 12) solutions for preparing, isolating, enriching, and purifying miRNAs or miRNA probes or arrays. Other reagents include those generally used for manipulating RNA, such as formamide, loading dye, ribonuclease inhibitors, and DNase. Buffers, as well as other solutions, are contemplated to have a pH of about, at least about, or at most about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0 or more (or any range derivable therein) in certain embodiments of the invention.

Poly(A) polymerase may be from any source, but specifically contemplated is a poly(A) polymerase from yeast or *E. coli*, which may be recombinant or purified from the organism. A reaction buffer for poly(A) polymerase may be included in any kit of the invention. Typically, such a poly(A) polymerase reaction buffer includes a volume exclusion reagent, such as PEG, magnesium, and sodium. In certain embodiments, the poly(A) polymerase reaction buffer in the kit contains at least: about 5, 6, 7, 8, 9, 10, 11, 12, 13, 14, 15% or more (or any range derivable therein) PEG; about 5, 10, 15, 20, 25, 30, 35, 40, 45, 50 mM or more $MgCl_2$ (or any range derivable therein); about 100, 200, 300, 400, 500, 600, 700, 800, 900 mM NaCl (or any range derivable therein); about 50, 60, 70, 80, 90, 100, 110, 120, 130, 140, 150 mM or more MES (or any range derivable therein); and about 0.5, 1, 1.5, 2, 2.5, 3, 3.5, 4 mM or more DTT (or any range derivable therein). The kits may also include a manganese source, which may be included as a separate component of a kit or in a solution or buffer with other components, such as in the reaction buffer. It is contemplated that about 5, 10, 15, 20, 25, 30, 35, 40, 45, 50 mM or more of $MnCl_2$ is included in the kit.

Nucleotides may also be included in kits of the invention. Nucleotides may be for DNA or RNA. Concentrations of a nucleotide or of a nucleotide mix (total concentration of all nucleotides) include, but are not limited to, about, at least about, or at most about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mM or more (or any range derivable therein). Moreover, they may be modified or not modified. If they are modified, they may have a reactive group or they may have a label attached to it. In certain embodiments, one or more nucleotides in a kit has a reactive group, such as an amine-reactive group. In other embodiments, a nucleotide is already labeled. It may be labeled with a chemiluminescent or fluorescent label, such as a dye. Specifically contemplated are amine-reactive dyes. Moreover, it is specifically contemplated that kits may or may not contain both modified and unmodified nucleotides. Also, kits may contain the label that will be attached to the nucleotide. Any label that can be attached to a nucleotide, as well as any specifically identified herein, can be included in kits of the invention.

Other solutions that may be included in a kit are those solutions involved in isolating and/or enriching miRNA from a mixed sample. A lysis solution may comprise a chaotropic salt, a detergent, a salt, and/or a reducing agent. In certain embodiments, a lysis solution contains one or more of the following: about 1, 2, 3, 4, 5, 6, 7, or 8 M guanidinium thiocyanate (or any range derivable therein); about 0.1, 0.2, 0.3, 0.4, 0.5, 0.6, 0.7, 0.8, 0.9, 1.0% or more N lauryl sarcosine (or any range derivable therein); about 5, 10, 15, 20, 25, 30, 35, 40, 45, 50 mM or more NaCitrate; and/or, about 0.0.5, 0.1, 0.15, 0.2 M or more 2-mercaptoethanol (or any range derivable therein). Wash solutions that may be contained in kits include wash solutions having a chaotropic salt and ethanol and wash solutions having a salt and buffer. In specific embodiments wash solutions include: about 1.0, 1.1, 1.2, 1.3, 1.4, 1.5, 1.6, 1.7, 1.8, 1.9, 2.0, 2.1, 2.2, 2.3, 2.4, 2.5 M or more guanidinium thiocyanate (or any range derivable therein) and/or 10, 15, 20, 25, 30, 35, 40, 45, 50, 55, 60% or more ethanol (or any range derivable therein). Other wash solutions can include: about 50, 60, 70, 80, 90, 100, 110, 120, 130, 140, 150 mM NaCl (or any range derivable therein); 3.0, 3.5, 4.0, 4.5, 5.0, 5.5, 6.0, 6.5, 7.0 mM or more EDTA (or any range derivable therein); about 5, 10, 15, 20, 25, 30, 35, 40 mM or more Tris (or any range derivable therein).

It is also contemplated that reagents for purifying miRNA using gel or tube electrophoresis can be included in kits of the invention.

A variety of microfilters can be used, and specifically contemplated in some embodiments of the invention is a glass fiber or silica filter column. Solutions that can be used with such microfilters include a binding buffer and/or wash buffer. In certain embodiments the binding buffer includes a salt and an alcohol. In particular cases, the binding or washing buffer has about 0.2, 0.3, 0.4, 0.5, 0.6, 0.7, 0.8, 0.9, 1.0 M or more NaCl (or any range derivable therein) and/or about 40, 45, 50, 55, 60, 65, 70, 75, 80, 85, 90% or more ethanol (or any range derivable therein).

Reagents and materials for preparing miRNA arrays can be included in a kit. The solid support for an array can be included in a kit, such as one or more slides. A kit may contain slide wash buffer, which in some embodiments includes a salt, buffer, and/or detergent. In certain embodiments, the slide wash buffer has about 100, 110, 120, 130, 140, 150, 160, 170, 180, 190, 200 mM or more NaCl (or any range derivable therein); 50, 60, 70, 80, 90, 100, 110, 120, 130, 140, 150 mM or more Tris (or any range derivable therein); and/or, 0.05. 0.06. 0.07. 0.08. 0.09, 0.1, 0.15, 0.02% or more Tween 20 (or any range derivable therein). Kits may include one or more miRNA probes described herein for use on an array.

Reagents for using miRNA arrays are also contemplated to be included as kit components. In some embodiments, there is a hybridization solution and/or an array wash solution. Such solutions can contain about 1.5, 2.0, 2.3, 3.0, 3.5, 4.0× or more SSC (or any range derivable therein).

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using miRNA arrays of the invention for therapeutic, prognostic, or diagnostic applications are included as part of the invention. Such kits can include an miRNA array, as well as information regarding a standard or normalized miRNA profile for the miRNAs on the array.

Control RNA or DNA is included in some kit embodiments. Control RNA is miRNA that can be used as a positive control for labeling and/or array analysis.

Other embodiments of the invention involve a system and/or apparatus for electrophoresis of a sample to isolate nucleic acids. In one embodiment, the present invention provides a micro-electrophoresis apparatus. The micro-electrophoresis apparatus of the present invention may be used to isolate any nucleic acid molecules. In some embodiments, the apparatus is used to isolate miRNA or other small nucleic acid molecules. In one embodiment, the micro-electrophoresis apparatus comprises: an upper buffer chamber electronically coupled to a negative electrode; a lower buffer collection chamber electronically coupled to a positive electrode; and a gel matrix disposed between the upper buffer chamber and the lower buffer collection chamber. In one embodiment, the micro-electrophoresis apparatus is the flashPAGE Fractionator (Ambion, Inc.).

In certain embodiments, the upper buffer chamber has a volume equal to or less than about 10 milliliters (ml). In certain aspects, the upper buffer chamber has a volume equal to or less than about 9 ml, 8 ml, 7 ml, 6 ml, 5 ml, 4 ml, 3 ml, 2 ml, 1 ml, or 500 microliters (µl). In certain embodiments, the lower buffer collection chamber has a volume equal to or less than about 10 ml. In certain aspects, the lower buffer collection chamber has a volume equal to or less than about 9 ml, 8 ml, 7 ml, 6 ml, 5 ml, 4 ml, 3 ml, 2 ml, 1 ml, or 500 µl.

In certain embodiments of the invention, the gel matrix is a polyacrylamide gel matrix. The gel matrix may be a pre-cast gel matrix such as flashPAGE Pre-Cast Gel cartridges (Ambion, Inc.).

The micro-electrophoresis apparatus of the present invention may be configured to operate on any low-current DC power source. For example, the apparatus may operate on a 50-100 V and 2-5 mA DC source.

Any embodiments discussed with respect to compositions and methods of the invention, as well as any embodiments in the Examples, is specifically contemplated as being part of a kit.

It is contemplated that any method or composition described herein can be implemented with respect to any other method or composition described herein.

Throughout this application, the term "about" is used to indicate that a value includes the standard deviation of error for the device or method being employed to determine the value.

The use of the word "a" or "an" when used in conjunction with the term "comprising" in the claims and/or the specification may mean "one," but it is also consistent with the meaning of "one or more," "at least one," and "one or more than one."

It is specifically contemplated that any embodiments described in the Examples section are included as an embodiment of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9. Tumor/NAT samples. miRNArray analysis was used to compare the miRNA expression profiles of tumors and NAT samples from patients with lung, colon, breast, thyroid, and bladder cancer. miRNAs that are expressed at higher levels in the normal than the corresponding tumor sample are noted with black boxes. miRNAs that are expressed at lower levels in the normal than the corresponding tumor sample are noted with white boxes. It is interesting to note that some miRNAs are differentially expressed in all tumors whereas others are differentially expressed in only one or two tumor types. The differentially expressed miRNAs represent potential diagnostic, prognostic, and therapeutic targets.

DESCRIPTION OF ILLUSTRATIVE EMBODIMENTS

Figure 1:
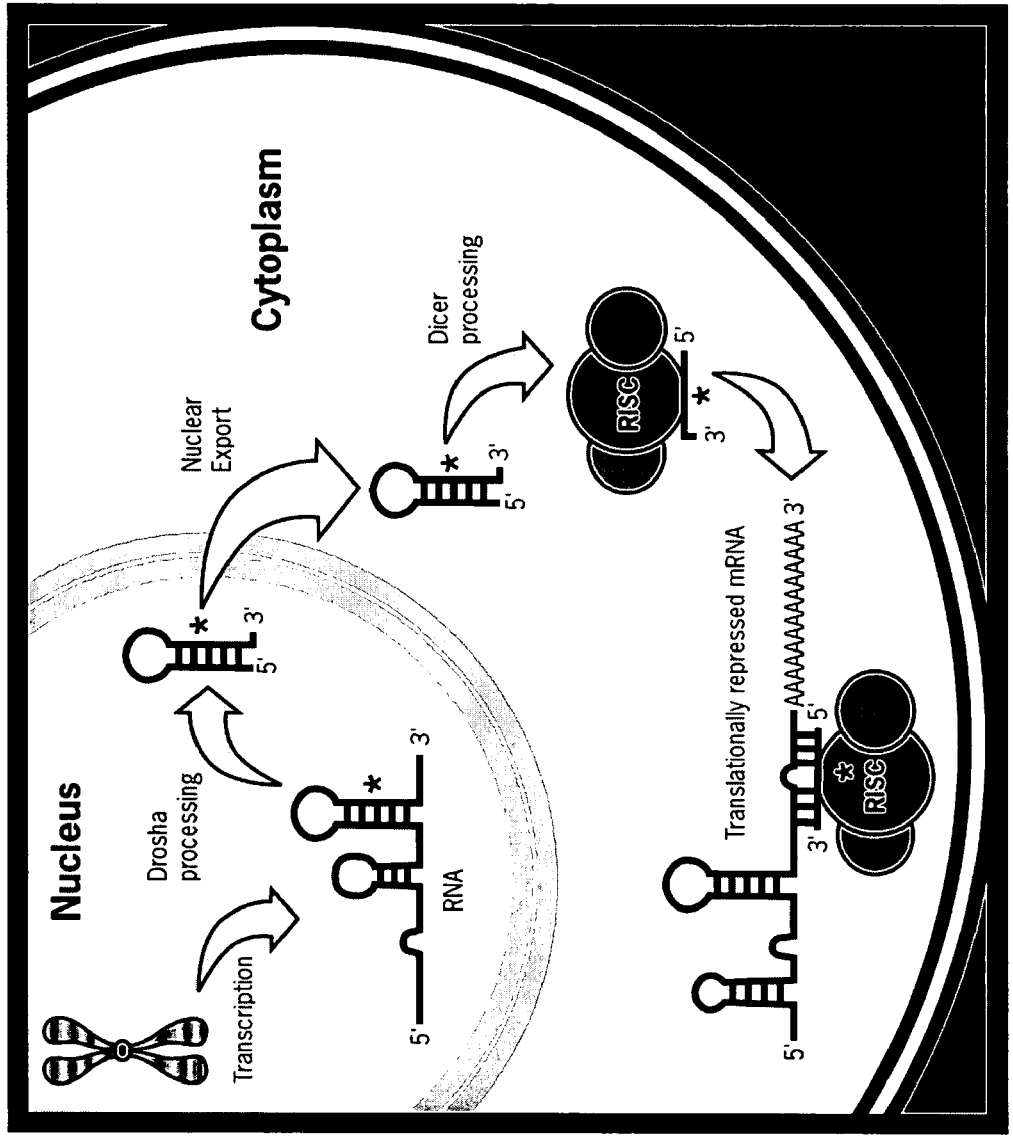
FIG. 1. Overview of miRNA Expression and Activation. miRNAs are transcribed as part of longer RNA molecules that can be as long as a thousand nucleotides (Lee, 2002). The RNAs are processed in the nucleus into hairpin RNAs of 70-100 nucleotides by the dsRNA-specific ribonuclease Drosha (Lee 2003) (FIG. 1). The hairpin RNAs are transported to the cytoplasm and digested by a second, double-strand specific ribonuclease called Dicer. The resulting 19-23mer miRNA is bound by a complex that is similar to or identical to the RNA-Induced Silencing Complex (RISC) that participates in RNA interference (Hutvagner 2002). The complex-bound, single-stranded miRNA binds mRNAs with sequences that are significantly, though not completely, complementary to the miRNA. By a mechanism that is not fully understood, but that does not involve mRNA degradation, the bound mRNA is not translated, resulting in reduced expression of the corresponding gene.
Figure 2:
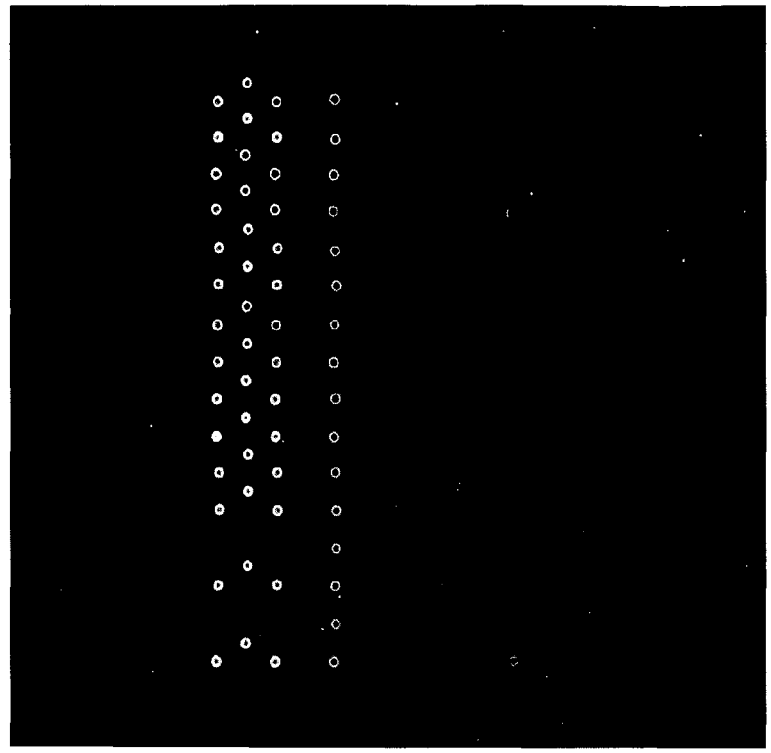
FIG. 2. Schematic for the miRNArray labeling procedure. Isolated miRNA is tailed using the Poly(A) Polymerase. The tailing reaction incorporates an amine modified nucleotide that can react with an amine-reactive dye molecule like Cy3-NHS ester or Cy5 NHS-ester. The labeled miRNA sample is hybridized to probes that are arrayed on a solid support like a glass slide. Gel matrices and filters could also be used as the solid support. The signal from the labeled and hybridized miRNAs are visualized and used to estimate the amount of miRNA in the sample.
Figure 2:
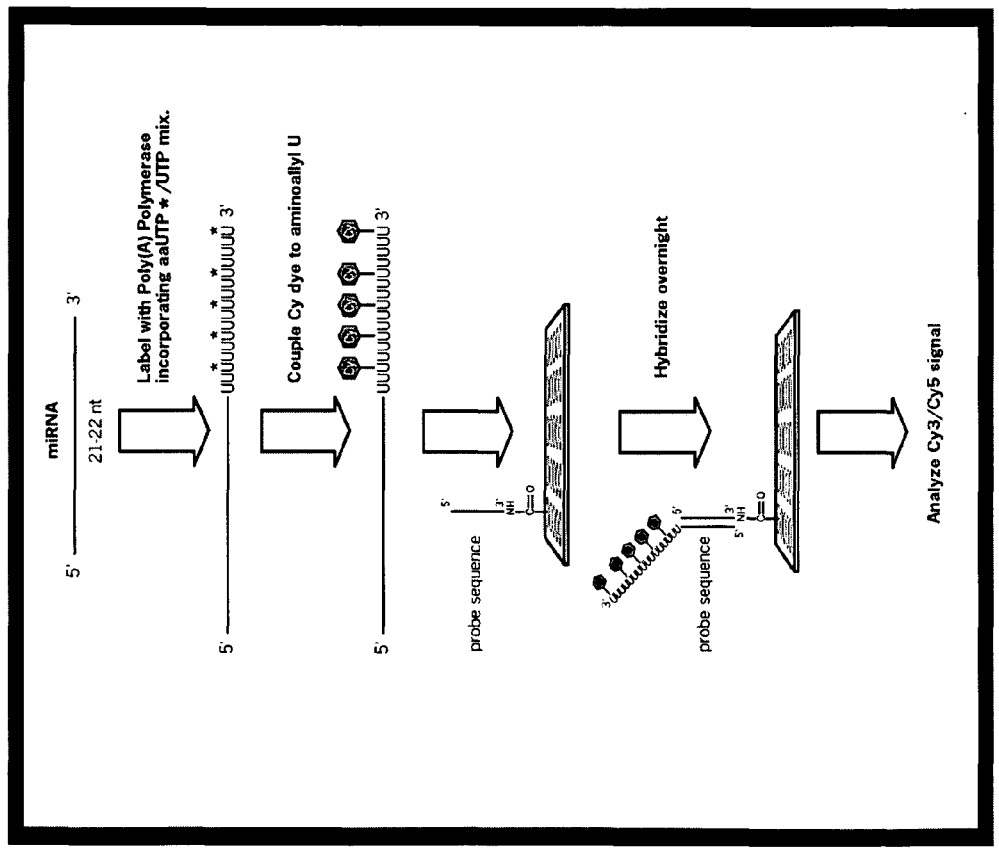

The present invention is directed to compositions and methods relating to preparation and characterization of miRNAs, as well as use of miRNAs for therapeutic, prognostic, and diagnostic applications.

I. miRNA Molecules

MicroRNA molecules ("miRNAs") are generally 21 to 22 nucleotides in length, though lengths of 19 and up to 23 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved by an enzyme called Dicer in animals. Dicer is ribonuclease III-like nuclease. The processed miRNA is typically a portion of the stem.

The processed miRNA (also referred to as "mature miRNA") become part of a large complex to down-regulate a particular target gene. Examples of animal miRNAs include those that imperfectly basepair with the target, which halts translation (Olsen et al., 1999; Seggerson et al., 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al., 2003).

A. Nucleic Acids

The present invention concerns miRNAs that can be labeled, used in array analysis, or employed in diagnostic, therapeutic, or prognostic applications. The RNA may have been endogenously produced by a cell, or been synthesized or produced chemically or recombinantly. They may be isolated and/or purified. The term "miRNA," unless otherwise indicated, refers to the processed RNA, after it has been cleaved from its precursor. Table 1 indicates which SEQ ID NO corresponds to the particular precursor sequence of an miRNA and what sequences within the SEQ ID NO correspond to the mature sequence. The name of the miRNA is often abbreviated and referred to without the prefix and will be understood as such, depending on the context. Unless otherwise indicated, miRNAs referred to in the application are human sequences identified as mir-X or let-X, where X is a number and/or letter.

In certain experiments, an miRNA probe designated by a suffix "5P" or "3P" can be used. "5P" indicates that the mature miRNA derives from the 5' end of the precursor and a corresponding "3P" indicates that it ferives from the 3' end of the precursor, as described on the world wide web at sanger.ac.uk/cgi-bin/rfam/mirna. Moreover, in some embodiments, an miRNA probe is used that does not correspond to a known human miRNA. It is contemplated that these non-human miRNA probes may be used in embodiments of the invention or that there may exist a human miRNA that is homologous to the non-human miRNA. While the invention is not limited to human miRNA, in certain embodiments, miRNA from human cells or a human biological sample is evaluated. In other embodiments, any mammalian cell or biological sample may be employed.

In some embodiments of the invention, methods and compositions involving miRNA may concern miRNA and/or other nucleic acids. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, miRNA probes, precursor miRNA, control nucleic acids, and other probes and primers. In many embodiments, miRNA are 19-24 nucleotides in length, while miRNA probes are 19-35 nucleotides in length, depending on the length of the processed miRNA and any flanking regions added. miRNA precursors are generally between 62 and 110 nucleotides in humans.

Nucleic acids of the invention may have regions of identity or complementarity to another nucleic acid. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides. It is further understood that the length of complementarity within a precursor miRNA or between an miRNA probe and an miRNA or an miRNA gene are such lengths. Moreover, the complementarity may be expressed as a percentage, meaning that the complementarity between a probe and its target is 90% or greater over the length of the probe. On some embodiments, complementarity is or is at least 90%, 95% or 100%. In particular, such lengths may be applied to any SEQ ID NO identified in any of SEQ ID NO:1 through SEQ ID NO:898, inclusive ("SEQ ID NO:1-SEQ ID NO:898") or any other sequence disclosed herein. Each of these SEQ ID NOs is disclosed in the tables below. The tables list known human miRNAs (Table 1A), mouse miRNAs (Table 2), and rat miRNAs (Table 3). In the tables, the commonly used name of the miRNA is given (with its identifying source in the prefix, for example, "hsa" for human sequences), the miRNA precursor sequence as identified in the corresponding SEQ ID NO:, and the processed miRNA sequence relative to the nucleotides identified in the miRNA precursor sequence. Unless otherwise indicated, an miRNA without a prefix will understood to refer to a human miRNA. An miRNA designated, for example, as miR-1-2 in the application will be understood to refer to hsa-mir-1-2 below. Moreover, a lowercase letter in the table below may or may not be lowercase; for example, hsa-mir-130b can also be referred to as miR-130B. In addition, miRNA sequences with a "mu" or "mmu" sequence will be understood to refer to a mouse miRNA.

TABLE 1A

Human miRNA Sequences

| miRNA name | Precursor | Processed Sequence Relative to Precursor |
|---|---|---|
| hsa-mir-1-2 | SEQ ID NO: 1 | 53-73 |
| hsa-mir-1-1 | SEQ ID NO: 2 | 46-66 |
| hsa-let-7a-1 | SEQ ID NO: 3 | 6-27 |
| hsa-let-7a-2 | SEQ ID NO: 4 | 5-26 |
| hsa-let-7a-3 | SEQ ID NO: 5 | 4-25 |
| hsa-let-7b | SEQ ID NO: 6 | 6-27 |
| hsa-let-7c | SEQ ID NO: 7 | 11-32 |
| hsa-let-7d | SEQ ID NO: 8 | 8-28 |
| hsa-let-7e | SEQ ID NO: 9 | 8-28 |
| hsa-let-7f-1 | SEQ ID NO: 10 | 7-28 |
| hsa-let-7f-2 | SEQ ID NO: 11 | 8-29 |
| hsa-mir-7-1 | SEQ ID NO: 12 | 24-44 |
| hsa-mir-7-2 | SEQ ID NO: 13 | 32-52 |
| hsa-mir-7-3 | SEQ ID NO: 14 | 31-51 |
| hsa-let-7g | SEQ ID NO: 15 | 5-25 |
| hsa-let-7i | SEQ ID NO: 16 | 6-24 |
| hsa-mir-9-1 | SEQ ID NO: 17 | 16-38 and/or 56-76 |
| hsa-mir-9-2 | SEQ ID NO: 18 | 16-38 and/or 54-74 |
| hsa-mir-9-3 | SEQ ID NO: 19 | 16-38 and/or 56-76 |
| hsa-mir-10a | SEQ ID NO: 20 | 22-44 |
| hsa-mir-10b | SEQ ID NO: 21 | 27-48 |
| hsa-mir-15a | SEQ ID NO: 22 | 14-35 |
| hsa-mir-15b | SEQ ID NO: 23 | 20-41 |
| hsa-mir-16-1 | SEQ ID NO: 24 | 14-35 |
| hsa-mir-16-2 | SEQ ID NO: 25 | 10-31 |
| hsa-mir-17 | SEQ ID NO: 26 | 14-37 and/or 51-70 |
| hsa-mir-18 | SEQ ID NO: 27 | 6-27 |
| hsa-mir-19a | SEQ ID NO: 28 | 49-71 |
| hsa-mir-19b-1 | SEQ ID NO: 29 | 54-76 |
| hsa-mir-19b-2 | SEQ ID NO: 30 | 62-84 |
| hsa-mir-20 | SEQ ID NO: 31 | 8-29 |
| hsa-mir-21 | SEQ ID NO: 32 | 8-29 |
| hsa-mir-22 | SEQ ID NO: 33 | 53-74 |
| hsa-mir-23a | SEQ ID NO: 34 | 45-65 |
| hsa-mir-23b | SEQ ID NO: 35 | 58-80 |
| hsa-mir-24-1 | SEQ ID NO: 36 | 6-28 and/or 44-65 |
| hsa-mir-24-2 | SEQ ID NO: 37 | 50-71 |
| hsa-mir-25 | SEQ ID NO: 38 | 52-73 |
| hsa-mir-26a-1 | SEQ ID NO: 39 | 10-31 |
| hsa-mir-26b | SEQ ID NO: 40 | 12-32 |
| hsa-mir-26a-2 | SEQ ID NO: 41 | 14-35 |
| hsa-mir-27a | SEQ ID NO: 42 | 51-72 |
| hsa-mir-27b | SEQ ID NO: 43 | 61-80 |
| hsa-mir-28 | SEQ ID NO: 44 | 14-35 |
| hsa-mir-29a | SEQ ID NO: 45 | 41-62 |
| hsa-mir-29b-1 | SEQ ID NO: 46 | 51-70 |
| hsa-mir-29b-2 | SEQ ID NO: 47 | 52-71 |
| hsa-mir-29c | SEQ ID NO: 48 | 54-75 |
| hsa-mir-30a | SEQ ID NO: 49 | 47-68 |
| hsa-mir-30c-2 | SEQ ID NO: 50 | 7-29 |

TABLE 1A-continued

Human miRNA Sequences

| miRNA name | Precursor | Processed Sequence Relative to Precursor |
|---|---|---|
| hsa-mir-30d | SEQ ID NO: 51 | 6-27 |
| hsa-mir-30b | SEQ ID NO: 52 | 17-37 |
| hsa-mir-30c-1 | SEQ ID NO: 53 | 17-39 |
| hsa-mir-30e | SEQ ID NO: 54 | 2-21 |
| hsa-mir-31 | SEQ ID NO: 55 | 9-29 |
| hsa-mir-32 | SEQ ID NO: 56 | 6-26 |
| hsa-mir-33 | SEQ ID NO: 57 | 6-24 |
| hsa-mir-34a | SEQ ID NO: 58 | 22-43 |
| hsa-mir-34b | SEQ ID NO: 59 | 14-35 |
| hsa-mir-34c | SEQ ID NO: 60 | 13-34 |
| hsa-mir-92-1 | SEQ ID NO: 61 | 48-69 |
| hsa-mir-92-2 | SEQ ID NO: 62 | 48-69 |
| hsa-mir-93 | SEQ ID NO: 63 | 12-33 |
| hsa-mir-95 | SEQ ID NO: 64 | 49-70 |
| hsa-mir-96 | SEQ ID NO: 65 | 9-30 |
| hsa-mir-98 | SEQ ID NO: 66 | 2-23 |
| hsa-mir-99a | SEQ ID NO: 67 | 13-34 |
| hsa-mir-99b | SEQ ID NO: 68 | 7-28 |
| hsa-mir-100 | SEQ ID NO: 69 | 13-34 |
| hsa-mir-101-1 | SEQ ID NO: 70 | 47-68 |
| hsa-mir-101-2 | SEQ ID NO: 71 | 49-70 |
| hsa-mir-103-2 | SEQ ID NO: 72 | 48-70 |
| hsa-mir-103-1 | SEQ ID NO: 73 | 48-70 |
| hsa-mir-105-1 | SEQ ID NO: 74 | 13-32 |
| hsa-mir-105-2 | SEQ ID NO: 75 | 13-32 |
| hsa-mir-106a | SEQ ID NO: 76 | 13-36 |
| hsa-mir-106b | SEQ ID NO: 77 | 12-32 |
| hsa-mir-107 | SEQ ID NO: 78 | 50-72 |
| hsa-mir-122a | SEQ ID NO: 79 | 15-37 |
| hsa-mir-124a-1 | SEQ ID NO: 80 | 52-73 |
| hsa-mir-124a-2 | SEQ ID NO: 81 | 61-82 |
| hsa-mir-124a-3 | SEQ ID NO: 82 | 52-73 |
| hsa-mir-125b-1 | SEQ ID NO: 83 | 15-36 |
| hsa-mir-125a | SEQ ID NO: 84 | 15-37 |
| hsa-mir-125b-2 | SEQ ID NO: 85 | 17-38 |
| hsa-mir-126 | SEQ ID NO: 86 | 15-35 and/or 52-72 |
| hsa-mir-127 | SEQ ID NO: 87 | 57-78 |
| hsa-mir-128a | SEQ ID NO: 88 | 50-71 |
| hsa-mir-128b | SEQ ID NO: 89 | 52-73 |
| hsa-mir-129-2 | SEQ ID NO: 90 | 15-35 |
| hsa-mir-130a | SEQ ID NO: 91 | 55-74 |
| hsa-mir-130b | SEQ ID NO: 92 | 51-72 |
| hsa-mir-132 | SEQ ID NO: 93 | 59-80 |
| hsa-mir-133a-1 | SEQ ID NO: 94 | 54-75 |
| hsa-mir-133a-2 | SEQ ID NO: 95 | 60-81 |
| hsa-mir-133b | SEQ ID NO: 96 | 67-87 |
| hsa-mir-134 | SEQ ID NO: 97 | 8-28 |
| hsa-mir-135a-1 | SEQ ID NO: 98 | 17-39 |
| hsa-mir-135a-2 | SEQ ID NO: 99 | 23-45 |
| hsa-mir-135b | SEQ ID NO: 100 | 16-37 |
| hsa-mir-136 | SEQ ID NO: 101 | 15-37 |
| hsa-mir-137 | SEQ ID NO: 102 | 60-81 |
| hsa-mir-138-2 | SEQ ID NO: 103 | 10-26 |
| hsa-mir-138-1 | SEQ ID NO: 104 | 23-39 |
| hsa-mir-139 | SEQ ID NO: 105 | 7-24 |
| hsa-mir-140 | SEQ ID NO: 106 | 24-44 |
| hsa-mir-141 | SEQ ID NO: 107 | 60-80 |
| hsa-mir-142 | SEQ ID NO: 108 | 16-35 and/or 52-74 |
| hsa-mir-143 | SEQ ID NO: 109 | 61-82 |
| hsa-mir-144 | SEQ ID NO: 110 | 52-73 |
| hsa-mir-145 | SEQ ID NO: 111 | 16-39 |
| hsa-mir-146 | SEQ ID NO: 112 | 21-42 |
| hsa-mir-147 | SEQ ID NO: 113 | 47-66 |
| hsa-mir-148a | SEQ ID NO: 114 | 44-65 |
| hsa-mir-148b | SEQ ID NO: 115 | 63-84 |
| hsa-mir-149 | SEQ ID NO: 116 | 15-36 |
| hsa-mir-150 | SEQ ID NO: 117 | 16-37 |
| hsa-mir-151 | SEQ ID NO: 118 | 46-67 |
| hsa-mir-152 | SEQ ID NO: 119 | 54-74 |
| hsa-mir-153-1 | SEQ ID NO: 120 | 54-73 |
| hsa-mir-153-2 | SEQ ID NO: 121 | 53-72 |
| hsa-mir-154 | SEQ ID NO: 122 | 15-36 |
| hsa-mir-155 | SEQ ID NO: 123 | 4-25 |
| hsa-mir-181a | SEQ ID NO: 124 | 39-61 |

TABLE 1A-continued

Human miRNA Sequences

| miRNA name | Precursor | Processed Sequence Relative to Precursor |
|---|---|---|
| hsa-mir-181b-1 | SEQ ID NO: 125 | 36-59 |
| hsa-mir-181c | SEQ ID NO: 126 | 27-48 |
| hsa-mir-181b-2 | SEQ ID NO: 127 | 16-39 |
| hsa-mir-182 | SEQ ID NO: 128 | 23-44 and/or 67-87 |
| hsa-mir-183 | SEQ ID NO: 129 | 27-49 |
| hsa-mir-184 | SEQ ID NO: 130 | 53-74 |
| hsa-mir-185 | SEQ ID NO: 131 | 15-32 |
| hsa-mir-186 | SEQ ID NO: 132 | 15-37 |
| hsa-mir-187 | SEQ ID NO: 133 | 71-91 |
| hsa-mir-188 | SEQ ID NO: 134 | 15-36 |
| hsa-mir-190 | SEQ ID NO: 135 | 15-36 |
| hsa-mir-191 | SEQ ID NO: 136 | 16-37 |
| hsa-mir-192 | SEQ ID NO: 137 | 24-44 |
| hsa-mir-193 | SEQ ID NO: 138 | 55-75 |
| hsa-mir-194-1 | SEQ ID NO: 139 | 15-36 |
| hsa-mir-194-2 | SEQ ID NO: 140 | 15-36 |
| hsa-mir-195 | SEQ ID NO: 141 | 15-35 |
| hsa-mir-196-1 | SEQ ID NO: 142 | 7-27 |
| hsa-mir-196-2 | SEQ ID NO: 143 | 25-45 |
| hsa-mir-197 | SEQ ID NO: 144 | 48-69 |
| hsa-mir-198 | SEQ ID NO: 145 | 6-24 |
| hsa-mir-199a-1 | SEQ ID NO: 146 | 6-28 and/or 46-67 |
| hsa-mir-199a-2 | SEQ ID NO: 147 | 31-53 and/or 69-90 |
| hsa-mir-199b | SEQ ID NO: 148 | 26-48 |
| hsa-mir-200b | SEQ ID NO: 149 | 54-77 |
| hsa-mir-200c | SEQ ID NO: 150 | 45-66 |
| hsa-mir-200a | SEQ ID NO: 151 | 54-75 |
| hsa-mir-203 | SEQ ID NO: 152 | 65-86 |
| hsa-mir-204 | SEQ ID NO: 153 | 33-54 |
| hsa-mir-205 | SEQ ID NO: 154 | 34-55 |
| hsa-mir-206 | SEQ ID NO: 155 | 53-74 |
| hsa-mir-208 | SEQ ID NO: 156 | 44-65 |
| hsa-mir-210 | SEQ ID NO: 157 | 66-86 |
| hsa-mir-211 | SEQ ID NO: 158 | 26-47 |
| hsa-mir-212 | SEQ ID NO: 159 | 71-91 |
| hsa-mir-213 | SEQ ID NO: 160 | 24-46 and/or 64-85 |
| hsa-mir-214 | SEQ ID NO: 161 | 71-91 |
| hsa-mir-215 | SEQ ID NO: 162 | 27-47 |
| hsa-mir-216 | SEQ ID NO: 163 | 19-39 |
| hsa-mir-217 | SEQ ID NO: 164 | 35-58 |
| hsa-mir-218-1 | SEQ ID NO: 165 | 25-45 |
| hsa-mir-218-2 | SEQ ID NO: 166 | 25-45 |
| hsa-mir-219-1 | SEQ ID NO: 167 | 21-41 |
| hsa-mir-219-2 | SEQ ID NO: 168 | 19-39 |
| hsa-mir-220 | SEQ ID NO: 169 | 23-43 |
| hsa-mir-221 | SEQ ID NO: 170 | 65-87 |
| hsa-mir-222 | SEQ ID NO: 171 | 69-92 |
| hsa-mir-223 | SEQ ID NO: 172 | 68-88 |
| hsa-mir-224 | SEQ ID NO: 173 | 8-30 |
| hsa-mir-296 | SEQ ID NO: 174 | 14-34 |
| hsa-mir-299 | SEQ ID NO: 175 | 7-28 |
| hsa-mir-301 | SEQ ID NO: 176 | 51-73 |
| hsa-mir-302 | SEQ ID NO: 177 | 44-66 |
| hsa-mir-320 | SEQ ID NO: 178 | 48-70 |
| hsa-mir-321 | SEQ ID NO: 179 | 10-30 |
| hsa-mir-323 | SEQ ID NO: 180 | 50-71 |
| hsa-mir-324 | SEQ ID NO: 181 | 16-38 and/or 51-72 |
| hsa-mir-326 | SEQ ID NO: 182 | 60-79 |
| hsa-mir-328 | SEQ ID NO: 183 | 48-69 |
| hsa-mir-330 | SEQ ID NO: 184 | 57-79 |
| hsa-mir-331 | SEQ ID NO: 185 | 61-81 |
| hsa-mir-335 | SEQ ID NO: 186 | 16-38 |
| hsa-mir-337 | SEQ ID NO: 187 | 56-78 |
| hsa-mir-338 | SEQ ID NO: 188 | 42-64 |
| hsa-mir-339 | SEQ ID NO: 189 | 15-35 |
| hsa-mir-340 | SEQ ID NO: 190 | 58-80 |
| hsa-mir-342 | SEQ ID NO: 191 | 61-84 |
| hsa-mir-345 | SEQ ID NO: 573 | 17-37 |
| hsa-mir-346 | SEQ ID NO: 574 | 4-26 |
| hsa-mir-367 | SEQ ID NO: 575 | 44-65 |
| hsa-mir-368 | SEQ ID NO: 576 | 44-65 |
| hsa-mir-369 | SEQ ID NO: 577 | 44-64 |
| hsa-mir-370 | SEQ ID NO: 578 | 48-68 |
| hsa-mir-371 | SEQ ID NO: 579 | 44-64 |
| hsa-mir-372 | SEQ ID NO: 580 | 42-64 |
| hsa-mir-373 | SEQ ID NO: 581 | 44-66 |
| hsa-mir-374 | SEQ ID NO: 582 | 12-33 |
| hsa-mir-375 | SEQ ID NO: 677 | 40-61 |
| hsa-mir-376a | SEQ ID NO: 678 | 44-64 |
| hsa-mir-377 | SEQ ID NO: 679 | 45-66 |
| hsa-mir-378 | SEQ ID NO: 680 | 5-26 and 44-65 |
| hsa-mir-379 | SEQ ID NO: 681 | 6-24 |
| hsa-mir-380 | SEQ ID NO: 682 | 5-26 and 40-61 |
| hsa-mir-381 | SEQ ID NO: 683 | 49-70 |
| hsa-mir-382 | SEQ ID NO: 684 | 11-32 |
| hsa-mir-383 | SEQ ID NO: 685 | 7-28 |
| hsa-mir-384 | SEQ ID NO: 686 | 57-76 |
| hsa-mir-422a | SEQ ID NO: 687 | 11-32 |
| hsa-mir-423 | SEQ ID NO: 688 | 53-74 |
| hsa-mir-424 | SEQ ID NO: 689 | 11-32 |
| hsa-mir-425 | SEQ ID NO: 690 | 55-75 |
| hsa-mir-448 | SEQ ID NO: 691 | 71-92 |
| hsa-mir-429 | SEQ ID NO: 692 | 51-72 |
| hsa-mir-449 | SEQ ID NO: 693 | 16-37 |
| hsa-mir-450 | SEQ ID NO: 694 | 17-38 |
| Has-mir-361 | SEQ ID NO: 899 | 6-27 |

The term "miRNA probe" refers to a nucleic acid probe that can identify a particular miRNA or structurally related miRNAs. Table 1B shows what probe was used to identify or screen for which miRNA. Table 1C provides the sequence of the probe. It is contemplated that all or part of any of the probes disclosed in Tables 1B or 1C can be implemented in any embodiments of the invention involving miRNA probes. Moreover, any of the miRNA identified in Table 1B may be screened for or profiled in embodiments of the invention.

TABLE 1B

| miRNA | Probe | miRNA | Probe | miRNA | Probe |
|---|---|---|---|---|---|
| hsa-mir-1-2 | miR1_2 | hsa-mir-24-1 | miR24_1 | hsa-mir-101-2 | miR101_1 |
| hsa-mir-1-1 | miR1_2 | hsa-mir-24-2 | miR24_1 | hsa-mir-103-2 | miR103_1 |
| hsa-let-7a-1 | let7a_1 | hsa-mir-25 | miR25 | hsa-mir-103-1 | miR103_1 |
| hsa-let-7a-2 | let7a_1 | hsa-mir-26a-1 | miR26a_1 | hsa-mir-105-1 | miR105_1 |
| hsa-let-7a-3 | let7a_1 | hsa-mir-26b | miR26a_1 | hsa-mir-105-2 | miR105_1 |
| hsa-let-7b | let7b | hsa-mir-26a-2 | miR26a_1 | hsa-mir-106a | miR106a |
| hsa-let-7c | let7c | hsa-mir-27a | miR27a | hsa-mir-106b | miR106a |
| hsa-let-7d | let7d | hsa-mir-27b | miR27a | hsa-mir-107 | miR107 |
| hsa-let-7e | let7e | hsa-mir-28 | miR28 | hsa-mir-122a | miR122a |
| hsa-let-7f-1 | let7f_1 | hsa-mir-29a | miR29b | hsa-mir-124a-1 | miR124a_1 |
| hsa-let-7f-2 | let7f_2 | hsa-mir-29b-1 | miR29b | hsa-mir-124a-2 | miR124a_1 |
| hsa-mir-7-1 | miR7_1 | hsa-mir-29b-2 | miR29b | hsa-mir-124a-3 | miR124a_1 |

TABLE 1B-continued

| miRNA | Probe | miRNA | Probe | miRNA | Probe |
|---|---|---|---|---|---|
| hsa-mir-7-2 | miR7_1 | hsa-mir-29c | miR29b | hsa-mir-125b-1 | miR125b_1 |
| hsa-mir-7-3 | miR7_1 | hsa-mir-30a | miR30a | hsa-mir-125a | miR125a |
| hsa-let-7g | let7g | hsa-mir-30c-2 | miR30a | hsa-mir-125b-2 | miR125b_1 |
| hsa-let-7i | let7i | hsa-mir-30d | miR30a | hsa-mir-126 | miR126 |
| hsa-mir-9-1 | miR9_1 | hsa-mir-30b | miR30b | hsa-mir-127 | miR127 |
| hsa-mir-9-2 | miR9_1 | hsa-mir-30c-1 | miR30a | hsa-mir-128a | miR128a |
| hsa-mir-9-3 | miR9_1 | hsa-mir-30e | miR30b | hsa-mir-128b | miR128a |
| hsa-mir-10a | miR10a | hsa-mir-31 | miR31 | hsa-mir-129-2 | miR129_2 |
| hsa-mir-10b | miR10a | hsa-mir-32 | miR32 | hsa-mir-130a | miR130a |
| hsa-mir-15a | miR15a | hsa-mir-33 | miR33 | hsa-mir-130b | miR130b |
| hsa-mir-15b | miR15b | hsa-mir-34a | miR34a | hsa-mir-132 | miR132 |
| hsa-mir-16-1 | miR16_1 | hsa-mir-34b | miR34b | hsa-mir-133a-1 | miR133a_1 |
| hsa-mir-16-2 | miR16_1 | hsa-mir-34c | miR34b | hsa-mir-133a-2 | miR133a_1 |
| hsa-mir-17 | miR17_3p | hsa-mir-92-1 | miR92_1 | hsa-mir-133b | miR133a_1 |
| hsa-mir-18 | miR18 | hsa-mir-92-2 | miR92_1 | hsa-mir-134 | miR134 |
| hsa-mir-19a | miR19a | hsa-mir-93 | miR93 | hsa-mir-135a-1 | miR135a_1 |
| hsa-mir-19b-1 | miR19a | hsa-mir-95 | miR95 | hsa-mir-135a-2 | miR135a_1 |
| hsa-mir-19b-2 | miR19a | hsa-mir-96 | miR96 | hsa-mir-135b | miR135a_1 |
| hsa-mir-20 | miR20 | hsa-mir-98 | miR98 | hsa-mir-136 | miR136 |
| hsa-mir-21 | miR21 | hsa-mir-99a | miR99a | hsa-mir-101-2 | miR101_1 |
| hsa-mir-22 | miR22 | hsa-mir-99b | miR99b | hsa-mir-103-2 | miR103_1 |
| hsa-mir-23a | miR23a | hsa-mir-100 | miR100 | hsa-mir-103-1 | miR103_1 |
| hsa-mir-23b | miR23b | hsa-mir-101-1 | miR101_1 | hsa-mir-105-1 | miR105_1 |
| hsa-mir-137 | miR137 | hsa-mir-191 | miR191 | hsa-mir-221 | miR221 |
| hsa-mir-138-2 | miR138_1 | hsa-mir-192 | miR192 | hsa-mir-222 | miR222 |
| hsa-mir-138-1 | miR138_1 | hsa-mir-193 | miR193 | hsa-mir-223 | miR223 |
| hsa-mir-139 | miR139 | hsa-mir-194-1 | miR194_1 | hsa-mir-224 | miR224 |
| hsa-mir-140 | miR140 | hsa-mir-194-2 | miR194_1 | hsa-mir-296 | miR296 |
| hsa-mir-141 | miR141 | hsa-mir-195 | miR195 | hsa-mir-299 | miR299 |
| hsa-mir-142 | miR142_5p | hsa-mir-196-1 | miR196a_1 | hsa-mir-301 | miR301 |
| hsa-mir-143 | miR143 | hsa-mir-196-2 | miR196a_1 | hsa-mir-302 | miR302a |
| hsa-mir-144 | miR144 | hsa-mir-197 | miR197 | hsa-mir-320 | miR320 |
| hsa-mir-145 | miR145 | hsa-mir-198 | miR198 | hsa-mir-323 | miR323 |
| hsa-mir-146 | miR146 | hsa-mir-199a-1 | miR199a_1 | hsa-mir-324 | miR324_3p |
| hsa-mir-147 | miR147 | hsa-mir-199a-2 | miR199a_1 | hsa-mir-326 | miR326 |
| hsa-mir-148a | miR148a | hsa-mir-199b | miR199a_1 | hsa-mir-328 | miR328 |
| hsa-mir-148b | miR148a | hsa-mir-200b | miR200b | hsa-mir-330 | miR330 |
| hsa-mir-149 | miR149 | hsa-mir-200c | miR200a | hsa-mir-331 | miR331 |
| hsa-mir-150 | miR150 | hsa-mir-200a | miR200a | hsa-mir-335 | miR335 |
| hsa-mir-151 | miR151 | hsa-mir-203 | miR203 | hsa-mir-337 | miR337 |
| hsa-mir-152 | miR152 | hsa-mir-204 | miR204 | hsa-mir-338 | miR338 |
| hsa-mir-153-1 | miR153_1 | hsa-mir-205 | miR205 | hsa-mir-339 | miR339 |
| hsa-mir-153-2 | miR153_1 | hsa-mir-206 | miR206 | hsa-mir-340 | miR340 |
| hsa-mir-154 | miR154 | hsa-mir-208 | miR208 | hsa-mir-342 | miR342 |
| hsa-mir-155 | miR155 | hsa-mir-210 | miR210 | hsa-mir-345 | miR345 |
| hsa-mir-181a | miR181a | hsa-mir-211 | miR211 | hsa-mir-346 | miR346 |
| hsa-mir-181b-1 | miR181b_1 | hsa-mir-212 | miR212 | hsa-mir-367 | miR367 |
| hsa-mir-181c | miR181b_1 | hsa-mir-213 | miR213 | hsa-mir-368 | miR368 |
| hsa-mir-181b-2 | miR181b_1 | hsa-mir-214 | miR214 | hsa-mir-369 | miR369 |
| hsa-mir-182 | miR182 | hsa-mir-215 | miR215 | hsa-mir-370 | miR370 |
| hsa-mir-183 | miR183 | hsa-mir-216 | miR216 | hsa-mir-371 | miR371 |
| hsa-mir-184 | miR184 | hsa-mir-217 | miR217 | hsa-mir-372 | miR372 |
| hsa-mir-185 | miR185 | hsa-mir-218-1 | miR218_1 | hsa-mir-373 | miR373 |
| hsa-mir-186 | miR186 | hsa-mir-218-2 | miR218_1 | hsa-mir-374 | miR374 |
| hsa-mir-187 | miR187 | hsa-mir-219-1 | miR219_1 | hsa-mir-221 | miR221 |
| hsa-mir-188 | miR188 | hsa-mir-219-2 | miR219_1 | hsa-mir-222 | miR222 |
| hsa-mir-190 | miR190 | hsa-mir-220 | miR220 | hsa-mir-223 | miR223 |
| hsa-mir-137 | miR137 | hsa-mir-191 | miR191 | hsa-mir-224 | miR224 |

TABLE 1C

| Probe name | Probe Sequences | SEQ ID NO: |
|---|---|---|
| let7a_1 | CTAAAACTATACAACCTACTACCTCATCCC | 704 |
| let7b | CTGAAACCACACAACCTACTACCTCACCC | 705 |
| let7c | TCTAAACCATACAACCTACTACCTCAACCC | 706 |
| let7d | TAAAACTATGCAACCTACTACCTCTTCCT | 707 |
| let7d_AS | CCTAAGAAAGGCAGCAGGTCGTATAGTTAA | 708 |
| let7e | CTCAACTATACAACCTCCTACCTCAGCCC | 709 |

TABLE 1C-continued

| Probe name | Probe Sequences | SEQ ID NO: |
|---|---|---|
| let7f_1 | CCACAACTATACAATCTACTACCTCACTCT | 710 |
| let7f_2 | CTAAAACTATACAATCTACTACCTCATCCC | 711 |
| let7g | TCAAACTGTACAAACTACTACCTCAGCCT | 712 |
| let7i | AAACAGCACAAACTACTACCTCAGCCA | 713 |
| miR100 | ATACCACAAGTTCGGATCTACGGGTTTGTG | 714 |
| miR101_1 | CATCCTTCAGTTATCACAGTACTGTACCTT | 715 |
| miR103_1 | TCTTTCATAGCCCTGTACAATGCTGCTTGAT | 716 |
| miR105_1 | CACCACAGGAGTCTGAGCATTTGACCAC | 717 |
| miR106a | AAAAGCTACCTGCACTGTAAGCACTTTTACAT | 718 |
| miR107 | GCTTTGATAGCCCTGTACAATGCTGCTTGAA | 719 |
| miR10a | CTTACACAAATTCGGATCTACAGGGTATATA | 720 |
| miR1_2 | CAAAAATACATACTTCTTTACATTCCATAGC | 721 |
| miR122a | AGACACAAACACCATTGTCACACTCCACAGC | 722 |
| miR124a_1 | TTCTTGGCATTCACCGCGTGCCTTAATTGT | 723 |
| miR125a | TCCTCACAGGTTAAAGGGTCTCAGGGACCTA | 724 |
| miR125b_1 | AACATCACAAGTTAGGGTCTCAGGGACTGA | 725 |
| miR126 | CGGCGCATTATTACTCACGGTACGAGTTT | 726 |
| miR126_AS | ACAGCGCGTACCAAAAGTAATAATGTCCC | 727 |
| miR127 | GACCAGCCAAGCTCAGACGGATCCGATGAT | 728 |
| miR128a | CTGAAAAGAGACCGGTTCACTGTGAGAAA | 729 |
| miR129_2 | TACAGCAAGCCCAGACCGCAAAAAGATTC | 730 |
| miR130a | CAATGCCCTTTTAACATTGCACTGCTAG | 731 |
| miR130b | ACCGATGCCCTTTCATCATTGCACTGCTTC | 732 |
| miR132 | GGGGCGACCATGGCTGTAGACTGTTACCTC | 733 |
| miR133a_1 | AGCTACAGCTGGTTGAAGGGGACCAAATCC | 734 |
| miR134 | ATGCCCCTCTGGTCAACCAGTCACACACC | 735 |
| miR135a_1 | AGAATCACATAGGAATAAAAAGCCATAGAGA | 736 |
| miR136 | AGAATCCATCATCAAAACAAATGGAGTCCTC | 737 |
| miR137 | TCGACTACGCGTATTCTTAAGCAATAACAA | 738 |
| miR138_1 | GCCTGATTCACAACACCAGCTGCCC | 739 |
| miR139 | CTGGAGACACGTGCACTGTAGAATAC | 740 |
| miR140 | TAACCTACCATAGGGTAAAACCACTGGCA | 741 |
| miR141 | GGAGCCATCTTTACCAGACAGTGTTAGGA | 742 |
| miR142_3p | CTCATCCATAAAGTAGGAAACACTACACCCT | 743 |
| miR142_5p | GTTAGTAGTGCTTTCTACTTTATGGGTG | 744 |
| miR143 | TTCCTGAGCTACAGTGCTTCATCTCAGACT | 745 |
| miR144 | CGGACTAGTACATCATCTATACTGTAGTGT | 746 |
| miR145 | ATCTAAGGGATTCCTGGGAAAACTGGACCGTG | 747 |
| miR146 | ACACAACCCATGGAATTCAGTTCTCAAAGC | 748 |
| miR147 | TCTAGCAGAAGCATTTCCACACACTGGC | 749 |
| miR148a | GAGAACAAAGTTCTGTAGTGCACTGATTCT | 750 |
| miR149 | CACGGGAGTGAAGACACGGAGCCAGAGCTC | 751 |
| miR150 | CCAGCACTGGTACAAGGGTTGGGAGACAGG | 752 |
| miR151 | CTGTCCTCAAGGAGCTTCAGTCTAGTAGGG | 753 |
| miR152 | GGGCCCAAGTTCTGTCATGCACTGACTGC | 754 |
| miR153_1 | ATGATCACTTTTGTGACTATGCAACTGG | 755 |
| miR154 | AAAGCGAAGGCAACACGGATAACCTATCTT | 756 |
| miR155 | AAAAACCCCTATCACGATTAGCATTAACAG | 757 |
| miR15a | AATCCACAAACCATTATGTGCTGCTACTTT | 758 |
| miR15b | AGCATGTAAACCATGATGTGCTGCTACAGT | 759 |
| miR16_1 | TTAACGCCAATATTTACGTGCTGCTAAGGC | 760 |
| miR17_3p | TGCTACAAGTGCCTTCACTGCAGTAGAT | 761 |
| miR17_5p | TATCACTACCTGCACTGTAAGCACTTTGACAT | 762 |
| miR18 | TCACTATCTGCACTAGATGCACCTTAGAAC | 763 |
| miR181a | CCAAACTCACCGACAGCGTTGAATGTTCTT | 764 |
| miR181b_1 | GTTCAACCCACCGACAGCAATGAATGTTGATT | 765 |
| miR182 | CCAGTGTGAGTTCTACCATTGCCAAAAACG | 766 |
| miR182_AS | CCCATAGTTGGCAAGTCTAGAACCACCGG | 767 |
| miR183 | TTCACAGTGAATTCTACCAGTGCCATACACA | 768 |
| miR184 | ACCTACCCTTATCAGTTCTCCGTCCAACAC | 769 |
| miR185 | TCAGGAACTGCCTTTCTCTCCAATCC | 770 |
| miR186 | CAGAAAGCCCAAAAGGAGAATTCTTTGAAA | 771 |
| miR187 | CCTCCGGCTGCAACACAAGACACGAGGGG | 772 |
| miR188 | GCTCACCCTCCACCATGCAAGGGATGTGAG | 773 |
| miR189 | GAGAACTGATATCAGCTCAGTAGGCACCGGA | 774 |
| miR190 | AACAACCTAATATATCAAACATATCACACA | 775 |
| miR191 | CAACAGCTGCTTTTGGGATTCCGTTGCCCG | 776 |
| miR192 | CACTGGCTGTCAATTCATAGGTCAGAGCC | 777 |
| miR193 | AGAACTGGGACTTTGTAGGCCAGTTGATC | 778 |
| miR194_1 | ACAGTCCACATGGAGTTGCTGTTACACTTG | 779 |
| miR195 | CTGTGCCAATATTTCTGTGCTGCTAGAGC | 780 |
| miR196a_1 | AGGCCCAACAACATGAAACTACCTAATTC | 781 |
| miR197 | CCATGCTGGGTGGAGAAGGTGGTGAAGGGT | 782 |
| miR198 | GGAACCTATCTCCCCTCTGGACCAATG | 783 |
| miR199a_AS_1 | GCCTAACCAATGTGCAGACTACTGTACACA | 784 |

TABLE 1C-continued

| Probe name | Probe Sequences | SEQ ID NO: |
|---|---|---|
| miR199a_AS_2 | GTCTAACCAATGTGCAGACTACTGTACAAC | 785 |
| miR199a_1 | TCCTGAACAGGTAGTCTGAACACTGGGTTGG | 786 |
| miR199a_2 | TCCTGAACAGGTAGTCTGAACACTGGGGCGA | 787 |
| miR19a | ACCATCAGTTTTGCATAGATTTGCACAACTA | 788 |
| miR20 | ACACTACCTGCACTATAAGCACTTTAGTGC | 789 |
| miR200a | TTGAACATCGTTACCAGACAGTGTTAGAGT | 790 |
| miR200b | CCGTCATCATTACCAGGCAGTATTAGAGACCT | 791 |
| miR201 | TAGAAGAACAATGCCTTACTGAGTAAGGT | 792 |
| miR202 | TCCATCTTCCCATGCGCTATACCTCTTTAG | 793 |
| miR203 | GGGTCTAGTGGTCCTAAACATTTCACAATT | 794 |
| miR204 | TCTCAGGCATAGGATGACAAAGGGAAGTCC | 795 |
| miR205 | GAGACAGACTCCGGTGGAATGAAGGATCTG | 796 |
| miR206 | GAAACCACACACTTCCTTACATTCCATAGC | 797 |
| miR207 | AAGAGAGGGAGGAGAGCCAGGAGAAGCGAA | 798 |
| miR208 | ACCAACAAGCTTTTTGCTCGTCTTATACGT | 799 |
| miR21 | ACAGTCAACATCAGTCTGATAAGCTACCCG | 800 |
| miR210 | AGATCAGCCGCTGTCACACGCACAGTGGG | 801 |
| miR211 | CCCTAGGCGAAGGATGACAAAGGGAAGCCC | 802 |
| miR212 | CGGTGGCCGTGACTGGAGACTGTTACTGA | 803 |
| miR213 | ATAGGGTACAATCAACGGTCGATGGTTTTG | 804 |
| miR214 | GTGACTGCCTGTCTGTGCCTGCTGTACAG | 805 |
| miR215 | TATTGTCTGTCAATTCATAGGTCATTTTC | 806 |
| miR216 | ATCTCACAGTTGCCAGCTGAGATTAAGCC | 807 |
| miR217 | TCTTATCCAATCAGTTCCTGATGCAGTATCTG | 808 |
| miR218_1 | AACCACATGGTTAGATCAAGCACAACAGA | 809 |
| miR219_1 | CTCGAGAATTGCGTTTGGACAATCAGGAG | 810 |
| miR22 | GGCAACAGTTCTTCAACTGGCAGCTTTAGC | 811 |
| miR220 | GCCCAAAGTGTCAGATACGGTGTGGAGCC | 812 |
| miR221 | GCCTGAAACCCAGCAGACAATGTAGCTGTTG | 813 |
| miR222 | ATCAGAGACCCAGTAGCCAGATGTAGCTGCTG | 814 |
| miR223 | ACTTGGGGTATTTGACAAACTGACACTCT | 815 |
| miR224 | CTACTAAACGGAACCACTAGTGACTTGAAAG | 816 |
| miR23a | GGTTGGAAATCCCTGGCAATGTGATTTGT | 817 |
| miR23b | TTGCGTGGTAATCCCTGGCAATGTGATTTTA | 818 |
| miR24_1 | CTCCTGTTCCTGCTGAACTGAGCCAGTGTG | 819 |
| miR25 | ACTGTCAGACCGAGACAAGTGCAATGCCCA | 820 |
| miR26a_1 | GCACAGCCTATCCTGGATTACTTGAACGAG | 821 |
| miR27a | GGGGGGCGGAACTTAGCCACTGTGAACACG | 822 |
| miR28 | GTAACTCAATAGACTGTGAGCTCCTTGAGG | 823 |
| miR290 | AAAAAAAAAGTGCCCCCATAGTTTGAGTACC | 824 |
| miR291_3p | CAGTGGCACACAAAGTGGAAGCACTTTCTCA | 825 |
| miR291_5p | CTCAAGAGAGGGCCTCCACTTTGATGGCCG | 826 |
| miR292_3p | GGTGACACTCAAAACCTGGCGGCACTTTTCT | 827 |
| miR292_5p | AATCCAAAAGAGCCCCCAGTTTGAGTATCA | 828 |
| miR293 | GGCAACACTACAAACTCTGCGGCACTTCTT | 829 |
| miR294 | GGCAACACACAAAAGGGAAGCACTTTCCAC | 830 |
| miR295 | GGAGAGACTCAAAAGTAGTAGCACTTTCTAT | 831 |
| miR296 | CACAACAGGATTGAGGGGGGCCCTCTGG | 832 |
| miR297_1 | TGCACATGCACATGCACACATACATACAT | 833 |
| miR298 | CAAGGGAAGAACAGCCCTCCTCTGCCAAAG | 834 |
| miR299 | CAAAATGTATGTGGGACGGTAAACCATTTC | 835 |
| miR29b | GAACACTGATTTCAAATGGTGCTAGACA | 836 |
| miR300 | CCTCGAAGAGAGCTTGCCCTTGCATATTCA | 837 |
| miR301 | AGATGCTTTGACAATACTATTGCACTGCTAG | 838 |
| miR302a | CCATCACCAAAACATGGAAGCACTTACTTCT | 839 |
| miR302b_AS | TCACAGAAAGCACTTCCATGTTAAAGTTGAA | 840 |
| miR302c | CCTCCACTGAAACATGGAAGCACTTACTTTT | 841 |
| miR302c_AS | CACACAGCAGGTACCCCCATCTTAAAGCAA | 842 |
| miR30a_3p | GCAGGCTGCAAACATCCGACTGAAAGCCAT | 843 |
| miR30a_5p | CACAGCTTCCAGTCGAGGATGTTTACAGTCG | 844 |
| miR30b | TACAGCTGAGTGTAGGATGTTTACATGAA | 845 |
| miR31 | TCAACAGCTATGCCAGCATCTTGCCTCCT | 846 |
| miR32 | ACATGCAACTTAGTAATGTGCAATATCTC | 847 |
| miR320 | CTTTTTCGCCCTCTCAACCCAGCTTTTCCCG | 848 |
| miR322 | GGGGTGTTGCAGCGCTTCATGTTTTGAA | 849 |
| miR323 | GCAAAGAGGTCGACCGTGTAATGTGCGCCA | 850 |
| miR324_3p | ACCCCCAGCAGCACCTGGGGCAGTGGGTCT | 851 |
| miR324_5p | CTTTACACCAATGCCCTAGGGGATCGGGGA | 852 |
| miR325 | AAACACTTACTGGACACCTACTAGGAACC | 853 |
| miR326 | GGGGCTGGAGGAAGGGCCCAGAGGCGAT | 854 |
| miR328 | GGGGACGGAAGGGCAGAGAGGGCCAGGGGC | 855 |
| miR329 | TGAAAAAAAGGTTAGCTGGGTGTGTTTCAT | 856 |
| miR33 | CATGCAATGCAACTACAATGCACCACA | 857 |
| miR330 | TGCCTCTCTGCAGGCCGTGTGCTTTGCTCGG | 858 |
| miR331 | TTGGTTCTAGGATAGGCCCAGGGGCCTGG | 859 |

TABLE 1C-continued

| Probe name | Probe Sequences | SEQ ID NO: |
|---|---|---|
| miR337 | GAAGAAAGGCATCATATAGGAGCTGGATAAC | 860 |
| miR338 | TCTTCAACAAAATCACTGATGCTGGAGTCGC | 861 |
| miR339 | CACGTGAGCTCCTGGAGGACAGGGAGAGC | 862 |
| miR340 | GTATGGCTATAAAGTAACTGAGACGGATCC | 863 |
| miR341 | GCCGACTGACCGACCGACCGATCGACCGA | 864 |
| miR342 | AGGTGACGGGTGCGATTTCTGTGTGAGACAAT | 865 |
| miR344 | GCTTACAGTCAGGCTTTGGCTAGATCAGGTA | 866 |
| miR345 | ACGAGCCCTGGACTAGGAGTCAGCAGACC | 867 |
| miR346 | AACAGAGAGGCAGGCATGCGGGCAGACAGC | 868 |
| miR34a | CACAACAACCAGCTAAGACACTGCCAAAGA | 869 |
| miR34c | TTAGCAATCAGCTAACTACACTGCCTAGTA | 870 |
| miR350 | AAGGGTGAAAGTGTATGGGCTTTGTGAACATT | 871 |
| miR351 | ACTCCAGGCTCAAAGGGCTCCTCAGGGAAACG | 872 |
| miR367 | CCATCACCATTGCTAAAGTGCAATTCCAAT | 873 |
| miR368 | AAAACGTGGAATTTCCTCTATGTTTAACCA | 874 |
| miR369 | GAGAAAAGATCAACCATGTATTATTCGAA | 875 |
| miR370 | CAGACCAGGTTCCACCCCAGCAGGCACTCCC | 876 |
| miR371 | GTAACACTCAAAAGATGGCGGCACTTTCAC | 877 |
| miR372 | GTGACGCTCAAATGTCGCAGCACTTTCCACT | 878 |
| miR373 | GGGACACCCCAAAATCGAAGCACTTCCCAGT | 879 |
| miR373_AS | AAAAGGAAAGCGCCCCCATTTTGAGTATCC | 880 |
| miR374 | ATAACACTTATCAGGTTGTATTATAATGGC | 881 |
| miR376a | GAAAACGTGGATTTTCCTCTACGATTAGT | 882 |
| miR376b | TGAAAAGTGGATGTTCCTCTATGATTAT | 883 |
| miR380 | AAGATGTGGACCATACTACATACGACCCA | 884 |
| miR409 | CGAAAGGGGTTCACCGAGCAACATTCGT | 885 |
| miR410 | TGAAAACAGGCCATCTGTGTTATATTCGTC | 886 |
| miR411 | TGATACTGAGGGTTAGTGGACCGTGTTACAT | 887 |
| miR412 | ACCGACGGCTAGTGGACCAGGTGAAGTACAT | 888 |
| miR7_1 | AAACAACAAAATCACTAGTCTTCCACACA | 889 |
| miR9_1 | CCACTCATACAGCTAGATAACCAAAGATAAC | 890 |
| miR9_1_AS | TTTTACTTTCGGTTATCTAGCTTTATGAA | 891 |
| miR92_1 | CTCAACAGGCCGGGACAAGTGCAATACCAT | 892 |
| miR93 | CACACTACCTGCACGAACAGCACTTTGGAG | 893 |
| miR95 | TGGGTGCTCAATAAATACCCGTTGAATGTA | 894 |
| miR96 | ACAAGCAAAAATGTGCTAGTGCCAAAATCG | 895 |
| miR98 | ACCCCACAACAATACAACTTACTACCTCAC | 896 |

TABLE 1C-continued

| Probe name | Probe Sequences | SEQ ID NO: |
|---|---|---|
| miR99a | TCACCACAAGATCGGATCTACGGGTTTATG | 897 |
| miR99b | GCCCCGCAAGGTCGGTTCTACGGGTGGGTG | 898 |

TABLE 2

Mouse miRNA Sequences

| miRNA name | Precursor | Processed Sequence Relative to Precursor |
|---|---|---|
| mmu-mir-1-1 | SEQ ID NO: 192 | 49-69 |
| mmu-mir-1-2 | SEQ ID NO: 193 | 47-67 |
| mmu-let-7g | SEQ ID NO: 194 | 7-27 |
| mmu-let-7i | SEQ ID NO: 195 | 6-24 |
| mmu-let-7d | SEQ ID NO: 196 | 16-36 + 70-91 |
| mmu-let-7a-1 | SEQ ID NO: 197 | 13-34 |
| mmu-let-7a-2 | SEQ ID NO: 198 | 17-38 |
| mmu-let-7b | SEQ ID NO: 199 | 7-28 |
| mmu-let-7c-1 | SEQ ID NO: 200 | 16-37 |
| mmu-let-7c-2 | SEQ ID NO: 201 | 14-35 |
| mmu-let-7e | SEQ ID NO: 202 | 15-35 |
| mmu-let-7f-1 | SEQ ID NO: 203 | 8-29 |
| mmu-let-7f-2 | SEQ ID NO: 204 | 8-29 |
| mmu-mir-7-1 | SEQ ID NO: 205 | 24-44 |
| mmu-mir-7-2 | SEQ ID NO: 206 | 19-39 |
| mmu-mir-7b | SEQ ID NO: 207 | 30-50 |
| mmu-mir-9-2 | SEQ ID NO: 208 | 8-30 and/or 46-66 |
| mmu-mir-9-1 | SEQ ID NO: 209 | 16-38 and/or 56-76 |
| mmu-mir-9-3 | SEQ ID NO: 210 | 16-38 and/or 56-76 |
| mmu-mir-10b | SEQ ID NO: 211 | 7-28 |
| mmu-mir-10a-1 | SEQ ID NO: 212 | 22-44 |
| mmu-mir-10a-2 | SEQ ID NO: 213 | 22-44 |
| mmu-mir-15b | SEQ ID NO: 214 | 4-25 |
| mmu-mir-15a | SEQ ID NO: 215 | 15-36 |
| mmu-mir-16-1 | SEQ ID NO: 216 | 16-37 |
| mmu-mir-16-2 | SEQ ID NO: 217 | 17-38 |
| mmu-mir-17 | SEQ ID NO: 218 | 14-37 and/or 51-70 |
| mmu-mir-18 | SEQ ID NO: 219 | 17-38 |
| mmu-mir-19b-2 | SEQ ID NO: 220 | 54-76 |
| mmu-mir-19a | SEQ ID NO: 221 | 49-71 |
| mmu-mir-19b-1 | SEQ ID NO: 222 | 54-76 |
| mmu-mir-20 | SEQ ID NO: 223 | 27-49 |
| mmu-mir-21 | SEQ ID NO: 224 | 18-39 |
| mmu-mir-22 | SEQ ID NO: 225 | 57-78 |
| mmu-mir-23b | SEQ ID NO: 226 | 46-68 |
| mmu-mir-23a | SEQ ID NO: 227 | 46-66 |
| mmu-mir-24-1 | SEQ ID NO: 228 | 6-28 and/or 44-65 |
| mmu-mir-24-2 | SEQ ID NO: 229 | 61-82 |
| mmu-mir-25 | SEQ ID NO: 230 | 52-73 |
| mmu-mir-26a-1 | SEQ ID NO: 231 | 16-37 |
| mmu-mir-26b | SEQ ID NO: 232 | 15-36 |
| mmu-mir-26a-2 | SEQ ID NO: 233 | 14-35 |
| mmu-mir-27b | SEQ ID NO: 234 | 49-68 |
| mmu-mir-27a | SEQ ID NO: 235 | 56-76 |
| mmu-mir-28 | SEQ ID NO: 236 | 14-35 |
| mmu-mir-29b-1 | SEQ ID NO: 237 | 47-68 |
| mmu-mir-29a | SEQ ID NO: 238 | 53-74 |
| mmu-mir-29c | SEQ ID NO: 239 | 54-75 |
| mmu-mir-29b-2 | SEQ ID NO: 240 | 52-73 |
| mmu-mir-30a | SEQ ID NO: 241 | 47-68 |
| mmu-mir-30b | SEQ ID NO: 242 | 2-22 |
| mmu-mir-30e | SEQ ID NO: 243 | 2-21 |
| mmu-mir-30c-1 | SEQ ID NO: 244 | 17-39 |
| mmu-mir-30c-2 | SEQ ID NO: 245 | 14-36 |
| mmu-mir-30d | SEQ ID NO: 246 | 12-33 |
| mmu-mir-31 | SEQ ID NO: 247 | 28-49 |
| mmu-mir-32 | SEQ ID NO: 248 | 6-26 |
| mmu-mir-33 | SEQ ID NO: 249 | 6-24 |
| mmu-mir-34c | SEQ ID NO: 250 | 13-35 |
| mmu-mir-34b | SEQ ID NO: 251 | 13-35 |

TABLE 2-continued

Mouse miRNA Sequences

| miRNA name | Precursor | Processed Sequence Relative to Precursor |
|---|---|---|
| mmu-mir-34a | SEQ ID NO: 252 | 20-42 |
| mmu-mir-92-2 | SEQ ID NO: 253 | 55-75 |
| mmu-mir-92-1 | SEQ ID NO: 254 | 50-70 |
| mmu-mir-93 | SEQ ID NO: 255 | 15-37 |
| mmu-mir-96 | SEQ ID NO: 256 | 24-46 |
| mmu-mir-98 | SEQ ID NO: 257 | 2-23 |
| mmu-mir-99a | SEQ ID NO: 258 | 6-25 |
| mmu-mir-99b | SEQ ID NO: 259 | 7-28 |
| mmu-mir-100 | SEQ ID NO: 260 | 13-34 |
| mmu-mir-101 | SEQ ID NO: 261 | 38-57 |
| mmu-mir-101b | SEQ ID NO: 262 | 61-82 |
| mmu-mir-103-1 | SEQ ID NO: 263 | 52-74 |
| mmu-mir-103-2 | SEQ ID NO: 264 | 52-74 |
| mmu-mir-106a | SEQ ID NO: 265 | 5-26 |
| mmu-mir-106b | SEQ ID NO: 266 | 12-32 |
| mmu-mir-107 | SEQ ID NO: 267 | 52-74 |
| mmu-mir-122a | SEQ ID NO: 268 | 6-28 |
| mmu-mir-124a-3 | SEQ ID NO: 269 | 43-64 |
| mmu-mir-124a-1 | SEQ ID NO: 270 | 52-73 |
| mmu-mir-124a-2 | SEQ ID NO: 271 | 61-82 |
| mmu-mir-125a | SEQ ID NO: 272 | 6-28 |
| mmu-mir-125b-2 | SEQ ID NO: 273 | 7-28 |
| mmu-mir-125b-1 | SEQ ID NO: 274 | 15-36 |
| mmu-mir-126 | SEQ ID NO: 275 | 9-29 and/or 46-66 |
| mmu-mir-127 | SEQ ID NO: 276 | 43-64 |
| mmu-mir-128a | SEQ ID NO: 277 | 44-65 |
| mmu-mir-128b | SEQ ID NO: 278 | 48-69 |
| mmu-mir-129-1 | SEQ ID NO: 279 | 6-27 |
| mmu-mir-129-2 | SEQ ID NO: 280 | 15-36 |
| mmu-mir-130a | SEQ ID NO: 281 | 42-61 |
| mmu-mir-130b | SEQ ID NO: 282 | 51-72 |
| mmu-mir-132 | SEQ ID NO: 283 | 42-63 |
| mmu-mir-133a-1 | SEQ ID NO: 284 | 44-65 |
| mmu-mir-133a-2 | SEQ ID NO: 285 | 60-81 |
| mmu-mir-133b | SEQ ID NO: 286 | 67-87 |
| mmu-mir-134 | SEQ ID NO: 287 | 7-27 |
| mmu-mir-135a-1 | SEQ ID NO: 288 | 17-39 |
| mmu-mir-135b | SEQ ID NO: 289 | 16-37 |
| mmu-mir-135a-2 | SEQ ID NO: 290 | 23-45 |
| mmu-mir-136 | SEQ ID NO: 291 | 5-27 |
| mmu-mir-137 | SEQ ID NO: 292 | 46-67 |
| mmu-mir-138-2 | SEQ ID NO: 293 | 2-18 |
| mmu-mir-138-1 | SEQ ID NO: 294 | 23-39 |
| mmu-mir-139 | SEQ ID NO: 295 | 7-24 |
| mmu-mir-140 | SEQ ID NO: 296 | 7-27 |
| mmu-mir-141 | SEQ ID NO: 297 | 49-69 |
| mmu-mir-142 | SEQ ID NO: 298 | 4-23 and/or 40-61 |
| mmu-mir-143 | SEQ ID NO: 299 | 40-61 |
| mmu-mir-144 | SEQ ID NO: 300 | 43-64 |
| mmu-mir-145 | SEQ ID NO: 301 | 7-30 |
| mmu-mir-146 | SEQ ID NO: 302 | 6-27 |
| mmu-mir-148a | SEQ ID NO: 303 | 61-82 |
| mmu-mir-149 | SEQ ID NO: 304 | 4-25 |
| mmu-mir-150 | SEQ ID NO: 305 | 6-27 |
| mmu-mir-151 | SEQ ID NO: 306 | 43-63 |
| mmu-mir-152 | SEQ ID NO: 307 | 47-67 |
| mmu-mir-153 | SEQ ID NO: 308 | 44-63 |
| mmu-mir-154 | SEQ ID NO: 309 | 6-27 |
| mmu-mir-155 | SEQ ID NO: 310 | 4-25 |
| mmu-mir-181a | SEQ ID NO: 311 | 7-29 |
| mmu-mir-181b-1 | SEQ ID NO: 312 | 12-35 |
| mmu-mir-181c | SEQ ID NO: 313 | 17-38 |
| mmu-mir-181b-2 | SEQ ID NO: 314 | 16-39 |
| mmu-mir-182 | SEQ ID NO: 315 | 7-28 |
| mmu-mir-183 | SEQ ID NO: 316 | 6-28 |
| mmu-mir-184 | SEQ ID NO: 317 | 45-66 |
| mmu-mir-185 | SEQ ID NO: 318 | 7-24 |
| mmu-mir-186 | SEQ ID NO: 319 | 7-29 |
| mmu-mir-187 | SEQ ID NO: 320 | 40-61 |
| mmu-mir-188 | SEQ ID NO: 321 | 6-27 |
| mmu-mir-190 | SEQ ID NO: 322 | 6-27 |
| mmu-mir-191 | SEQ ID NO: 323 | 7-28 |
| mmu-mir-192 | SEQ ID NO: 324 | 14-31 |
| mmu-mir-193 | SEQ ID NO: 325 | 41-61 |
| mmu-mir-194-1 | SEQ ID NO: 326 | 7-28 |
| mmu-mir-194-2 | SEQ ID NO: 327 | 16-37 |
| mmu-mir-195 | SEQ ID NO: 328 | 1-21 |
| mmu-mir-196-1 | SEQ ID NO: 329 | 24-44 |
| mmu-mir-196-2 | SEQ ID NO: 330 | 16-36 |
| mmu-mir-199a-1 | SEQ ID NO: 331 | 6-28 and/or 45-66 |
| mmu-mir-199a-2 | SEQ ID NO: 332 | 31-53 and/or 69-90 |
| mmu-mir-199b | SEQ ID NO: 333 | 26-48 |
| mmu-mir-200b | SEQ ID NO: 334 | 45-67 |
| mmu-mir-200a | SEQ ID NO: 335 | 54-75 |
| mmu-mir-200c | SEQ ID NO: 336 | 46-67 |
| mmu-mir-201 | SEQ ID NO: 337 | 6-26 |
| mmu-mir-202 | SEQ ID NO: 338 | 45-66 |
| mmu-mir-203 | SEQ ID NO: 339 | 49-69 |
| mmu-mir-204 | SEQ ID NO: 340 | 6-28 |
| mmu-mir-205 | SEQ ID NO: 341 | 7-28 |
| mmu-mir-206 | SEQ ID NO: 342 | 46-67 |
| mmu-mir-207 | SEQ ID NO: 343 | 52-74 |
| mmu-mir-208 | SEQ ID NO: 344 | 50-71 |
| mmu-mir-210 | SEQ ID NO: 345 | 66-86 |
| mmu-mir-211 | SEQ ID NO: 346 | 26-47 |
| mmu-mir-212 | SEQ ID NO: 347 | 56-76 |
| mmu-mir-213 | SEQ ID NO: 348 | 14-36 and/or 54-75 |
| mmu-mir-214 | SEQ ID NO: 349 | 71-91 |
| mmu-mir-215 | SEQ ID NO: 350 | 30-50 |
| mmu-mir-216 | SEQ ID NO: 351 | 7-27 |
| mmu-mir-217 | SEQ ID NO: 352 | 34-57 |
| mmu-mir-218-2 | SEQ ID NO: 353 | 25-45 |
| mmu-mir-219-1 | SEQ ID NO: 354 | 21-41 |
| mmu-mir-219-2 | SEQ ID NO: 355 | 19-39 |
| mmu-mir-221 | SEQ ID NO: 356 | 60-81 |
| mmu-mir-222 | SEQ ID NO: 357 | 49-71 |
| mmu-mir-223 | SEQ ID NO: 358 | 68-88 |
| mmu-mir-224 | SEQ ID NO: 359 | 8-30 |
| mu-miR-290 | SEQ ID NO: 360 | 15-37 |
| mmu-mir-291 | SEQ ID NO: 361 | 14-35 and/or 50-72 |
| mmu-mir-292 | SEQ ID NO: 362 | 12-33 and/or 51-73 |
| mmu-mir-293 | SEQ ID NO: 363 | 48-69 |
| mmu-mir-294 | SEQ ID NO: 364 | 51-72 |
| mmu-mir-295 | SEQ ID NO: 365 | 43-65 |
| mmu-mir-296 | SEQ ID NO: 366 | 13-33 |
| mmu-mir-297-1 | SEQ ID NO: 367 | 15-35 |
| mmu-mir-297-2 | SEQ ID NO: 368 | 36-56 |
| mmu-mir-298 | SEQ ID NO: 369 | 11-32 |
| mmu-mir-299 | SEQ ID NO: 370 | 7-28 |
| mmu-mir-300 | SEQ ID NO: 371 | 51-72 |
| mmu-mir-301 | SEQ ID NO: 372 | 51-73 |
| mmu-mir-302 | SEQ ID NO: 373 | 44-66 |
| mmu-mir-320 | SEQ ID NO: 374 | 48-70 |
| mmu-mir-321 | SEQ ID NO: 375 | 10-30 |
| mmu-mir-323 | SEQ ID NO: 376 | 50-71 |
| mmu-mir-324 | SEQ ID NO: 377 | 18-40 and/or 53-74 |
| mmu-mir-325 | SEQ ID NO: 378 | 16-38 |
| mmu-mir-326 | SEQ ID NO: 379 | 60-80 |
| mmu-mir-328 | SEQ ID NO: 380 | 61-82 |
| mmu-mir-329 | SEQ ID NO: 381 | 61-82 |
| mmu-mir-330 | SEQ ID NO: 382 | 61-83 |
| mmu-mir-331 | SEQ ID NO: 383 | 61-81 |
| mmu-mir-337 | SEQ ID NO: 384 | 61-83 |
| mmu-mir-338 | SEQ ID NO: 385 | 61-83 |
| mmu-mir-339 | SEQ ID NO: 386 | 16-36 |
| mmu-mir-340 | SEQ ID NO: 387 | 61-83 |
| mmu-mir-341 | SEQ ID NO: 388 | 61-81 |
| mmu-mir-342 | SEQ ID NO: 389 | 61-84 |
| mmu-mir-344 | SEQ ID NO: 390 | 61-83 |
| mmu-mir-345 | SEQ ID NO: 391 | 16-36 |
| mmu-mir-346 | SEQ ID NO: 392 | 16-38 |
| mmu-mir-350 | SEQ ID NO: 393 | 61-84 |
| mmu-mir-351 | SEQ ID NO: 583 | 16-39 |
| mmu-mir-370 | SEQ ID NO: 584 | 48-70 |
| mmu-mir-376a | SEQ ID NO: 585 | 44-64 |
| mmu-mir-376b | SEQ ID NO: 586 | 51-72 |
| mmu-mir-380 | SEQ ID NO: 587 | 40-61 |
| mmu-mir-409 | SEQ ID NO: 588 | 47-69 |

TABLE 2-continued

Mouse miRNA Sequences

| miRNA name | Precursor | Processed Sequence Relative to Precursor |
|---|---|---|
| mmu-mir-410 | SEQ ID NO: 589 | 50-71 |
| mmu-mir-411 | SEQ ID NO: 590 | 56-78 |
| mmu-mir-412 | SEQ ID NO: 591 | 50-72 |
| mmu-mir-425 | SEQ ID NO: 695 | 54-74 |
| mmu-mir-429 | SEQ ID NO: 696 | 51-72 |
| mmu-mir-448 | SEQ ID NO: 697 | 72-93 |
| mmu-mir-449 | SEQ ID NO: 698 | 16-37 |
| mmu-mir-450 | SEQ ID NO: 699 | 17-38 |

TABLE 3

Rat miRNA Sequences

| miRNA name | Precursor | Processed Sequence Relative to Precursor |
|---|---|---|
| rno-let-7d | SEQ ID NO: 394 | 14-34 and/or 68-89 |
| rno-mir-7-1 | SEQ ID NO: 395 | 19-39 and/or 61-82 |
| rno-let-7a-1 | SEQ ID NO: 396 | 13-34 |
| rno-let-7a-2 | SEQ ID NO: 397 | 17-38 |
| rno-let-7b | SEQ ID NO: 398 | 7-28 |
| rno-let-7c-1 | SEQ ID NO: 399 | 16-37 |
| rno-let-7c-2 | SEQ ID NO: 400 | 14-35 |
| rno-let-7e | SEQ ID NO: 401 | 15-35 |
| rno-let-7f-1 | SEQ ID NO: 402 | 8-29 |
| rno-let-7f-2 | SEQ ID NO: 403 | 8-29 |
| rno-let-7i | SEQ ID NO: 404 | 6-24 |
| rno-mir-7-2 | SEQ ID NO: 405 | 19-39 |
| rno-mir-7b | SEQ ID NO: 406 | 29-49 |
| rno-mir-9-1 | SEQ ID NO: 407 | 16-38 |
| rno-mir-9-3 | SEQ ID NO: 408 | 16-38 |
| rno-mir-9-2 | SEQ ID NO: 409 | 16-38 |
| rno-mir-10a | SEQ ID NO: 410 | 22-44 |
| rno-mir-10b | SEQ ID NO: 411 | 26-47 |
| rno-mir-15b | SEQ ID NO: 412 | 20-41 |
| rno-mir-16 | SEQ ID NO: 413 | 17-38 |
| rno-mir-17 | SEQ ID NO: 414 | 14-37 |
| rno-mir-18 | SEQ ID NO: 415 | 17-38 |
| rno-mir-19b-1 | SEQ ID NO: 416 | 54-76 |
| rno-mir-19b-2 | SEQ ID NO: 417 | 62-84 |
| rno-mir-19a | SEQ ID NO: 418 | 49-71 |
| rno-mir-20 | SEQ ID NO: 419 | 16-38 and/or 52-72 |
| rno-mir-21 | SEQ ID NO: 420 | 18-39 |
| rno-mir-22 | SEQ ID NO: 421 | 57-78 |
| rno-mir-23a | SEQ ID NO: 422 | 46-66 |
| rno-mir-23b | SEQ ID NO: 423 | 58-80 |
| rno-mir-24-1 | SEQ ID NO: 424 | 44-65 |
| rno-mir-24-2 | SEQ ID NO: 425 | 61-82 |
| rno-mir-25 | SEQ ID NO: 426 | 52-73 |
| rno-mir-26a | SEQ ID NO: 427 | 16-37 |
| rno-mir-26b | SEQ ID NO: 428 | 15-36 |
| rno-mir-27b | SEQ ID NO: 429 | 61-80 |
| rno-mir-27a | SEQ ID NO: 430 | 56-76 |
| rno-mir-28 | SEQ ID NO: 431 | 14-35 |
| rno-mir-29b-2 | SEQ ID NO: 432 | 52-73 |
| rno-mir-29a | SEQ ID NO: 433 | 53-74 |
| rno-mir-29b-1 | SEQ ID NO: 434 | 51-72 |
| rno-mir-29c | SEQ ID NO: 435 | 54-75 |
| rno-mir-30c-1 | SEQ ID NO: 436 | 17-39 |
| rno-mir-30e | SEQ ID NO: 437 | 2-21 |
| rno-mir-30b | SEQ ID NO: 438 | 16-36 |
| rno-mir-30d | SEQ ID NO: 439 | 12-33 |
| rno-mir-30a | SEQ ID NO: 440 | 47-68 |
| rno-mir-30c-2 | SEQ ID NO: 441 | 14-36 |
| rno-mir-31 | SEQ ID NO: 442 | 28-49 |
| rno-mir-32 | SEQ ID NO: 443 | 6-26 |
| rno-mir-33 | SEQ ID NO: 444 | 6-24 |
| rno-mir-34b | SEQ ID NO: 445 | 13-35 |
| rno-mir-34c | SEQ ID NO: 446 | 13-35 |
| rno-mir-34a | SEQ ID NO: 447 | 20-42 |
| rno-mir-92-1 | SEQ ID NO: 448 | 48-68 |

TABLE 3-continued

Rat miRNA Sequences

| miRNA name | Precursor | Processed Sequence Relative to Precursor |
|---|---|---|
| rno-mir-92-2 | SEQ ID NO: 449 | 55-75 |
| rno-mir-93 | SEQ ID NO: 450 | 15-37 |
| rno-mir-96 | SEQ ID NO: 451 | 24-46 |
| rno-mir-98 | SEQ ID NO: 452 | 2-23 |
| rno-mir-99a | SEQ ID NO: 453 | 13-34 |
| rno-mir-99b | SEQ ID NO: 454 | 7-28 |
| rno-mir-100 | SEQ ID NO: 455 | 13-34 |
| rno-mir-101b | SEQ ID NO: 456 | 61-82 |
| rno-mir-101 | SEQ ID NO: 457 | 47-68 |
| rno-mir-103-2 | SEQ ID NO: 458 | 52-74 |
| rno-mir-103-1 | SEQ ID NO: 459 | 52-74 |
| rno-mir-106b | SEQ ID NO: 460 | 12-32 |
| rno-mir-107 | SEQ ID NO: 461 | 52-74 |
| rno-mir-122a | SEQ ID NO: 462 | 15-37 |
| rno-mir-124a-3 | SEQ ID NO: 463 | 52-73 |
| rno-mir-124a-1 | SEQ ID NO: 464 | 52-73 |
| rno-mir-124a-2 | SEQ ID NO: 465 | 61-82 |
| rno-mir-125a | SEQ ID NO: 466 | 15-37 |
| rno-mir-125b-1 | SEQ ID NO: 467 | 15-36 |
| rno-mir-125b-2 | SEQ ID NO: 468 | 17-38 |
| rno-mir-126 | SEQ ID NO: 469 | 9-29 and/or 46-66 |
| rno-mir-127 | SEQ ID NO: 470 | 57-78 |
| rno-mir-128a | SEQ ID NO: 471 | 50-71 |
| rno-mir-128b | SEQ ID NO: 472 | 52-73 |
| rno-mir-129-2 | SEQ ID NO: 473 | 19-40 and/or 61-82 |
| rno-mir-129-1 | SEQ ID NO: 474 | 6-27 |
| rno-mir-130a | SEQ ID NO: 475 | 55-74 |
| rno-mir-130b | SEQ ID NO: 476 | 51-72 |
| rno-mir-132 | SEQ ID NO: 477 | 59-80 |
| rno-mir-133a | SEQ ID NO: 478 | 53-74 |
| rno-mir-134 | SEQ ID NO: 479 | 8-28 |
| rno-mir-135b | SEQ ID NO: 480 | 16-37 |
| rno-mir-135a | SEQ ID NO: 481 | 23-45 |
| rno-mir-136 | SEQ ID NO: 482 | 15-37 |
| rno-mir-137 | SEQ ID NO: 483 | 60-81 |
| rno-mir-138-2 | SEQ ID NO: 484 | 9-25 |
| rno-mir-138-1 | SEQ ID NO: 485 | 23-39 |
| rno-mir-139 | SEQ ID NO: 486 | 7-24 |
| rno-mir-140 | SEQ ID NO: 487 | 23-43 and/or 61-84 |
| rno-mir-141 | SEQ ID NO: 488 | 59-79 |
| rno-mir-142 | SEQ ID NO: 489 | 16-35 and/or 52-74 |
| rno-mir-143 | SEQ ID NO: 490 | 60-81 |
| rno-mir-144 | SEQ ID NO: 491 | 50-71 |
| rno-mir-145 | SEQ ID NO: 492 | 16-39 |
| rno-mir-146 | SEQ ID NO: 493 | 17-38 |
| rno-mir-148b | SEQ ID NO: 494 | 61-82 |
| rno-mir-150 | SEQ ID NO: 495 | 16-37 |
| rno-mir-151 | SEQ ID NO: 496 | 16-37 and/or 50-71 |
| rno-mir-152 | SEQ ID NO: 497 | 53-73 |
| rno-mir-153 | SEQ ID NO: 498 | 53-72 |
| rno-mir-154 | SEQ ID NO: 499 | 15-36 |
| rno-mir-181c | SEQ ID NO: 500 | 24-45 |
| rno-mir-181a | SEQ ID NO: 501 | 39-61 |
| rno-mir-181b-1 | SEQ ID NO: 502 | 36-59 |
| rno-mir-181b-2 | SEQ ID NO: 503 | 15-38 |
| rno-mir-183 | SEQ ID NO: 504 | 27-49 |
| rno-mir-184 | SEQ ID NO: 505 | 47-68 |
| rno-mir-185 | SEQ ID NO: 506 | 14-31 |
| rno-mir-186 | SEQ ID NO: 507 | 15-37 |
| rno-mir-187 | SEQ ID NO: 508 | 66-86 |
| rno-mir-190 | SEQ ID NO: 509 | 15-36 |
| rno-mir-191 | SEQ ID NO: 510 | 15-36 |
| rno-mir-192 | SEQ ID NO: 511 | 24-44 |
| rno-mir-193 | SEQ ID NO: 512 | 54-74 |
| rno-mir-194-1 | SEQ ID NO: 513 | 15-36 |
| rno-mir-194-2 | SEQ ID NO: 514 | 15-36 |
| rno-mir-195 | SEQ ID NO: 515 | 15-35 |
| rno-mir-196 | SEQ ID NO: 516 | 25-45 |
| rno-mir-199a | SEQ ID NO: 517 | 31-53 |
| rno-mir-200c | SEQ ID NO: 518 | 46-67 |
| rno-mir-200a | SEQ ID NO: 519 | 54-75 |
| rno-mir-200b | SEQ ID NO: 520 | 54-77 |
| rno-mir-203 | SEQ ID NO: 521 | 52-73 |
| rno-mir-204 | SEQ ID NO: 522 | 33-54 |

TABLE 3-continued

Rat miRNA Sequences

| miRNA name | Precursor | Processed Sequence Relative to Precursor |
|---|---|---|
| rno-mir-205 | SEQ ID NO: 523 | 33-54 |
| rno-mir-206 | SEQ ID NO: 524 | 51-72 |
| rno-mir-208 | SEQ ID NO: 525 | 50-71 |
| rno-mir-210 | SEQ ID NO: 526 | 66-86 |
| rno-mir-211 | SEQ ID NO: 527 | 26-47 |
| rno-mir-212 | SEQ ID NO: 528 | 72-92 |
| rno-mir-213 | SEQ ID NO: 529 | 55-76 |
| rno-mir-214 | SEQ ID NO: 530 | 71-91 |
| rno-mir-216 | SEQ ID NO: 531 | 19-39 |
| rno-mir-217 | SEQ ID NO: 532 | 32-55 |
| rno-mir-218-2 | SEQ ID NO: 533 | 25-45 |
| rno-mir-218-1 | SEQ ID NO: 534 | 25-45 |
| rno-mir-219-1 | SEQ ID NO: 535 | 21-41 |
| rno-mir-219-2 | SEQ ID NO: 536 | 19-39 |
| rno-mir-221 | SEQ ID NO: 537 | 65-87 |
| rno-mir-222 | SEQ ID NO: 538 | 62-85 |
| rno-mir-223 | SEQ ID NO: 539 | 68-88 |
| rno-mir-290 | SEQ ID NO: 540 | 14-36 |
| rno-mir-291 | SEQ ID NO: 541 | 14-35 and/or 50-72 |
| rno-mir-292 | SEQ ID NO: 542 | 12-33 and/or 51-73 |
| rno-mir-296 | SEQ ID NO: 543 | 13-33 |
| rno-mir-297 | SEQ ID NO: 544 | 26-48 |
| rno-mir-298 | SEQ ID NO: 545 | 11-32 |
| rno-mir-299 | SEQ ID NO: 546 | 7-28 |
| rno-mir-300 | SEQ ID NO: 547 | 51-72 |
| rno-mir-301 | SEQ ID NO: 548 | 61-85 |
| rno-mir-320 | SEQ ID NO: 549 | 48-70 |
| rno-mir-321 | SEQ ID NO: 550 | 10-30 |
| rno-mir-322 | SEQ ID NO: 551 | 61-80 |
| rno-mir-323 | SEQ ID NO: 552 | 50-71 |
| rno-mir-324 | SEQ ID NO: 553 | 16-38 and/or 51-72 |
| rno-mir-325 | SEQ ID NO: 554 | 16-38 |
| rno-mir-326 | SEQ ID NO: 555 | 60-80 |
| rno-mir-328 | SEQ ID NO: 556 | 48-69 |
| rno-mir-329 | SEQ ID NO: 557 | 61-82 |
| rno-mir-330 | SEQ ID NO: 558 | 60-82 |
| rno-mir-331 | SEQ ID NO: 559 | 61-81 |
| rno-mir-333 | SEQ ID NO: 560 | 16-35 |
| rno-mir-336 | SEQ ID NO: 561 | 16-36 |
| rno-mir-337 | SEQ ID NO: 562 | 60-82 |
| rno-mir-338 | SEQ ID NO: 563 | 41-63 |
| rno-mir-339 | SEQ ID NO: 564 | 16-36 |
| rno-mir-341 | SEQ ID NO: 565 | 61-81 |
| rno-mir-342 | SEQ ID NO: 566 | 61-84 |
| rno-mir-344 | SEQ ID NO: 567 | 61-83 |
| rno-mir-345 | SEQ ID NO: 568 | 16-36 |
| rno-mir-346 | SEQ ID NO: 569 | 16-38 |
| rno-mir-349 | SEQ ID NO: 570 | 61-82 |
| rno-mir-350 | SEQ ID NO: 571 | 61-84 |
| rno-mir-351 | SEQ ID NO: 572 | 16-39 |
| rno-mir-352 | SEQ ID NO: 592 | 61-81 |
| rno-mir-421 | SEQ ID NO: 593 | 10-30 |
| rno-mir-429 | SEQ ID NO: 700 | 53-74 |
| rno-mir-448 | SEQ ID NO: 701 | 72-93 |
| rno-mir-449 | SEQ ID NO: 702 | 16-37 |
| rno-mir-450 | SEQ ID NO: 703 | 17-38 |

It is understood that an miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary. miRNA probes of the invention can be or be at least 60, 65, 70, 75, 80, 85, 90, 95, or 100% complementary to their target.

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15

M to about 0.9 M NaCl at a temperature range of about 20° C. to about 50° C. Of course, it is within the skill of one in the art to further modify the low or high stringency conditions to suite a particular application.

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or Iodo), thiol or alkylthiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652, 099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446, 137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466, 786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777, 092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'deoxyguanosine nucleotides and nucleic acid analogs thereof).

5. Modified Nucleotides

Labeling methods and kits of the invention specifically contemplate the use of nucleotides that are both modified for attachment of a label and can be incorporated into an miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the invention are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and NEN. Functional groups may be prepared according to ways known to those of skill in the art, including the representative information found in U.S. Pat. Nos. 4,404,289; 4,405,711; 4,337,063 and 5,268,486, and Br. Pat. No. 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; $N^6$-(4-amino)butyl-ATP, $N^6$-(6-amino)butyl-ATP, $N^4$-[2,2-oxy-bis-(ethylamine)]-CTP; $N^6$-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; $N^6$-(4-amino)butyl-dATP, $N^6$-(6-amino)butyl-dATP, $N^4$-[2,2-oxy-bis-(ethylamine)]-dCTP; $N^6$-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

B. Preparation of Nucleic Acids

A nucleic acid may be made by any technique known to one of ordinary skill in the art, such as for example, chemical synthesis, enzymatic production or biological production. It is specifically contemplated that miRNA probes of the invention are chemically synthesized.

In some embodiments of the invention, miRNAs are recovered from a biological sample. The miRNA may be recombinant or it may be natural or endogenous to the cell (produced from the cell's genome). It is contemplated that a biological sample may be treated in a way so as to enhance the recovery of small RNA molecules such as miRNA. U.S. patent application Ser. No. 10/667,126 describes such methods and it is specifically incorporated by reference herein. Generally, methods involve lysing cells with a solution having guanidinium and a detergent, as described in Example 1.

Alternatively, nucleic acid synthesis is performed according to standard methods. See, for example, Itakura and Riggs (1980). Additionally, U.S. Pat. No. 4,704,362, U.S. Pat. No. 5,221,619, and U.S. Pat. No. 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester method. The diester method was the first to be developed to a usable state, primarily by Khorana and coworkers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester method. The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method. This is an enzymatic method of DNA synthesis that can be used to synthesize many useful oligonucleotides (Gillam et al., 1978; Gillam et al., 1979). Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods. Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant methods. Recombinant methods for producing nucleic acids in a cell are well known to those of skill in the art. These include the use of vectors (viral and non-viral), plasmids, cosmids, and other vehicles for delivering a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

C. Isolation of Nucleic Acids

Nucleic acids may be isolated using techniques well known to those of skill in the art, though in particular embodiments, methods for isolating small nucleic acid molecules and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased, such as from C.B.S. Scientific Co., Inc. or Scie-Plas.

Methods may involve the use of organic solvents and/or alcohol to isolate nucleic acids, particularly miRNA used in methods and compositions of the invention. Some embodiments are described in U.S. patent application Ser. No. 10/667,126, which is hereby incorporated by reference. Generally, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column has worked particularly well for such isolation procedures.

In specific embodiments, miRNA isolation processes include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the miRNA molecules from the solid support with an ionic solution; and, f) capturing the miRNA molecules. Typically the sample is dried down and resuspended in a liquid and volume appropriate for subsequent manipulation.

II. Labels and Labeling Techniques

In some embodiments, the present invention concerns miRNA that are labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

A. Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to an miRNA, and the unlabeled nucleotide is modified with a chemical moiety that enables it to be subsequently labeled. In embodiments of the invention, the chemical moiety is a reactive amine such that the nucleotide is an amine-modified nucleotide.

Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNA is how to label the already existing molecule. The present invention concerns the use of an enzyme capable of using a di- or tri-phosphate ribonucleotide or deoxyribonucleotide as a substrate for its addition to an miRNA, a small RNA molecule. Moreover, in specific embodiments, it involves using a modified di- or tri-phosphate ribonucleotide, which is added to the 3' end of an miRNA. The source of the enzyme is not limiting. Examples of sources for the enzymes include yeast, gram-negative bacteria such as E. coli, lactococcus lactis, and sheep pox virus.

Enzymes capable of adding such nucleotides include, but are not limited to, poly(A) polymerase, terminal transferase, and polynucleotide phosphorylase. In specific embodiments of the invention, ligase is contemplated as NOT being the enzyme used to add the label, and instead, a non-ligase enzyme is employed.

Poly(A) polymerase has been cloned from a number of organisms from plants to humans. It has been shown to catalyze the addition of homopolymer tracts to RNA (Martin et al., 1998).

Terminal transferase catalyzes the addition of nucleotides to the 3' terminus of a nucleic acid.

Polynucleotide phosphorylase can polymerize nucleotide diphosphates without the need for a primer.

B. Labels

Labels on miRNA or miRNA probes may be colorimetric (includes visible and UV spectrum, including fluorescent), luminescent, enzymatic, or positron emitting (including radioactive). The label may be detected directly or indirectly. Radioactive labels include $^{125}I$, $^{32}P$, $^{33}P$, and $^{35}S$. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

It is contemplated that nucleic acids may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

C. Visualization Techniques

A number of techniques for visualizing or detecting labeled nucleic acids are readily available. The reference by Stanley T. Crooke, 2000 has a discussion of such techniques (Chapter 6), which is incorporated by reference. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997, spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize the dsRNA. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

III. Array Preparation and Screening

A. Array Preparation

The present invention concerns the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect miRNA; consequently, methods and compositions may be used with a variety of different types of miRNA arrays.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

B. Sample Preparation

It is contemplated that the miRNA of a wide variety of samples can be analyzed using the array technology of the invention. While endogenous miRNA is contemplated for use with compositions and methods of the invention, recombinant miRNA—including nucleic acids that are complementary or identical to endogenous miRNA or precursor miRNA—can also be handled and analyzed as described herein. Samples may be biological samples, in which case, they can be from blood, tissue, organs, semen, saliva, tears, other bodily fluid, hair follicles, skin, or any sample containing or constituting biological cells. Alternatively, the sample may not be a biological sample, but be a chemical mixture, such as a cell-free reaction mixture (which may contain one or more biological enzymes).

C. Hybridization

After the array is prepared and the miRNA in the sample is labeled, the population of target nucleic acids is contacted with the array under hybridization conditions, where such conditions can be adjusted, as desired, to provide for an optimum level of specificity in view of the particular assay being performed. Suitable hybridization conditions are well known to those of skill in the art and reviewed in Sambrook et al., 1989 and WO 95/21944. Of particular interest in many embodiments is the use of stringent conditions during hybridization. Stringent conditions are known to those of skill in the art.

It is specifically contemplated that a single array may be contacted with multiple samples. The samples may be labeled with different labels to distinguish the samples. For example, a single array can be contacted with a tumor tissue sample labeled with Cy3, and normal tissue sample labeled with Cy5. Differences between the samples for particular miRNAs corresponding to probes on the array can be readily ascertained and quantified.

The small surface area of the array permits uniform hybridization conditions, such as temperature regulation and salt content. Moreover, because of the small area occupied by the high density arrays, hybridization may be carried out in extremely small fluid volumes (e.g., about 250 µl or less, including volumes of about or less than about 5, 10, 25, 50, 60, 70, 80, 90, 100 µl, or any range derivable therein). In small volumes, hybridization may proceed very rapidly.

D. Differential Expression Analyses

Arrays of the invention can be used to detect differences between two samples. Specifically contemplated applications include identifying and/or quantifying differences between miRNA from a sample that is normal and from a sample that is not normal or between two differently treated samples. Also, miRNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic.

Particularly arrays can be used to evaluate samples with respect to diseases or conditions that include, but are not limited to, the following: AIDS, autoimmune diseases (rheumatoid arthritis, multiple sclerosis, diabetes-insulin-dependent and non-independent, systemic lupus erythematosus and Graves disease); cancer (e.g., malignant, benign, metastatic, precancer); cardiovascular diseases (heart disease or coronary artery disease, stroke—ischemic and hemorrhagic, and rheumatic heart disease); diseases of the nervous system; and infection by pathogenic microorganisms (Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis); inflammation (allergy, asthma); prion diseases (e.g., CJD, kuru, GSS, FFI).

Moreover, miRNA can be evaluated with respect to the following diseases, conditions, and disorders: Abdominal Adhesions; Anal Abscess; Brain Abscess; Peritonsillar Abscess; Absence Seizures; Achalasia; Acne; Acoustic Neuroma; Acquired Immunodeficiency Syndrome (AIDS); Acrochordon; Actinic Keratosis; Adenocarcinoma of the Lung; ADHD; Adult-Onset Diabetes; Aero-Otitis; Age Spots; Age-Related Hearing Loss; Age-Related Macular Degeneration; Age-Related Vision Change (Presbyopia); Agoraphobia; Alcohol Withdrawal; Alcoholism; Allergen Immunotherapy; Allergic Rhinitis; Allergies; Alopecia (Areata, Hereditary-Patterned, and Traumatic); Altitude Sickness; Alzheimer's Disease; Amaurotic Familial Infantile Idiocy; Amblyopia; Amenorrhea; Amyloidosis; Amyotrophic Lateral Sclerosis (ALS); Anaphylaxis; Androgenetic Alopecia; Anemia (Aplastic, Hemolytic, Pernicious, and Sickle Cell); Angina; Angiomas, Spider; Angioplasty; Ankylosing Spondylitis; Anorexia Nervosa; Anovulatory Bleeding; Antibiotic-Associated Diarrhea; Antiphospholipid Antibody Syndrome; Antisocial Personality Disorder; Anus Fissure, Fistula, Hemorrhoids, Anus Itch, Stricture; Anxiety Disorders (Generalized, Obsessive-Compulsive Disorder, Panic Disorder, Phobia, and Post-Traumatic Stress Disorder); Aortic Aneurysm; Aortic Arch Syndrome; Appendicitis; Arrhythmias, Cardiac; Arteritis, Takayasu's; Arthritic Diseases (Ankylosing Spondylitis, Gout, Infectious, Juvenile, Osteoarthritis, Pseudogout, Psoriatic Arthritis, and Rheumatoid); Asbestosis; Ascending Cholangitis; Asteatotic Eczema; Asthma; Astigmatism; Asymptomatic Bacteriuria; Ataxia, Friedreich's; Atherosclerosis; Athlete's Foot; Atopic Dermatitis; Atrial Fibrillation; Atrophic Vaginitis; Attention-Deficit Hyperactivity Disorder; Autism; Autoimmune Diseases (Celiac Disease, Crohn's Disease, Diabetes Mellitus, Type I (Insulin-Dependent; Juvenile-Onset), Diabetes Mellitus, Type 2 (Non-Insulin-Dependent; Adult-Onset), Graves' Disease, Hyperthyroidism, Immune Thrombocytopenic Purpura, Lupus, Myasthenia Gravis, Polyarteritis Nodosa, Rheumatoid Arthritis, Scleroderma, Takayasu's Arteritis, and Ulcerative Colitis); B12 Deficiency; Bacillary Dysentery; Bacterial Gastroenteritis; Bacterial Vaginosis; Balanitis; Baldness, Hereditary-Patterned; Barber's Itch; Barotitis; Barotrauma; Bartholin's Gland Cyst; Basal-Cell Carcinoma; Bed-Wetting; Bedsores; Behcet's Syndrome; Bell's Palsy; Bends; Benign Prostatic Hyperplasia; Bile-Duct Diseases; Biliary Colic; Biopsy; Bipolar Disorder; Bladder conditions (Infection; Interstitial Cystitis; Prolapse; Urethritis; Urinary Incontinence; Urinary Tract Infection); Blepharitis; Blepharoptosis; Blighted Ovum; Friction Blisters; Blood Pressure, High; Boils; Bone diseases and conditions (Osteoporosis; Paget's Disease); Bone Yaws; Borderline Personality Disorder; Bornholm Disease; Botulism; Bowel Obstruction; Bradycardia; Bronchitis; Bulimia Nervosa; Bunion; Bursitis; C. Difficile Colitis; Calcaneal Apophysitis; Calcium Pyrophosphate Deposition Disease; Campylobacteriosis; Cancer; Candidiasis; Carbon-Monoxide Poisoning; Carbuncles; Cardiac Arrhythmias (Atrial Fibrillation, Bradycardia); Cardiomyopathy; Carpal Tunnel Syndrome; Cataracts; Cellulitis; Central Serous Retinopathy; Cerebral Palsy; Cerebromacular Degeneration; Cerumen Impaction; Cervicitis, Nabothian Cysts, Cervical Polyps, Cervical Warts; Chalazion; Chickenpox; Chlamydia; Chloasma; Cholangitis; Cholecystitis; Cholesteatoma; Chondromalacia; Chorea; Choroidal Melanoma; Chronic Bronchitis; Chronic Fatigue Syndrome; Chronic Hepatitis; Chronic Leukemia; Chronic Obstructive Pulmonary Disease; Chronic Otitis Media; Cirrhosis; Cluster Headache; Cogan's Syndrome; Cold, Common; Colic, Biliary; Pseudomembranous Colitis, Ulcerative Colitis, Collapsed Lung; Collarbone Fracture; Coma; Complex Regional Pain Syndrome; Congestive Heart Failure; Conjunctivitis; Constipation; Contact Dermatitis; Conversion Disorder; COPD; Cornea Abrasion, Cornea Keratitis; Corns; Coronary Artery Disease; Creutzfeldt-Jakob Disease; Crossed Eyes; Croup; Cryptorchidism; Cystic Fibrosis; Interstitial Cystitis; Cystocele; Cysts; Cytomegalovirus infection; Dacryocystitis; Dandruff; Decompression Sickness; Decubitus Ulcers; Delirium Tremens; Delusional Disorder; Dementia; Depressive Disorders (Bipolar Disorder, Dysthymia, Major Depression, Manic Depression, Postpartum Depression); Dermatitis; Dermatofibroma; Dermatomyositis; Detached Retina; Developmental Dysplasia of the Hip; Deviated Septum; Devil's Grip; Diabetes (Gestational Diabetes; Type 1 Diabetes (Insulin-Dependent; Juvenile); Type 2 Diabetes (Non-Insulin-Dependent; Adult-Onset); Hypoglycemia, Ketoacidosis, Nephropathy, Neuropathies, Retinopathy) Antibiotic-Associated Diarrhea; Diplopia; Herniated Disk; Dislocated Lens; Hip Dislocation (Developmental); Diverticulitis; Diverticulosis; Dizziness; Doerderland's Vaginitis; Double Vision; Down Syndrome; Drooping Eyelid; Dry Skin; Sun-Damaged Skin; Dry-Eye Syndrome; Duck-Foot; Dysautonomia, Familial; Dysfunctional Uterine Bleeding; Dyslexia; Dyspareunia; Dysthymia; Dysuria; Eating Disorders (Anorexia Nervosa, Bulimia Nervosa); Eclampsia; Eczema; Edema; Emphysema; Encephalitis; Encopresis; End-Stage Renal Disease; Endocarditis; Endometriosis; Endophthalmitis; Endoscopy; Enlarged Prostate; Enuresis; Epidemic Benign Dry Pleurisy; Epididymitis; Epiglottitis; Epilepsy; Epistaxis; Erectile Dysfunction; Erythema Infectiosum; Esophagitis; Esophagus Achalasia; Esophagitis; Essential Hypertension; Essential Tremor; Ewing's Sarcoma; Familial Dysautonomia; Farsightedness; Febrile Seizures; Fecal Incontinence; Fever; Fever-Induced Seizures; Fibroids; Fibromyalgia; Fifth Disease; Filiform Warts; Flat Warts; Flatulence; Flu; Focal Seizures; Food Allergy; Food Poisoning; Forefoot Neuroma; Fragile X Syndrome; Friction Blisters; Friedreich's Ataxia; Frostbite; Fungal Infections (Athlete's Foot, Brain Abscess, Infectious Arthritis, Jock Itch, Onychomycosis, Ringworm, Swimmer's Ear, Tinea Cruris, Tinea Unguium, Tinea Versicolor); Furuncle; Gallstones; Gardnerella Vaginitis; Gastritis; Gastrocnemius Strain; Gastroenteritis; Gastroesophageal Reflux Disease; Gastrointestinal Amebiasis; Generalized Anxiety Disorder; Generalized Barotrauma; Genital Herpes; Genital Warts; GERD; Germ Cell Tumors, Extragonadal; Giant Cell Arteritis; Giardiasis; Glaucoma; Glomerulonephritis; Gluten-Sensitive Enteropathy; GM2 Gangliosidosis; Gonorrhea; Gout; Grand Mal Seizures; Graves' Disease; Graves' Ophthalmopathy; Guillain-Barre Syndrome; Hammertoe; Hay Fever; Headache; Hearing Loss; Heart Attack; Heat Stroke; Heel Spur; Heloma; Spider Hemangiomas; Hematoma; Hematuria; Hemochromatosis; Hemolytic Anemia; Hemophilia; Hemorrhagic Stroke; Subarachnoid Hemorrhagic Stroke; Hemorrhoids; Hepatitis A; Hepatitis B; Hepatitis C; Hereditary-Patterned Baldness; Hernia; Herniated Disk; High Blood Pressure; High Cholesterol; Hirsutism; Histiocytosis X; HIV/AIDS; Hordeolum; Human Papilloma Virus (HPV); Huntington's Disease; Hydatidiform Mole; Hydrocephalus; Hyperactivity; Hypercholesterolemia; Hyperkeratosis; Hyperopia; Hypertension; Ocular Hypertension; Secondary Hypertension; Hypertensive Retinopathy; Hyperthermia; Hyperthyroidism; Hypochondriasis; Hypoglycemia; Hypoparathyroidism; Hypothyroidism; IBS; ICD; Ichthyosis; Immune Thrombocytopenic Purpura; Impetigo; Impotence; Incontinence; Infantile Ganglioside Lipidosis; Infectious Arthritis; Infectious Mononucleosis; Infertility; Inflammatory Bowel Disease; Inguinal Hernia; Insomnia; Intercerebral Hemorrhage; Interdigital Neuroma; Intermetatarsal Neuroma; Intermittent Claudication; Interstitial Cystitis; Intestinal Obstruction; Iron Deficiency; Irritable Bowel Syndrome; Juvenile Arthritis; Kaposi's Sarcoma; Kawasaki Syndrome; Keloids; Keratitis; Actinic Keratosis; Labyrinthitis; Lactose Intolerance; Lacunar Stroke; Langerhans' Cell Histiocytosis; Laryngitis; Laryngotracheitis; Lateral Epicondylitis; Latex Allergy; Lazy Eye; Lead Poisoning; Intermittent Claudication; Restless Legs Syndrome; Shin Splints; Leg Strain; Cataract; Dislocated Lens; Leukemia; Lice; Lichen Simplex Chronicus; Cirrhosis; Hepatitis; Liver Spots; Lockjaw; Lou Gehrig's Disease; Lupus Erythematosus, Systemic; Lyme Disease; Lymphedema; Lymphoma; Macular Degeneration; Malabsorption Syndromes; Malaria; Male Pattern Baldness; Malignant Hyperthermia; Manic Depression; Marfan's Syndrome; Mastoiditis; Measles; Meckel's Diverticulum; Melasma; Meniere's Disease; Meningitis; Menopause; Mental Retardation; Phenylketonuria; Migraine; Miscarriage; Mitral-Valve Prolapse; Mittelschmerz; Molar Pregnancy; Molluscum Contagiosum; Mononucleosis; Morton's Neuroma; Mosaic Warts; Motor Tics; Mucocutaneous Lymph Node Syndrome; Multiple Sclerosis; Mumps; Muscular Dystrophy; Musculoskeletal Disorders (Fibromyalgia, Giant Cell Arteritis, Gout, Infectious Arthritis, Muscular Dystrophy, Myositis, Osteoarthritis, Osteoporosis, Paget's Disease Of Bone, Polymyalgia Rheumatica, Pseudogout, Reflex Sympathetic Dystrophy, Rheumatoid Arthritis, Scleroderma, Systemic Lupus Erythematosus, Tendonitis); Myasthenia Gravis; Myocardial Infarction; Myocarditis; Myopia; Myositis; Nail Felon; Onycholysis; Onychomycosis; Paronychia; Subungual Hematoma; Narcolepsy; Nasal Polyps; Nausea; Nearsightedness; Needle Biopsy; Nephrectomy; Nephroblastoma; Nephrolithiasis; Nephropathy, Diabetic; Neuritis, Retrobulbar; Neuroblastoma; Neuromuscular Disorders; Neuropathies; Guillain-Barre Syndrome; Retrobulbar; Nevi; Nevus Flammeus; Nevus Simplex; Nocturnal Enuresis; Non-Tropical Sprue; Obesity; Obsessive-Compulsive Disorder; Occupational Hearing Loss; Ocular Hypertension; Ocular Rosacea; Onycholysis; Onychomycosis; Glaucoma; Retrobulbar Neuritis; Optic Nerve Swelling; Orbit Fracture; Orchitis; Osgood-Schlatter Disease; Osteoarthritis; Osteoporosis; Osteosarcoma; Otitis Externa; Otitis Media; Chronic Otitis Media; Otosclerosis; Ototoxicity; Pelvic Inflammatory Disease; Polycystic Ovary Syndrome; Painful-Bladder Syndrome; Pancreatitis; Panic Disorder; Papilledema; Paraphimosis; Parkinson's Disease; Paronychia; Partial Seizures; PCL Injuries; Pedunculated Warts; Pelvic Relaxation; Paraphimosis; Peyronie's Disease; Peptic Ulcer; Perforated Eardrum; Pericarditis; Perimenopause; Peripheral Vascular Disease; Peritonsillar Abscess; Persistent Vegetative State; Personality Disorders; Petit Mal Seizures; Peyronie's Disease; Pharyngitis; Pharynx Cancer; Phenylketonuria; Phimosis; Phobia; Photosensitivity; Pigmentation Disorders (Chloasma, Melasma, Vitiligo); Piles; Pinkeye; Pityriasis Rosea; PKU; Plague; Plantar Fascuitis; Plantar Warts; Plantaris Strain; Pleurisy; Pleurodynia; PMS; Pneumoconiosis; Pneumonectomy; Pneumonia; Pneumothorax; Lead Poisoning; Polio; Poliomyelitis; Polyarteritis Nodosa; Polychondritis; Polymyalgia Rheumatica; Polymyositis; Colonic Polyps; Nasal Polyps; Vocal Cord Polyps; Port-Wine Stain; Post-Polio Syndrome; Postinfectious Thrombocytopenia; Postpartum Depression; Preeclampsia; Pregnancy-Induced Hypertension; Premenstrual Syndrome; Pressure Sores; Primary Sclerosing Cholangitis; Prolapse; Enlarged Prostate; Acute Prostatitis; Chronic Prostatitis; Pruritus Ani; Pseudogout; Psoriasis; Psoriatic Arthritis; Ptosis; Pulseless Disease; Pyelonephritis; Quadriceps Strain; Quinsy; Rash; Raynaud's Phenomenon; Rectal Itch; Rectocele; Reflex Sympathetic Dystrophy; Renal Failure; Respiratory Disorders Respiratory Syncytial Virus; Retina Detachment; Retinitis Pigmentosa; Retinopathy; Retrobulbar Neuritis; Reye's Syndrome; Rhabdomyosarcoma; Rheumatoid Arthritis; Allergic Rhinitis; Viral Rhinitis (Common Cold); Riley-Day Syndrome; Ringworm; Rocky Mountain Spotted Fever; Rosacea; Rubeola; Mumps; Salivary Gland Disorders; Salmon Patch; Sarcoidosis; Scabies; Scarlet Fever; Scars; Schizophrenia; Schizotypal Personality Disorder; Sciatica; Scleritis; Scleroderma; Scoliosis; Sebaceous Cysts; Seborrhea; Seborrheic Keratoses; Secondary Hypertension; Seizures; Sexual Dysfunction; Sexually Transmitted Diseases; Shigellosis; Shingles; Sialadenitis; Sialadenosis; Sialolithiasis; Sickle-Cell Anemia; Siderosis; Silicosis; Sinus Cancer; Sjögren's Syndrome; Sleep Disorders; Smallpox; Social Anxiety Disorder; Solar Lentigo; Somatoform Disorders (Hypochondriasis, Somatization Disorder); Somnambulism; Spastic Colon; Spider Veins; Spina Bifida; Spinal Cord Trauma; Spontaneous Abortion; Stasis Dermatitis; Strabismus; Strep Throat; Streptococcal Toxic Shock Syndrome; Stroke; Subarachnoid Hemorrhage; Transient Ischemic Attack; Stuttering; Subungual Hematoma; Sun Allergy; Sun-Damaged Skin; Sylvest's Disease; Systemic Lupus Erythematosus; Systemic Sclerosis; Tachycardia; Takayasu's Arteritis; Tay-Sachs Disease; Tear-Duct Infection; Telogen Effluvium; Temporal Arteritis; Tendonitis; Tennis Elbow; Tension Headache; Testicular Torsion; Undescended Testicles; Tetanus; Thrombocytopenia; Thrombophlebitis; Thrombotic Stroke; Tinea; Tinnitus; Tonsillitis; Torsional Deformities; Toxemia Of Pregnancy; Toxic Shock Syndrome, Streptococcal; Toxoplasmosis; Trichomoniasis; Trigeminal Neuralgia (Tic Douloureux); Tuberculosis; Tylosis; Ulcer; Urethritis; Urinary Tract disorders and conditions; Uroliniasis; Urticaria; Uterine disorders; Uterine Prolapse; Uveitis; Vaginitis; Bacterial (Gardnerella) Vaginosis; Varicella; Varices, Esophageal; Varicose Veins; Vascular Disorders (Hypertension, Intermittent Claudication, Peripheral Vascular Disease, Polyarteritis Nodosa, Raynaud's Phenomenon, Takayasu's Arteritis, Thrombophlebitis, Vasculitis, Wegener's Granulomatosis); Vein Inflammation; Varicose Veins; Vertigo; Vestibular Schwannoma; Viral Rhinitis; Vitamin B12 Deficiency; Vitiligo; Vocal Tics; Vocal-Cord Disorders; Common Warts; Genital Warts; Plantar Warts; Water On The Brain; Wax Blockage Of Ear Canal; Esophageal Webs; Werlhof's Disease; Wrinkles; *Yersinia Pestis* Infection.

Cancers that may be evaluated by methods and compositions of the invention include cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, miRNA can be evaluated in precancers, such as metaplasia, dysplasia, and hyperplasia.

It is specifically contemplated that the invention can be used to evaluate differences between stages of disease, such as between pre-cancer and cancer, or between a primary tumor and a metastasized tumor.

Moreover, it is contemplated that samples that have differences in the activity of certain pathways may also be compared. These pathways include the following and those involving the following factors: antibody response, apoptosis, calcium/NFAT signaling, cell cycle, cell migration, cell adhesion, cell division, cytokines and cytokine receptors, drug metabolism, growth factors and growth factor receptors, inflammatory response, insulin signaling, NFκ-B signaling, angiogenesis, adipogenesis, cell adhesion, viral infection, bacterial infection, senescence, motility, glucose transport, stress response, oxidation, aging, telomere extension, telomere shortening, neural transmission, blood clotting, stem cell differentiation, G-Protein Coupled Receptor (GPCR) signaling, and p53 activation.

Cellular pathways that may be profiled also include but are not limited to the following: any adhesion or motility pathway including but not limited to those involving cyclic AMP, protein kinase A, G-protein couple receptors, adenylyl cyclase, L-selectin, E-selectin, PECAM, VCAM-1, α-actinin, paxillin, cadherins, AKT, integrin-α, integrin-β, RAF-1, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, RhoA, RAC1, myosin light chain kinase, platelet-derived growth factor receptor or ezrin; any apoptosis pathway including but not limited to those involving AKT, Fas ligand, NF$_K$B, caspase-9, PI3 kinase, caspase-3, caspase-7, ICAD, CAD, EndoG, Granzyme B, Bad, Bax, Bid, Bak, APAF-1, cytochrome C, p53, ATM, Bcl-2, PARP, Chk1, Chk2, p21, c-Jun, p73, Rad51, Mdm2, Rad50, c-Abl, BRCA-1, perform, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, $H_2O_2$, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RIP, cyclin-D1, PCNA, Bcl-XL, PIP2, PIP3, PTEN, ATM, Cdc2, protein kinase C, calcineurin, IKKα, IKKβ, IKKγ, SOS-1, c-FOS, Traf-1, Traf-2, I$_K$Bβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p16, p34, p20, PP2A, angiotensin, angiotensin-converting enzyme, protease-activated receptor-1, protease-activated receptor-4, Ras, RAF-1, PLCβ, PLCγ, COX-1, G-protein-coupled receptors, phospholipase A2, IP3, SUMO1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCC1, CD40, CD40 ligand, p38, IKKα, IKKβ, NF$_K$B, TRAF2, TRAF3, TRAF5, TRAF6, IL-4, IL-4 receptor, CDK5, AP-1 transcription factor, CD45, CD4, T cell receptors, MAP kinase, nerve growth factor, nerve growth factor receptor, c-Jun, c-Fos, Jun kinase, GRB2, SOS-1, ERK-1, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-1, BRCA-2, SKP1, the proteasome, CUL1, E2F, p107, steroid hormones, steroid hormone receptors, I$_K$Bα, I$_K$Bβ, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCC1, Sonic Hedgehog, Crml, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, IKB, NF$_K$B, RAC1, RAF1, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-1 receptor, the urea cycle, vesicular transport, or salvage pathways. It is further contemplated that nucleic acids molecules of the invention can be employed in diagnostic and therapeutic methods with respect to any of the above pathways or factors. Thus, in some embodiments of the invention, an miRNA may be differentially expressed with respect to one or more of the above pathways or factors.

Phenotypic traits also include characteristics such as longevity, morbidity, appearance (e.g., baldness, obesity), strength, speed, endurance, fertility, susceptibility or receptivity to particular drugs or therapeutic treatments (drug efficacy), and risk of drug toxicity. Samples that differ in these phenotypic traits may also be evaluated using the arrays and methods described.

In certain embodiments, miRNA profiles may be generated to evaluate and correlate those profiles with pharmacokinetics. For example, miRNA profiles may be created and evaluated for patient tumor and blood samples prior to the patient's being treated or during treatment to determine if there are miRNAs whose expression correlates with the outcome of the patient. Identification of differential miRNAs can lead to a diagnostic assay involving them that can be used to evaluate tumor and/or blood samples to determine what drug regimen the patient should be provided. In addition, it can be used to identify or select patients suitable for a particular clinical trial. If an miRNA profile is determined to be correlated with drug efficacy or drug toxicity, that may be relevant to whether that patient is an appropriate patient for receiving the drug or for a particular dosage of the drug.

In addition to the above prognostic assay, blood samples from patients with a variety of diseases can be evaluated to determine if different diseases can be identified based on blood miRNA levels. A diagnostic assay can be created based on the profiles that doctors can use to identify individuals with a disease or who are at risk to develop a disease. Alternatively, treatments can be designed based on miRNA profiling. Examples of such methods and compositions are described in the U.S. Provisional Patent Application entitled "Methods and Compositions Involving miRNA and miRNA Inhibitor Molecules" filed on May 23, 2005 in the names of David brown, Lance Ford, Angie Cheng and Rich Jarvis, which is hereby incorporated by reference in its entirety.

E. Other Assays

In addition to the use of arrays and microarrays, it is contemplated that a number of difference assays could be employed to analyze miRNAs, their activities, and their effects. Such assays include, but are not limited to, RT-PCR, in situ hybridization, hybridization protection assay (HPA) (GenProbe), branched DNA (bDNA) assay (Chiron), rolling circle amplification (RCA), single molecule hybridization detection (US Genomics), Invader assay (ThirdWave Technologies), Bridge Litigation Assay (Genaco).

III. Kits

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits of the invention may include components for making a nucleic acid array comprising miRNA, and thus, may include, for example, a solid support.

Kits are also included as part of the invention. Kits for implementing methods of the invention described herein are specifically contemplated. In some embodiments, there are kits for preparing miRNA for multi-labeling and kits for preparing miRNA probes and/or miRNA arrays. In these embodiments, kit comprise, in suitable container means, 1, 2, 3, 4, 5, 6, 7, 8, 9, 10, 11, 12 or more of the following: 1) poly(A) polymerase; 2) unmodified nucleotides (G, A, T, C, and/or U); 3) a modified nucleotide (labeled or unlabeled); 4) poly(A) polymerase buffer; and, 5) at least one microfilter; 6) label that can be attached to a nucleotide; 7) at least one miRNA probe; 8) reaction buffer; 9) an miRNA array or components for making such an array; 10) acetic acid; 11) alcohol; 12) solutions for preparing, isolating, enriching, and purifying miRNAs or miRNA probes or arrays. Other reagents include those generally used for manipulating RNA, such as formamide, loading dye, ribonuclease inhibitors, and DNase.

In specific embodiments, kits of the invention include an array containing miRNA probes, as described in the application. An array may have probes corresponding to all known miRNAs of an organism, or to a subset of such probes. The subset of probes on arrays of the invention may be or include those identified as relevant to a particular diagnostic, therapeutic, or prognostic application. For example, the array may contain one or more probes that is indicative or suggestive of 1) a disease or condition, 2) susceptibility or resistance to a particular drug or treatment; 3) susceptibility to toxicity from a drug or substance; 4) the stage of development or severity of a disease or condition (prognosis); and 5) genetic predisposition to a disease or condition.

For any kit embodiment, including an array, there can be nucleic acid molecules that contain a sequence that is identical or complementary to all or part of any of SEQ ID NOS: 1-899. In certain embodiments, a kit or array of the invention can contain one or more probes for SEQ ID NOS: 1-703 and SEQ ID NO:899 and/or include one or more probes having all or part of the sequence in any of SEQ ID NOs:704-898. Any nucleic acid discussed above may be implemented as part of a kit.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 μg or at least or at most those amounts of dried dye are provided in kits of the invention. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that facilitate isolation of the labeled miRNA. It may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: Control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors.

It is contemplated that such reagents are embodiments of kits of the invention. Such kits, however, are not limited to the particular items identified above and may include any reagent used for the manipulation or characterization of miRNA.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Unless otherwise designated, catalog numbers refer to products available by that number from Ambion, Inc.®, The RNA Company.

Example 1 miRNA Isolation and Enrichment miRNA was obtained from cell or tissue samples using a two-step process. In the first, all of the RNA in the sample is isolated away from the other contents of the sample. In the second step, the small RNAs that include miRNAs are preferentially extracted from the sample to create an RNA fraction that is significantly enriched for miRNAs.

A. Total RNA Isolation

Although there are a variety of methods that can be used to recover all of the RNA in a sample, silica binding and RNA elution were used as described below:

For tissue samples, 1 ml of Lysis/Binding Solution [4 M Guanidinium Thiocyanate, 0.5% N Lauryl Sarcosine, 25 mM NaCitrate pH 7.2, 0.1 M 2-Mercaptoethanol] per 0.1 g of tissue was added. The samples were kept cold, and the tissue was thoroughly disrupted in Lysis/Binding Solution using a motorized rotor-stator homogenizer. For cell samples, 0.6 ml of Lysis/Binding Solution was added per $10^7$ cells. The cells were lysed by vortexing for 30-60 seconds.

A $\frac{1}{10}$ volume of glacial acetic acid was added to the homogenate. For example, if the lysate volume was 300 µl, 30 µl glacial acetic acid was added. The sample was then mixed well by vortexing or inverting the tube several times before leaving it on ice for 10 min.

A volume of Acid-Phenol:Chloroform equal to the sample lysate volume was added to the sample and then vortexed for 30-60 sec to mix it. The mixture was centrifuged for 5 min at maximum speed (10,000×g) at room temp to separate the aqueous and organic phases. The aqueous (upper) phase was carefully removed without disturbing the lower phase and transferred to a fresh tube. 1.25 volumes of 100% ethanol was added to the aqueous phase (e.g., if 300 µl was recovered from the aqueous phase, 375 µl of ethanol was added). The lysate/ethanol mixture (from the previous step) was pipetted onto a glass fiber filter column. The column was then centrifuged at RCF (relative centrifugal force) 10,000×g for approximately 15 sec to pass the mixture through the filter. After discarding the flow-through, the process was repeated until all of the lysate/ethanol mixture passed through the filter.

700 µl of miRNA Wash Solution 1 [1.6 M Guanidinium Thiocyanate, 30% EtOH] was applied to the filter column, which was subsequently centrifuged for ~5-10 sec or placed under a vacuum to pull the solution through the filter. The flow-through was discarded. 500 µl of Wash Solution ⅔ [100 mM NaCl, 4.5 mM EDTA, 10 mM Tris pH 7.5] was applied to the filter column and drawn through it as in the previous step. The wash was repeated with a second 500 µl aliquot of Wash Solution ⅔. After discarding the flow-through from the last wash, the assembly was spun for 1 min to remove residual fluid from the filter. 100 µl of room temp nuclease-free water was added to the center of the filter, and the cap was closed. It was spun for approximately 20-30 seconds at maximum speed to recover the RNA.

B. miRNA Enrichment

The miRNA labeling process is most effective with samples that lack most of the larger mRNAs and rRNAs that are in a total RNA sample. To remove these RNAs from the samples, one of the following was employed: an enrichment process to remove the vast majority of the RNA in a sample that is greater than 70 nucleotides or a gel purification process to obtain a population of RNAs that were 15-30 nucleotides in length.

1. Removal of Other RNAs

To the isolated total RNA, 300 µl of Lysis/Binding Solution was added. 100 µl of 100% ethanol was then added. It was mixed thoroughly by vortexing or inverting the tube several times.

The lysate/ethanol mixture was pipetted onto a glass fiber filter column and centrifuged for ~15 sec at RCF 10,000×g (typically 10,000 rpm). The filtrate was collected and A ⅔ volume of 100% ethanol was added to the filtrate (i.e., flow-through) and it was mixed thoroughly.

The filtrate/ethanol mixture (from the previous step) was pipetted onto a new glass fiber filter column. The column was centrifuged at RCF (relative centrifugal force) 10,000×g for approximately 15 sec to pass the mixture through the filter. 700 µl of miRNA Wash Solution 1 [1.6 M Guanidinium Thiocyanate, 30% EtOH] was applied to the filter column, which was subsequently centrifuged for ~5-10 sec or placed under a vacuum to pull the solution through the filter. The flow-through was discarded. 500 µl of Wash Solution 2/3 [100 mM NaCl, 4.5 mM EDTA, 10 mM Tris pH 7.5] was applied to the filter column and drawn through it as in the previous step. The wash was repeated with a second 500 µl aliquot of Wash Solution 2/3. After discarding the flow-through from the last wash, the assembly was spun for 1 min to remove residual fluid from the filter. 100 µl of room temp nuclease-free water was added to the center of the filter, and the cap was closed. It was spun for approximately 20-30 seconds at maximum speed to recover the miRNA. The miRNA was lyophilized and stored until labeled for analysis.

2. Gel Purification

Isolating the miRNAs in a sample away from contaminating mRNAs, tRNAs, and rRNAs can be done using gel electrophoresis. Two methods for gel electrophoresis were used. The first features standard gel conditions and excision of the miRNA fraction of the gel following electrophoresis. The second features a method called tube electrophoresis wherein gel-filled tubes are used to fractionate RNA samples and facilitate recovery of the miRNA fraction.

a. Standard Gel Purification

An equal volume of Gel Loading Buffer (95% formamide, 18 mM EDTA, 0.01% xylene cyanol and 0.01% bromophenol blue) was added to as much as 150 µg of total RNA. The mixture was then heated for 5 minutes at 95° C. in a water bath and applied to a 15% denaturing polyacrylamide gel to fractionate the RNA.

After the gel was run, the gel slice corresponding to 19-30 nt (from under xylene cyanol to between bromophenol blue and xylene cyanol) was excised. The miRNA was extracted by incubating the gel slice in 10 volumes of Gel Elution Buffer (0.5 mM NaCl, 10 mM EDTA) at 4° C. overnight. This was then centrifuged at 2500 rpm (1000×G) and the Gel Elution Buffer was removed and placed into a new tube. Two volumes of Gel Elution Buffer was added to the gel and incubated for 60 min at room temperature. Again, this was centrifuged and the Gel Elution Buffer samples were pooled.

The recovered and pooled buffer samples were mixed with enough 100% ethanol to create a 60% final ethanol concentration. The sample/ethanol was loaded onto glass fiber filter column and a vacuum was applied. Two volumes of miRNA Binding/Washing Buffer (0.5 mM NaCl, 55% ethanol) was applied to the column. The column was then placed in a sample collection tube. The column was washed with 0.6 ml of miRNA Binding/Washing Buffer. The column was then centrifuged at 10,000×G for at least 1 minute. The filtrate was removed and the column was centrifuged again at 10,000×G for 1 minute. 50 µl of hot (95° C.) nuclease-free water was added to the column and centrifuged at 10,000×G for 30 seconds. The previous two steps were repeated with a second 50 µl wash. The miRNA was lyophilized and stored until labeling.

b. Gel Purification by Tube Electrophoresis

Tube electrophoresis is a method whereby nylon tubing is filled with a polyacrylamide gel matrix and the gel tube is placed in a special electrophoresis device. The total RNA sample is added to the top of the tube and an electric current is applied to fractionate the RNA based on size. The miRNA fraction is captured when it flows from the end of the tube into the electrophoresis buffer. The miRNA is then recovered from the buffer. This process is described in greater detail below.

The gel cartridge was prepared by cutting nylon 6 tubing into lengths of approximately 10-15 inches. Gentle pressure was applied during the cutting to avoid crushing and/or cracking it. The tubing was placed on a glass plate and heated in an oven for 6-12 minutes at 180° C. After the tubing was removed from the oven, each end of the tubing was held to straighten the length until the plastic cooled.

A 16% Denaturing Acrylamide solution was prepared by mixing 4 mL 20% acrylamide/7M Urea/1×TBE with 1 mL 7M Urea/1×TBE. Added to this was 50 µL of 10% APS+5 µL TEMED. After mixing the solution, the gel mix was drawn up into the tubing using a Drummond pipettor. The gel was allowed to polymerize for 30 minutes.

The tubing was then cut to fit in a 50 mL conical. The tubing was soaked overnight in 1×TBE solution (10×TBE Cat #9866). Upon use, 1.2 cm tube lengths were cut using gentle pressure. The cartridge was loaded into the tube electrophoresis apparatus using the lower buffer chamber platform. The gel cartridge was placed on its end and the upper plate cartridge receptacle hole was aligned. With firm and even pressure, the tube cartridge was slid into place. 200 µL 1×TBE was added to the bottom cartridge so that it surrounded the bottom of the gel cartridge, and the top platform was put in place. 125 µL 1×TBE was put into the upper buffer chamber, which was checked for leaks before the sample was added.

The sample was prepared by adding an equal volume of deionized formamide (Cat#9342) to total RNA (total volume≦50 µL). 2 µL of filtered serva blue R dye (5 mg/mL) was added to the sample, which was then heated at 95° C. for 2 minutes. The sample was then applied to the upper buffer chamber just above the gel surface. The gel was run at 70V for 7-10 minutes. The miRNA fraction (≦40 bp) was allowed to migrate off the gel into the lower buffer chamber. The gel was stopped when the serva blue dye, which designates a 40 nucleotide species, reached the bottom of the gel. The 200 µL buffer was collected from the lower chamber and placed in an eppendorf tube.

15 µL 0.5 mg/mL linear acrylamide (5 mg/mL Cat# 7118), 60 µL 5 M NaCl, and 400 µL absolute EtOH were added to the sample. A glass filter fiber column (Cat#10066G) was prepared by prewetting with Wash Solution #1 (0.5 M NaCl; 55% EtOH). The sample was added to the column. The column was spun for 1 min at 5000 rpm. 500 µL of wash solution #2 (80% EtOH) was added to the column, which was spun again for 1 min at 5000 rpm. The column was spun again for 1 min at 10000 rpm to get rid of any excess EtOH. 15 µL of $H_2O$, heated at 95° C., was applied to the column, which was allowed to sit at room temperature (RT) for 2 min. The column was then spun for 1 min at 10000 rpm. Another 15 µL of heated elution solution was added. After sitting at RT for 2 min, the column was spun for 1 min at 10000 rpm. The sample was lyophilized and stored until labeling.

Example 2

Labeling miRNAs: Factors Affecting Reaction

A. Appending Various Nucleotides to the 3' Ends of miRNAs with *E. coli* Poly(A) Polymerase PolyA tails of several hundred nucleotides were efficiently added to the 3' ends of miRNAs using ATP and *E. coli* Poly(A) Polymerase. Other nucleotides could also serve as substrates for the enzyme, most notably UTP. Modified nucleotides like 5-(3-aminoallyl)-UTP, adenosine'5'-(1-thiotriphosphate), uridine'5'-(1-thiotriphosphate), 8-[(4-amino)butyl]-amino-ATP, and 8-[(6-amino)butyl]-amino-ATP were substrates for *E. coli* Poly(A) Polymerase, but the lengths of the 3' tails were significantly shorter than those generated with ATP and UTP. When only modified nucleotides were in the Poly(A) Polymerase reaction, the tails were typically 3-10 nucleotides long.

Various mixtures of standard and modified NTP (ATP or UTP) were tested for their capacity to be incorporated by polyA polymerase. The length of the tail could be extended tremendously adding as little as 10 µM standard NTP to the reaction. The labeling efficiency of miRNAs samples tailed with fluorescent NTP only was compared to the labeling efficiency of ones with fluorescent NTP to various ratios of standard NTP. The optimal modified NTP:standard NTP ratio was 5:1 under these conditions.

B. Radio-Labeling and Fluorescently Labeling miRNAs miRNAs were labeled in a variety of ways. For radiolabeling, $\alpha$-$^{32}$P-ATP or $\alpha$-$^{32}$P-UTP at 0.5-5 µM was used in a Poly(A) Polymerase reaction. Several hundred nucleotides can be appended to each miRNA, providing substantial radioactive signal for each miRNA. For fluorescent labeling, either a dye-labeled nucleotide (in addition to a carrier standard nucleotide) is incorporated or a nucleotide with a reactive group to which can be appended a dye molecule following the tailing reaction is incorporated. The latter method generated longer tails with greater fluorescence. The use of aminoallyl UTP at a final concentration of 500 µM and UTP at a final concentration of 100 µM were conditions that provided favorable results. This combination typically yielded tails of 10-50 nucleotides and presumably as many as 20 dye molecules per miRNA.

C. Poly(A) Polymerase Reaction Optimization

The Poly(A) Polymerase reaction conditions described in the literature were not very efficient when using the ng and sub-nanogram amounts of miRNA that were isolated from samples of total RNA. The addition of volume exclusion reagents like polyethylene glycol (PEG) significantly improved the labeling reaction. 10% PEG provides as much as ten times more labeled material in samples with 0.1 ng of miRNA.

D. pH Optimization

Optimization of the pH of the miRNA poly-A tailing reactions revealed that pH 6-7 provides much better tailing efficiency than the pH 7.9 that is recommended in the literature (Sillero et al., 2001). miRNAs tailed with poly(A) polymerase at pH 6.5 provided as much as ten times more signal than the pH 7.9 that is described in the literature. Our final reaction buffer for miRNA labeling was: 10% Polyethylene glycol (MW 3,350), 10 mM MgCl$_2$, 250 mM NaCl, 50 mM MES pH 6.5, and 1 mM DTT.

Example 3

Labeling miRNAs: Two-Step Fluorescent miRNA Labeling

1. PolyA Polymerase Reaction

Isolated miRNA was resuspended in 4.0 µL H2O. The following were added to the miRNA sample: 10 µL 2× Poly (A) Polymerase (PAP) Buffer (20% Polyethylene glycol (MW 3,350), 20 mM MgCl2, 500 mM NaCl, 100 mM MES pH 6.5, 2 mM DTT); 2.0 µL 25 mM MnCl2; 2.0 µL NTP mix (1 mM UTP, 5 mM aminoallyl-UTP); 2.0 µL PAP (2 U/µL) (Cat# 2030G). The reaction mixture was incubated at 37° C. for 2 hours.

To begin the process of obtaining the tailed miRNA from the mixture, 10 µg of sheared yeast RNA and 80 µL of miRNA binding buffer (0.6 M NaCl, 70% EtOH) were added to the reaction mix and incubated at RT for 5 minutes. The mix was subsequently applied to a glass fiber filter column, which was then spun at 5000 rpm for 1 min. 300 µL of miRNA Wash Buffer (0.5 M NaCl, 55% EtOH) was added, and the column spun again at 5000 rpm for 1 min. The Wash/spin step was repeated before the column was spun again at 10000 rpm for 1 min. 25 µL of ddH2O heated at 95° C. was added to the column, which was then incubated at 65° C. for 5 min. The column was spun at 10000 rpm for 1 minute and the eluted fraction was dried down and resuspended, typically in 4 or 7 µL.

2. Labeling Reaction

Amine-modified miRNA was reacted with amine-modified labeled moieties like NHS-ester Cy3, Cy5, AlexaFluor 555, AlexaFluor 647, and biotin. This was accomplished by the following procedure.

Amine-modified dye was resuspended in 8 µL dimethyl sulfoxide (DMSO). Two samples were labeled per dye tube. The labeling reaction was set up by mixing 7 µL of RNA with 9 µL 0.2 M Sodium Bicarbonate pH 9.0 and 4 µL of the amine-reactive dye in DMSO. This reaction was incubated in the dark at RT for 1 hr. 4.5 µL of 4M Hydroxylamine was added, and the mixture was incubated in the dark at RT for 15 min.

To isolate the labeled miRNA, 80 µL of miRNA binding buffer was added to the mixture. This was incubated at RT for 5 min. This was then applied to a glass fiber filter column, which was spun at 5000 rpm for 1 min. 300 µL of miRNA Wash Buffer (0.5 M NaCl, 55% EtOH) was applied to the microfilter, which was spun at 5000 rpm for 1 min. The wash/spin step was repeated before spinning it again at 10,000 rpm for 1 min. 25 µL of 95° C. ddH$_2$O was incubated with the microfilter at 65° C. for 5 min. It was then spun at 10,000 rpm for 1 min.

Example 4

Labeling miRNAs: One-Step Fluorescent miRNA Labeling

The miRNA was resuspended in 4.0 µL H$_2$O. The reaction contained 10 µL 2×PAP Buffer (20% Polyethylene glycol (MW 3,350), 20 mM MgCl$_2$, 500 mM NaCl, 100 mM MES pH 6.5, 2 mM DTT); 2.0 µL 25 mM MnCl$_2$; 2.0 µL NTP mix (1 mM UTP, 5 mM Cy3 UTP); and, 2.0 µL PAP (2 U/mL) (Cat#2030G). The reaction mixture was incubated at 37° C. for 2 hrs. Then 10 µg sheared yeast RNA (Cat #7118) and 80 µL miRNA binding buffer were added, and the mixture was incubated at RT for 5 min. The mixture was applied to a microfilter (silica filter column), which was then spun at 5000 rpm for 1 min. 300 µL of miRNA Wash Buffer (0.5 M NaCl, 55% EtOH) was applied to the microfilter, which was spun at 5000 rpm for 1 min. The wash/spin step was repeated before spinning it again at 10,000 rpm for 1 min. 25 µL of 95° C. ddH$_2$O was incubated with the microfilter at 65° C. for 5 min. It was then spun at 10,000 rpm for 1 min. The eluted fraction was dried down and resuspended.

Example 5

Labeling miRNAs: One-Step miRNA Radiolabeling

The miRNA was resuspended in 4.0 µL H$_2$O. The reaction contained 10 µL 2×PAP Buffer (20% Polyethylene glycol (MW 3,350), 20 mM MgCl$_2$, 500 mM NaCl, 100 mM MES pH 6.5, 2 mM DTT); 2.0 µL 25 mM MnCl$_2$; 2.0 µL α-[$^{32}$P]-ATP mix; and, 2.0 µL PAP (2 U/µL) (Cat#2030G). The reaction mixture was incubated at 37° C. for 2 hrs. Then 10 µg sheared yeast RNA (Cat #7118) and 80 µL miRNA binding buffer were added, and the mixture was incubated at RT for 5 min. The mixture was applied to a microfilter (silica filter column), which was then spun at 5000 rpm for 1 min. 300 µL of miRNA Wash Buffer (0.5 M NaCl, 55% EtOH) was applied to the microfilter, which was spun at 5000 rpm for 1 min. The wash/spin step was repeated before spinning it again at 10,000 rpm for 1 min. 25 µL of 95° C. ddH$_2$O was incubated with the microfilter at 65° C. for 5 min. It was then spun at 10,000 rpm for 1 min. The eluted fraction was dried down and resuspended in 7 µL.

Example 6 miRNAs Probe Optimization

Various probe designs were tested in order to get the best level of detection from the labeled miRNAs. Amine modification, position of amine modification, and the benefits of extraneous nucleotides were factors that were examined. Based on hybridization with both chemically synthesized and endogenous miRNAs, it was determined that a linker having 21 nts resulted in the best signal, however, it was also concluded that the linker length can be decreased to 15 nts, if necessary, while still getting a comparable signal. The amine group required for slide attachment located at the 3' end, rather than the 5' end, gave better results, and the addition of 4 bps on each side of the miRNA probe sequence, which are complementary to the miRNA precursor, increased the signal in some miRNAs.

Figure 3:
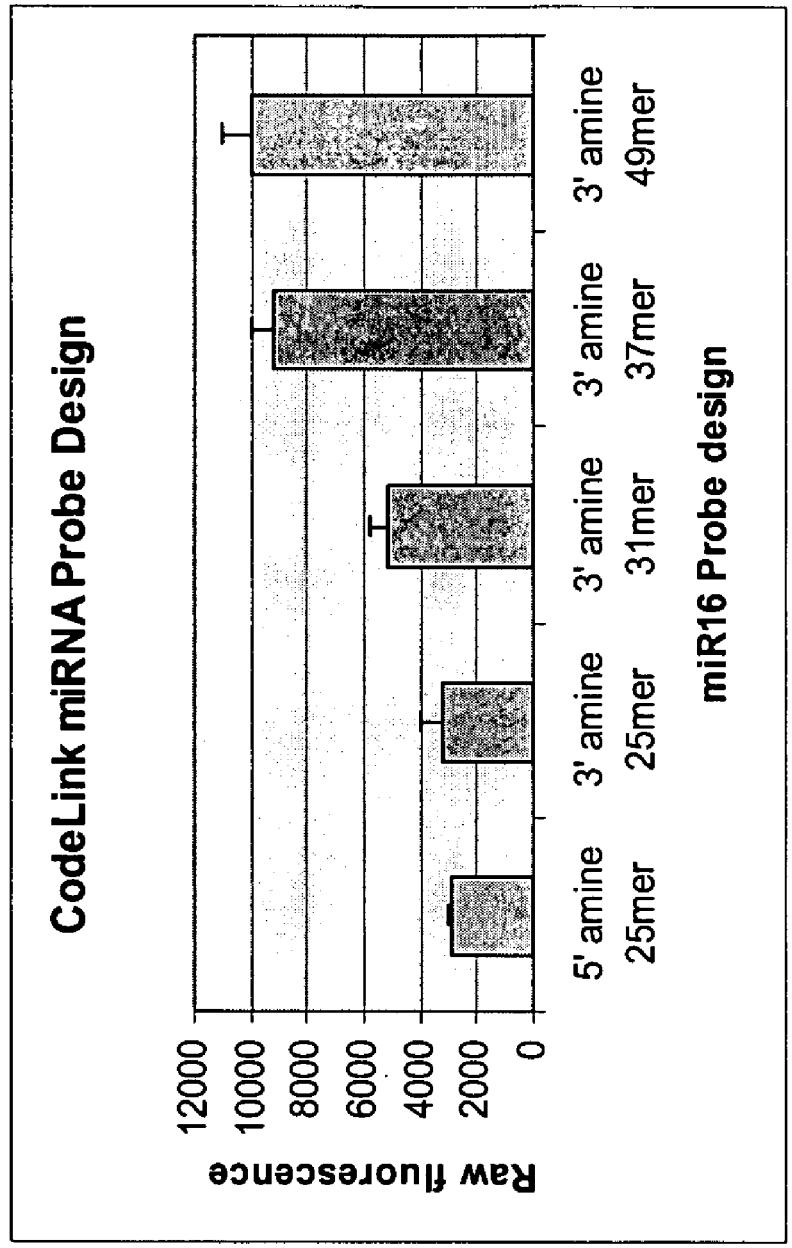
FIG. 3. Impact of probe length on miRNArray performance. DNA probes with a domains complementary to several different miRNAs were prepared and arrayed. Each probe had a unique linker length between the terminal attachment group and the sequence complementary to the miRNA. The miRNA from a total RNA was labeled and hybridized to the arrays and the signal from the various probes was quantified and plotted. The graph is representative of the data in that longer linkers with a 3' attachment provided greater signal intensity.

MicroRNA probes with 3' and 5' amines and linker lengths of 3-21 nucleotides between the terminal amine and the microRNA probe sequence were prepared. The probes were spotted on glass slides to create microarrays. miRNAs that had been 3' end labeled using the procedure described above were hybridized to the microarrays. In general, the probes with longer linker lengths provided greater signal. The miRNA probes with 3' amines performed much better than the equivalent probes with 5' amines (FIG. 3).

The sequence of the linker between the terminal amine and the miRNA probe sequence was varied without impacting the hybridization signal. Five repeats of the sequence ACC were used at the 3' end of the miRNA probes.

The performance of probes that had only the 19-24 nt predicted to be in the final mature miRNAs was compared to the performance of probes that included 4 nucleotides of flanking region from both sides of the miRNA coding region. The theory was that miRNA processing is not always precise and thus some miRNAs might include sequence from either side of the predicted mature sequence.

Example 7 miRNArray Protocol

A. Array Preparation miRNA probes were prepared and spotted using a SpotBot (TeleChem) according to the manufacturer's recommendations. The arrays were then processed using the method described below.

Up to five slides were placed in a 50 ml slide washer. 40 mls of slide wash buffer (150 mM NaCl; 100 mM Tris pH 7.5; 0.1% Tween 20) were added, and the buffer and slides were mixed by inversion for 60 seconds. The first wash buffer was discarded. Another 40 mls of fresh slide buffer were added and inverted with the slides for 60 seconds before they were allowed to set without agitation for 5 minutes. The buffer was poured off and the slides were rinsed with de-ionized water. The water was poured off and another 40 mls of de-ionized water were added and mixed vigorously with the slides by inversion for 60 seconds. The wash process was repeated. The arrays were removed one at a time. They were then dried in either a microfuge or 50 ml conical. If they were dried by picofuge, up to 4 slides were included and the picofuge was spun for 10 seconds.

B. Hybridization

Hybridization Solution (3×SSC) was heated at 65° C. for 10 minutes and mixed thoroughly several times throughout the incubation. 35 µl of pre-warmed were added to the labeled miRNA and vortexed. The mixture was heated to 95° C. for 3 minutes in a heat temperature block. While the miRNA/Hybridization Solution mixture was being heated, 35 µl of Hybridization Solution was added to the top and bottom humidity reservoirs of the hybridization chamber and an additional 150 µl spread throughout the central span of the chamber. The array was placed in the chamber and precautions were taken to ensure the slide did not come into contact with the sides of the chamber. A coverslip was placed over the sub-arrays outlined by the etched regions. The 35 µl of heated miRNA mixture was added to the array and it was allowed to travel by capillary action to the other side of the coverslip. The hybridization chamber was sealed and the array incubated at 42° C. for 4-16 hours, but no longer than 16 hours.

C. Washing

The slides were removed from the hybridization chamber and submerged in 2×SSC/0.1 SDS to remove the coverslip. Once the cover slip was removed, the slides were moved up and down 10 times and immediately placed in 2×SSC buffer. They were washed for 2 minutes with gentle stirring (150-200 rpm) in a wash chamber. The slides were transferred to a new slide holder in a new container containing fresh 2×SSC and washed for 1 min with up and down motion. The holder was transferred to a new container with fresh buffer and washed for 1 additional minute. The slides were then dried using a centrifuge or picofuge.

Example 8 miRNArray Reproducibility

For any method that is used to compare the abundance of biomolecules like RNA in one sample to the biomolecules in another sample, it is critical that the process be highly reproducible. The reproducibility of the miRNArray system was tested by repeatedly comparing the miRNA profiles of human prostate and colon samples.

Total RNA from a single human prostate sample was isolated using the glass fiber filter method described above. The total RNA was fractionated by tube electrophoresis to recover the miRNAs. The miRNAs were fluorescently labeled with Cy3 using the two-step fluorescent labeling process described above. Total RNA from a single human colon sample was isolated using the glass fiber filter method described above. The total RNA was split into six independent samples and each sample was fractionated by tube electrophoresis to recover the miRNAs. The six miRNA samples were fluorescently labeled with Cy5 using the two-step fluorescent labeling process described above.

Figure 4:
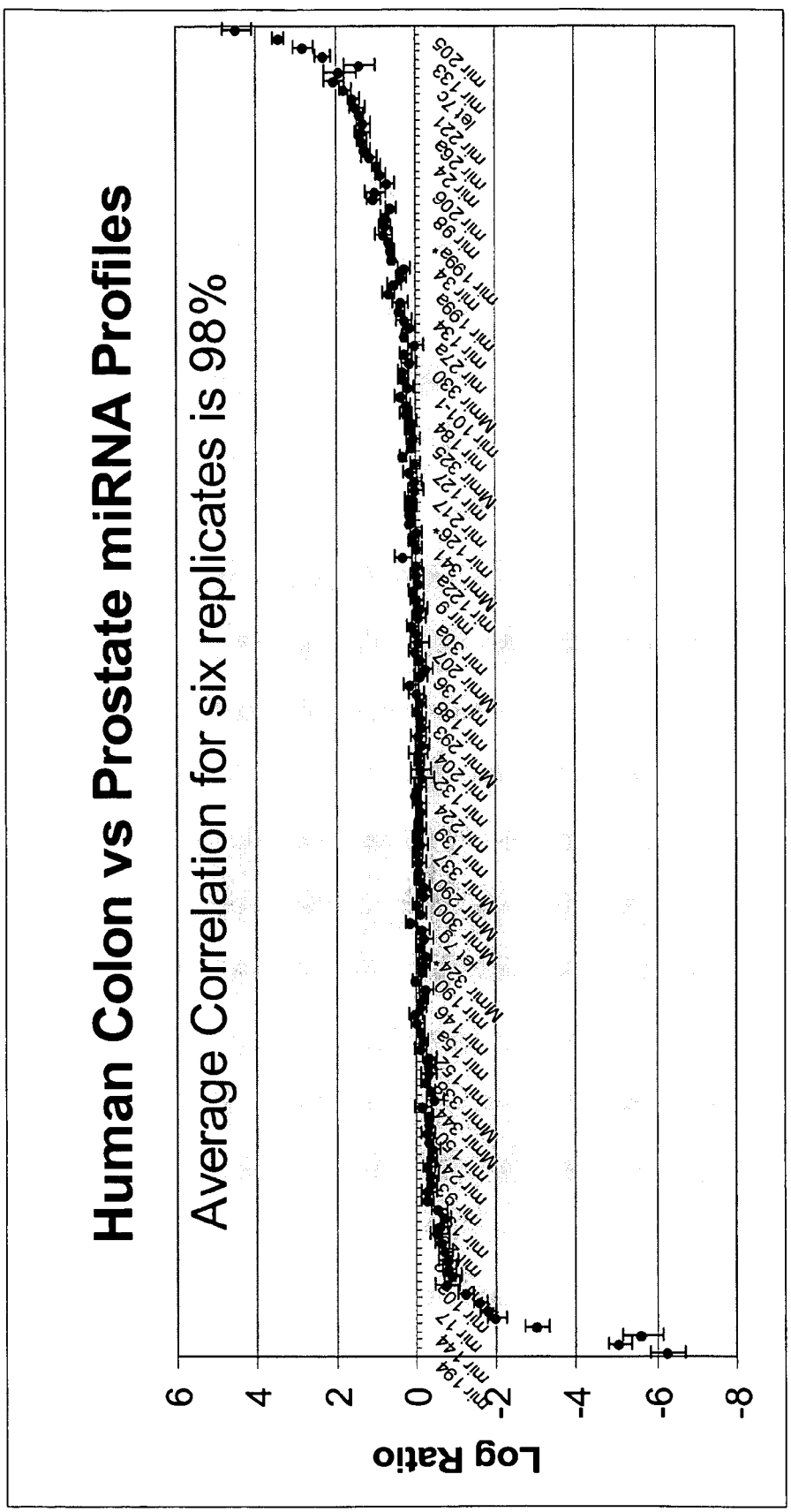
FIG. 4. miRNArray reproducibility. A human colon total RNA sample was split six ways and each aliquot was processed and labeled using the miRNArray system. The labeled samples were compared to a similarly prepared human prostate sample. The average differential expression between the colon and prostate samples for each of the six replicates was determined. The average differential expression for each miRNA is plotted with error bars. The average correlation for six replicates was 98% showing the highly reproducible nature of the miRNArray system.

The Cy3-labeled prostate miRNAs were split into six equal samples and each was mixed with one of the Cy5-labeled colon samples. The six independently labeled miRNA mixtures were hybridized to the miRNA probes arrayed on six different glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the prostate and colon samples. Signal ratios at each element are expressed as a log ratio and shown in FIG. 4. The average correlation between the six independent reactions was 98%, indicating that the miRNArray process is highly reproducible.

Example 9 miRNA Expression Normal Human Tissues

Molecular methods that distinguish the tissue origin of unknown samples are needed. An example is where a metastatic tumor has been found and its origin is unknown. Identifying the originating tissue allows a physician to identify other affected organs as well as create a therapeutic regimen with a higher likelihood of success.

Total RNA from 24 human tissues was isolated using the glass fiber filter method described above. Each of the total RNAs were fractionated by tube electrophoresis to recover the miRNAs from each sample. One half of each sample was placed in a single tube to create a miRNA pool comprising the miRNAs from all 24 samples. The miRNAs from the pooled sample as well as each of the 24 single-tissue samples were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signal from each single-tissue sample was compared to the signal from the pooled sample. The relative signal intensities of the single and pooled samples were compared for each miRNA. Shown in the table below is the list of miRNAs that were exclusively or primarily expressed in one or a few related tissues. The expression of these miRNAs could be used to determine the origin of a human tissues sample. Similarly, age, sex, race, etc might also be determined using miRNA profiling.

TABLE 4 miRNAs expressed exclusively/preferentially in specific human organs.

| miRNA | Tissue where Over-Expressed |
|---|---|
| miR-124 | Brain |
| miR-9 | Brain |
| miR-138 | Brain |
| miR-7 | Brain, Adrenal Gland |
| miR-128 | Brain, Sk. Muscle |
| miR-206 | Sk. Muscle |
| miR-1-2 | Heart, Sk. Muscle |
| miR-133 | Heart, Sk. Muscle |
| miR-134 | Heart, Sk. Muscle |
| miR-122 | Liver |
| miR152 | Colon, Liver |
| miR-215 | Colon, Sm. Intestine, Ileum |
| mu-miR-341 | Ileum, Sm. Intestine, Prox. Colon |
| miR-321 | Colon, Sm. Intestine, Prostate |
| miR-143 | Prostate, Colon |
| miR-145 | Prostate, Colon |
| miR-17 | Colon, Stomach |
| miR-24* | Stomach |
| miR-191 | Placenta |
| miR-224 | Placenta |
| miR-137 | Placenta, Brain |
| miR-98 | Cervix, Uterus, Brain |
| miR-130 | Cervix, Uterus |
| miR-99 | Cervix, Uterus |
| miR-195 | Cervix, Uterus |
| miR-26a | Cervix, Uterus |
| miR-320 | Cervix, Uterus |
| miR-28 | Cervix, Uterus |
| miR-142 | Lymph Node |
| miR-34 | Lymph Node |
| miR-216 | Pancreas |
| miR-217 | Pancreas |
| miR-30a | Kidney, Placenta |

*indicates that a strand complementary to this miRNA has also been detected in cells.

Example 10

Confirmation of Array Results—Normal Samples

The ultimate test of array results is confirming microarray expression profiles with a second method of RNA quantification. A ribonuclease protection assay was used to compare the expression of three different miRNAs in 9 human tissue samples to the miRNArray data generated in the previous example.

Total RNA from human samples of adrenal gland, colon, kidney, liver, lung, skeletal muscle, pancreas, prostate, spleen, and thymus was isolated using the glass fiber filter method described above. Each of the total RNAs were analyzed using the procedure below to measure the expression of let-7, miR-16, and miR-200b.

Radiolabeled RNAs with sequences complementary to let-7, miR-16, and miR-200b were produced according to the miRNA Probe Labeling kit (Ambion). 104 cpm of each probe was mixed in separate tubes with 1 ug of each of the nine human tissue sample RNAs listed above. 5 μg of yeast RNA (Ambion) and hybridization buffer (40% formamide, 50 mM Na Citrate pH 6.4, 150 mM Na Acetate pH 6.4, 1 mM EDTA, 2.5% PEG 8000) were added to each sample. The samples were heated to 95° C. for three minutes and then incubated overnight at 42° C. To each sample, 150 μl of RNAse Digestion solution (300 mM Na Acetate pH 7.5, 10 mM HEPEs pH 7.5, 5 mM EDTA, 20 ug/ml Salmon Sperm DNA, 150 ug/ml Glyco Blue, 2.5 U/ml RNase A, and 100 U/ml RNase T1) was added. The resulting mixtures were incubated for 30 minutes at 37° C. 220 μl of RNAse Inactivation/Precipitation buffer (1 M Guanidinium Thiocyanate, 0.167% N-Lauryl Sarcosine, 10 mM DTT, 83% Isopropanol) was added to each sample. The samples were incubated at −20° C. for fifteen minutes. The sample tubes were centrifuged at 12,000 RPM for fifteen minutes. The pellets were washed with 70% ethanol, dried, and dissolved in gel loading buffer (95% formamide, 18 mM EDTA pH 8.0, 0.025% bromophenol blue, 0.025% xylene cyanol). The samples were heated to 95° C. and fractionated using a 15% denaturing polyacrylamide gel.

Figure 5A:
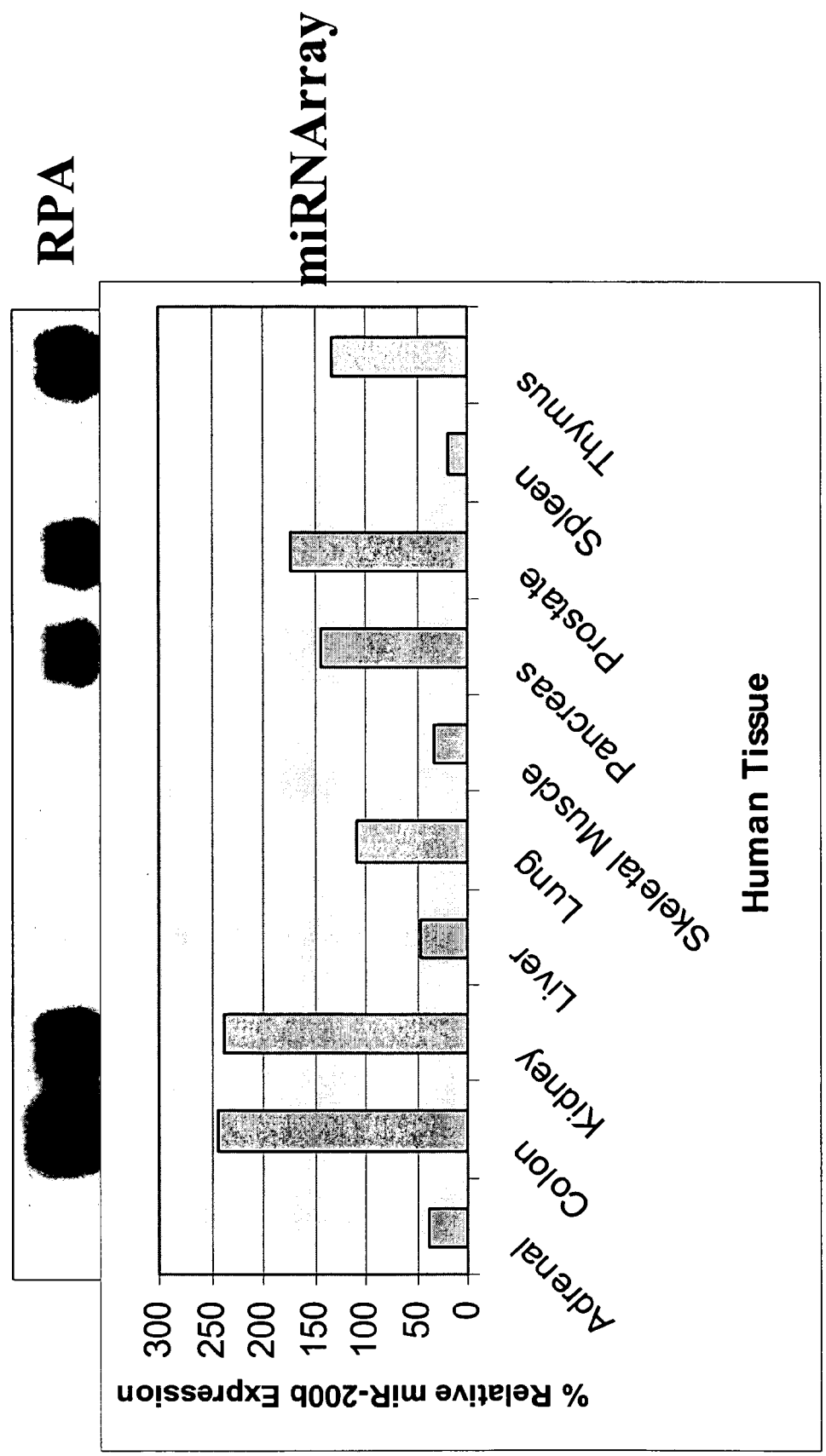
FIG. 5. Confirmation of miRNArray results using ribonuclease protection assay (RPA). miRNArray analysis was used to compare the miRNA expression profiles of 9 human tissues to an "average" sample comprising 24 human tissues. The relative expression of three miRNAs in the 9 tissues are plotted in the bar graphs wherein 100% is the measured expression of each miRNA in the average sample. The levels of the three miRNAs were also measured in the nine samples using the mirVana miRNA detection kit (Ambion) using the manufacturer's recommended procedure. The miRNA product bands are displayed in the autoradiographs above each miRNArray bar graph. Panel A. RPA and miRNArray results for miR-200b expression. Panel B. RPA and miRNArray for miR-16 expression. Panel C. RPA and miRNArray for let-7 expression. The expression profiles for the three miRNAs across the nine samples are very similar, providing independent confirmation that the miRNArrays are providing accurate quantification of the miRNAs in a sample.
Figure 5B:
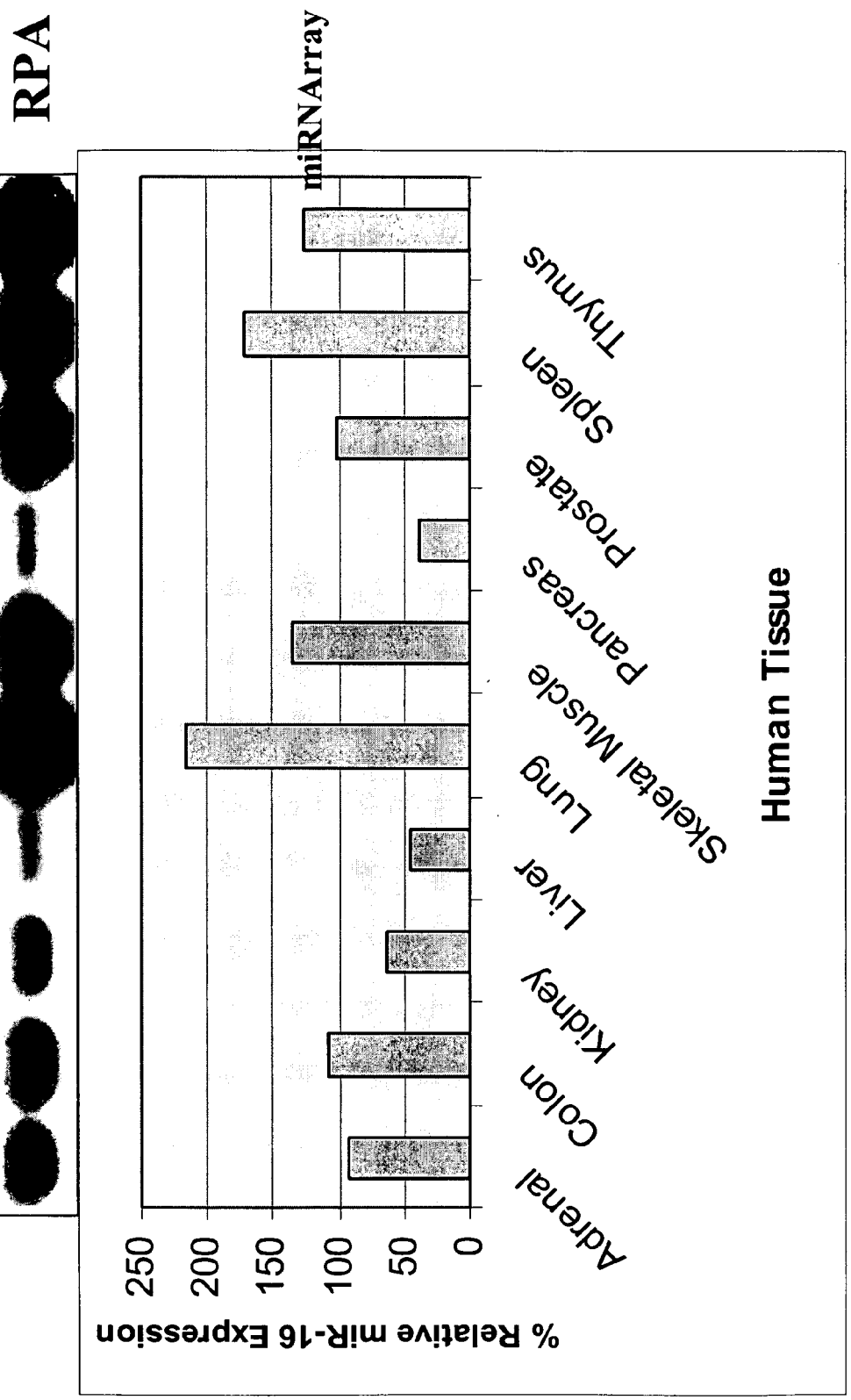
Figure 5C:
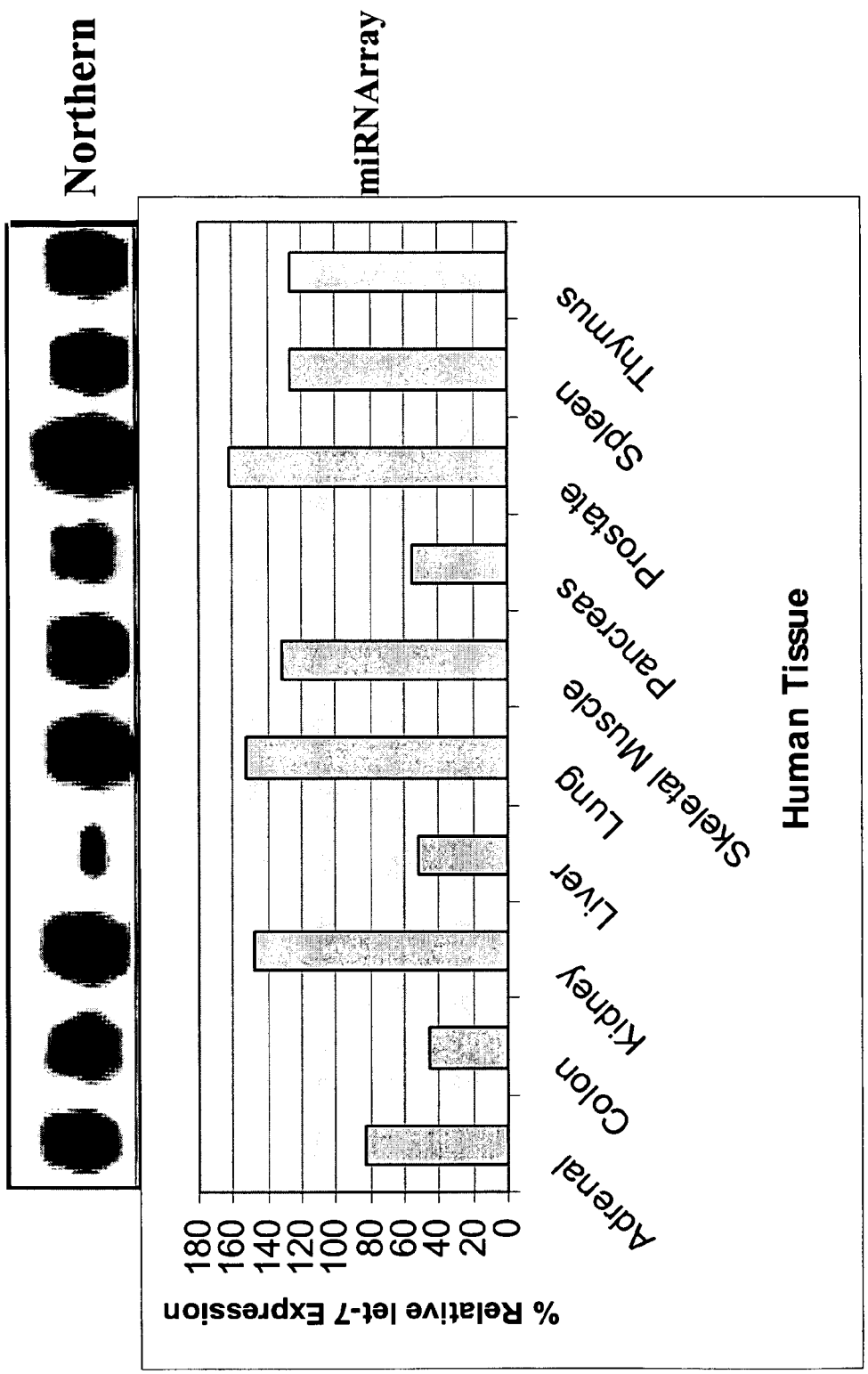

Radiolabeled probes that were hybridized to target miRNAs were protected from nuclease digestion and were seen as bands on autoradiographs that were exposed to the gels upon which the miRNA samples were fractionated. The intensities of the bands in the various samples correlates with the abundances of the miRNAs in the samples. As shown in FIG. 5, the Ribonuclease Protection Assay data mirror the miRNArray data for the same 9 samples that were generated in the experiment described in the previous example. This confirms that the miRNArray system is accurate in estimating the abundance of miRNAs in samples.

Example 11 miRNA Analysis of Lung Tumor Samples

In a one set of experiments tumor and normal adjacent tissue (NAT) samples were obtained from seven lung cancer patients. In a second set of experiments, tumor and NAT samples were evaluated from 16 additional lung cancer patients. The final data set comprise the first seven samples shown in the first table+16 additional samples.

Figure 6:
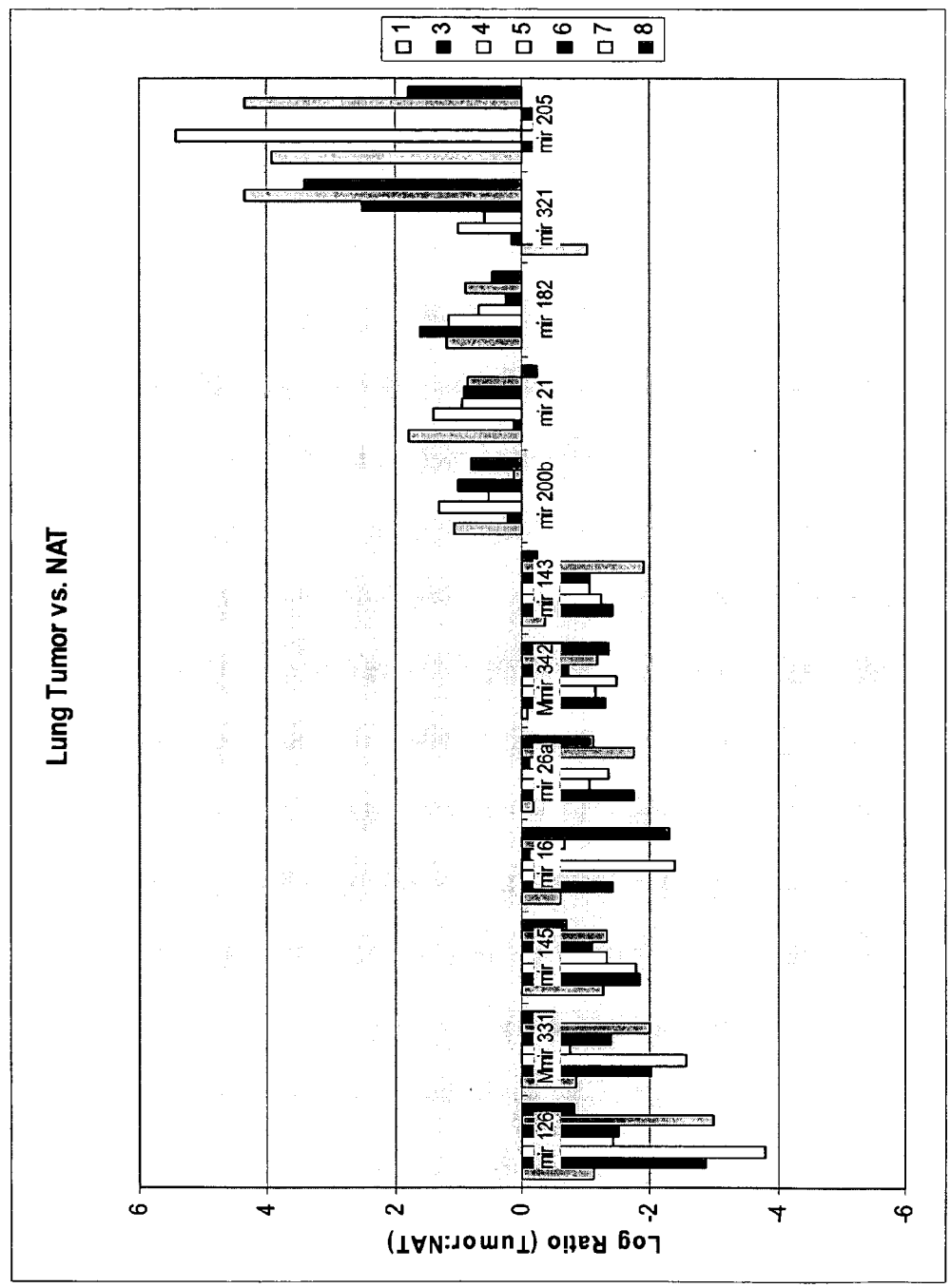
FIG. 6. Lung tumor/NAT samples. miRNArrays on tumor and normal adjacent tissues from 7 different lung tumor patients revealed a number of miRNAs that were differentially expressed between the tumor and normal samples. The differences in expression for the most prevalent of these miRNAs were plotted as a log ratio of the differential expression. The two- to four-fold differences in expression for many of these miRNAs would be easy to detect in patient samples and could provide an effective diagnostic or prognostic tool in clinical settings.

Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the tumor and NAT samples from each patient. Signal ratios of tumor:NAT for some of the miRNA elements are shown in FIG. 6. A table listing the miRNAs that were differentially expressed in at least four of the seven lung tumor/NAT samples from the first set of experiments is provided in Table 5A below. 16 additional lung cancer samples were analyzed using arrays. Those miRNAs that are significantly and reproducibly up- or down-regulated in the tumors relative to normal tissues from the combined 23 samples are shown in Table 5B. The miRNAs shown in Table 5B could be used to determine if a given sample were cancerous. These miRNAs represent potential targets for therapeutic development. Likewise, the genes that are regulated by these miRNAs might provide effective targets for therapeutic development. The miRNAs that are differentially expressed in only a subset of the samples likely represent molecular markers of the sub-classes of the cancer samples. These will likely prove to be valuable as prognostic indicators.

TABLE 5A miRNAs differentially expressed in lung tumor/NAT samples

| miRNA | # of tumor samples with >30% lower miRNA expression (out of 7 total) | # of tumor samples with >50% higher miRNA expression (out of 7 total) |
|---|---|---|
| miR-145 | 7 | |
| miR-126 | 7 | |
| miR-331 | 7 | |
| miR-342 | 6 | |
| miR-143 | 5 | |
| Let-7 | 5 | |
| miR-30a | 5 | |
| miR-16 | 5 | |
| miR-26a | 5 | |
| miR-125a | 5 | |
| miR-29b | 5 | 2 |
| miR-24 | 4 | |
| miR-328 | 4 | |
| mu-miR-201 | 4 | |
| miR-195 | 4 | |
| miR-22 | 4 | |
| miR-181a | 4 | |
| miR-21 | | 5 |
| miR-200b | | 5 |
| miR-321 | 1 | 5 |
| miR-182* | | 5 |
| miR-183 | | 4 |
| miR-17 | | 4 |
| miR-205 | | 4 |

*indicates that a strand complementary to this miRNA has also been detected in cells.

TABLE 5B miRNAs differentially expressed in lung tumor/NAT samples

| miRNA | % of tumor samples with >30% lower miRNA expression | % of tumor samples with >50% higher miRNA expression |
|---|---|---|
| miR-30A-as | 93% | |
| miR-126 | 100% | |
| miR-331 | 96% | |
| let-7a | 75% | |
| let-7c | 72% | |
| miR-95 | 87% | |
| miR-26a | 65% | |
| miR-125a | 68% | |
| Mu-miR-344 | 77% | |
| miR-21 | | 87% |
| miR-200b | | 81% |
| miR-205 | | 87% |

Example 12

Confirmation of Array Results-Lung Tumor/NAT Samples

Figure 7:
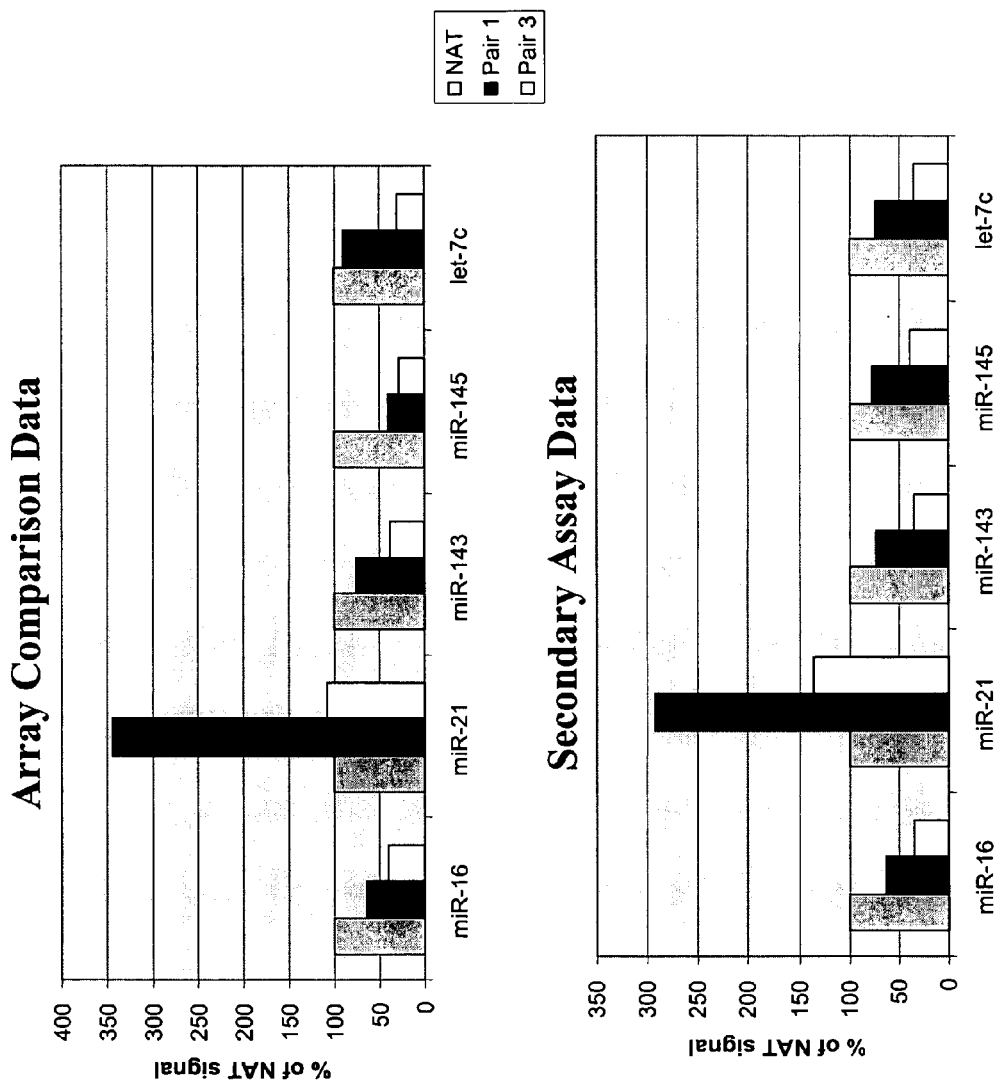
FIG. 7. Lung tumor marker verification. Several of the miRNA markers identified as in FIG. 6 were further evaluated to verify their validity. The top chart shows array comparison data while the bottom charts shows the relative expression of the miRNAs in the tumor compared to the normal samples from the lung cancer patients. As expected, the data from the miRNArray analysis were confirmed by a second method of analysis.

As with the normal tissue samples described above, a second method of RNA quantification was used to confirm that the miRNAs that were observed to be differentially expressed by the miRNArray process in the first set of experiments were indeed differentially expressed. Tumor/NAT samples from two of the lung cancer patients were analyzed for expression of miR-16, miR-21, miR-143, miR-145, and let-7. As was observed in the comparisons of the miRNA expression profiles in the normal samples, the quantitative data from the miRNArray system were very similar to the secondary analysis (FIG. 7). As above, this is validation of the miRNArray system. Furthermore, it shows that an alternative RNA analysis system could be used to analyze the expression of defined miRNAs in a clinical setting.

Example 13 miRNA Analysis of Colon Tumor Samples

Figure 8:
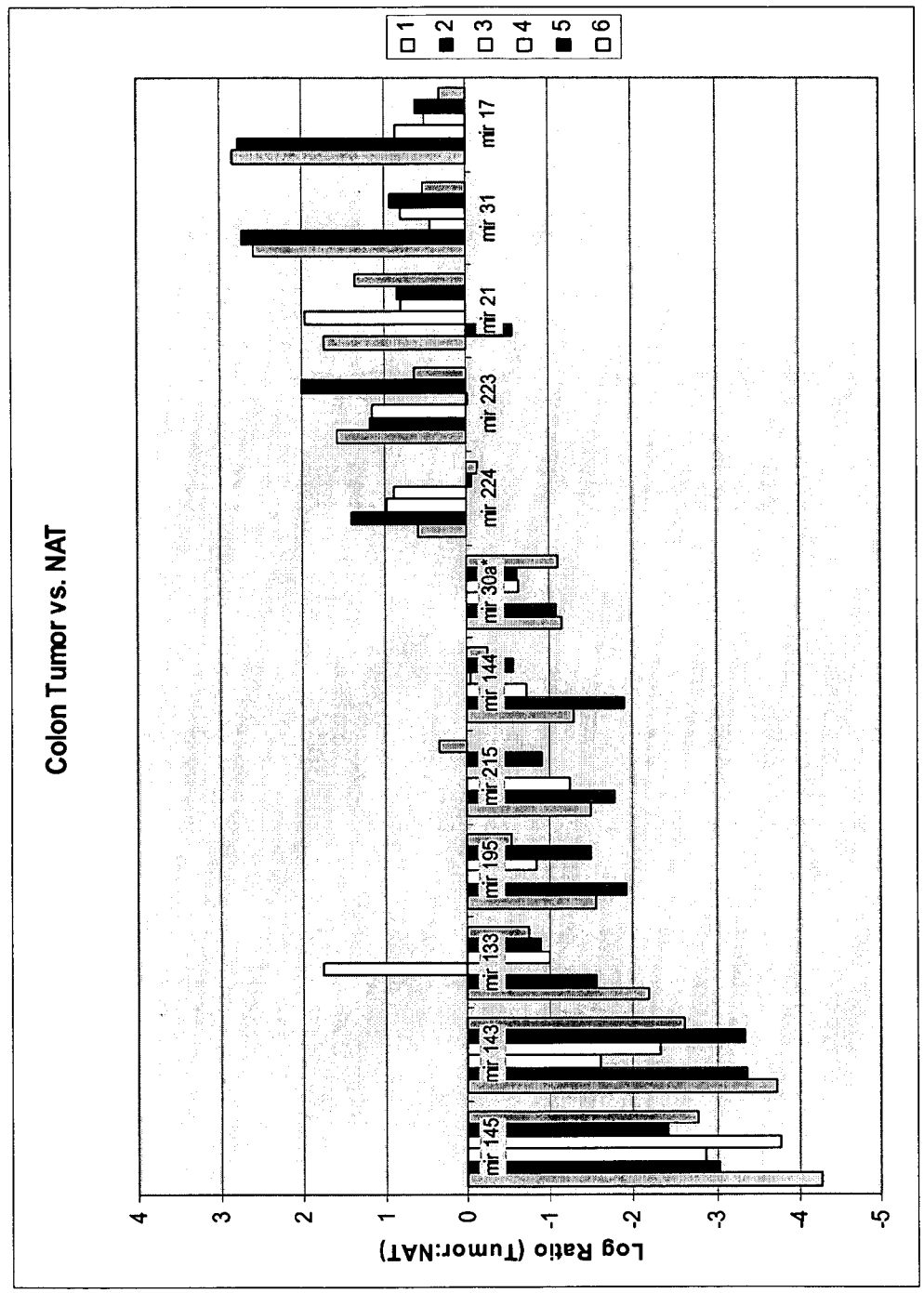
FIG. 8. Colon tumor/NAT samples. miRNArrays on tumor and normal adjacent tissues from 6 different colon tumor patients revealed a number of miRNAs that were differentially expressed between the tumor and normal samples. The differences in expression for the most prevalent of these miRNAs were plotted as a log ratio of the differential expression. The two- to four-fold differences in expression for many of these miRNAs would be easy to detect in patient samples and could provide an effective diagnostic or prognostic tool in clinical settings.

Tumor and normal adjacent tissue (NAT) samples were obtained from six colon cancer patients in a first set of experiments. In a second set of experiments, tumor and NAT samples were evaluated from 18 additional colon cancer patients. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the tumor and NAT samples from each patient. Signal ratios of tumor:NAT for some of the miRNA elements are shown in FIG. 8. A table listing the miRNAs that were differentially expressed in at least four of the first six colon tumor/NAT samples from the first set of experiments is provided below in Table 6A Data from the combination of the first and second set of experiments is provided in Table 6B. Those miRNAs that are consistently seen to be down- or up-regulated in tumor samples could be used to determine if a given sample were cancerous. Likewise, these miRNAs represent potential targets for therapeutic development. Also, the genes that are regulated by these miRNAs might provide effective targets for therapeutic development. The miRNAs that are differentially expressed in only a subset of the samples likely represent molecular markers of the sub-classes of the cancer samples. These will likely prove to be valuable as prognostic indicators.

TABLE 6A miRNAs differentially expressed in colon tumor/NAT samples

| miRNA | # of tumor samples with >30% lower miRNA expression (out of 6 total) | # of tumor samples with >50% higher miRNA expression (out of 6 total) |
|---|---|---|
| miR-145 | 6 | |
| miR-143 | 6 | |
| miR-133 | 5 | |
| miR-342 | 5 | |
| miR-125a | 5 | |
| miR-195 | 5 | |
| miR-30a* | 5 | |
| miR-10a | 5 | |
| miR-130 | 5 | |
| miR-192 | 4 | |
| miR-194 | 4 | |
| miR-215 | 4 | |
| miR-144 | 4 | |
| miR-23 | 4 | |
| miR-26a | 4 | |
| miR-126 | 4 | |
| miR-199a* | 4 | |
| miR-21 | 1 | 5 |
| miR-223 | | 5 |
| miR-224 | | 4 |
| miR-17 | | 4 |

*indicates that a strand complementary to this miRNA has also been detected in cells.

TABLE 6B miRNAs differentially expressed in colon tumor/NAT samples

| miRNA | % of tumor samples with >30% lower miRNA expression | % of tumor samples with >50% higher miRNA expression |
|---|---|---|
| miR-145 | 93% | |
| miR-143 | 93% | |
| miR-133 | 87% | |
| miR-125a | 75% | |
| miR-130a | 81% | |
| miR-135 | 79% | |
| miR-21 | | 79% |
| miR-200B | | 79% |
| miR-203 | | 83% |
| miR-223 | | 76% |
| miR-106A | | 71% |
| miR-31 | | 67% |

Example 14 miRNA Analysis of Various Tumor Samples

Tumor and normal adjacent tissue (NAT) samples were obtained from three breast cancer patients, two thyroid cancer patients, and one bladder cancer patient. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the tumor and NAT samples from each patient.

Interestingly, many of the miRNAs that were differentially expressed in the lung and colon tumor samples were likewise differentially expressed in the breast thyroid, and bladder samples. A heat map showing a subset of the differentially expressed miRNAs is shown in FIG. 9. Note that green squares represent miRNAs that are expressed at least 50% lower in the tumor than the normal adjacent tissue and red represents miRNAs that are expressed at least 50% higher in tumor than in normal adjacent tissues. A table listing the miRNAs that were differentially expressed in samples from each of cancer types is provided below. These miRNAs appear to be the functional equivalents of the known protein-expressing oncogenes and are likely involved in regulating cell proliferation and cell death as well as angiogenesis. These miRNAs represent potential targets for therapeutic development. Likewise, the genes that are regulated by these miRNAs might provide effective targets for therapeutic development.

TABLE 7 miRNAs differentially expressed in different tumor/NAT samples

| miRNA | # of tumor samples with >30% lower miRNA expression (out of 19 total) | # of tumor samples with >50% higher miRNA expression (out of 19 total) |
|---|---|---|
| miR-145 | 18 | |
| miR-143 | 15 | |
| miR-126 | 16 | |
| miR-30a* | 11 | |
| miR-125a | 12 | 2 |
| miR-21 | 1 | 15 |
| miR-195 | 11 | 2 |
| miR-321 | 4 | 9 |
| miR-17 | 1 | 8 |
| miR-182* | | 10 |
| miR-183 | | 11 |

*indicates that a strand complementary to this miRNA has also been detected in cells.

Example 15

Sample Variability

An assumption of many molecular diagnostic methods is that a tumor sample is relatively the same throughout the cancerous tissue. The validity of this assumption was tested by measuring the miRNA profiles of two isolates of a single thyroid tumor from one patient.

Figure 10:
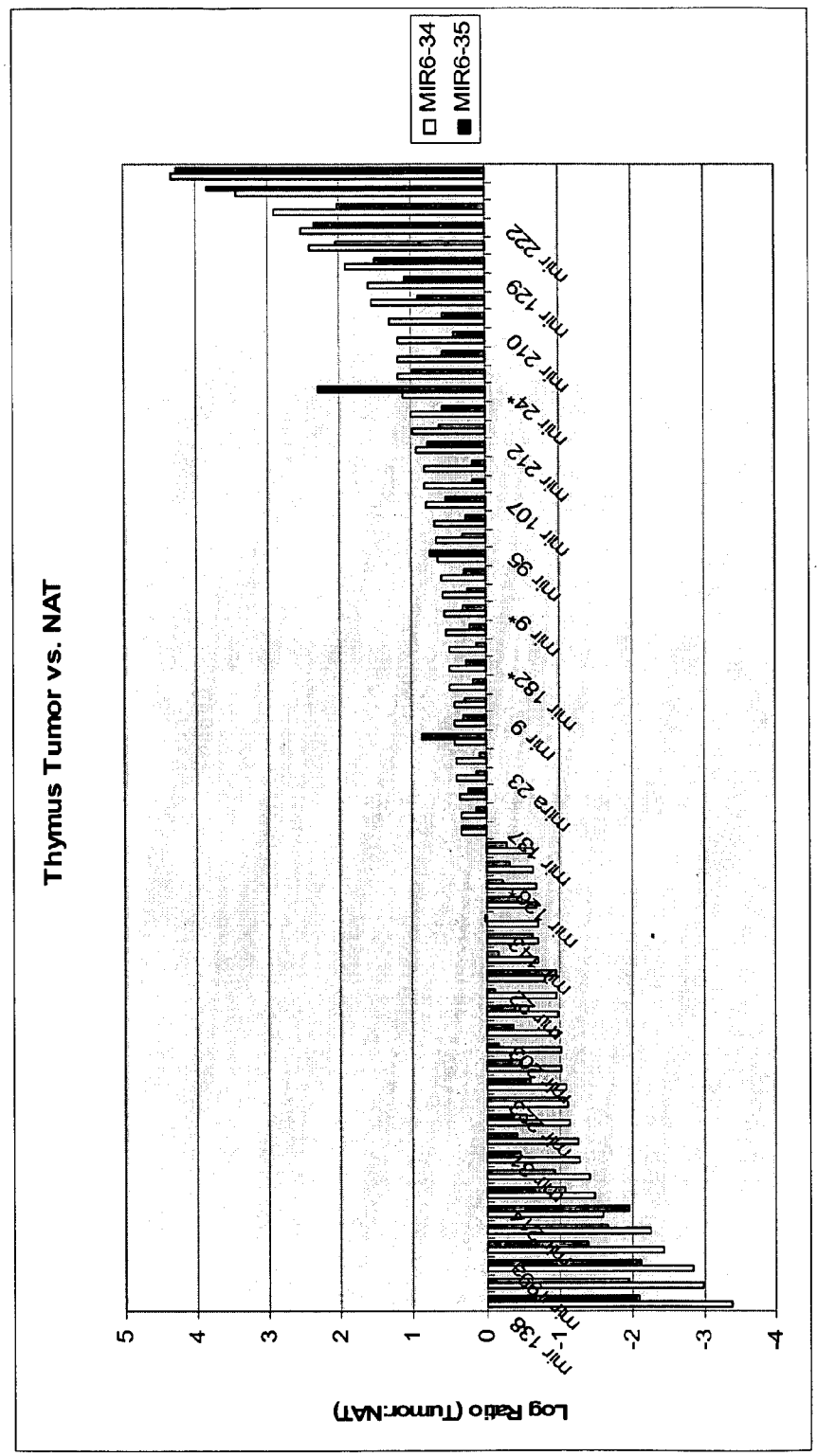
FIG. 10. Similarity of miRNA expression profiles from different regions of a single tumor. Two different tumor and normal adjacent samples from the thyroid of a single cancer patient were evaluated by miRNArray analysis. The relative expression of the miRNAs in the two tumor and NAT samples are plotted as log ratios. The two independent samples have a correlation of 92%, showing that miRNA profiles are very similar between tumor isolates. This is important when considering using an analyte like a miRNA as a diagnostic sample.

Total RNA from the two thyroid tumor and normal adjacent samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to the miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the isolates of the same tumor. Signal ratios at each element are expressed as a log ratio and shown in FIG. 10. The average correlation between the two isolates was 92%, indicating that there is little variation between different regions of the same sample.

Example 16 miRNA Profiling from Fixed Tissue Samples

Formaldehyde- and paraformaldehyde-fixed tissues represent a huge resource of clinically interesting samples. In clinical setting, most tumors and other disease tissues are fixed, analyzed, and stored indefinitely. Analyzing these historical samples provide scientists with the opportunity to match molecular characteristics of the fixed samples to clinical outcomes for the patients from which the samples derived. Although researchers have long recognized the benefits of performing RNA analysis on fixed tissues, the fixed tissues have not been used because it is essentially impossible to isolate high quality RNA from the samples. This is due to the fact that the fixatives introduce chemical moieties into the RNA molecules that make them incompatible with essentially all quantitative RNA techniques.

It was tested whether miRNAs could be extracted and analyzed from fixed tissues. Mouse kidney and brain samples were either fixed in 4% paraformaldehyde for three weeks or frozen and stored at −80° C. for three weeks. Following the three week incubations, the fixed samples were processed using the Optimum™ kit (Ambion) according to manufacturer's recommendation. Total RNA was isolated from both the fixed and frozen samples using the glass fiber filter method described above. Each of the total RNAs was fractionated by tube electrophoresis to recover the miRNAs from each sample. The miRNAs from each sample were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signal from each fixed sample was compared to the signal from its corresponding frozen sample. The relative signal intensities of the fixed and frozen samples were compared for each miRNA. The correlations between the fixed and frozen samples approached 99%, indicating that miRNAs can be used to analyze fixed tissues. A representative array profile for one of the sample comparisons is provided in FIG. 11.

Example 17 miRNA Profiling from Samples with Degraded RNA

Another problem that is encountered by researchers who are comparing the gene expression profiles of different samples is that RNA is fragile. Nucleases in tissues as well as those introduced by mishandling can degrade mRNAs and other interesting RNA molecules in samples. Most methods of RNA analysis are affected by RNA degradation making it essentially impossible to get reliable data when one or more RNA samples in the analysis are at least partially degraded. Given the surprising results with miRNAs in fixed tissues, it was decided to test the impact of RNA degradation in tissues on miRNA expression profiles.

Figure 11:
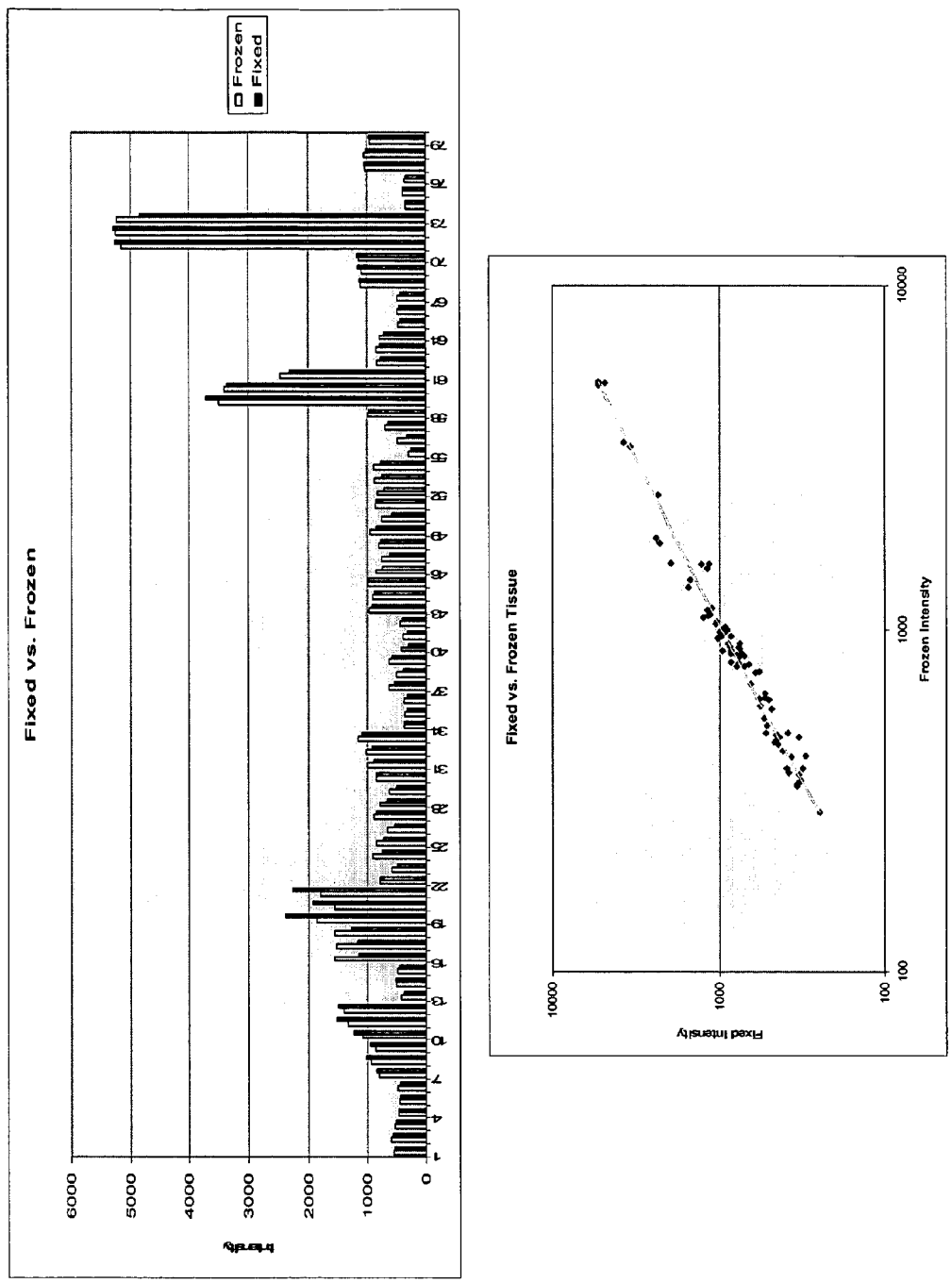
FIG. 11. miRNArray analysis of fixed tissues. Most hospitals formaldehyde fix tumor samples as part of the diagnostic process. Fixation cross-links many of the biomolecules in the sample and renders them incompatible with molecular analysis. Several tissues were removed from a mouse and either fixed or frozen. miRNAs from the fixed and frozen samples were then analyzed using the miRNArray system. A representative of these samples is shown. The top panel shows signal intensities for the various miRNA probe elements on the miRNArray. The bottom panel is a scatter plot of the signal intensities for the fixed vs frozen samples. The miRNA profiles were essentially identical between the fixed and frozen samples, indicating that miRNAs can be effectively analyzed in fixed samples. This means that miRNA diagnostic assays will be compatible with existing medical protocols. In addition, it will also be possible to perform retrospective studies using old fixed tissues that have been banked by hospitals.
Figure 12A:
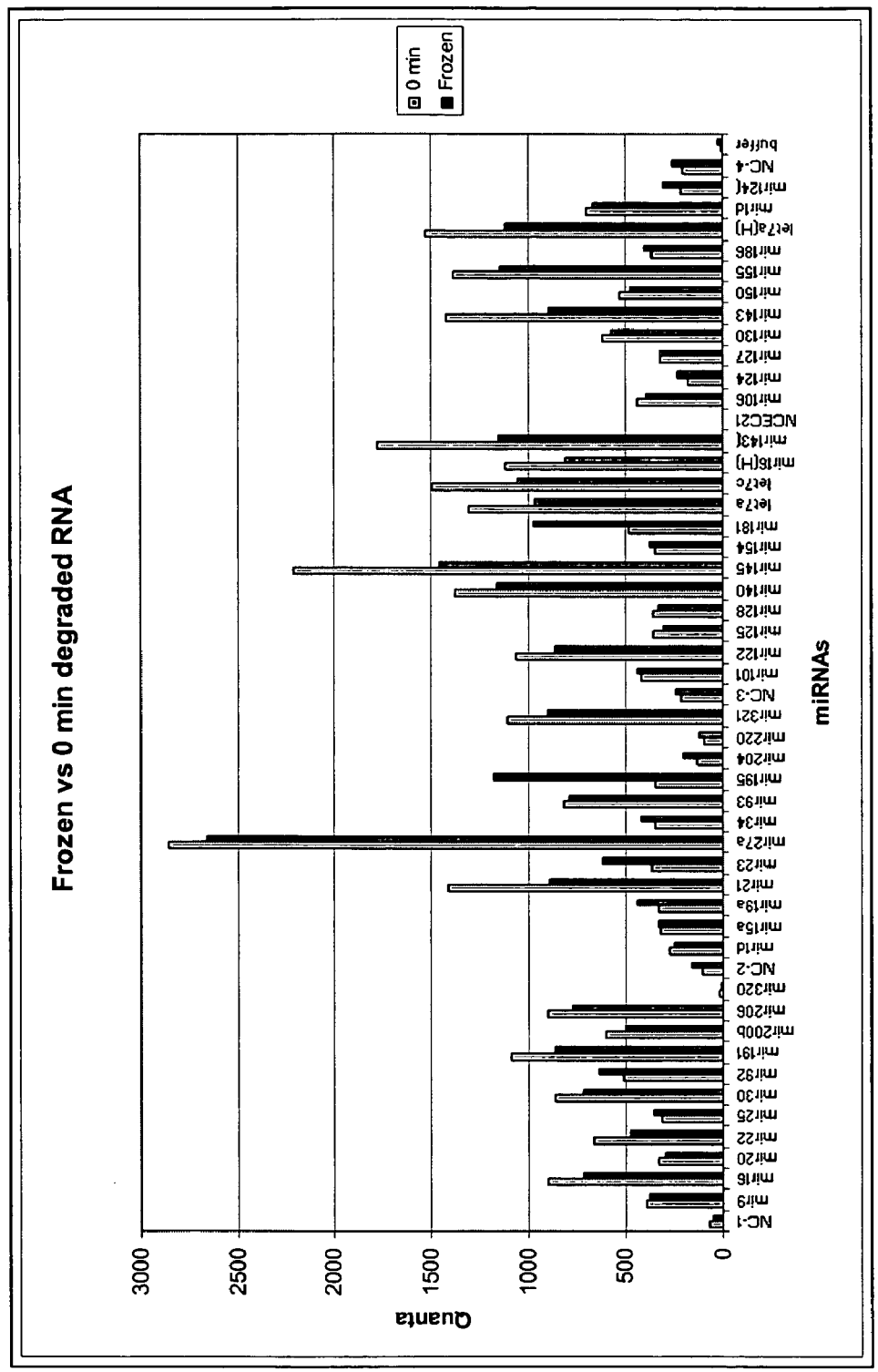
FIG. 12A-E. miRNArray analysis of on degraded RNA samples. A mouse tissue sample was incubated at room temperature for various periods of time to create RNA samples that were degraded at increasing levels. The degraded (and undegraded) samples were evaluated using the miRNArray system to establish the level of tolerance for degradation that miRNA profiling can accommodate. Panel A. miRNArray analysis comparing miRNAs from sample of undegraded frozen tissue to a sample with RNA degraded for 0 minutes. Panel B. miRNArray analysis comparing miRNAs from sample of frozen tissue to sample with RNA degraded for 5 minutes. Panel C. miRNArray analysis comparing miRNAs from sample of frozen tissue to sample with RNA degraded for 20 minutes. Panel D. miRNArray analysis comparing miRNAs from sample of frozen tissue to sample with RNA degraded for 120 minutes. Panel E. Polyacrylamide gel showing extent of degradation in different samples. Interestingly, the miRNA profiles appear to be unperturbed by conditions that degrade other RNAs in a sample. This could either be because the miRNAs are bound and protected from nuclease digestion by the protein complex that uses them in cells or the miRNAs are too small to be effectively digested by nucleases. Regardless of why they are protected, the observation that miRNAs are stable increases their usefulness as diagnostic/prognostic analytes because their levels are unlikely to be affected by poor sample handling which is a problem for mRNA-based assays.
Figure 12B:
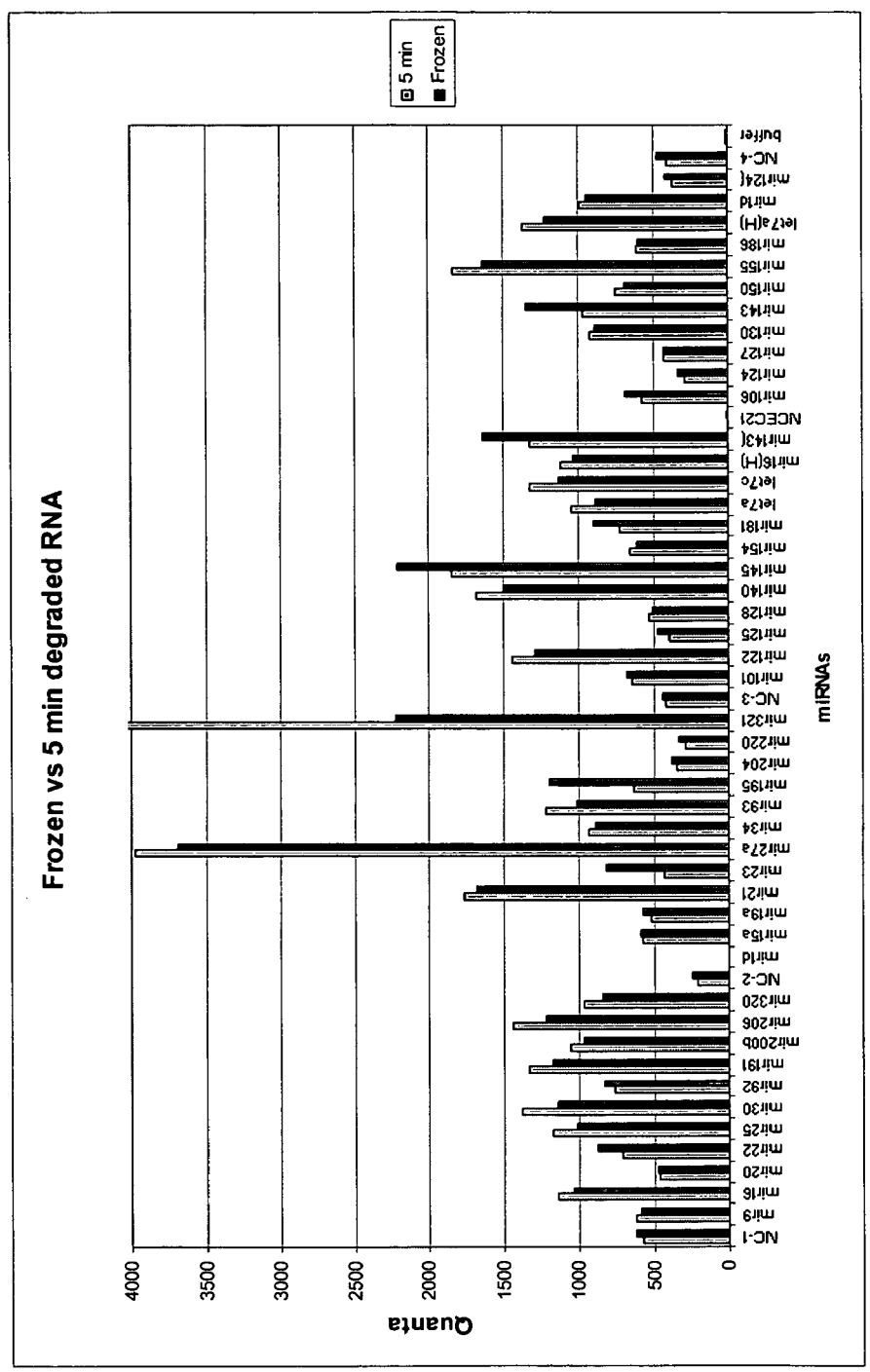
Figure 12C:
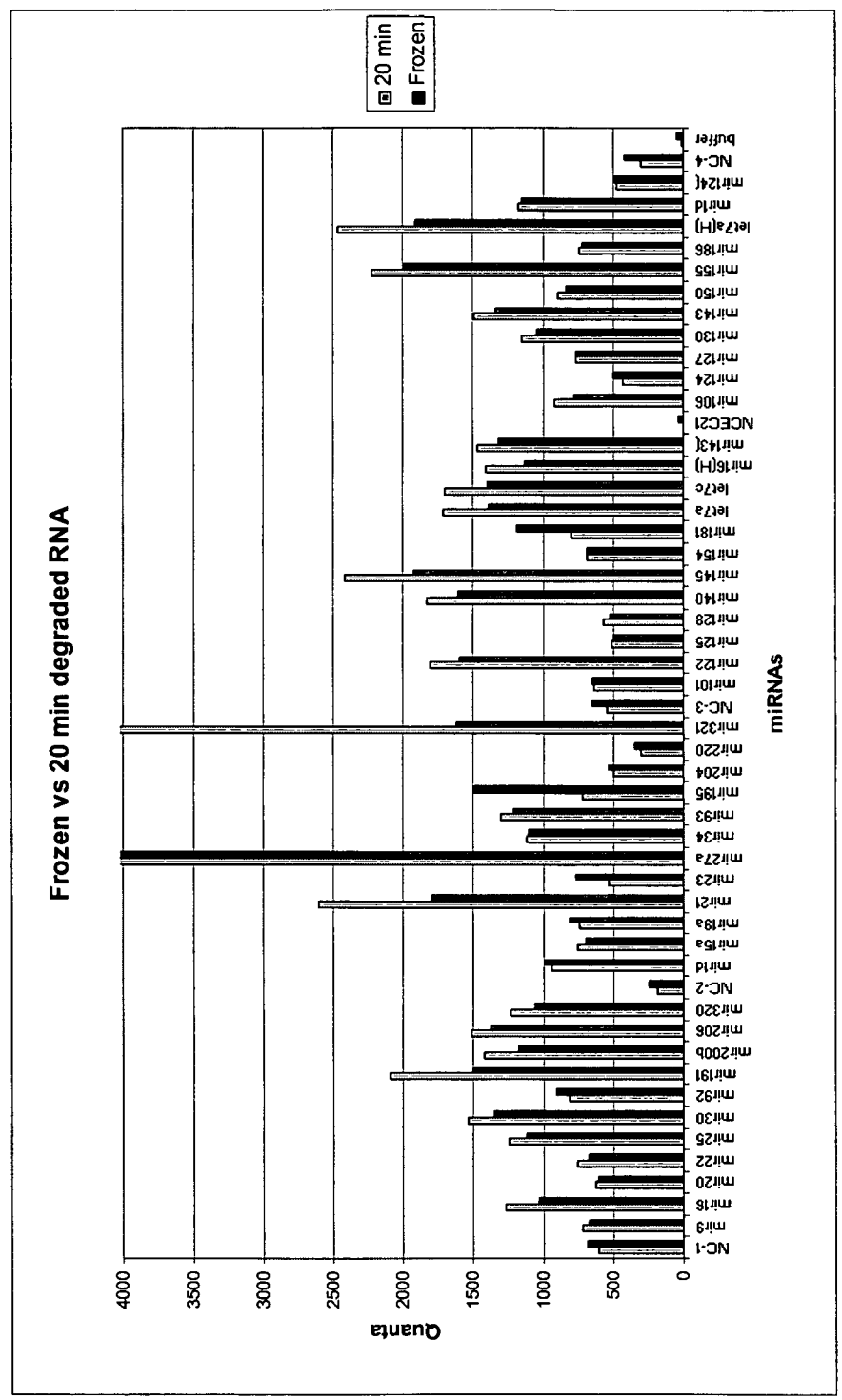
Figure 12D:
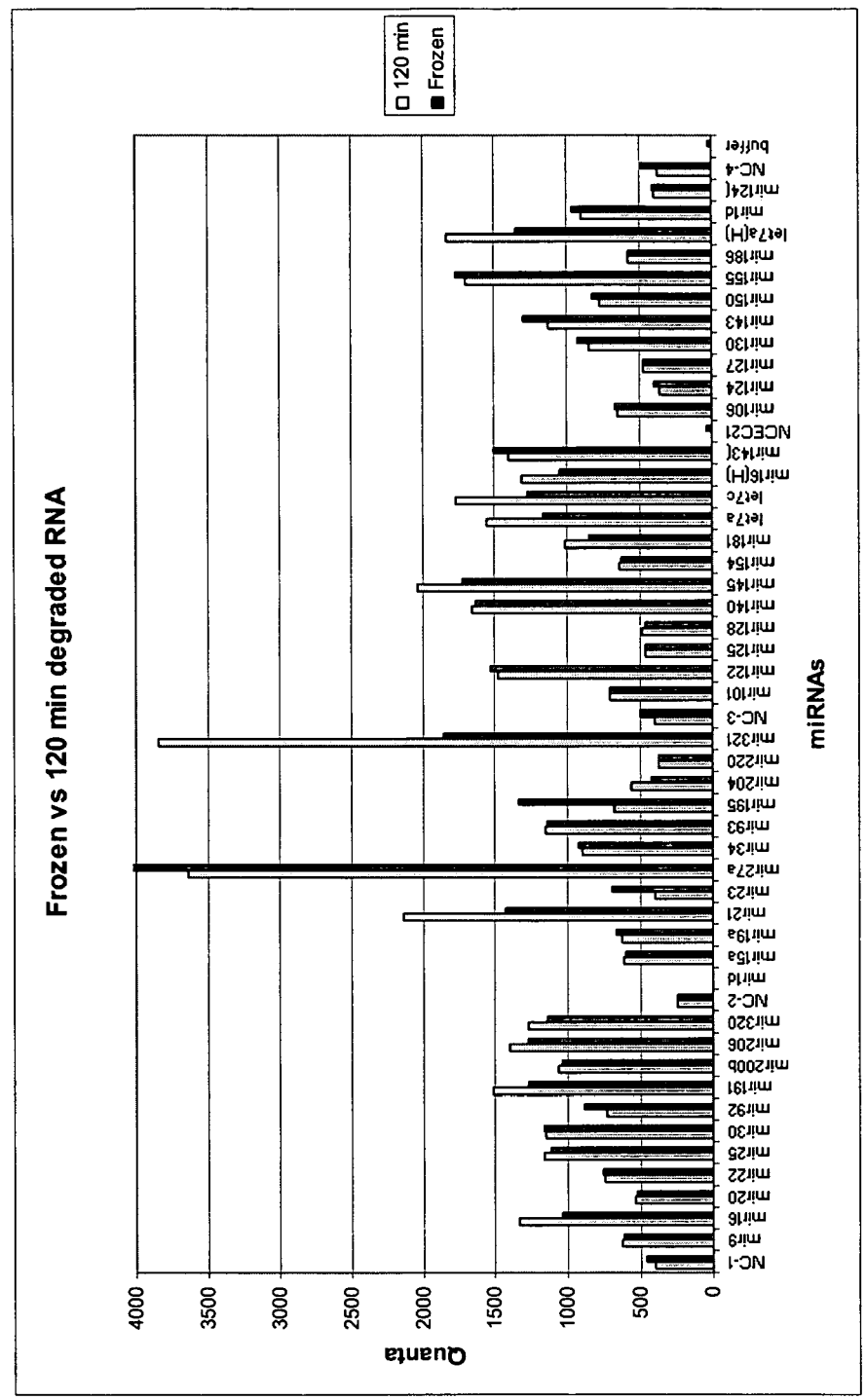
Figure 12E:
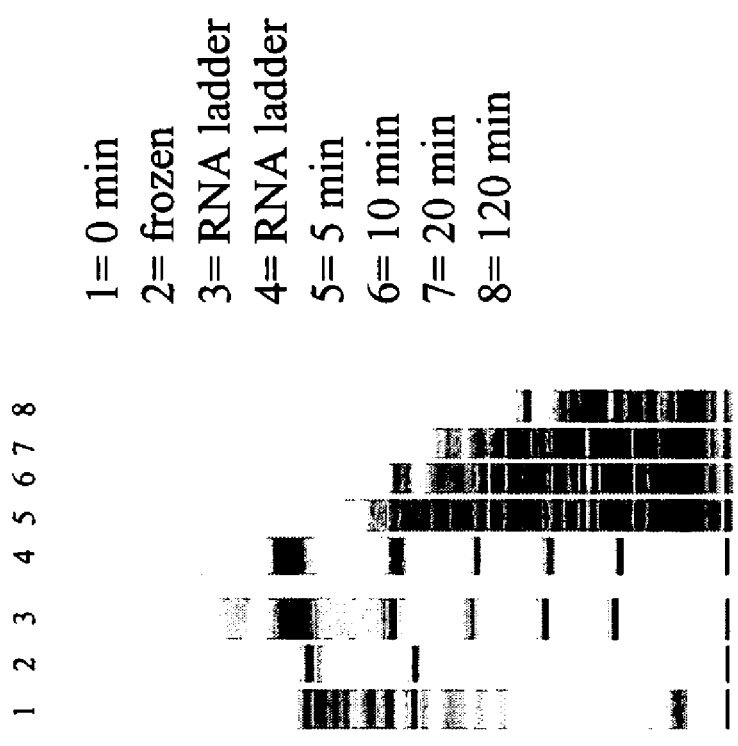

A series of RNA samples was created with variable levels of degradation by harvesting the colon of a mouse and dividing the sample into two equal parts. RNA from one of the parts was isolated using the glass fiber filter method described above. This RNA represented the non-degraded control. The second part was sub-divided into five equal samples. The five samples were placed in phosphate-buffered saline and incubated for 0-120 minutes at room temperature. RNA was isolated from one of the five samples at 0, 5, 10, 20, and 120 minutes using the glass fiber filter method described above. Each of the total RNA samples was analyzed using the Bio-Analyzer (Agilent) according to the manufacturer's recommended protocol. Profiles of the various samples are shown in FIG. 11. Note that the non-degraded (noted as frozen) sample has two distinct bands corresponding to the 18S rRNAs and 28S rRNAs in the sample. The 18S rRNA and 28S rRNA bands disappear as the nucleases in the colon samples are allowed to degrade the RNA in the tissues during the room temperature incubation.

Each of the total RNAs was fractionated by tube electrophoresis to recover the miRNAs from each sample. The miRNAs from each sample were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signal from each degraded sample was compared to the signal from the non-degraded sample. The relative signal intensities of the degraded and non-degraded samples were compared for each miRNA (FIG. 12). The correlations between the degraded and non-degraded samples approached 95% indicating that miRNAs can be used to analyze degraded RNA samples. The benefits to using miRNAs profiling to compare samples is that it reduces the stringency required for sample handing (this is especially important for clinical and field settings) and it allows many historical samples that were prepared poorly to be used for comparative analyses.

Example 18 miRNA Analysis of Blood Samples

Many diagnostic assays are designed to assay blood samples since blood is readily available and often representative of the health of the patient. To confirm that miRNA can be analyzed in blood samples, samples from ten different individuals were obtained. Total RNA from each of the samples was isolated by pouring whole blood into a 10 ml syringe attached to a LK4 leukocyte depletion filter (Pall) in a reusable syringe device. The blood was passed thru the LK4 filter over a time period of ~75 sec. per sample. The filter device was then transferred to a 3 ml syringe containing 3 ml of Ambion's RNAlater®, which was passed thru the filter containing the captured WBCs, in a drop-wise fashion. The plunger was then retracted and residual drops of RNAlater® were expelled but the filters were left damp. The filters with treated WBCs were then removed from the devices and transferred to 15 ml conicals. Filters were stored at room temp. for approximately 1 hour before beginning the RNA extraction.

Figure 13A:
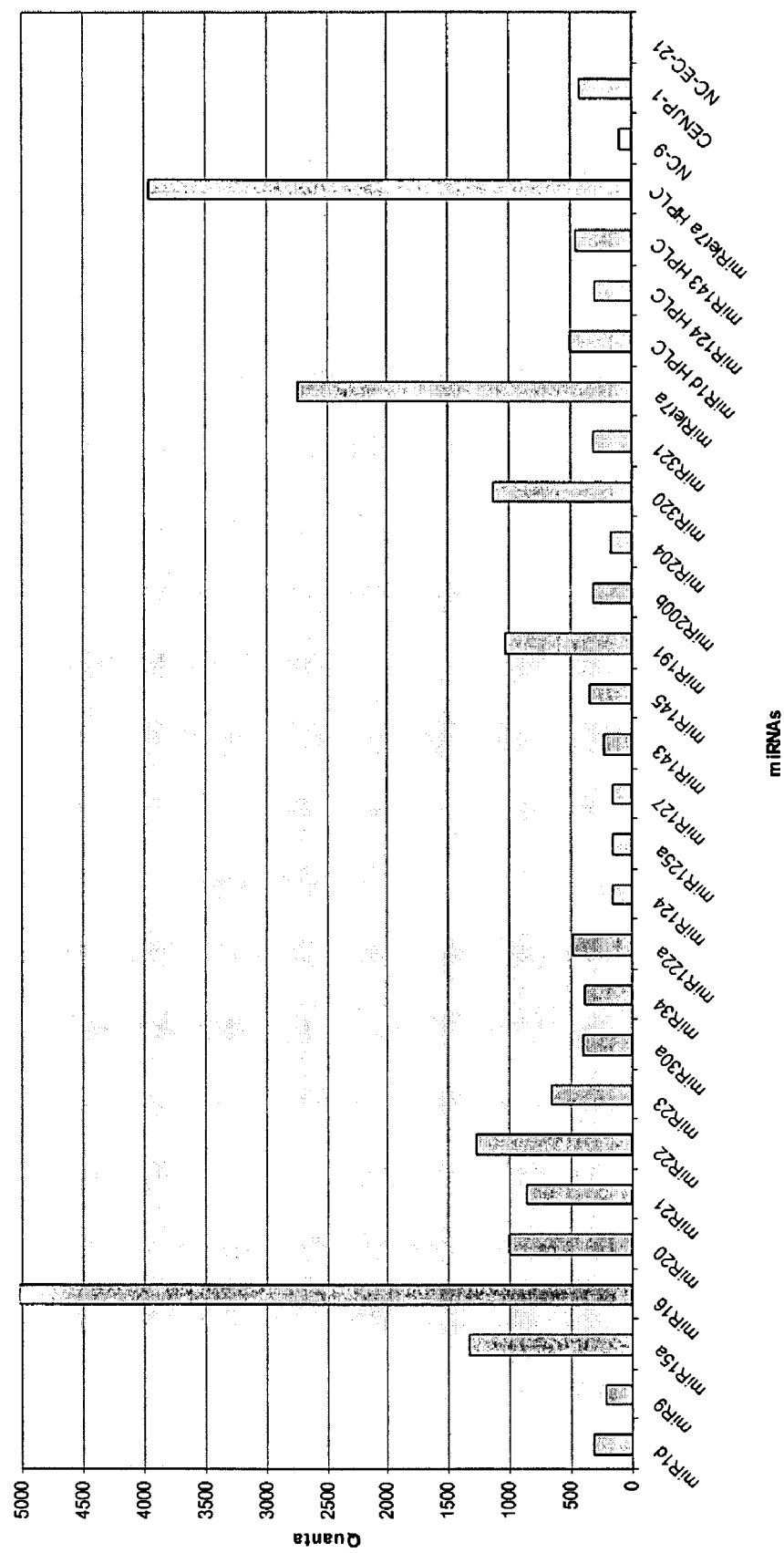
FIG. 13. miRNArray analysis of blood samples from different patients. One of the most prevalent samples used in clinics is blood. The miRNArray system was used to analyze the miRNA profiles of ten different blood donors. The three panels show the relative signal intensity from a select set of miRNAs in three of the representative patients. The data show that miRNA profiles can be obtained from blood. In addition, it is important to not the similarity in the miRNA profiles of the various donors, suggesting that different individuals have very similar miRNA expression patterns, which should make it easy to identify individuals with conditions that perturb their miRNA profiles.
Figure 13B:
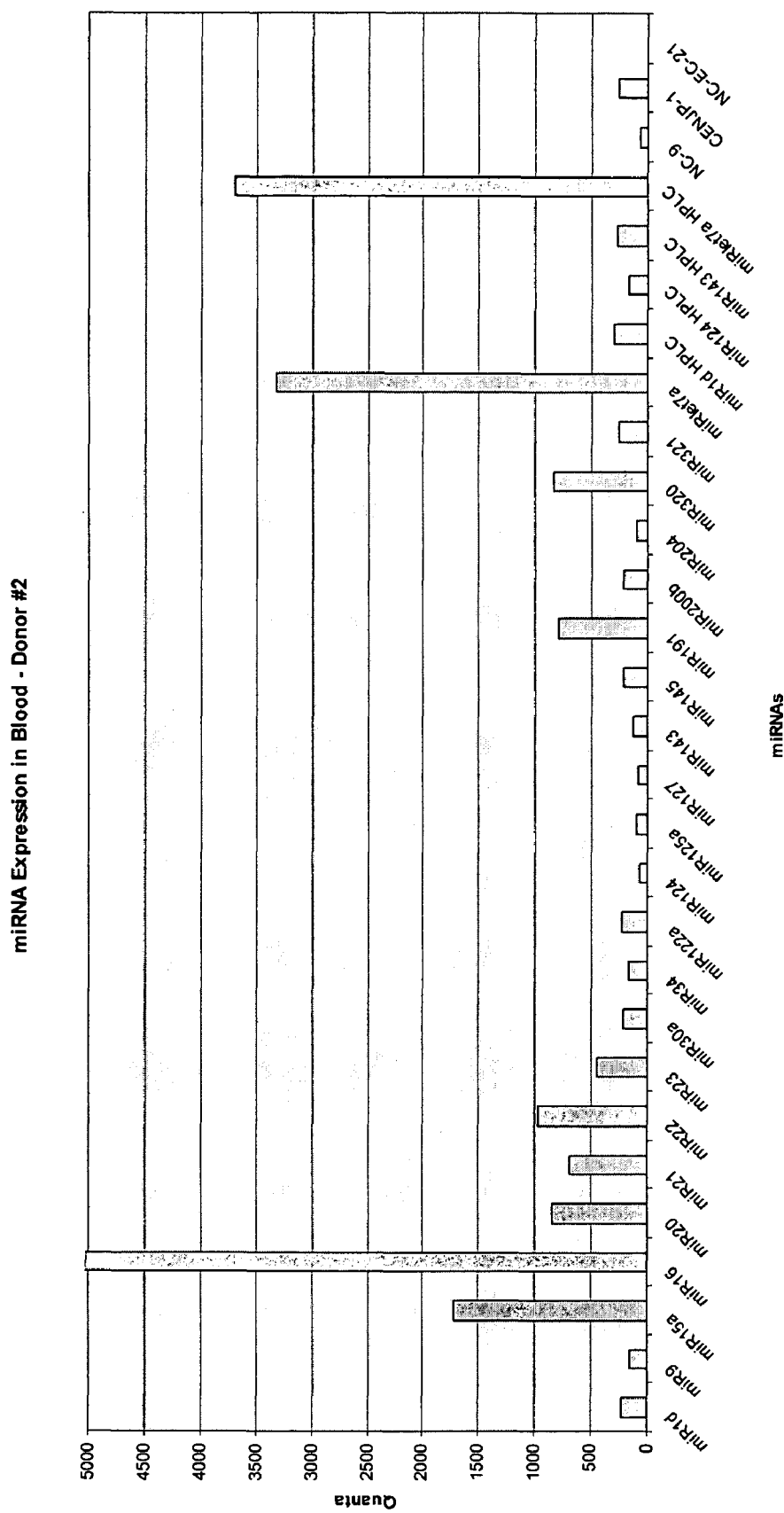
Figure 13C:
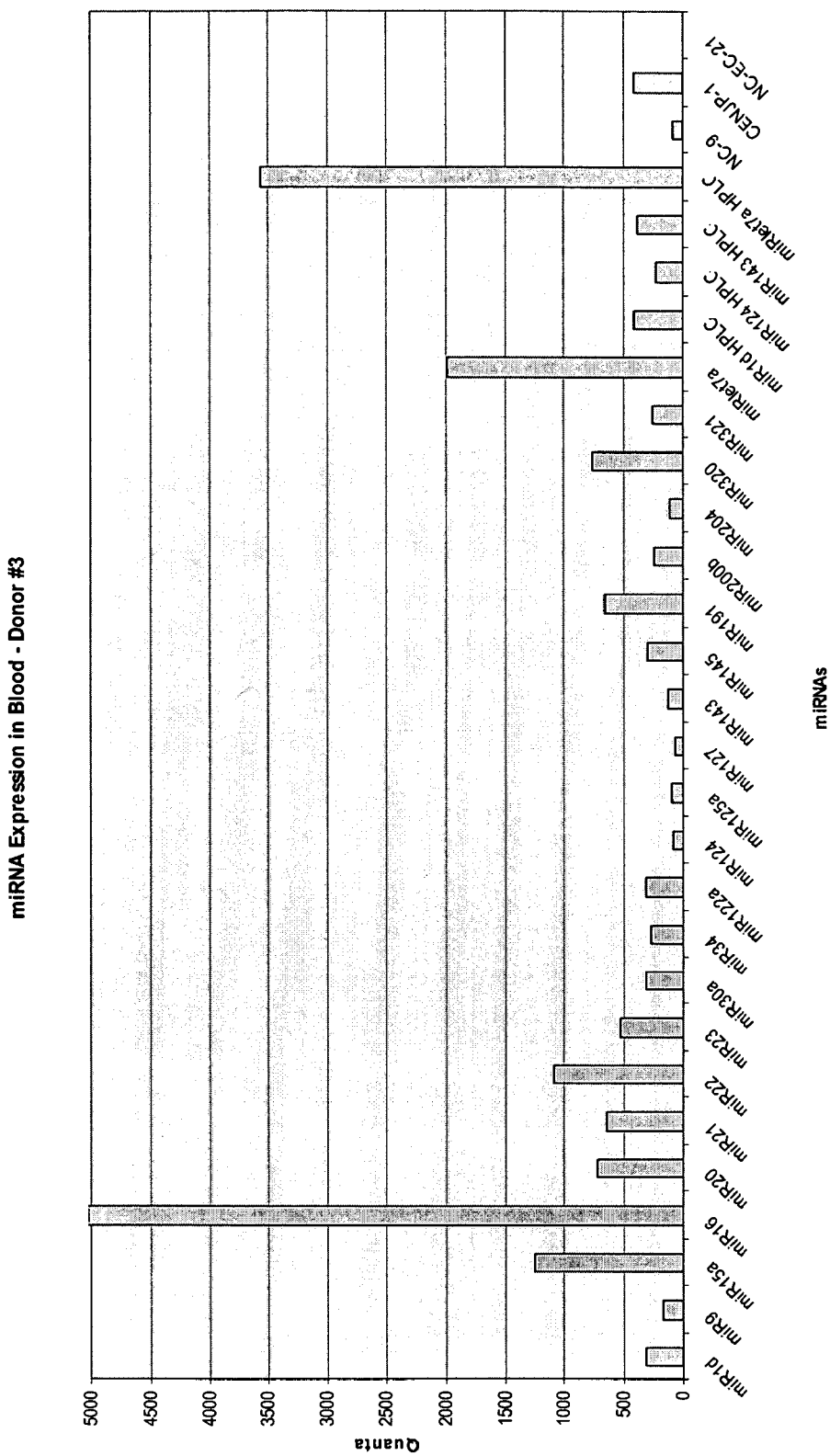

2.5 ml Lysis Solution. from RiboPure™ Blood kit (Ambion) and 0.25 ml of 2 M NaOAc was added to each 15 ml conical containing an LK4 filter with captured treated cells, and these were shaken vigorously for 30 sec. and then stored for 5 min. on ice. 2.5 ml acid phenol/$ChCl_3$ was added to each tube and contents mixed by vigorous shaking for 30 sec. Preps were centrifuged at 3,200 rpm for 10 min. in swinging bucket table-top centrifuge, then the aqueous phase was removed to a second 15 ml conical. 1.25 volumes of 100% ethanol was added to each prep (using calibration marks on the 15 ml tubes to determine volume of prep prior to adding EtOH) and contents mixed by vortexing. Preps were filtered thru silica filters in RiboPure™ Blood kit (Ambion) using vacuum suction, vacuum manifold. Silica filters were transferred to 2 ml microfuge tubes and washed by adding 0.75 ml of Wash 1 (1.6 M GuSCN/70% EtOH) and centrifuging briefly to pass the solution thru the filters. Silica filters were washed twice with 0.75 ml of Wash 2/3 from RiboPure™ Blood kit (Ambion) as above, then centrifuged for 1 min. at 13.2 K rpm to remove residual fluid. RNA was eluted by transferring the silica filters to fresh 2 ml collection tubes, adding 200 ul of nuclease-free water, heated to 78° C., to each silica filter, storing for 1 min. at room temp., then centrifuging for 1 min. at 13.2 K rpm. The miRNAs from each sample were isolated using standard gel purification as described above. The miRNAs from each sample were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon). The signal intensities of the various miRNAs were plotted. FIG. 13 provides miRNA profiles for three of the donors. The signals for many of the miRNAs are on par with what we observe for tissue samples, indicating that miRNAs are indeed present in blood samples and might be used for diagnostic assays. Interestingly, the miRNA profiles were very similar for the ten different donors, suggesting that there is a global norm for miRNAs in blood. This could make it easier to identify individuals who are sick given that minor miRNA perturbations would be seen against the relatively non-variable background of normal individuals.

Example 19

Oncogeneic miRNAs—Differential Expression and Cancer Regulation

As noted in previous examples, a number of miRNAs have been identified that are differentially expressed between tumor and normal adjacent tissue samples from the same cancer patients. Interestingly, there is significant overlap in the miRNAs that are differentially expressed between different cancers, suggesting there is a core set of miRNAs that influence cellular processes that when altered, lead to cancer. The following describes experiments aimed at developing a link between miRNA mis-regulation and cancer.

miRNA Expression in Lung Cancer

Figure 14:
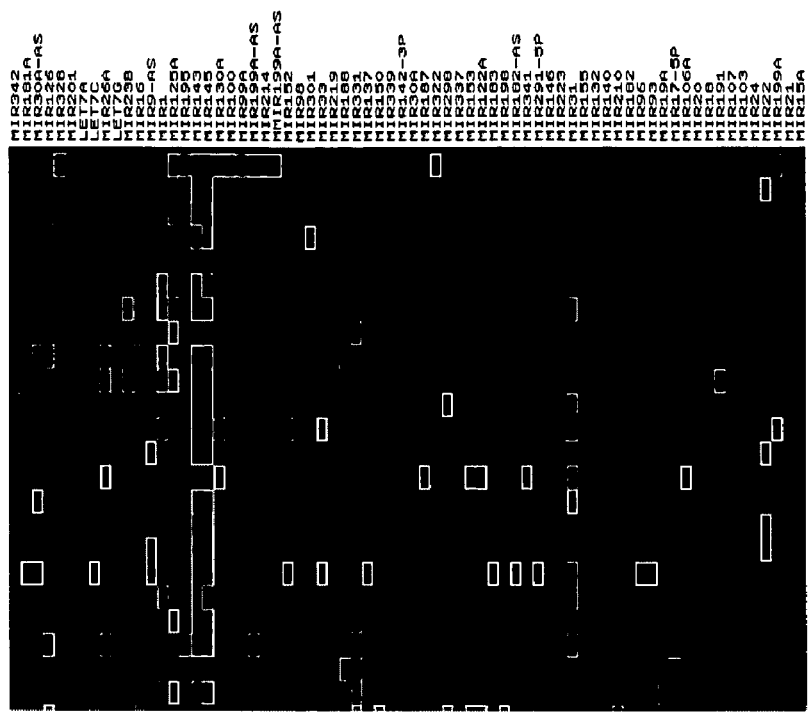
FIG. 14. miRNA Expression in Lung and Colon Cancer Patients. The miRNA expression profiles of tumor vs normal adjacent tissues were compared for lung and colon cancer patients. The miRNAs are provided in rows; the patients are presented in columns. Shown are miRNAs that are down-regulated in the tumor sample relative to the normal adjacent tissue sample, and miRNAs that are up-regulated in the tumor sample relative to the normal adjacent tissue sample.
Figure 14:
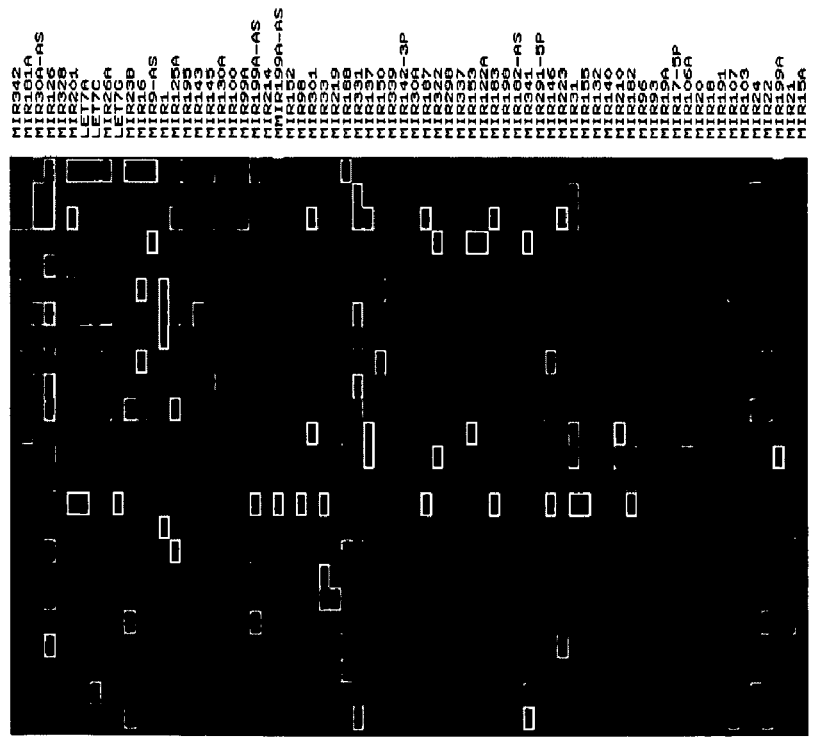
Figure 15:
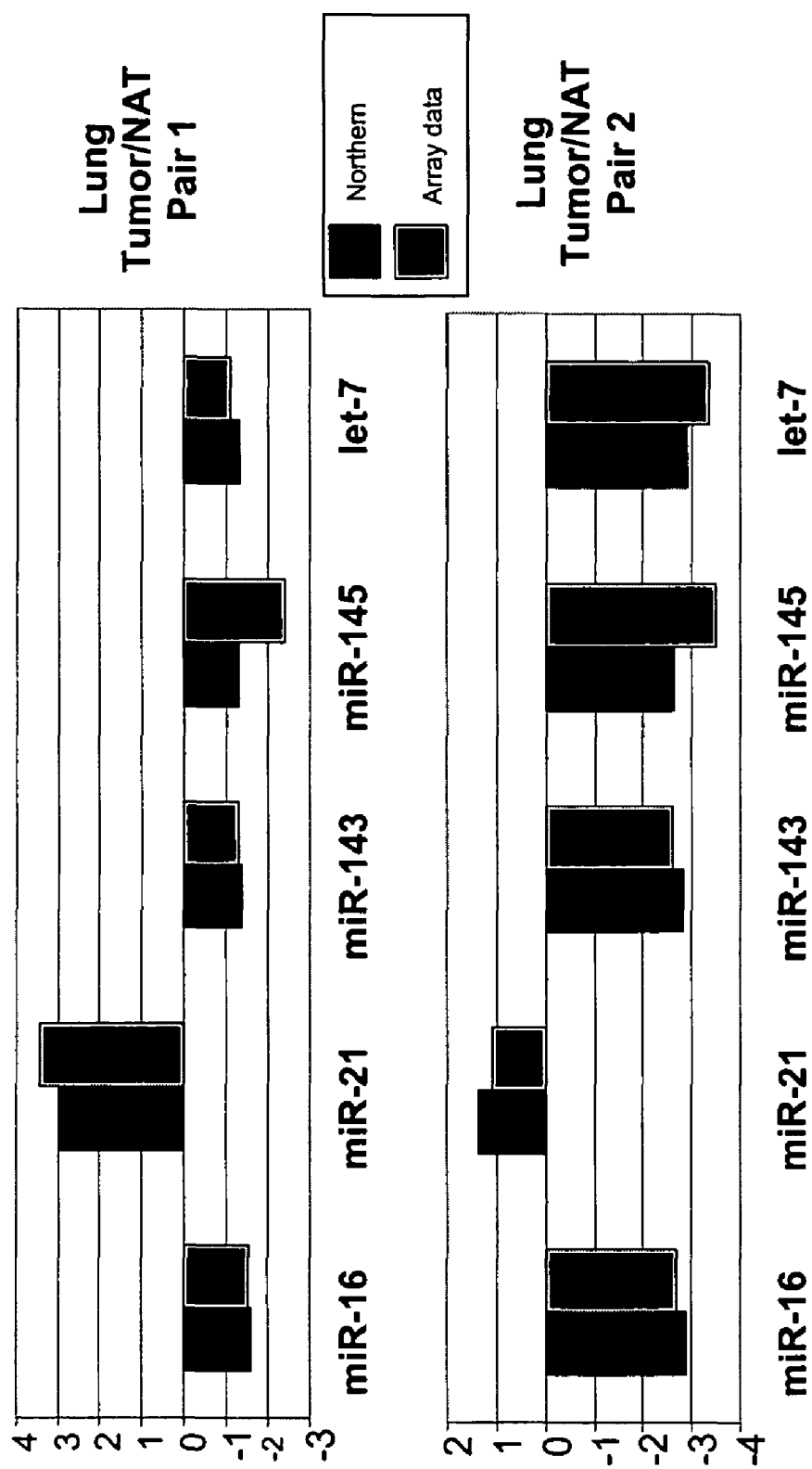
FIG. 15. Validation of miRNA Array Expression Results in Lung Cancer Patients. Total RNA samples from two lung cancer patients were analyzed for expression of miR-16, miR-21, miR-143, miR-145, and let-7 using Northern analysis. The graphs show the relative abundance of each miRNA (ratio of tumor:NAT) from the array analysis and Northern phosphoimager analysis.

Twenty-two tumor and normal adjacent tissue (NAT) samples from lung cancer patients were analyzed using the miRNA array system described above. The arrays were analyzed and the relative expression of each miRNA was compared between the tumor and normal adjacent tissues from each patient. The various miRNAs were clustered based on their relative expression in tumors across different patients (FIG. 14). Six miRNAs (miR-126, 30a, 143, 145, 188, and 331) were expressed at significantly lower levels in the tumors of more than 70% of the patients. Three miRNAs (miR-21 and 200b) were expressed at significantly higher levels in the tumors of more than 70% of the patients. The differential expression of a number of these miRNAs was verified by Northern analysis (FIG. 15).

miRNA Expression in Colon Cancer

Twenty-five tumor and NAT samples from colon cancer patients were analyzed using our miRNA array process. Like the lung cancer comparisons, the various miRNAs were clustered based on their relative expression in tumors across the different colon cancer patients (FIG. 14). Five miRNAs (miR-143, 145, 195, 130a, and miR-331) were expressed at significantly lower levels in the tumors of more than 70% of the patients. Five miRNAs (miR-223, 31, 21, 17, and 106) were expressed at significantly higher levels in the tumors of more than 70% of the patients.

miRNAs as Cancer Markers

Figure 16:
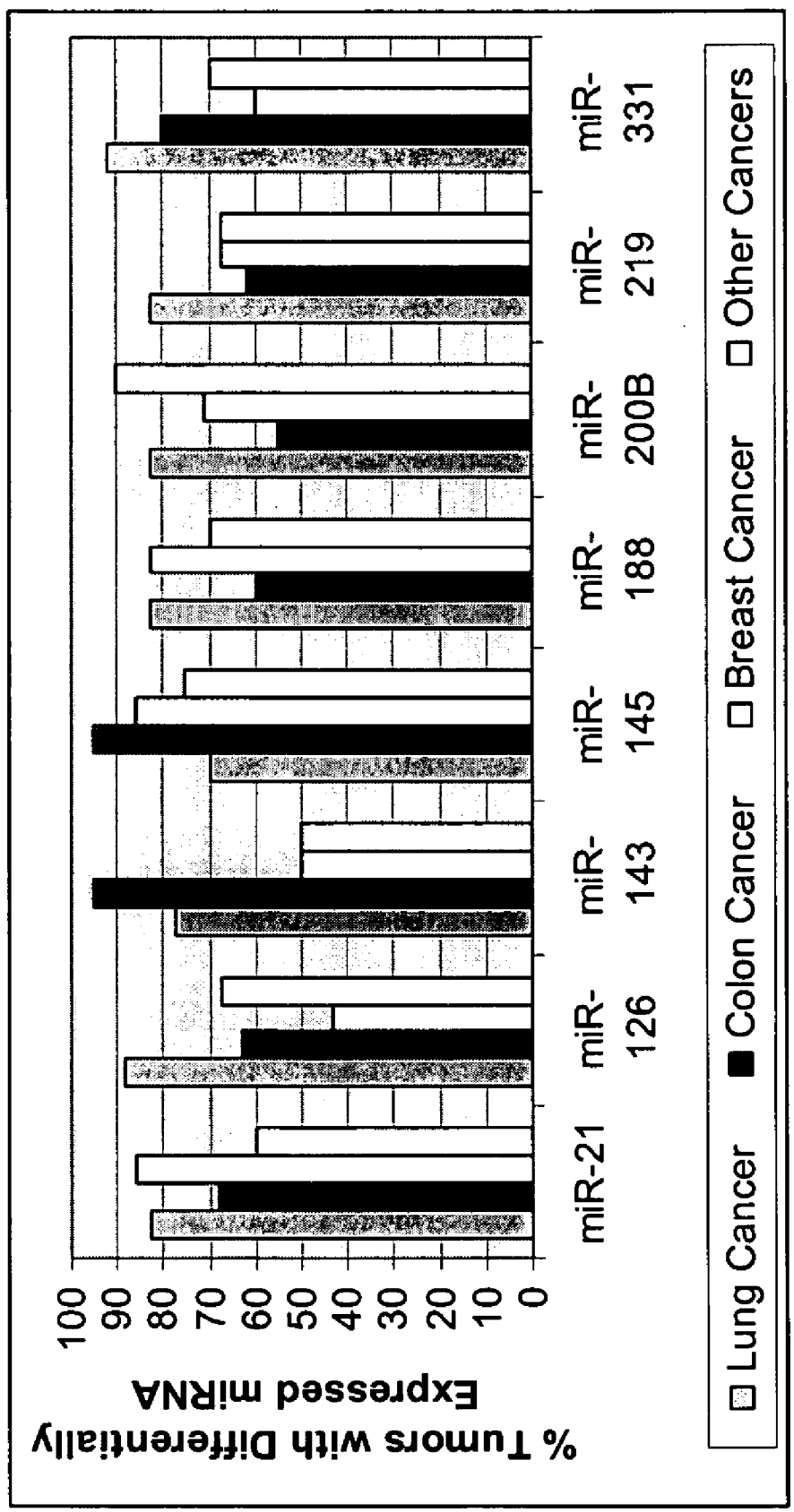
FIG. 16. Some miRNAs are differentially expressed in multiple cancer types. miRNA array analysis comparing tumor and normal adjacent tissues from patients with various types of cancer was used to identify miRNAs that are differentially expressed in cancer. The percentage of patients exhibiting up- or down-regulation of a given miRNA was calculated for each cancer type. The eight that were most often differentially expressed across sample types are presented.

It is interesting that eight different miRNAs were differentially expressed between the tumor and normal adjacent samples for most of the lung and colon patient samples that we analyzed (FIG. 16). These same miRNAs were also found to be differentially expressed in the breast, thymus, bladder, pancreatic, and prostate cancer patients that we analyzed, suggesting that these miRNAs might control cellular processes that when altered lead to cancer.

miRNAs as Regulators of Oncogene Expression

To address whether specific miRNAs might be participating in cancer through the mis-regulation of oncogenes, we scanned the 3' untranslated regions (UTRs) of 150 well-known oncogenes for sequences with significant homology to the miRNAs identified in our microarray analysis. Potential target sites were selected based on two criteria:

(1) Perfect complementarity between positions 2-9 of the miRNA and the oncogene. This miRNA core sequence has been identified as critical to the activities of miRNAs and the known miRNA target sites have essentially 100% complementarity at this site (Doench et al. 2004).

(2) Overall $T_m$ of the miRNA/mRNA interaction. In addition to the core sequence, overall binding stability between miRNAs and mRNAs has been shown to be an important indicator of miRNA activity (Doench et al., 2004).

As seen in Table 8, potential target sites in the 3'UTRs of known oncogenes were identified for all of the miRNAs that were observed to be routinely differentially expressed in tumor samples. Interestingly, KRAS2, MYCL1, and CBL have multiple predicted miRNA binding sites which could provide the cooperative miRNA binding that has been implicated as an important factor in miRNA regulation (Doench et al. 2003); Zeng et al., 2003). Many of the genes listed in Table 8 become oncogenic when they are over-expressed, thus it is conceivable that reduced expression of a miRNA could lead to up-regulation of one or more oncogenes and subsequently lead to oncogenesis.

TABLE 8

Cancer-related miRNAs and their putative oncogene targets

| miRNA | Predicted Gene Target |
|---|---|
| let-7 | RAS |
| let-7 | C-MYC |
| miR-21 | mutS homolog 2 (MSH2) |
| miR-21 | v-ski sarcoma viral oncogene homolog (avian) (SKI) |
| miR-143 | breakpoint cluster region (BCR) |
| miR-143 | MCF.2 cell line derived transforming sequence (MCF2) |
| miR-143 | von Hippel-Lindau tumor suppressor (VHL) |
| miR-143 | v-Ki-ras2 Kirsten rat sarcoma 2 viral oncogene homolog (KRAS2) |
| miR-143 | v-Ki-ras2 Kirsten rat sarcoma 2 viral oncogene homolog (KRAS2) |
| miR-143 | Cas-Br-M (murine) ecotropic retroviral transforming sequence (CBL) |
| miR-143 | Cas-Br-M (murine) ecotropic retroviral transforming sequence (CBL) |
| miR-145 | v-myc myelocytomatosis viral related oncogene (MYCN) |
| miR-145 | fibroblast growth factor receptor 2 (FGFR2) |
| miR-145 | Cas-Br-M (murine) ecotropic retroviral transforming sequence (CBL) |
| miR-188 | v-myc myelocytomatosis viral oncogene homolog 1 (MYCL1) |
| miR-200b | cadherin 13 (CDH13) |
| miR-200b | v-kit Hardy-Zuckerman 4 feline sarcoma viral oncogene homolog (KIT) |
| miR-219 | v-myc myelocytomatosis viral oncogene homolog 1 (MYCL1) |
| miR-219 | B-cell CLL/lymphoma 2 (BCL2) |
| miR-219 | E-cadherin 1, type 1, E-cadherin (epithelial) (CDH1) |
| miR-331 | vav 1 oncogene (VAV1) |
| miR-331 | fibroblast growth factor receptor 1 (FGFR1) |
| miR-331 | BCL2-antagonist/killer 1 (BAK1) |
| miR-331 | retinoic acid receptor, alpha (RARA) |
| miR-331 | v-src sarcoma (Schmidt-Ruppin A-2) viral oncogene homolog (SRC) |

Example 20

Measuring the Effect of miRNAs on Oncogene Expression

Confirming miRNA target site predictions can be done in a variety of ways. In *Drosophila* and *C. elegans*, genetic approaches have been applied wherein mutations in the miRNA and the putative miRNA target site(s) are made and shown to result in similar phenotypes (Ha et al., 1996; Vella et al., 2004). In mammalian cells, where genetic approaches are far more difficult, reporter constructs have been used to show that the 3' UTRs of putative target genes are regulated in cells at levels that are disproportionate to reporter vector controls that contain mutations in the putative miRNA binding sites (Lewis et al. 2003). In addition, vectors and oligonucleotides have been used to introduce or inhibit miRNAs in cells to determine the effects on endogenous levels of putative target genes (Lewis et al., 2003; Kiriakidou et al. 2004). The latter approach has been undertaken to validate the miRNA target site predictions.

Synthetic miRNAs and miRNA inhibitors have been developed that can be transfected into mammalian cells to either introduce miRNAs into cells or inhibit the activity of miRNAs in cells, respectively. See U Ser. No. 60/627,171, and 60/649,634, both of which are hereby incorporated by reference. A synthetic miRNA and a miRNA inhibitor corresponding to let-7 were used to determine if the target site predictions were correct. In these experiments, cultured cells that express undetectable levels of the miRNA were transfected with the synthetic miRNA using siPORT™ NeoF™ Transfection Agent (Ambion). Immunofluorescence assays were used to RAS and C-MYC in the transfected cells. The proteins from both oncogenes were expressed at almost three-fold lower levels in cells transfected with the synthetic miRNA than cells transfected with a Negative Control miRNA (Ambion). In a reciprocal experiment, cells that naturally express high levels of the miRNA were transfected with the let-7 miRNA inhibitor. As expected, the proteins from both oncogenes were higher in cells transfected with the miRNA inhibitor than in cells transfected with the Negative Control inhibitor (Ambion). These results are consistent with the model that the miRNA regulates the expression of the two oncogenes. These data suggest that mis-regulation of a key miRNA could participate in cancer progression by failing to regulate the expression of one or more oncogenes.

Example 21 miRNAs in Lupus

Systemic lupus erythematosus (SLE; Lupus) is a chronic inflammatory auto-immune disease that ultimately leads to immune complex-mediated end-organ failure. It is characterized by an over activation of CD4+ T helper cells and repression of CD8+ T cytotoxic activity, leading to an overproduction of natural antibodies and pathogenic autoantibodies. Recently several histone modifications were reported in peripheral blood mononuclear cells (PBMCs) isolated from lupus patients. Diagnosis of lupus is still frequently incorrect mainly because the symptoms vary so widely and they come and go frequently, and because the disease mimics so many other disorders. Furthermore, diagnosis does not indicate the particular therapy to be used. In the absence of a cure, present-day treatment of lupus is still primarily tailored to symptomatic relief and not to the diagnosis. A diagnostic assay with high specificity and sensitivity would be very important.

Samples were analyzed from 16 individuals, 8 with clinically verified lupus and 8 non-lupus patients that were age- and gender-matched with the lupus patients. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the lupus and normal sample signals were compared to identify differentially expressed miRNAs. Each array experiment included duplicate arrays.

Fourteen miRNAs were differentially expressed in all of the lupus samples relative to the matched samples. miR-301, miR-199, miR-95, miR-105, mu-miR-290, miR-215, miR-188, miR-186, miR-211, miR-331, and miR-137 were expressed at 50% or less in the lupus samples than the corresponding normal samples. miR-21, miR-223, and miR-342 were expressed at 50% or greater in the lupus samples than the corresponding normal samples. Several of the miRNAs were differentially expressed by as much as ten-fold between the lupus and normal samples. These miRNAs represent targets for diagnostic assay of therapeutic development.

In a further analysis of these samples, twenty-three miRNAs were differentially expressed (1.5 fold or greater) in at least 50% of the lupus samples relative to the matched samples. Among these miRNAs, miR-95, miR-144, miR-184 and miR-186 were differentially express in all the lupus samples. Together with let7D-AS, miR-21, miR-32, miR-133A, miR-137, miR-141, miR-181A, miR-188, miR-199, miR-201, miR-203, miR-204, miR-211, miR-212, miR-223, miR-224, mu-miR-329, miR-331 and miR-344, these miRNAs represent targets for diagnostic assay or therapeutic development.

Example 22 miRNAs and Prion Diseases

Novel infectious particles, termed prions, composed largely and perhaps solely of a single protein, are the likely causative agents of a group of transmissible spongiform encephalopathies that produce lethal decline of cognitive and motor function. Evidence indicates that the responsible protein arrives at a pathogenic state by misfolding from a normal form that has ubiquitous tissue distribution.

Using two cell-based prion model systems, the identification of miRNAs that might be associated with the process was pursued. One model system comprises two cell lines, one of which is susceptible to prion formation and one that is not. The second model system involves cells before and after they have been infected with prions. Total RNA from prion-sensitive cells, prion-insensitive cells, and prion-infected cells was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signal from each of the samples was compared to identify differentially expressed miRNAs.

Figure 17:
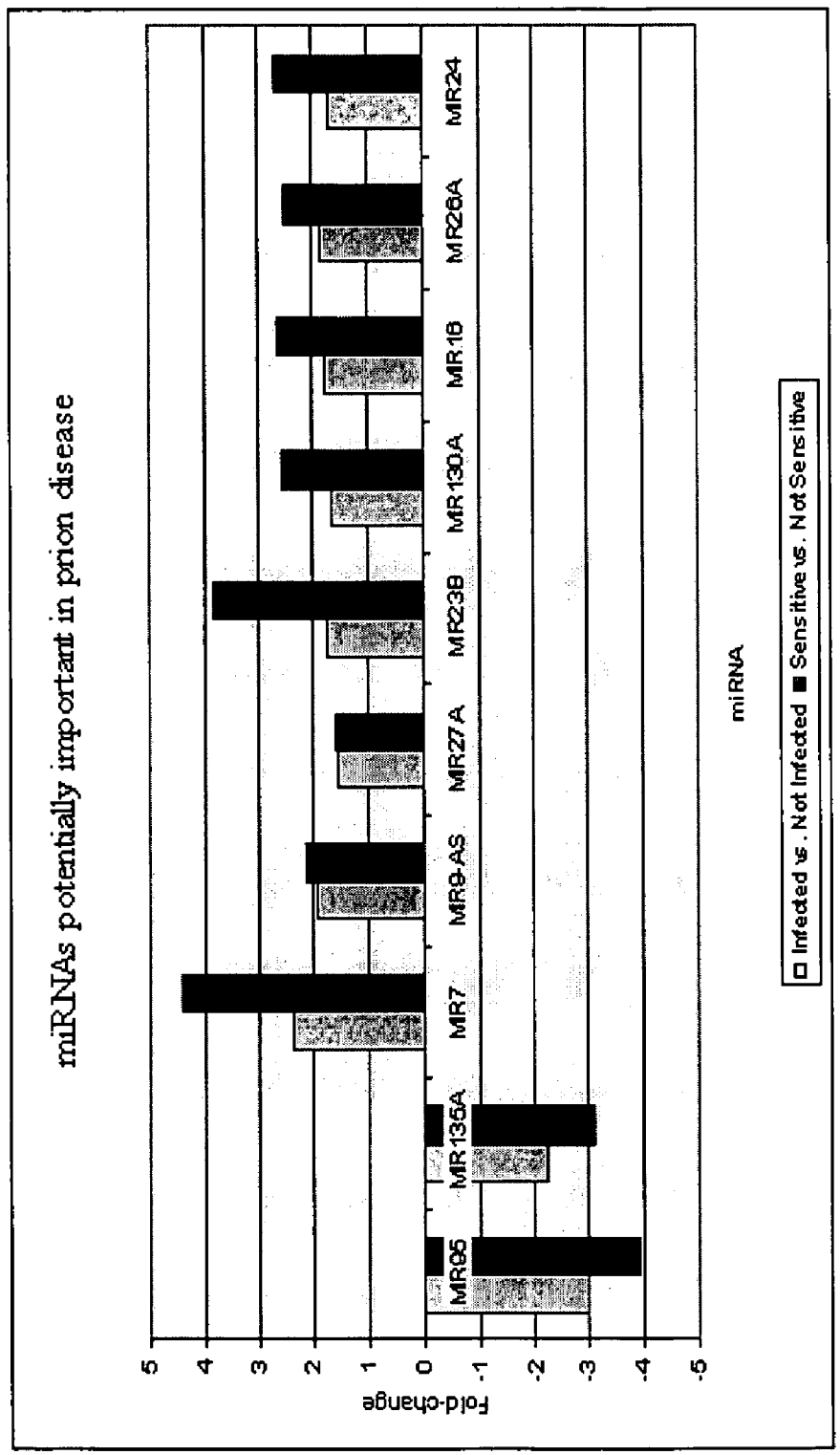
FIG. 17. Shown are miRNAs having >1.5-fold expression changes between both infected vs. uninfected and sensitive vs. insensitive. On the right is a cluster of the results from 2 arrays of each model.

As seen in FIG. 17, ten miRNAs were significantly up- or down-regulated in both prion-sensitive and prion-infected cells relative to prion resistant, uninfected cells. Arrays on multiple biological replicates for both model systems have confirmed these results. Based on their expression profiles, miR-95, 135A, 7, 9-as, 27A, 130A, 16, 26A, and 24 likely are involved directly or indirectly in prion infection and might represent diagnostic or therapeutic targets for prion disease.

Additional analyses revealed that about 40 miRNAs were found differentially expressed between cells sensitive and resistant to infection, and about 20 miRNAs were found differentially expressed during infection by prion. Ten miRNAs were significantly up- or down-regulated in both model systems. miR-7, miR-9-as, miR-16, miR-24, miR-26A, miR-27A, miR-130A and miR-239 are induced during infection and expressed at higher levels in cells sensitive to infection. These miRNAs might be involved in the mechanism of prion infection. miR-95 and miR-135A are repressed during infection and expressed at higher levels in cells not sensitive to infection, and therefore might confer some type of resistance to prion infection. Arrays on multiple biological replicates for both model systems have confirmed these results. Based on their expression profiles, miR-95, 135A, 7, 9-as, 27A, 239, 130A, 16, 26A, and 24 likely are involved directly or indirectly in prion infection and might represent diagnostic or therapeutic targets for prion disease.

Example 23

Stroke-Associated miRNAs

Stroke is a major cause of death and permanent disability in humans. They occur when blood flow to a region of the brain is obstructed and may result in death of brain tissue. There are two main types of stroke: ischemic and hemorrhagic. Ischemic stroke is caused by blockage in an artery that supplies blood to the brain, resulting in a deficiency in blood flow (ischemia). Hemorrhagic stroke is caused by the bleeding of ruptured blood vessels (hemorrhage) in the brain. Understanding miRNAs involved in stroke might enhance detection and/or treatment.

A stroke model system was used wherein mice are "preconditioned" by reducing oxygen flow to the brain (Kitagawa, 1991). An equivalent set of six mice were used; three were preconditioned and three were untreated. 24 hours after preconditioning, the mice were sacrificed. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the preconditioned and normal sample signals were compared to identify differentially expressed miRNAs.

Figure 18:
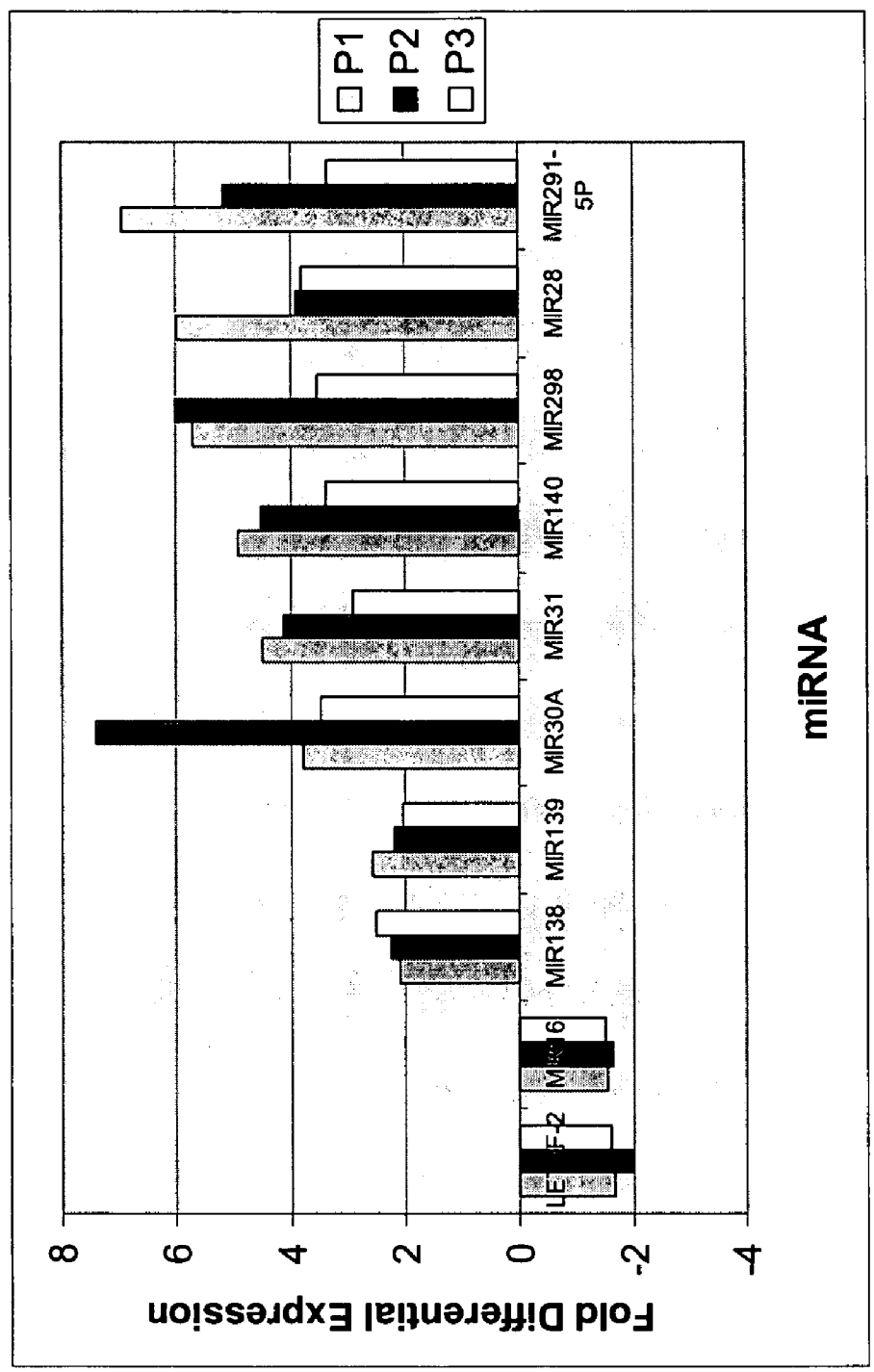
FIG. 18. Differentially expressed miRNAs in 3 preconditioned mice relative to non-treated mice.

Analysis of the miRNA profiles of the preconditioned animals (labeled P1, P2, and P4) revealed 10 miRNAs that were expressed at significantly different levels in all three preconditioned animals relative to the three non-treated animals (FIG. 18). These miRNAs resulted from ischemic pre-conditioning and represent potential targets for stroke diagnosis, prevention, or treatment.

Example 24 miRNA Analysis of Breast Tumor Samples

Tumor and normal adjacent tissue (NAT) samples were obtained from six breast cancer patients. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the tumor and NAT samples from each patient. A table listing the miRNAs that were differentially expressed in at least 80% of the breast tumor/NAT samples is provided in Table 9. Those miRNAs that are consistently seen to be down- or up-regulated in tumor samples could be used to determine if a given sample were cancerous. Likewise, these miRNAs represent potential targets for therapeutic development. Also, the genes that are regulated by these miRNAs might provide effective targets for therapeutic development. The miRNAs that are differentially expressed in only a subset of the samples likely represent molecular markers of the sub-classes of the cancer samples. These will likely prove to be valuable as prognostic indicators.

TABLE 9 miRNAs differentially expressed in breast tumor/NAT samples

| miRNA | % of tumor samples with >30% lower miRNA expression | % of tumor samples with >50% higher miRNA expression |
|---|---|---|
| miR-145 | 87% | |
| miR-135A | 100% | |
| mu-miR-329 | 100% | |
| miR-211 | 87% | |
| Mu-miR-298 | 87% | |
| miR-205 | 80% | |
| miR-21 | | 100% |
| miR-200B | | 83% |
| miR-15A | | 100% |
| miR-24 | | 83% |

Example 25 miRNA Analysis of Thyroid Tumor Samples

Tumor and normal adjacent tissue (NAT) samples were obtained from six thyroid cancer patients. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the tumor and NAT samples from each patient. A table listing the miRNAs that were differentially expressed in at least 80% of the thyroid tumor/NAT samples is provided in Table 10. Those miRNAs that are consistently seen to be down- or up-regulated in tumor samples could be used to determine if a given sample were cancerous. Likewise, these miRNAs represent potential targets for therapeutic development. Also, the genes that are regulated by these miRNAs might provide effective targets for therapeutic development. The miRNAs that are differentially expressed in only a subset of the samples likely represent molecular markers of the sub-classes of the cancer samples. These will likely prove to be valuable as prognostic indicators.

TABLE 10 miRNAs differentially expressed in thyroid tumor/NAT samples

| miRNA | % of tumor samples with >30% lower miRNA expression | % of tumor samples with >50% higher miRNA expression |
|---|---|---|
| miR-31 | 83% | |
| miR-135A | 100% | |
| miR-331 | 83% | |
| miR-203 | 83% | |

TABLE 10-continued miRNAs differentially expressed in thyroid tumor/NAT samples

| miRNA | % of tumor samples with >30% lower miRNA expression | % of tumor samples with >50% higher miRNA expression |
|---|---|---|
| miR-152 | 83% | |
| miR-138 | 80% | |
| miR-199A-as | 80% | |
| miR-30A-as | 80% | |
| miR-21 | | 80% |
| miR-200B | | 100% |
| miR-15A | | 83% |

Example 26 miRNA Analysis of Prostate Tumor Samples

Tumor and normal adjacent tissue (NAT) samples were obtained from prostate cancer patients. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the tumor and NAT samples from each patient. A table listing the miRNAs that were differentially expressed in the prostate tumor/NAT samples is provided in Table II. Those miRNAs that are consistently seen to be down- or up-regulated in tumor samples could be used to determine if a given sample were cancerous. Likewise, these miRNAs represent potential targets for therapeutic development. Also, the genes that are regulated by these miRNAs might provide effective targets for therapeutic development. The miRNAs that are differentially expressed in only a subset of the samples likely represent molecular markers of the sub-classes of the cancer samples. These will likely prove to be valuable as prognostic indicators.

TABLE 11 miRNAs differentially expressed in prostate tumor/NAT samples

| miRNA | tumor samples with >30% lower miRNA expression? | tumor samples with >50% higher miRNA expression? |
|---|---|---|
| miR-331 | yes | |
| miR-188 | yes | |
| Mu-miR-290 | yes | |
| miR-29 | | yes |
| miR-21 | | yes |
| miR-141 | | yes |
| miR-15A | | yes |

Example 27 miRNA Analysis of Bladder Tumor Samples

Tumor and normal adjacent tissue (NAT) samples were obtained from bladder cancer patients. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the tumor and NAT samples from each patient. A table listing the miRNAs that were differentially expressed in the bladder tumor/NAT samples is provided in Table 12. Those miRNAs that are consistently seen to be down- or up-regulated in tumor samples could be used to determine if a given sample were cancerous. Likewise, these miRNAs represent potential targets for therapeutic development. Also, the genes that are regulated by these miRNAs might provide effective targets for therapeutic development. The miRNAs that are differentially expressed in only a subset of the samples likely represent molecular markers of the sub-classes of the cancer samples. These will likely prove to be valuable as prognostic indicators.

TABLE 12 miRNAs differentially expressed in bladder tumor/NAT samples

| miRNA | tumor samples with >30% lower miRNA expression? | tumor samples with >50% higher miRNA expression? |
|---|---|---|
| miR-143 | yes | |
| miR-145 | yes | |
| miR-133 | yes | |
| miR-200B | | yes |
| miR-182 | | yes |
| miR-21 | | yes |
| miR-9as | | yes |

Example 28 miRNAs in Crohn's Disease

Crohn's disease is also called regional ileitis; it is a chronic, progressive, inflammatory disease of the bowel. The symptoms are most commonly that of diarrhea and pain. Weight loss, fatigue, and irritability are characteristic of the disease. The bowel movements often include mucus, blood and pus because of the infection. Fat may occur in the bowel movements, making them bulky and foul smelling. The root cause of Crohn's disease is unknown and there are commercially available therapeutic options available for patients with the disease. Identifying the molecular cause of Crohn's could lead to enhanced diagnostics as well as therapeutics.

Intestinal tissue was recovered from Crohn's patients and normal individuals. Total RNA from these samples was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the Crohn's disease and normal sample signals were compared to identify differentially expressed miRNAs. Each array experiment included duplicate arrays.

Seven miRNAs were differentially expressed in all of the Crohn's patient samples relative to the normal controls. miR-126 as, miR-194, miR-192, and mu-miR-207 were expressed at more than two-fold lower levels in the Crohn's patient intestinal samples while miR-150, miR-125B, and miR-223 were expressed at more than two-fold higher levels in Crohn's patients. These miRNAs represent targets for diagnostic assay or therapeutic development for Crohn's disease.

Example 29 miRNAs and Cervical Cancer

Cancer of the uterine cervix is the second-leading cause of cancer-related deaths among women worldwide. Epidemiological and molecular studies have demonstrated that human papillomaviruses (HPVs) are the etiological agents of the majority (~99%) of cervical cancers. More than a hundred of different HPV types have been characterized so far, and new types are regularly added to this list. Among the HPVs identified, about the third (46) infect the genital tract. These HPV types are sexually transmitted and can be further categorized into low-risk or high-risk groups according to the propensity for malignant progression of the lesions that they cause. The high-risk mucosal HPV types cause intraepithelial lesions that can progress to invasive carcinomas. Although routine cytology screening and reflexive HPV testing has improved cervical cancer detection and reduced mortality, significant problems and barriers remain, including the low predictive value of current testing which leads to costly and invasive testing and emotional stress in patients.

To identify host human miRNAs signatures in patients carrying high-risk HPV type(s), total RNA from HPV negative or high-risk HPV positive liquid-based cervical Pap smears was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signal from each of the samples was compared to identify differentially expressed miRNAs. Four miRNAs were consistently expressed at levels at least 1.5 fold higher in the high-risk HPV positive patients relative to the HPV negative controls. Based on their expression profiles, miR-29B, miR-326, miR-361 and miR-425 likely are involved directly or indirectly in viral infection and/or cervical cancer onset, and might represent diagnostic or therapeutic targets for cervical cancer.

Example 30 miRNA Analysis of Leukemia Samples

Leukemia is cancer of T-cells. The two most prevalent forms of leukemia are acute myelogenous leukemia and chronic lymphocytic leukemia. Acute myelogenous leukemia is a rapidly progressing disease that affects mostly cells that are unformed or primitive (not yet fully developed or differentiated). These immature cells cannot carry out their normal functions. Chronic leukemia progresses slowly and permits the growth of greater numbers of more developed cells. In general, these more mature cells can carry out some of their normal functions. To understand how miRNAs are affected by leukemia or might be contributing to leukemia, samples from leukemia patients were compared to samples from normal individuals.

Total RNA from white blood cells of patients with acute myelogenous leukemia (AML), chronic lymphocytic leukemia (CLL), and no disease was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the tumor and NAT sample signals were compared to identify differentially expressed miRNAs. The relative signal intensities for each element were compared between the leukemia and normal samples from each patient.

The following miRNAs were expressed at lower levels in all of the AML samples than the corresponding normal samples: miR-425, miR-361, miR-25, and mu-miR-291-5P. The following miRNAs were expressed at higher levels in all of the AML samples than the corresponding normal samples: miR-126, miR-126-AS, miR-222, miR-221, and miR-181B. Those miRNAs that are consistently seen to be down- or up-regulated in AML patients could be used to diagnose patients. Likewise, these miRNAs represent potential targets for therapeutic development. Likewise, the genes that are regulated by these miRNAs might provide effective targets for therapeutic development.

The following miRNAs were expressed at lower levels in all of the CLL samples than the corresponding normal samples: miR-361, miR-425, and mu-miR-341. The following miRNAs were expressed at higher levels in all of the CLL samples than the corresponding normal samples: miR-92, miR-99B, miR-23A, miR-23B, miR-223, miR-26A, miR-221, miR-222, miR-21, miR-20, miR-181A, miR-181B, miR-16, miR-15, miR-106A, let-7, and miR-103. Those miRNAs that are consistently seen to be down- or up-regulated in CLL patients could be used to diagnose patients. Likewise, these miRNAs represent potential targets for therapeutic development. Likewise, the genes that are regulated by these miRNAs might provide effective targets for therapeutic development.

Example 31 miRNA Analysis of Alzheimer's Samples

Alzheimer's disease is a progressive brain disorder that gradually destroys a person's memory and ability to learn, reason, make judgments, communicate and carry out daily activities. As Alzheimer's progresses, individuals may also experience changes in personality and behavior, such as anxiety, suspiciousness or agitation, as well as delusions or hallucinations.

There is currently no cure for Alzheimer's and positive diagnosis of the disease can only be achieved post-mortem by analyzing the patient brain for two abnormal microscopic structures called "plaques" and "tangles." Amyloid plaques are clumps of protein that accumulate outside the brain's nerve cells. Tangles are twisted strands of another protein that form inside cells. Understanding the molecular basis of Alzheimer's will be critical to the development of effective drugs and diagnostic assays. We analyze the miRAN expression profiles of the brains of Alzheimer's patients to identify those miRNAs that are differentially expressed.

Alzheimer's and normal amygdala tissue samples were obtained from eight individuals. Total RNA from these samples was isolated using the glass fiber filter method described above. The total RNA was fractionated by tube electrophoresis to recover the miRNAs. The amygdala miRNAs were fluorescently labeled with Cy3 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signals from the Alzheimer's and normal amygdale samples were compared to identify differentially expressed miRNAs. The relative signal intensities for each element were compared between the tumor and NAT samples from each patient. The following miRNAs were down-regulated in all of the Alzheimer samples than corresponding normal samples: miR-425, mu-miR-291-5P, miR-204, and miR-338. The following miRNAs were up-regulated in all of the Alzheimer samples than corresponding normal samples: miR-145, miR-16, miR-223, miR-126, let-7F2, and miR-143. Those miRNAs that are consistently seen to be down- or up-regulated in Alzheimer's samples could be used to diagnose Alzheimer's patients. Likewise, these miRNAs represent potential targets for therapeutic development. The genes that are regulated by these miRNAs might provide effective targets for therapeutic development.

Example 32 miRNA Analysis of Alzheimer's Mouse Model

Although Alzheimer Disease (AD) is the most common form of dementia, there is currently no molecular test for AD, and definitive diagnosis can only be made by post-mortem histological examination to identify extracellular amyloid plaques and intracellular neurofibrillary tangles in human brain sections. Promising new therapies offer the prospect of better management of AD provided methods for definitive diagnosis can be developed. Both early and late-onset human AD have been linked to specific haplotypes of the sequence encoding the ApoE apolipoprotein transporter. Apo E mice (JAX strain 02052) serve as an animal model for human Alzheimer Disease (1, 2, 3). These mice are homozygous for the Apoe$^{tm/Unc}$ knockout mutation in the apolipoprotein E gene, which leads to defects in lipid transport, defects in cholesterol metabolism, and xanthomatous lesions in the brain. These mice also show altered responses to stress, impaired learning and memory, and synaptic damage. In order to identify biomarkers associated with AD, we carried out global expression profiling of mRNA and microRNA (miRNA) transcripts in brain regions of ApoE and control mice using a novel microarray system developed at Ambion, followed by qRT-PCR assays to validate differentially expressed miRNAs. These studies resulted in identification of a miRNA, miR-182, that is differentially expressed in specific brain regions of the ApoE compared to control mice. The miR-182 molecule was dysregulated in all the brain regions tested (cortex, hypothalamus, cerebellum, and hippocampus), with the most dramatic difference being ~10-fold down-regulation in cortex of the AD mouse (as determined by qRT-PCR). Computational analysis was used to identify candidate mRNA targets, and the relevant gene product levels were assessed in AD mice. These efforts may lead to discovery of new RNA-based biomarkers useful for diagnosis and treatment of AD.

Example 33 miRNA Analysis of Multiple Sclerosis Brain Samples

Total RNA from the brains of patients with multiple sclerosis along with normal brains was isolated using the glass fiber filter method described above. The total RNA was fractionated by tube electrophoresis to recover the miRNAs. The miRNAs were fluorescently labeled with Cy3 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signals from the Multiple Sclerosis and normal samples were compared to identify differentially expressed miRNAs. The following miRNAs were expressed at higher levels in each of the multiple sclerosis brain samples: miR-370, miR-30A, miR-132, mu-miR-298, miR-422A, miR-31, and miR-155. The following miRNAs were expressed at lower levels in each of the multiple sclerosis brain samples: mu-miR-322, miR-326, miR-328, miR-9 as, miR-137, miR-126, miR-21, miR-181B, and miR-218. Those miRNAs that are consistently seen to be down- or up-regulated in multiple sclerosis samples could be used to determine if a person has multiple sclerosis. Likewise, these miRNAs represent potential targets for therapeutic development. Also, the genes that are regulated by these miRNAs might provide effective targets for therapeutic development.

Example 34 miRNAs Associated with T-Cell Development

T-cells are the primary component of both leukemia and lymphoma, as well as HIV infection. Understanding these diseases requires understanding the molecular components of T-cells. A significant amount is already known about T-cell development. T cell development occurs in the thymus; the thymic microenvironment directs differentiation as well as positive and negative selection. Lymphoid progenitors which have developed from hematopoietic stem cells in the bone marrow migrate to the thymus to complete their antigen-independent maturation into functional T cells. In the thymus, T cells develop their specific T cell markers, including TCR, CD3, CD4 or CD8, and CD2. When progenitor cells begin to express CD2 but have not yet rearranged their TCR genes ($CD2^+$ $CD3^-$), they are double negative for CD4 and CD8 ($CD4^-$ $CD8^-$), the markers for Th and Tc lineages. Of the double negative cells in the thymus, about 20% have rearranged gd TCR, about 20% have very homogenous ab TCR, and 60% are committed to becoming the majority of mature ab T cells. These cells next express the adhesion molecule CD44, then the alpha chain of the IL-2 receptor (CD25). $CD44^{low}$ $CD25^+$ double negative T cells rearrange TCR beta chain. beta chain rearrangement begins with D-J joining, followed by V-DJ joining. The chances of successful b chain rearrangement are increased by the presence of two DJCb gene clusters. If rearrangement in the first cluster fails, rearrangement in the second can occur Productive rearrangement of beta chain is followed by its expression on the T cell membrane with CD3 and surrogate a chain, pTa (analogous to 15 in B cells). Signaling through the preT receptor causes the cells to stop rearranging b chain, undergo a period of proliferation, and begin to express both CD4 and CD8, becoming double positive T cells.

Using a mouse model of T-cell development, we compared double positive T-cells to more mature, CD4+ cells. Total RNA from double positive and CD4+ T-cells was isolated using the glass fiber filter method described above. The total RNA was fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signals were compared to identify differentially expressed miRNAs. The relative signal intensities for each element were compared between the double positive and CD4+ samples. miRNAs that are expressed at more than two-fold higher levels in the more mature, CD4+ cells are miR-181A, miR-16, miR-15B, miR-128A, miR-17-5P, let-7A, let-7C, and miR-106. One miRNA was expressed at more than two-fold lower levels in the more mature CD4+ cells: miR-326.

Example 35 miRNAs Associated with Cardiac Hypertrophy

Patients with chronic heart failure develop an enlargement of the heart called cardiac hypertrophy. The causes and effects of cardiac hypertrophy have been extensively documented, but the underlying molecular mechanisms that link the molecular signals to cell changes, or cardiac signaling pathways, remain poorly understood. miRNAs that induce cardiac hypertrophy would supply targets for diagnostic or therapeutic intervention.

The miRNA expression profiles of two different hypertrophic mouse models was examined. The first mouse model was a knockout that eliminated the Gq-coupled receptor-signaling pathway, which has been implicated in the cardiac hypertrophic response to stress. The second mouse model was a double knockout that eliminated both the Gq-coupled receptor signaling pathway and the STE20 HGK pathway, both of which have been implicated in cardiac hypertrophy.

Total RNA from the hearts of Gq and Gq/HGK transgenics as well as normal mouse hearts was isolated using the glass fiber filter method described above. The total RNAs were fractionated by tube electrophoresis to recover the miRNAs. The miRNAs were fluorescently labeled with Cy3 or Cy5 using the two-step fluorescent labeling process described above. The labeled miRNAs were hybridized to miRNA probes arrayed on glass slides as described above. The signal from the hybridized miRNAs was quantified using a GenePix 4000B Scanner (Axon) and the signals were compared to identify differentially expressed miRNAs. The relative signal intensities for each element were compared between the transgenic mouse samples and the normal heart samples. miRNAs that are expressed at more than two-fold lower levels in the Gq transgenic hearts are miR-23B, miR-326, miR-126, miR-133A, miR-23A, and miR-99B. Interestingly, only miR-326 was also down-regulated in the Gq/HGK transgenic mice.

Example 36

Electrophoretic Purification System

The previous examples involved purification of miRNA using a micro-electrophoresis system that contains small electrode buffer chambers with a small volume of separating gel matrix (each less than 0.5 ml). This purification relies on the fact that all desired species are at the small end of the size spectrum. This allows the collection of the sample simply by the removal of all lower electrode buffer after these species have migrated completely through the gel matrix. Species can be concentrated either by alcohol precipitation or immobilization on glass fiber filters in high alcohol concentrations (covered in Ambion Patent App). Although this is similar to passing the sample through a filter with pores of a particulae nm size, it is distinguishable in that the driving force is electrophoretic movement of the species rather than passage of the carrier fluid under atmospheric or centrifugal pressure. Also, since the total thickness of the separation matrix being passed through is substantially greater (~150 vs. <1 mm), the separation is much more efficient. The system can also be used to make successive collections by removing and replenishing the lower electrode buffer.

To accomplish this, the sample was mixed with an equal volume of denaturing solution containing 95% formamide to a volume of up to 100 µl and applied under the upper electrode buffer (250 µl) to the top of the separating gel matrix. The gel was a polyacrylamide matrix in a urea solution. The use of denaturing conditions ensured both that the small RNAs were separated from any hybrids they form, and that their migration rates reflected their size rather than their structure. The gel buffers were a standard Tris-Borate-EDTA system. By using a 10% polyacrylamide (9.33% monomer:0.67% methylene bis-acrylamide) gel matrix, xylene cyanol dye can be used to track the position of RNA chains of about 40 nt, so that standard procedure is to stop the gel as the dye begins to emerge. The samples were run at 60-80 V, drawing a current of ~3 mA, for 12-15 min. The entire contents of the lower electrode chamber (250 µl) were then collected and the RNA species purified from it using either precipitation in 80% ethanol or capture on glass fiber filters in the presence of 75% ethanol, 0.5 M guanidinium thiocyanate, 3.75 mM CaCl2, 16 mM NaAcetate, pH 4.0. After ethanolic washes, the sample were eluted in water at a temperature of >65° C.

All of the compositions and methods disclosed and claimed herein can be made and executed without undue experimentation in light of the present disclosure. While the compositions and methods of this invention have been described in terms of embodiments, it will be apparent to those of skill in the art that variations may be applied to the compositions and methods, and in the steps or in the sequence of steps of the methods, described herein without departing from the concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

U.S. patent application Ser. No. 10/667,126
U.S. Patent Appln. 60/627,171
U.S. Patent Appln. 60/649,634
U.S. Pat. No. 5,610,287
U.S. Pat. No. 4,337,063
U.S. Pat. No. 4,404,289
U.S. Pat. No. 4,405,711
U.S. Pat. No. 4,659,774
U.S. Pat. No. 4,682,195

U.S. Pat. No. 4,683,202
U.S. Pat. No. 4,704,362
U.S. Pat. No. 4,816,571
U.S. Pat. No. 4,959,463
U.S. Pat. No. 5,141,813
U.S. Pat. No. 5,143,854
U.S. Pat. No. 5,202,231
U.S. Pat. No. 5,214,136
U.S. Pat. No. 5,221,619
U.S. Pat. No. 5,223,618
U.S. Pat. No. 5,242,974
U.S. Pat. No. 5,264,566
U.S. Pat. No. 5,268,486
U.S. Pat. No. 5,288,644
U.S. Pat. No. 5,324,633
U.S. Pat. No. 5,378,825
U.S. Pat. No. 5,384,261
U.S. Pat. No. 5,405,783
U.S. Pat. No. 5,412,087
U.S. Pat. No. 5,424,186
U.S. Pat. No. 5,428,148
U.S. Pat. No. 5,429,807
U.S. Pat. No. 5,432,049
U.S. Pat. No. 5,436,327
U.S. Pat. No. 5,445,934
U.S. Pat. No. 5,446,137
U.S. Pat. No. 5,466,786
U.S. Pat. No. 5,468,613
U.S. Pat. No. 5,470,710
U.S. Pat. No. 5,470,967
U.S. Pat. No. 5,472,672
U.S. Pat. No. 5,480,980
U.S. Pat. No. 5,492,806
U.S. Pat. No. 5,503,980
U.S. Pat. No. 5,510,270
U.S. Pat. No. 5,525,464
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,574,146
U.S. Pat. No. 5,580,726
U.S. Pat. No. 5,580,732
U.S. Pat. No. 5,583,013
U.S. Pat. No. 5,593,839
U.S. Pat. No. 5,599,672
U.S. Pat. No. 5,599,695
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,624,711
U.S. Pat. No. 5,631,134
U.S. Pat. No. 5,637,683
U.S. Pat. No. 5,639,603
U.S. Pat. No. 5,645,897
U.S. Pat. No. 5,652,099
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,670,663
U.S. Pat. No. 5,672,697
U.S. Pat. No. 5,681,947
U.S. Pat. No. 5,695,940
U.S. Pat. No. 5,700,637
U.S. Pat. No. 5,700,922
U.S. Pat. No. 5,705,629
U.S. Pat. No. 5,708,154
U.S. Pat. No. 5,714,606
U.S. Pat. No. 5,728,525
U.S. Pat. No. 5,744,305
U.S. Pat. No. 5,763,167
U.S. Pat. No. 5,777,092
U.S. Pat. No. 5,792,847
U.S. Pat. No. 5,800,992
U.S. Pat. No. 5,807,522
U.S. Pat. No. 5,830,645
U.S. Pat. No. 5,837,196
U.S. Pat. No. 5,847,219
U.S. Pat. No. 5,858,988
U.S. Pat. No. 5,859,221
U.S. Pat. No. 5,871,928
U.S. Pat. No. 5,872,232
U.S. Pat. No. 5,876,932
U.S. Pat. No. 5,886,165
U.S. Pat. No. 5,919,626
U.S. Pat. No. 6,004,755
U.S. Pat. No. 6,087,102
U.S. Pat. No. 6,251,666
U.S. Pat. No. 6,368,799
U.S. Pat. No. 6,383,749
U.S. Pat. No. 6,617,112
U.S. Pat. No. 6,638,717
U.S. Pat. No. 6,720,138
U.S. Pat. No. 6,723,509
Ambros et al., *RNA,* 9(3):277-279, 2003.
Beaucage, and Lyer, *Tetrahedron,* 48:2223-2311, 1992.
Brennecke et al., *Cell,* 113:25-36, 2003.
British Patent 1,529,202
Calin et al., *Proc. Natl. Acad. Sci., USA,* 99:15524-15529, 2002.
Carrington et al., *Science,* 301(5631):336-338, 2003.
Cummins et al., In: *IRT: Nucleosides and nucleosides,* La Jolla Calif., 72, 1996.
Denli et al., *Trends Biochem. Sci.,* 28:196, 2003.
Didenko, *Biotechniques,* 31(5):1106-16, 1118, 1120-1, 2001.
Doench et al. 2004
Doench et al., *Genes & Dev.* 17: 438-442, 2003.
Dostie et al., *RNA,* 9: 180-186, 2003.
Emptage et al., *Neuron,* 29(1):197-208, 2001.
EP 373 203;
EP 785 280;
EP 799 897 and
European Patent 266,032
Froehler et al., *Nucleic Acids Res.,* 14(13):5399-5407, 1986.
Gillam et al., *J. Biol. Chem.,* 253:2532, 1978.
Gillam et al., *Nucleic Acids Res.,* 6:2973, 1979.
Griffey et al., *J Mass Spectrom,* 32(3):305-13, 1997.
Grishok et al., *Cell,* 106: 23-34, 2001.
Ha et al., *Genes Dev.,* 10, 3041-3050, 1996.
Hutvagner et al., *Science,* 297(5589):2056-60, 2002.
Itakura and Riggs, *Science,* 209:1401-1405, 1980.
Itakura et al., *J. Biol. Chem.,* 250:4592 1975.
Khorana, *Science,* 203, 614 1979.

Kiriakidou et al. *Genes Dev.* 18(10):1165-78, 2004.
Kitagawa et al., *Brain Res.*, 561:203-11, 1991.
Klostermeier and Millar, *Biopolymers,* 61(3):159-79, 2001-2002
Kornberg and Baker, *DNA Replication,* 2nd Ed., Freeman, San Francisco, 1992.
Krichevsky et al., *RNA,* 9(10):1274-1281, 2003.
Lagos-Quintana et al., *Science,* 294(5543):853-858, 2001.
Lau et al., *Science,* 294(5543):858-862, 2001.
Lee and Ambros, *Science,* 294(5543):862-864, 2001.
Lee et al., *EMBO J.* 21:4663-70, 2002.
Lee et al., *Nature* 425:415-419, 2003.
Lewis, *Cell,* 115(7):787-798 2003.
Martin et al., *RNA,* 4(2):226-230, 1998.
Martin et al., *RNA,* 4(2):226-30, 1998.
Miller and Mandell, *Clin. Chem.,* 51(2):289-290, 2005.
Olsen et al., *Dev. Biol.,* 216:671, 1999.
Pasquinelli and Ruvkun, *Ann. Rev. Cell Dev. Biol.,* 18:495-513, 2002.
PCT Appln. WO 0138580
PCT Appln. WO 0168255
PCT Appln. WO 03020898
PCT Appln. WO 03022421
PCT Appln. WO 03023058
PCT Appln. WO 03029485
PCT Appln. WO 03040410
PCT Appln. WO 03053586
PCT Appln. WO 03066906
PCT Appln. WO 03067217
PCT Appln. WO 03076928
PCT Appln. WO 03087297
PCT Appln. WO 03091426
PCT Appln. WO 03093810
PCT Appln. WO 03100012
PCT Appln. WO 03100448
PCT Appln. WO 04020085
PCT Appln. WO 04027093
PCT Appln. WO 09923256
PCT Appln. WO 09936760
PCT Appln. WO 93/17126
PCT Appln. WO 95/11995
PCT Appln. WO 95/21265
PCT Appln. WO 95/21944
PCT Appln. WO 95/21944
PCT Appln. WO 95/35505
PCT Appln. WO 96/31622
PCT Appln. WO 97/10365
PCT Appln. WO 97/27317;
PCT Appln. WO 9743450
PCT Appln. WO 99/35505;
Piedrahita et al., *Proc. Natl. Acad. Sci. USA,* 89(10):4471-4475, 1992.
Rademakers et al., *Scientific World J,* 3:497-519, 2003.
Reinhart et al., *Nature,* 403:901-906, 2000.
Sambrook et al., In: *DNA microaarays: a molecular cloning manual,* Cold Spring Harbor Laboratory Press, Cold Spring Harbor, N.Y., 2003.
Sambrook et al., In: Molecular cloning, Cold Spring Harbor Laboratory Press, Cold Spring Harbor, N.Y., 1989.
Sambrook et al., *In: Molecular cloning,* Cold Spring Harbor Laboratory Press, Cold Spring Harbor, N.Y., 2001.
Scheit, "Nucleotide Analogs," *In: Synthesis and Biological Function,* Wiley-Interscience, New York, pp. 171-172, 1980.
Seggerson et al., *Dev. Biol.,* 243:215, 2002.
Sillero et al., *Eur. J. Biochem.,* 268:3605-3611, 2001.
UK Appln 8 803 000
Vella et al., *Genes Dev.* 18(2):132-7, 2004.
Xu et al., *Curr. Biol.,* 13:790-795, 2003.
Zeng et al., *Proc. Natl. Acad. Sci.* 100: 9779-9784, 2003.

What is claimed is:

1. A method for identifying a patient as having a marker for lung cancer comprising
    a) analyzing mir-205 expression in a lung tissue sample from a patient suspected of having lung cancer; and
    b) identifying the patient as having a marker correlated with lung cancer when an increase in miR-205 of at least 50% in the lung tissue sample compared to a noncancerous lung tissue sample is determined or identifying the patient as not having the marker when the increase in miR-205 in the lung tissue sample fails to be determined.

2. The method of claim 1, wherein analyzing the sample comprises generating an miRNA profile from the sample, wherein the profile comprises multiple miRNAs.

3. The method of claim 2, wherein the generating the miRNA profile comprises:
    (a) labeling miRNA isolated from the lung tissue sample;
    (b) hybridizing the miRNA to an miRNA array; and,
    (c) determining miRNA hybridization to the array.

4. The method of claim 1, further comprising analyzing the lung tissue sample for a decrease in miR-126 expression compared to the noncancerous sample.

5. The method of claim 1, wherein the patient is determined to have an increase in miR-205 expression.

6. The method of claim 4, wherein the patient is determined to have a decrease in miR-126 expression.

7. The method of claim 1, further comprising analyzing the lung tissue sample for a decrease in expression of let-7, miR-26a, miR-30a-AS, miR-95, miR-125a, miR-331, or miR-342, or an increase in expression of miR-200b compared to the noncancerous sample.

8. A method for identifying a patient as having a marker correlated with lung cancer comprising:
    a) obtaining from a patient a lung tissue sample, wherein the patient is suspected of having lung cancer;
    b) identifying the patient as having a marker correlated with lung cancer if an increase of at least 50% in miR-205 expression in the lung tissue sample compared to a noncancerous lung tissue sample is determined or identifying the patient as not having the marker if the increase is not determined.

9. The method of claim 8, wherein the increase in the lung tissue sample was determined by generating an miRNA profile from the sample.

10. The method of claim 9, wherein generating the miRNA profile comprises:
    (a) labeling the miRNA isolated from the sample;
    (b) hybridizing the miRNA to an miRNA array; and,
    (c) determining miRNA hybridization to the array.

11. The method of claim 8, further comprising identifying the patient as having a marker correlated with lung cancer if a decrease in miR-126 expression compared to the noncancerous sample is determined.

12. The method of claim 8, wherein the patient is determined to have an increase in miR-205 expression.

13. The method of claim 11, wherein the patient is determined to have an decrease in miR-126 expression.

14. The method of claim 8, wherein the lung tissue sample from the patient is analyzed for a decrease in expression of let-7, miR-26a, miR-30a-AS, miR-95, miR-125a, miR-331, or miR-342 or an increase in expression of miR-200b compared to the noncancerous sample.

* * * * *

UNITED STATES PATENT AND TRADEMARK OFFICE
CERTIFICATE OF CORRECTION

| | | |
|---|---|---|
| PATENT NO. | : 7,888,010 B2 | Page 1 of 1 |
| APPLICATION NO. | : 11/141707 | |
| DATED | : February 15, 2011 | |
| INVENTOR(S) | : David Brown et al. | |

It is certified that error appears in the above-identified patent and that said Letters Patent is hereby corrected as shown below:

In claim 3, column 387, line 15, delete "wherein the generating" and insert -- wherein generating -- therefor.

Signed and Sealed this
Tenth Day of May, 2011

David J. Kappos
*Director of the United States Patent and Trademark Office*